US009994619B2

(12) United States Patent
Weiner et al.

(10) Patent No.: US 9,994,619 B2
(45) Date of Patent: Jun. 12, 2018

(54) NUCLEIC ACID MOLECULES ENCODING NOVEL HERPES ANTIGENS, VACCINE COMPRISING THE SAME, AND METHODS OF USE THEREOF

(71) Applicant: THE TRUSTEES OF THE UNIVERSITY OF PENNSYLVANIA, Philadelphia, PA (US)

(72) Inventors: David B Weiner, Merion, PA (US); Devon Shedlock, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days. days.

(21) Appl. No.: 15/001,825

(22) Filed: Jan. 20, 2016

(65) Prior Publication Data

US 2016/0130308 A1 May 12, 2016

Related U.S. Application Data

(62) Division of application No. 13/982,457, filed as application No. PCT/US2012/023398 on Jan. 31, 2012, now Pat. No. 9,243,041.

(60) Provisional application No. 61/438,089, filed on Jan. 31, 2011.

(51) Int. Cl.

| | |
|---|---|
| ***C07K 14/005*** | (2006.01) |
| ***C12N 7/00*** | (2006.01) |
| ***A61K 39/12*** | (2006.01) |
| ***A61K 39/245*** | (2006.01) |
| ***A61K 39/00*** | (2006.01) |
| ***A61K 39/25*** | (2006.01) |

(52) U.S. Cl.

CPC ............ *C07K 14/005* (2013.01); *A61K 39/12* (2013.01); *A61K 39/245* (2013.01); *A61K 39/25* (2013.01); *C12N 7/00* (2013.01); *A61K 2039/53* (2013.01); *C12N 2710/16011* (2013.01); *C12N 2710/16111* (2013.01); *C12N 2710/16122* (2013.01); *C12N 2710/16134* (2013.01); *C12N 2710/16622* (2013.01); *C12N 2710/16634* (2013.01); *C12N 2710/16722* (2013.01); *C12N 2710/16734* (2013.01)

(58) Field of Classification Search

CPC ...................... C12N 7/00; C12N 15/86; C12N 2710/16034; C12N 2710/16734; C12N 15/869; C12N 2710/16762; A61K 39/12; A61K 39/245; A61K 2039/525; A61K 2039/6075; A61K 39/25; A61K 39/42; A61K 35/763; C07K 14/005; C07K 14/03; C07K 14/035; C07K 16/085

See application file for complete search history.

(56) References Cited

U.S. PATENT DOCUMENTS

| | | | |
|---|---|---|---|
| 4,510,245 | A | 4/1985 | Cousens et al. |
| 4,554,101 | A | 11/1985 | Hopp et al. |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | David et al. |
| 4,945,050 | A | 7/1990 | Sanford et al. |
| 5,017,487 | A | 5/1991 | Stunnenberg et al. |
| 5,036,006 | A | 7/1991 | Sanford et al. |
| 5,077,044 | A | 12/1991 | Stocker et al. |
| 5,100,587 | A | 3/1992 | Clough et al. |
| 5,112,749 | A | 6/1992 | Hoshino et al. |
| 5,174,993 | A | 12/1992 | Paoletti et al. |
| 5,223,424 | A | 6/1993 | Cochran et al. |
| 5,225,336 | A | 7/1993 | Paoletti et al. |
| 5,240,703 | A | 8/1993 | Cochran et al. |
| 5,242,829 | A | 9/1993 | Panicali et al. |
| 5,273,525 | A | 12/1993 | Hofmann et al. |
| 5,294,441 | A | 3/1994 | Curtiss et al. |
| 5,294,548 | A | 3/1994 | McLinden et al. |
| 5,310,668 | A | 5/1994 | Ellis et al. |
| 5,387,744 | A | 2/1995 | Curtiss et al. |
| 5,389,368 | A | 2/1995 | Curtiss et al. |
| 5,424,065 | A | 6/1995 | Curtiss et al. |
| 5,451,499 | A | 9/1995 | Cochran et al. |
| 5,453,364 | A | 9/1995 | Paoletti et al. |
| 5,462,734 | A | 10/1995 | Letchworth et al. |
| 5,470,734 | A | 11/1995 | Sondermeijer et al. |
| 5,474,935 | A | 12/1995 | Chatterjee et al. |
| 5,482,713 | A | 1/1996 | Paoletti et al. |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten et al. |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |

(Continued)

FOREIGN PATENT DOCUMENTS

| | | | | |
|---|---|---|---|---|
| EP | 0244155 A1 | 4/1987 | | |
| WO | WO 2000043527 A1 * | 7/2000 | ........... | A61K 39/145 |
| WO | 2008011609 A2 | 1/2008 | | |
| WO | WO-2009012487 A2 * | 1/2009 | ........... | A61K 39/145 |
| WO | WO94/016737 | 10/2012 | | |

OTHER PUBLICATIONS

Kumar S, Nei M, Dudley J, Tamura K. MEGA: a biologist-centric software for evolutionary analysis of DNA and protein sequences. Brief Bioinform. Jul. 2008;9(4):299-306.*

(Continued)

*Primary Examiner* — Rachel B Gill

(74) *Attorney, Agent, or Firm* — Riverside Law LLP

(57) ABSTRACT

Provided herein are nucleic acid sequences that encode novel consensus amino acid sequences of herpes virus antigens, as well as genetic constructs/vectors and vaccines expressing the sequences. Also provide herein are methods for generating an immune response against herpes virus using the vaccines that are provided.

20 Claims, 26 Drawing Sheets

(56) References Cited

U.S. PATENT DOCUMENTS

| | | | |
|---|---|---|---|
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,110,161 | A | 8/2000 | Mathiesen et al. |
| 6,156,319 | A | 12/2000 | Cohen et al. |
| 6,261,281 | B1 | 7/2001 | Mathiesen et al. |
| 6,589,529 | B1 | 7/2003 | Choi et al. |
| 6,697,669 | B2 | 2/2004 | Dev et al. |
| 6,939,862 | B2 | 9/2005 | Bureau et al. |
| 6,958,060 | B2 | 10/2005 | Mathiesen et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 2004/0175727 | A1 | 9/2004 | Draghia-Akli et al. |
| 2005/0052630 | A1 | 3/2005 | Smith et al. |
| 2008/0091135 | A1 | 4/2008 | Draghia-Akli et al. |
| 2010/0160419 | A1 | 6/2010 | Vilalta et al. |

OTHER PUBLICATIONS

Peters GA, Tyler SD, Grose C, Severini A, Gray MJ, Upton C, Tipples GA. A full-genome phylogenetic analysis of varicella-zoster virus reveals a novel origin of replication-based genotyping scheme and evidence of recombination between major circulating clades. J Virol. Oct. 2006;80(19):9850-60.*

Davison AJ, Scott JE. The complete DNA sequence of varicella-zoster virus. J Gen Virol. Sep. 1986;67 ( Pt 9):1759-816.*

Davison AJ, Scott JE. Human herpesvirus 3, complete genome. NCBI Reference Sequence: NC_001348.1. First rev. Aug. 1, 2000.*

AAK19252. Cole,N.L., Faga,B.P. and Grose,C. ORF37 [Human herpesvirus 3 VZV-32]. Mar. 15, 2001.*

NP_040182. Davison AJ, Scott JE. envelope glycoprotein L [Human alphaherpesvirus 3]. Aug. 1, 2000.*

ABE03086. Loparev VN. unknown [Human alphaherpesvirus 3]. Mar. 15, 2007.*

NP_040189. Davison AJ, Scott JE. envelope glycoprotein I [Human alphaherpesvirus 3]. Aug. 1, 2000.*

GenBank Accession No. ACM48077.1, dated Jan. 9, 2009; https://www.ncbi.nlm.nih.gov/protein/ACM48077.1.

UniProtKB/Swiss-Prot Accession No. Q68671.1, dated Nov. 1, 1997;https://www.ncbi.nlm.nih.gov/protein/Q68671.1.

GenBank Accession No. ABY48954.1, dated Dec. 18, 2007; https://www.ncbi.nlm.nih.gov/protein/ABY48954.1.

GenBank Accession No. AAR31335.1, dated Oct. 22, 2003; https://www.ncbi.nlm.nih.gov/protein/AAR31335.1.

GenPept Accession No. YP_01565.1, dated Jul. 2, 2013; https://www.ncbi.nlm.nih.gov/proteintYP_081565.1.

GenPept Accession No. YP_081566.1, dated Jul. 2, 2013; https://www.ncbi.nlm.nih.gov/protein/YP_081566.1.

GenBank Accesion No. ACM48061.1, dated May 9, 2013; https://www.ncbi.nlm.nih.gov/protein/ACM48061.1.

GenBank Accesion No. AAA45928.1, dated Aug. 2, 1993; https://www.ncbi.nlm.nih.gov/protein/AAA45928.1.

GenBank Accesion No. AAL77782.1, dated Apr. 1, 2002; https://www.ncbi.nlm.nih.gov/protein/AAL77782.1.

Frelin L, et al., "Codon optimization and mRNA amplication effectively enhances the immunogenicity of the hepatitis C virus nonstructual 3/4A gene", Gene Ther, 2004, 11{6}:522-33.

Hirao LA, et al., "Intradermal/subcutaneous immunization by electroporation improves plasmid vaccine delivery and potency in pigs and rhesus macaques", Vaccine, 2008, 26{3}:440-8.

Luckay A, et al., "Effect of plasmid DNA vaccine design and in vivo electroporation on the resulting vaccine-specific immune respones in rhesus macques", J. Virol, 2007, 81(10):5257-69.

Ahlen G, et al., "In vivo electroporation enhances the immunogenicity of hepatitis C virus nonstructural 3/4A DNA by increased local DNA uptake, protein expression, inflammation, and infiltration of CD3+ T cells", J Immunol, 2007, 179, pp. 4741-4753.

Yan J, et al., "Enhanced cellular immune responses elicited by an engineered HIV-1 subtype B consensus-based envelope DNA vaccine", Mol Ther, 2007, 15(2):411-21.

Rolland M, et al., "Reconstruction and function of ancestral center-of-tree human immunodeficiency virus type 1 proteins", J Virol, 2007, 81(16):8507-14.

Kyte J and Doolittle RF, "A simple method for displaying the hydropathic character of a protein", J Mol Bio, 1982, 157(1):105-132.

Jung GS, et al., "Full genome sequencing and analysis of human cytomegalovirus strain JHC isolated from a Korean patient", Virus Res., 2011, 156(1-2):113-20.

Yan H, Koyano S, Suzutani T, Inoue N. glycoprotein O [Human herpesvirus 5]. GenBank: ABY48955.1. Sep. 10, 2008.

Davison AJ. envelope glycoprotein H [Human herpesvirus 5]. GenBank Acc. No. AGL96664.1. Dep Aug. 16, 2003.

Ishibashi K, Suzutani T, Fukushima E. glycoprotein H [Human herpesvirus 5]. GenBank Acc. No.BAF44189.1. Dep. Jun. 21, 2008.

Fukushima E, Ishibashi K, Kaneko H, Nishimura H, Inoue N, Tokumoto T, Tanabe K, Ishioka K, Ogawa H, Suzutani T. Identification of a highly conserved region in the human cytomegalovirus glycoprotein H gene and design of molecular diagnostic methods targeting the region. J Virol Methods. Jul. 2008;151(1):55-60. Epub May 6, 2008.

Vleck, Susan E. et al., "Anti-Glycoprotein H Antibody Impairs the Pathogenicity of Varicella-Zoster Virus in Skin Xenografts in the SCID Mouse Model", Journal of Virology, 2010. vol. 84(1):141-152.

Sung, Heungsup et al., "Update on the current status of cytomegalovirus vaccines", Expert Rev. Vaccines, 2010. vol. 9(11)1303-1314.

Peng, Tao et al., "The gH-gL Complex of Herpes Simplex Virus (HSV) Stimulates Neutralizing Antibody and protects mice against HSV Type 1 Challenge", Journal of Virology, 1998. vol. 72(1):65-72.

Kutinová, Lud'a et al., "Immune Response to Vaccinia Virus Recombinants Expressing Glycoproteins gE, gB, gH, and gL of Varicella-Zoster Virus", Virology, 2001. vol. 280:211-220.

Akahori, Yasushi et al., "Characterization of Neutralizing Epitopes of Varicella-Zoster Virus Glycoprotein H", Journal of Virology, 2009. vol. 83(4):2020-2024.

* cited by examiner

| | | | ELISpot T cell Epitopes (B6) | | | | | B cell responses | | |
|---|---|---|---|---|---|---|---|---|---|---|
| | pHCMV- | Ag | Total | Dom | # | Subdom | # | ELISA (1:x) | Neut Titr | Vaccine |
| 1 | gB | gB | 3,300 | 1 | 1,400 | 4 | 1,900 | 1,350 | 650 | Y |
| 2 | gH-gL | gH | 4,900 | 1 | 3,600 | 3 | 1,300 | 4,500 | 1,280 | Y |
| | | gL | | | | | | 4,500 | | |
| 3 | gM-gN | gM | 2,325 | 1 | 1,200 | 1 | 125 | | 160 | N |
| | | gN | | 1 | 900 | 2 | 100 | | | |
| 4 | gO | gO | 200 | | | 3 | 200 | | 350 | Y |
| 5 | gUL | UL128 | 6,900 | 2 | 3,300 | 2 | 1,200 | | 50 | Y |
| | | UL130 | | 2 | 2,100 | 1 | 200 | | | |
| | | UL131A | | | | 1 | 100 | | | |
| 6 | gUL83 | gUL83 | 800 | 1 | 650 | 2 | 150 | | ? | Maybe |

FIG. 15

NUCLEIC ACID MOLECULES ENCODING NOVEL HERPES ANTIGENS, VACCINE COMPRISING THE SAME, AND METHODS OF USE THEREOF

CROSS-REFERENCE TO RELATED APPLICATIONS

This application is a divisional of U.S. patent application Ser. No. 13/982,457, filed Oct. 4, 2013, which is the U.S. national phase application filed under 35 U.S.C. § 371 claiming benefit to International Patent Application No. PCT/US12/023398, filed Jan. 31, 2012, which is entitled to priority under 35 U.S.C § 119(e) to U.S. Provisional Patent Application No. 61/438,089, filed Jan. 31, 2011, each of which applications are incorporated by reference herein in their entireties.

FIELD OF THE INVENTION

The present invention relates to nucleic acid sequences encoding human herpes family viral (Herp) proteins and fragments thereof; to improved herpes vaccines, improved methods for inducing immune responses against herpes, improved methods for prophylactically and/or therapeutically immunizing individuals against herpes viruses.

BACKGROUND OF THE INVENTION

Herpesviridae (herpesviruses or herpes family viruses) is the name of a family of enveloped, double-stranded DNA viruses with relatively large complex genomes. They replicate in the nucleus of a wide range of vertebrate hosts, including eight varieties isolated in humans, several each in horses, cattle, mice, pigs, chickens, turtles, lizards, fish, and even in some invertebrates, such as oysters. Human herpesvirus infections are endemic and sexual contact is a significant method of transmission for several including both herpes simplex virus 1 and 2 (HSV-1, HSV-2), also human cytomegalovirus (HHV-5) and likely Karposi's sarcoma herpesvirus (HHV-8). The increasing prevalence of genital herpes and corresponding rise of neonatal infection and the implication of Epstein-Barr virus (HHV-4) and Karposi's sarcoma herpesvirus as cofactors in human cancers create an urgency for a better understanding of this complex, and highly successful virus family.

The virion structure of all herpesvirus virions are comprised of four structural elements: 1. Core: The core consists of a single linear molecule of dsDNA in the form of a torus. 2. Capsid: Surrounding the core is an icosahedral capsid with a 100 nm diameter constructed of 162 capsomeres. 3. Tegument: Between the capsid and envelope is an amorphous, sometimes asymmetrical, feature named the tegument. It consists of viral enzymes, some of which are needed to take control of the cell's chemical processes and subvert them to virion production, some of which defend against the host cell's immediate responses, and others for which the function is not yet understood. 4. Envelope: The envelope is the outer layer of the virion and is composed of altered host membrane and a dozen unique viral glycoproteins. They appear in electron micrographs as short spikes embedded in the envelope.

The herpesvirus genomes range in length from 120 to 230 kbp with base composition from 31% to 75% G+C content and contain 60 to 120 genes. Because replication takes place inside the nucleus, herpesviruses can use both the host's transcription machinery and DNA repair enzymes to support a large genome with complex arrays of genes. Herpesvirus genes, like the genes of their eukaryotic hosts, are not arranged in operons and in most cases have individual promoters. However, unlike eukaryotic genes, very few herpesvirus genes are spliced.

The genes are characterized as either essential or dispensable for growth in cell culture. Essential genes regulate transcription and are needed to construct the virion. Dispensable genes for the most part function to enhance the cellular environment for virus production, to defend the virus from the host immune system and to promote cell to cell spread. The large numbers of dispensable genes are in reality required for a productive in vivo infection. It is only in the restricted environment of laboratory cell cultures that they are dispensable. All herpesvirus genomes contain lengthy terminal repeats both direct and inverted. There are six terminal repeat arrangements and understanding how these repeats function in viral success is an interesting part of current research.

Four biological properties that characterize members of the herpesviridae family are that herpesviruses express a large number of enzymes involved in metabolism of nucleic acid (e.g. thymidine kinase), DNA synthesis (e.g. DNA helicase/primase) and processing of proteins (e.g. protein kinase); herpesviruses synthesize viral genomes and assemble capsids within the nucleus; their productive viral infection is accompanied by inevitable cell destruction; and herpesviruses are able to establish and maintain a latent state in their host and reactivate following cellular stress. Latency involves stable maintenance of the viral genome in the nucleus with limited expression of a small subset of viral genes.

Herpes virus family, which includes cytomeglavirus and herpes simplex virus, is found in the body fluids of infected individuals including urine, saliva, breast milk, blood, tears, semen, and vaginal fluids.

In the U.S., between 50% and 80% of adults are positive for HCMV by the age of 40 and there is no cure. While most infections are 'silent', HCMV can cause disease in unborn babies and immunocompromised people. HCMV in positive mothers can lead to Down syndrome, fetal alcohol syndrome, and neural tube defects. Furthermore, approximately 33% of women who become infected with HCMV for the first time during pregnancy pass the virus to unborn babies. Currently, 1 in 150 babies is born with congenital HCMV infection and 1 in 750 babies is born with or develops permanent disabilities dues to HCMV. Moreover, HCMV is widespread in developing countries and areas of lower socioeconomic conditions. Therefore, developing a preventative and/or therapeutic vaccine against HCMV would decrease morbidity and medical costs associated with virus-associated illness and disease worldwide.

Current vaccine strategies using attenuated/killed virus or recombinant proteins have been reported to yield levels of efficacy approaching 35% at best. Since antibodies (Abs) recognizing viral glycoproteins such as gB, gH, gM, and gN are observed in cases of protection, it is thought that the elicitation of neutralizing Abs against these viral surface targets are important. Furthermore, T cell epitopes are known to occur in particular viral proteins including UL83 (pp65), which specifically defines T-cell-based vaccine approaches targeting pp65 epitopes.

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp 120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutancous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

One method for delivering nucleic acid sequences such as plasmid DNA is the electroporation (EP) technique. The technique has been used in human clinical trials to deliver anti-cancer drugs, such as bleomycin, and in many preclinical studies on a large number of animal species.

There remains a need for nucleic acid constructs that encode herpesvirus antigens and for compositions useful to induce immune responses against herpesviruses. There remains a need for effective vaccines against herpesviruses that are economical and effective.

SUMMARY OF THE INVENTION

In one aspect of the invention, there are nucleic acid molecules comprising a coding sequence for a herpes virus antigen encoding one or more proteins selected from the group consisting of: proteins comprising SEQ ID NO:2; proteins that is 95% homologous to SEQ ID NO:2; proteins comprising SEQ ID NO:4; proteins that are 95% homologous to SEQ ID NO:4; proteins comprising SEQ ID NO:6; proteins that are 95% homologous to SEQ ID NO:6; proteins comprising SEQ ID NO:8; proteins that are 95% homologous to SEQ ID NO:8; proteins comprising SEQ ID NO:10; proteins that are 95% homologous to SEQ ID NO:10; proteins comprising SEQ ID NO:12; proteins that are 95% homologous to SEQ ID NO:12; proteins comprising SEQ ID NO:14; proteins that are 95% homologous to SEQ ID NO:14; proteins comprising SEQ ID NO:16; proteins that are 95% homologous to SEQ ID NO:16; proteins comprising SEQ ID NO:18; proteins that are 95% homologous to SEQ ID NO:18; proteins comprising proteins comprising SEQ ID NO:20; proteins that are 95% homologous to SEQ ID NO:20; proteins comprising SEQ ID NO:85, proteins that are 95% homologous to SEQ ID NO:85; proteins comprising HSV1-gH (N-terminal region up to position 838 of SEQ ID NO:87), proteins that are 95% homologous to HSV1-gH; proteins comprising HSV1-gL (C-terminal region from position 846 of SEQ ID NO:87), proteins that are 95% homologous to HSV1-gL; proteins comprising HSV1-gC (N-terminal region up to position 511 of SEQ TD NO:89), proteins that are 95% homologous to HSV1-gC; proteins comprising HSV1-gD (C-terminal region from position 519 of SEQ ID NO:89), proteins that are 95% homologous to HSV1-gD; proteins comprising SEQ ID NO:91, proteins that are 95% homologous to SEQ ID NO:91; proteins comprising HSV2-gH (N-terminal region up to position 838 of SEQ ID NO:93), proteins that are 95% homologous to HSV2-gH; proteins comprising HSV2-gL (C-terminal region from position 846 of SEQ ID NO:93), proteins that are 95% homologous to HSV2-gL; proteins comprising HSV2-gC (N-terminal region up to position 480 of SEQ ID NO:95), proteins that are 95% homologous to HSV2-gC; proteins comprising HSV2-gD (C-terminal region from position 488 of SEQ ID NO:95), proteins that are 95% homologous to HSV2-gD; proteins comprising SEQ ID NO:97, proteins that are 95% homologous to SEQ ID NO:97; proteins comprising VZV-gH (N-terminal region up to position 841 of SEQ TD NO:99), proteins that are 95% homologous to VZV-gH; proteins comprising VZV-gL (C-terminal region from position 849 of SEQ ID NO:99), proteins that are 95% homologous to VZV-gL; proteins comprising VZV-gM (N-terminal region up to position 435 of SEQ ID NO:101), proteins that are 95% homologous to VZV-gM; proteins comprising VZV-gN (C-terminal region from position 443 of SEQ ID NO:101), proteins that are 95% homologous to VZV-gN; proteins comprising SEQ ID NO:103, proteins that are 95% homologous to SEQ ID NO:103; proteins comprising CeHV1-gH (N-terminal region up to position 858 of SEQ ID NO:105), proteins that are 95% homologous to CeHV1-gH; proteins comprising CeHV1-gL (C-terminal region from position 866 of SEQ ID NO:105), proteins that are 95% homologous to CeHV1-gL;

proteins comprising CeHV1-gC (N-terminal region up to position 467 of SEQ ID NO:107), proteins that are 95% homologous to CeHV1-gC; proteins comprising CeHV1-gD (C-terminal region from position 475 of SEQ ID NO:107), proteins that are 95% homologous to CeHV1-gD; proteins comprising VZV-gE (N-terminal region up to position 623 of SEQ ID NO:109), proteins that are 95% homologous to VZV-gE; proteins comprising VZV-gI (C-terminal region from position 631 of SEQ ID NO:109), proteins that are 95% homologous to VZV-gI; proteins comprising SEQ ID NO:111, proteins that are 95% homologous to SEQ ID NO:111; and proteins comprising SEQ ID NO:113, proteins that are 95% homologous to SEQ ID NO:113; and immunogenic fragments thereof comprising at least 10 amino acids.

In some examples, proteins set forth above comprise a signal peptide, such as for example the IgE signal peptide (SEQ ID NO: 61) (e.g. SEQ ID NOs: 22, 24, 26, 28, 30, 32, 34, 36, 38 and 40) and/or an antigenic tag such as the HA Tag (SEQ ID NO: 62) (e.g. SEQ ID NOs: 42, 44, 46, 48, 50, 52, 54, 56, 58 and 60). Further, one or more proteins set forth above may be linked to each other to form a fusion protein. In some examples, the proteins are linked by way of a proteolytic cleavage site such as the furin site (SEQ ID NO: 63) (e.g. SEQ ID NOs:65, 67, 69, 71, 73, 75, 87, 89, 93, 95, 99, 101, 105, and 107).

Nucleic acid molecules comprising sequences that encode one or more protein molecules set forth above are also provided. In some embodiments, the nucleic acid molecule comprises a sequence selected from the group consisting of: nucleic acid sequences comprising SEQ ID NO:1; nucleic acid sequences that are 95% homologous to SEQ ID NO:1; nucleic acid sequences comprising SEQ ID NO:3; nucleic acid sequences that are 95% homologous to SEQ TD NO:3; nucleic acid sequences comprising SEQ TD NO:5; nucleic acid sequences that are 95% homologous to SEQ ID NO:5; nucleic acid sequences comprising SEQ ID NO:7; nucleic acid sequences that are 95% homologous to SEQ ID NO:7; nucleic acid sequences comprising SEQ ID NO:9; nucleic acid sequences that are 95% homologous to SEQ ID NO:9; nucleic acid sequences comprising SEQ ID NO:11; nucleic acid sequences that are 95% homologous to SEQ ID NO:11; nucleic acid sequences comprising SEQ ID NO:13; nucleic acid sequences that are 95% homologous to SEQ ID NO:13; nucleic acid sequences comprising SEQ ID NO:15; nucleic acid sequences that are 95% homologous to SEQ ID NO:15; nucleic acid sequences comprising SEQ ID NO:17; nucleic acid sequences that are 95% homologous to SEQ ID NO:17; nucleic acid sequences comprising SEQ ID NO:19; nucleic acid sequences that are 95% homologous to SEQ ID NO:19; nucleic acid sequences comprising SEQ ID NO:86; nucleic acid sequences that are 95% homologous to SEQ ID NO:86; nucleic acid sequences comprising DNA sequence encoding HSV1-gH; nucleic acid sequences that are 95% homologous to DNA sequence encoding HSV1-gH; nucleic acid sequences comprising DNA sequence encoding HSV1-gL; nucleic acid sequences that are 95% homologous to DNA sequence encoding HSV1-gL; nucleic acid sequences comprising DNA sequence encoding HSV1-gC; nucleic acid sequences that are 95% homologous to DNA sequence encoding HSV1-gC; nucleic acid sequences comprising DNA sequence encoding HSV1-gD; nucleic acid sequences that are 95% homologous to DNA sequence encoding HSV1-gD; nucleic acid sequences comprising SEQ ID NO:92; nucleic acid sequences that are 95% homologous to SEQ ID NO:92; nucleic acid sequences comprising DNA sequence encoding HSV2-gH; nucleic acid sequences that are 95% homologous to DNA sequence encoding HSV2-gH; nucleic acid sequences comprising DNA sequence encoding HSV2-gL; nucleic acid sequences that are 95% homologous to DNA sequence encoding HSV2-gL; nucleic acid sequences comprising DNA sequence encoding HSV2-gC; nucleic acid sequences that are 95% homologous to DNA sequence encoding HSV2-gC; nucleic acid sequences comprising DNA sequence encoding HSV2-gD; nucleic acid sequences that are 95% homologous to DNA sequence encoding HSV2-gD; nucleic acid sequences comprising SEQ ID NO:98; nucleic acid sequences that are 95% homologous to SEQ ID NO:98; nucleic acid sequences comprising DNA sequence encoding VZV-gH; nucleic acid sequences that are 95% homologous to DNA sequence encoding VZV-gH; nucleic acid sequences comprising DNA sequence encoding VZV-gL; nucleic acid sequences that are 95% homologous to DNA sequence encoding VZV-gL; nucleic acid sequences comprising DNA sequence encoding VZV-gM; nucleic acid sequences that are 95% homologous to DNA sequence encoding VZV-gM; nucleic acid sequences comprising DNA sequence encoding VZV-gN; nucleic acid sequences that are 95% homologous to DNA sequence encoding VZV-gN; nucleic acid sequences comprising SEQ ID NO:104; nucleic acid sequences that are 95% homologous to SEQ ID NO:104; nucleic acid sequences comprising DNA sequence encoding CeHV1-gH; nucleic acid sequences that are 95% homologous to DNA sequence encoding CeHV1-gH; nucleic acid sequences comprising DNA sequence encoding CeHV1-gL; nucleic acid sequences that are 95% homologous to DNA sequence encoding CeHV1-gL; nucleic acid sequences comprising DNA sequence encoding CeHV1-gC; nucleic acid sequences that are 95% homologous to DNA sequence encoding CeHV1-gC; nucleic acid sequences comprising DNA sequence encoding CeHV1-gD; nucleic acid sequences that are 95% homologous to DNA sequence encoding CeHV1-gD; nucleic acid sequences comprising DNA sequence encoding VZV-gE; nucleic acid sequences that are 95% homologous to DNA sequence encoding VZV-gE; nucleic acid sequences comprising DNA sequence encoding VZV-gI; nucleic acid sequences that are 95% homologous to DNA sequence encoding VZV-gI; nucleic acid sequences comprising SEQ ID NO:112; nucleic acid sequences that are 95% homologous to SEQ ID NO:112; and nucleic acid sequences comprising SEQ ID NO:114; nucleic acid sequences that are 95% homologous to SEQ ID NO:114; and fragments thereof that comprise nucleic acid sequences encoding immunogenic fragments comprising at least 10 amino acids.

In some examples, the nucleic acid sequences encode proteins that further comprise a signal peptide, such as for example the IgE signal peptide (DNA sequence encoding SEQ ID NO: 61) (e.g. SEQ ID NOs: 21, 23, 25, 27, 29, 31, 33, 35, 37 and 39) and/or an antigenic tag such as the HA Tag (DNA sequence encoding SEQ ID NO:62) (e.g. SEQ ID NOs: 41, 43, 45, 47, 49, 51, 53, 55, 57 and 59). Further, one or more nucleic acid sequences may be linked to each other to form a chimeric gene that encodes a fusion protein. In some examples, the nucleic acid sequences encode proteins that are linked by way of a proteolytic cleavage site such as the furin site (DNA sequence encoding SEQ ID NO:63) (e.g. SEQ ID NOs:64, 66, 68, 70, 72, 74, 88, 90, 94, 96, 100, 102, 106, 108, and 110).

In some embodiments, the nucleic acid molecules comprising sequences that encode one or more protein molecules set forth above are also provided in combination with a different second nucleic acid sequence, wherein the second nucleic acid sequence encodes a protein selected from the group consisting of: HCMV gB, HCMV gM, HCMV gN, HCMV gH, HCMV gL, HCMV gO, HCMV-UL131a, HCMV-UL130, HCMV-UL128, HCMV-UL83, HSV1-gB, HSV1-gH, HSV1-gL, HSV1-gC, HSV1-gD, HSV2-gB, HSV2-gH, HSV2-gL, HSV2-gC, HSV2-gD, VZV-gB, VZV-gH, VZV-gL, VZV-gM, VZV-gN, VZV-gE, VZV-gI, VZV-gC, VZV-gK, CeHV1-gB, CeHV1-gH, CeHV1-gL, CeHV1-gC, and CeHV1-gD. Preferably, an HCMV sequence will be combined with a different second HCMV sequence; an HSV1 sequence will be combined with a different second HSV1 sequence; an HSV2 sequence will be combined with a different second HSV2 sequence; an CeHV1 sequence will be combined with a different second CeHV1 sequence; and a VZV sequence will be combined with a different second VZV sequence.

Another aspect of the present invention includes compositions that comprise one or more of the nucleic acid molecules provided herein.

Some aspects of the invention provide method of inducing an immune response against a herpes virus antigen comprising administering the nucleic acid molecules provided herein. Preferably the herpes virus antigens comprise HCMV, HSV1, HSV2, CeHV1, and VZV antigens.

Additional aspects of the invention provide methods of protecting an individual from herpes virus infection comprising administering the nucleic acid molecules provided herein. In some embodiments, the individual is an individual who has been diagnosed with herpes virus infection.

In another aspect of the invention, there are proteins selected from the group consisting of: a protein comprising SEQ ID NO:2; a protein that is 95% homologous to SEQ ID NO:2; a protein comprising SEQ ID NO:4; a protein that is 95% homologous to SEQ ID NO:4; a protein comprising SEQ ID NO:6; a protein that is 95% homologous to SEQ ID NO:6; a protein comprising SEQ ID NO:8; a protein that is 95% homologous to SEQ ID NO:8; a protein comprising SEQ ID NO:10; a protein that is 95% homologous to SEQ ID NO:10; a protein comprising SEQ ID NO:12; a protein that is 95% homologous to SEQ ID NO:12; a protein comprising SEQ ID NO:14; a protein that is 95% homologous to SEQ ID NO:14; a protein comprising SEQ TD NO:16; a protein that is 95% homologous to SEQ TD NO:16; a protein comprising SEQ ID NO:18; a protein that is 95% homologous to SEQ ID NO:18; a protein comprising a protein comprising SEQ ID NO:20; a protein that is 95% homologous to SEQ ID NO:20; a protein comprising SEQ ID NO:85, proteins that are 95% homologous to SEQ ID NO:85; a protein comprising HSV1-gH (N-terminal region up to position 838 of SEQ ID NO:87), proteins that are 95% homologous to HSV1-gH; a protein comprising HSV1-gL (C-terminal region from position 846 of SEQ ID NO:87), proteins that are 95% homologous to HSV1-gL; a protein comprising HSV1-gC (N-terminal region up to position 511 of SEQ ID NO:89), proteins that are 95% homologous to HSV1-gC; a protein comprising HSV1-gD (C-terminal region from position 519 of SEQ ID NO:89), proteins that are 95% homologous to HSV1-gD; a protein comprising SEQ ID NO:91, proteins that are 95% homologous to SEQ ID NO:91; a protein comprising HSV2-gH (N-terminal region up to position 838 of SEQ ID NO:93), proteins that are 95% homologous to HSV2-gH; a protein comprising HSV2-gL (C-terminal region from position 846 of SEQ ID NO:93), proteins that are 95% homologous to HSV2-gL; a protein comprising HSV2-gC (N-terminal region up to position 480 of SEQ ID NO:95), proteins that are 95% homologous to HSV2-gC; a protein comprising HSV2-gD (C-terminal region from position 488 of SEQ ID NO:95), proteins that are 95% homologous to HSV2-gD; a protein comprising SEQ ID NO:97, proteins that are 95% homologous to SEQ ID NO:97; a protein comprising VZV-gH (N-terminal region up to position 841 of SEQ ID NO:99), proteins that are 95% homologous to VZV-gH; a protein comprising VZV-gL (C-terminal region from position 849 of SEQ ID NO:99), proteins that are 95% homologous to VZV-gL; a protein comprising VZV-gM (N-terminal region up to position 435 of SEQ ID NO:101), proteins that are 95% homologous to VZV-gM; a protein comprising VZV-gN (C-terminal region from position 443 of SEQ ID NO:101), proteins that are 95% homologous to VZV-gN; a protein comprising SEQ ID NO:103, proteins that are 95% homologous to SEQ ID NO:103; a protein comprising CeHV1-gH (N-terminal region up to position 858 of SEQ ID NO:105), proteins that are 95% homologous to CeHV1-gH; a protein comprising CeHV1-gL (C-terminal region from position 866 of SEQ ID NO:105), proteins that are 95% homologous to CeHV1-gL; a protein comprising CeHV1-gC (N-terminal region up to position 467 of SEQ ID NO:107), proteins that are 95% homologous to CeHV1-gC; a protein comprising CeHV1-gD (C-terminal region from position 475 of SEQ TD NO:107), proteins that are 95% homologous to CeHV1-gD; a protein comprising VZV-gE (N-terminal region up to position 623 of SEQ ID NO:109), proteins that are 95% homologous to VZV-gE; a protein comprising VZV-gI (C-terminal region from position 631 of SEQ ID NO:109), proteins that are 95% homologous to VZV-gI; a protein comprising SEQ ID NO:111, proteins that are 95% homologous to SEQ ID NO:111; and a protein comprising SEQ ID NO:113, proteins that are 95% homologous to SEQ ID NO:113; and immunogenic fragments thereof comprising at least 10 amino acids.

In some embodiments, there are provided methods of inducing an immune response against a herpes virus infection comprising delivering to an individual the proteins provided herein. In some embodiments, the individual is an individual who has been diagnosed with herpes virus infection.

Aspects of the invention relate to method of generating a multivalent vaccine against a herpes family virus, comprising: performing phylogenetic and molecular evolutionary analysis to estimate diversity among clinically relevant and publically available target protein sequences of the herpes virus; selecting at least two target protein sequence from the group comprising: a) a specific, clinically relevant subgroup of a divergent protein; or b) a highly conserved protein; generating a consensus sequence from the selected target protein sequences; and cloning the consensus target protein sequences from the generating step into one or more expression constructs for formulation of the multivalent vaccine. In some embodiments, the the selecting step comprises selecting target proteins that are associated to one another as part of a biological complex expressed by a herpes virus. In some embodiments, the selected target proteins are surface antigens. In some embodiments the surface antigens are selected from the group consisting of gH, gL, gM, gN, gC, and gD. In some embodiments, the surface antigens are gH and gL. In some embodiments, the specific, clinically relevant subgroup of a divergent protein further comprises, selecting a clinically relevant strain of the herpes virus that has passaged no more than four times in culture. In some embodiments, the step of selecting the specific, clinically relevant subgroup of a divergent protein further comprises, selecting a clinically relevant strain of the herpes virus that has passaged no more than six times in culture. In some embodiments, the herpes family virus is selected from the group consisting of CMV, HSV1, HSV2, VZV, CeHV1, EBV, roseolovirus, Kaposi's sarcoma-associated herpesvirus, and MuHV.

Another aspect of the invention comprises methods of generating a multivalent vaccine against a herpes family virus, comprising: performing phylogenetic and molecular evolutionary analysis to estimate diversity among clinically relevant and publically available target protein sequences of the herpes virus; selecting at least two target protein sequence from the group comprising: a) a specific, clinically relevant subgroup of a divergent protein; or b) a highly conserved protein; generating a consensus sequence from the selected target protein sequences; and cloning the consensus target protein sequences from the generating step into one or more expression constructs for formulation of the multivalent vaccine. The expression constructs can be formulated with known and available pharmaceutically acceptable excipients. In some embodiments, the multivalent vaccines can also include a known vaccine adjuvant, preferably IL-12, IL-15, IL-28, and RANTES.

In some embodiments the herpes family virus is selected from CMV, HSV1, HSV2, VZV, CeHV1, EBV, roseolovirus, Kaposi's sarcoma-associated herpesvirus, or MuHV, and preferably, CMV, HSV1, HSV2, CeHV1 or VZV.

In some embodiments, the selected target proteins are those associated to one another as part of a biological complex expressed by a herpes virus. Preferably, the selected target proteins are surface antigens, more preferably antigens gH, gL, gM, gN, gC, and gD, and even more preferably the surface antigens are gH and gL.

In some embodiments, the step of selecting the specific, clinically relevant subgroup of a divergent protein further comprises, selecting a clinically relevant strain of the herpes virus that has passaged no more than four times in culture, and preferably no more than six times.

Aspects of the invention relates to vaccines against viruses of the herpes families which comprise coding sequence for two or more antigens. In some embodiments, two or more such antigens are provided on the same vector such as a plasmid to ensure co-expression of both antigens in the same cell. Various permutations of antigens are provided as are various arrangements in which multiple plasmids are provided encoding such multiple antigens including embodiments in which two or more such antigens are provided on the same vector. For example, co-expression of the the combination of gH and gL antigens from HCMV and HSV1 have both been observed to provide antigen transport to the cell surface which does not occur when proteins are expressed in the absence of each other. Data show the coexpression of gH and gL provide more effective immune targets than when proteins are expressed in the absence of each other. According to aspects of the invention, multiple antigens may be delivered as coding sequences to provide effective vaccines. in some embodiments, coding sequences for multiple antigens are provided on single vectors such as single plasmids.

BRIEF DESCRIPTION OF THE FIGURES

FIG. 15 shows a summary of DNA vaccine data.

DETAILED DESCRIPTION

1. Definitions

Figure 1:
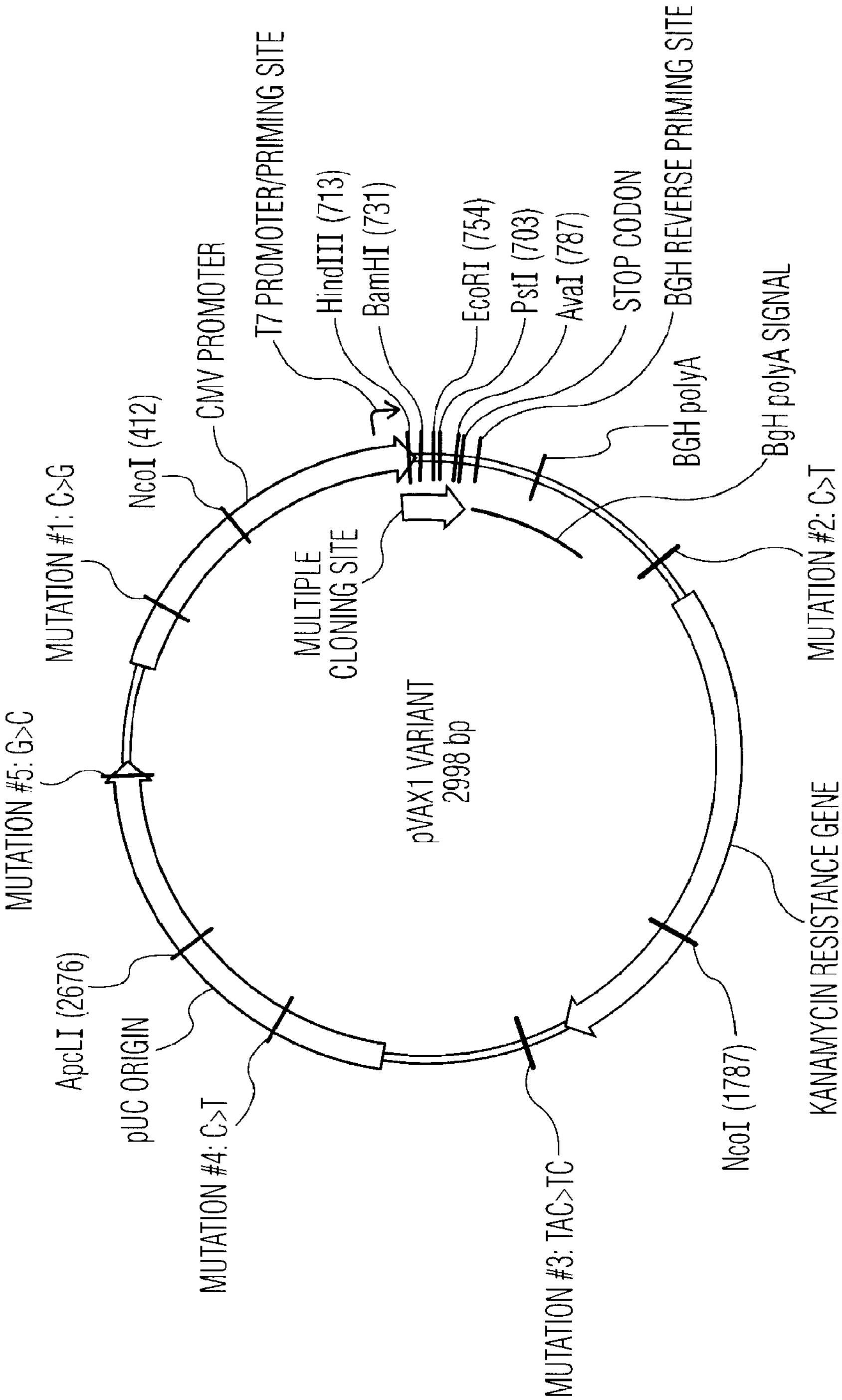
FIG. 1 is a map of the pVax1 variant used as a backbone for plasmids with herpes virus coding sequence inserts. The sequence of the pVax1 Variant is set forth in SEQ ID NO:76.

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein means a polypeptide sequence based on analysis of an alignment of multiple subtypes of a particular herpes family virus, comprising HCMV, HSV1, HSV2, CeHV1, VZV, Epstein-Barr virus (EBV), roseolovirus (or herpes lymphotropic virus), Kaposi-s sarcoma-associated herpesvirus, and murine gammaherpesvirus (MuHV-4), preferably HCMV, HSV1, HSV2, CeHV1, VZV, and more preferably HCMV, HSV1, HSV2, and VZV antigen. Nucleic acid sequences that encode a consensus polypeptide sequence may be prepared. Vaccines comprising proteins that comprise consensus sequences and/or nucleic acid molecules that encode such proteins can be used to induce broad immunity against multiple subtypes or serotypes of a particular HCMV antigen.

f. Constant Current

"Constant current" as used herein means a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" can be used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback can be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop can be instantaneous as it is an analog closed-loop feedback.

h. Decentralized Current

"Decentralized current" as used herein means the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein means a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism can be performed by an analog closed loop circuit.

k. Fragment

"Fragment" as used herein with respect to nucleic acid sequences means a nucleic acid sequence or a portion thereof, that encodes a polypeptide capable of eliciting an immune response in a mammal that cross reacts with a full length wild type strain herpes family virus, comprising HCMV, HSV1, HSV2, CeHV1, VZV, Epstein-Barr virus (EBV), roseolovirus (or herpes lymphotropic virus), Kaposi-s sarcoma-associated herpesvirus, and murine gammaherpesvirus (MuHV-4), preferably HCMV, HSV1, HSV2, CeHV1, VZV, and more preferably HCMV, HSV1, HSV2, and VZV antigen. The fragments can be DNA fragments selected from at least one of the various nucleotide sequences that encode protein fragments set forth below.

"Fragment" with respect to polypeptide sequences means a polypeptide capable of eliciting an immune response in a mammal that cross reacts with a full length wild type strain herpes family virus, comprising HCMV, HSV1, HSV2, CeHV1, VZV, Epstein-Barr virus (EBV), roseolovirus (or herpes lymphotropic virus), Kaposi-s sarcoma-associated herpesvirus, and murine gammaherpesvirus (MuHV-4), preferably HCMV, HSV1, HSV2, CeHV1, VZV, and more preferably HCMV, HSV1, HSV2, and VZV antigen. Fragments of consensus proteins may comprise at least 10%, at least 20%, at least 30%, at least 40%, at least 50%, at least 60%, at least 70%, at least 80%, at least 90% or at least 95% of a consensus protein.

l. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

m. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

n. Impedance

"Impedance" can be used when discussing the feedback mechanism and can be converted to a current value according to Ohm's law, thus enabling comparisons with the preset current.

o. Immune Response

"Immune response" as used herein means the activation of a host's immune system, e.g., that of a mammal, in response to the introduction of antigen such as an herpes family virus, comprising HCMV, HSV1, HSV2, CeHV1, VZV, Epstein-Barr virus (EBV), roseolovirus (or herpes lymphotropic virus), Kaposi-s sarcoma-associated herpesvirus, and murine gammaherpesvirus (MuHV-4), preferably HCMV, HSV1, HSV2, CeHV1, VZV, and more preferably HCMV, HSV1, HSV2, and VZV consensus antigens. The immune response can be in the form of a cellular or humoral response, or both.

p. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

q. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

r. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV 1E promoter.

s. Signal Peptide

"Signal peptide and leader sequence" are used interchangeably herein and refer to an amino acid sequence at the amino terminus of an herpes family virus, comprising HCMV, HSV1, HSV2, CeHV1, VZV, Epstein-Barr virus (EBV), roseolovirus (or herpes lymphotropic virus), Kaposi-s sarcoma-associated herpesvirus, and murine gammaherpesvirus (MuHV-4), preferably HCMV, HSV1, HSV2, CeHV1, VZV, and more preferably HCMV, HSV1, HSV2, and VZV protein. Signal peptides/leader sequences typically direct localization of a protein. Signal peptides/leader sequences used herein preferably facilitate secretion of a protein from the cell in which it is produced. Signal peptides/leader sequences are often cleaved from the remainder of the protein, often referred to as the mature protein, upon secretion from the cell. Signal peptides/leader sequences are linked at the N terminus of the protein. As referred to herein with regard to linking a signal peptide or leader sequence to the N terminus of a protein, the signal peptide/leader sequence replaces the N terminal methionine of a protein. Thus for example, SEQ ID NO:22 is SEQ ID NO:2 with the signal peptide/leader sequence linked at the N terminal of SEQ ID NO:2. The N terminal residue of SEQ TD NO:2 can be anything but if it is encoded by an initiation sequence it is methionine. the linkage of the signal peptide/leader sequence at the N terminal of SEQ ID NO:2 eliminates an N terminal methionine. As used herein, it is intended that SEQ ID NO:22 comprises SEQ ID NO:2 with a signal peptide/leader sequence linked at the N terminal of SEQ ID NO:2 notwithstanding the elimination of the N terminus Xaa residue of SEQ ID NO:2. Similarly, the coding sequences for SEQ ID NO:22 comprise coding sequences for SEQ ID NO:2 with coding sequences for a signal peptide/leader sequence linked to the 5' end of the coding sequences encoding SEQ ID NO:2. The initiation codon may be the nnn in the coding sequences for SEQ ID NO:2 but it is eliminated when the coding sequences for a signal peptide/leader sequence linked to the 5' end of the coding sequences encoding SEQ ID NO:2. As used herein, it is intended that coding sequences for SEQ ID NO:22 comprises coding sequences for SEQ ID NO:2 with coding sequences for a signal peptide/leader sequence linked at the 5' end of the coding sequence of SEQ ID NO:2 where nnn occurs. Thus, for example, it is intended that SEQ ID NO:21 comprises SEQ ID NO:1 with coding sequences for a signal peptide/leader sequence linked at the 5' end of SEQ ID NO:1, in place of the nnn. In some embodiments, the nnn is an initiation codon at the 5' end of SEQ ID NO:1. It is further intended that SEQ ID NOs:2, 4, 6, 8, 10, 12 14, 16, 18 and 20 are provided free of then terminal Xaa and that SEQ ID NOs:1, 3, 5, 7, 9, 11 13, 15, 17 and 19 are provided free the nnn.

t. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

u. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or that the two sequences hybridize under stringent hybridization conditions.

v. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or with respect to nucleic acids, if the first sequence is substantially complementary to the complement of the second sequence.

w. Subtype or Serotype

"Subtype" or "serotype": as used herein, interchangeably, and in reference to herpes virus, means genetic variants of an herpes virus such that one subtype is recognized by an immune system apart from a different subtype.

x. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

y. Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

2. Herpes Viruses, Including HCMV, HSV1, HSV2, CeHV1, and VZV, Antigens

In an aspect of the present invention, provided is a methodology to generate novel herpes virus antigens, useful across the various herpes family viruses, to increase the potential breadth of immunity elicited by each viral antigen (Ag)

Phylogenetic diversity was first examined to assess polymorphism and to aid in the production of clinically-relevant consensus amino acid sequences. Phylogenetic and molecular evolutionary analyses can be conducted using MEGA version 5 (Tamura, Peterson, Stecher, Nei, and Kumar 2011) to estimate diversity among clinically relevant and publically available herpes target protein sequences used for generating consensus vaccine Ags. Neighbor-joining phylogenetic reconstruction analysis using the bootstrap method with 1,000 bootstrap replications can be used to generate bootstrap consensus trees with radiation view.

Strategies for generating the consensus amino acid sequences for each herpes immunogen are outlined, below, in the examples. In general, consensus sequences from highly conserved herpes proteins can be used for vaccine immunogens while consensus sequences from specific, clinically relevant subgroups can be used for the highly divergent proteins.

Amino acid sequences of herpes vaccine proteins can be generated by taking the consensus of publically available (GenBank) and clinically relevant strains (passaged no more than six times in tissue culture) using Vector NTI software (Invitrogen) for sequence alignment. Preferably, the antigens can be combined in a vaccine formulation as multiple vectors having single antigen or single vector having multiple antigens therein, whether 2 or more antigens. In some embodiments, more than 2 or more of the specific herpes virus antigens are present in one vaccine formulation. When multiple antigens are present on a vector (for example a DNA plasmid, e.g., pHCMV-gHgL or HSV1-gHgL) such antigens are separated by a cleavage site, preferably a furin site, e.g., SEQ ID NO:63, for the co-expression of structurally-relevant macromolecules. Genetic optimization of DNA vaccines included codon and RNA optimization for protein expression in humans and all genes were synthesized and subcloned into a modified pVAX1 mammalian expression vector (GeneArt, Regensburg, Germany or GenScript, Piscataway, N.J.).

In another aspect, provided herein are antigens capable of eliciting an immune response in a mammal against one or more herpes viruses, including HCMV, HSV1, HSV2, CeHV1, and VZV, serotypes. The antigen can comprise epitopes that make them particularly effective as immunogens against which anti-herpes virus immune responses can be induced. The herpes virus antigen can comprise the full length translation product, a variant thereof, a fragment thereof or a combination thereof. The herpes virus antigen can be a wild type sequence or a consensus sequence derived from multiple different sequences.

Various nucleic acid sequences encoding different herpes viruses, including HCMV, HSV1, HSV2, CeHV1, and VZV, proteins have been identified for use alone or in various combinations as part of a vaccine against herpes viruses that can induce an immune response against the immunogenic protein and be used in prophylactic and therapeutic vaccines. Alternatively, the proteins themselves may be used. The immunogenic proteins include gB, gM, gN, gH, gL, gO, gE, gI, gK, gC, gD, UL128, UL130, UL-131A, UL-83 (pp65), whether from HCMV, HSV1, HSV2, CeHV1, or VZV, and vaccines may comprise one or more immunogenic proteins selected from this group and/or vaccines may comprise one or more nucleic acid sequences that encode one or more immunogenic proteins selected from this group.

In view of evolutionary divergence from clinical isolates and extensive genetic differences among prevalent circulating human strains consensus amino acid sequences for each of immunogenic proteins have been generated. Consensus amino acid sequences for gB, gM, gH, gL, gE, gI, gK, gC, gD, UL128, UL130, UL-131A and UL-83 (pp65) were based upon sequences from human clinical isolates as of the beginning of 2010. Due to the great evolutionary divergence of the gN protein, the consensus sequence was generated from only one (gN-4c) of seven serotypes that represents the most sero-prevalent (gN-4). Similarly, in the case gO, a consensus amino acid sequences was generated from one (gO-5) of eight sero-types due to that particular serotypes reported linkage with the gN-4c sero-type.

In some embodiments, consensus herpes virus antigens may be provided with a signal peptide. In some embodiments, the IgE leader (SEQ ID NO:61) is linked to the N terminus. As described herein, when referring to a signal peptide linked to the N terminus of a consensus sequence, it is intended to specifically include embodiments in which the N terminal Xaa residue of the consensus sequences is replaced with a signal peptide. That is, as used herein Xaa is intended to refer to any amino acid or no amino acid. The proteins which comprise a consensus sequence set forth herein SEQ ID NOs: 2, 4, 6, 8, 10, 12, 14, 16, 18, 20, 85, 91, 97, 103, 111, and 113, and proteins HSV1-gH, HSV1-gL, HSV1-gC, HSV1-gD, HSV2-gH, HSV2-gL, HSV2-gC, HSV2-gD, VZV-gH, VZV-gL, VZV-gM, VZV-gN, CeHV1-gH, CeHV1-gL, CeHV1-gC, CeHV1-gD, VZV-gE, and VZV-gI, may comprise those sequences free of the N terminal Xaa.

In some embodiments, the herpes virus antigens, whether with or without a signal peptide, may comprise an antigenic tag such as the HA Tag (SEQ ID NO:62 which is induced in each of SEQ ID NOs: 42, 44, 46, 48, 50, 52, 54, 56, 58 and 60). The antigenic tags can be used to detect expression. The HA Tag is a common antigenic tag used for this purpose. Further, one or more proteins set forth above may be linked to each other to form a fusion protein. In some examples, the proteins are linked by way of a proteolytic cleavage site such as the furin site (SEQ ID NO: 63 which is included in each of SEQ ID NOs:65, 67, 69, 71, 73, 75, 87, 89, 93, 95, 99, 101, 105, 107, and 109).)

A consensus protein HCMV-gB (SEQ ID NO:2), a consensus protein HCMV-gM (SEQ ID NO:4), a consensus protein HCMV-gN (SEQ ID NO:6), a consensus protein HCMV-gH (SEQ ID NO:8), a consensus protein HCMV-gL (SEQ ID NO:10), a consensus protein HCMV-gO (SEQ ID NO:12), a consensus protein HCMV-UL128 (SEQ ID NO:14), a consensus protein HCMV-UL130 (SEQ ID NO: 16), a consensus protein HCMV-UL-131A (SEQ ID NO:18), a consensus protein HCMV-UL-83 (pp65) (SEQ ID NO:20), a consensus protein HSV1-gB SEQ ID NO:85, a consensus protein HSV1-gH (N-terminal region up to position 838 of SEQ ID NO:87), a consensus protein HSV1-gL (C-terminal region from position 846 of SEQ ID NO:87), a consensus protein HSV1-gC (N-terminal region up to position 511 of SEQ ID NO:89), a consensus protein HSV1-gD (C-terminal region from position 519 of SEQ ID NO:89), a consensus protein HSV2-gB (SEQ ID NO:91), a consensus protein HSV2-gH (N-terminal region up to position 838 of SEQ ID NO:93), a consensus protein HSV2-gL (C-terminal region from position 846 of SEQ ID NO:93), a consensus protein HSV2-gC (N-terminal region up to position 480 of SEQ ID NO:95), a consensus protein HSV2-gD (C-terminal region from position 488 of SEQ ID NO:95), a consensus protein VZV-gB (SEQ ID NO:97), a consensus protein VZV-gH (N-terminal region up to position 841 of SEQ ID NO:99), a consensus protein VZV-gL (C-terminal region from position 849 of SEQ ID NO:99), a consensus protein VZV-gM (N-terminal region up to position 435 of SEQ ID NO:101), a consensus protein VZV-gN (C-terminal region from position 443 of SEQ TD NO:101), a consensus protein CeHV1-gB (SEQ TD NO:103), a consensus protein CeHV1-gH (N-terminal region up to position 858 of SEQ ID NO:105), a consensus protein CeHV1-gL (C-terminal region from position 866 of SEQ ID NO:105), a consensus protein CeHV1-gC (N-terminal region up to position 467 of SEQ ID NO:107), a consensus protein CeHV1-gD (C-terminal region from position 475 of SEQ ID NO:107), a consensus protein VZV-gE (N-terminal region up to position 623 of SEQ ID NO:109), a consensus protein VZV-gI (C-terminal region from position 631 of SEQ ID NO:109), a consensus protein VZV-gC (SEQ ID NO:111), and a consensus protein VZV-gK (SEQ ID NO:113) are provided. Amino acid sequences were generated which comprised in each particular instance, the IgE leader sequence at the N terminus of the herpes virus immunogenic protein consensus sequences. Thus, also provided are a protein with an IgE leader linked to consensus protein HCMV-gB (SEQ ID NO:22), a protein with an IgE leader linked to consensus protein HCMV-gM (SEQ ID NO:24), a protein with an IgE leader linked to consensus protein HCMV-gN (SEQ ID NO:26), a protein with an IgE leader linked to consensus protein HCMV-gH (SEQ ID NO:28), a protein with an IgE leader linked to consensus protein HCMV-gL (SEQ ID NO:30), a protein with an IgE leader linked to consensus protein HCMV-gO (SEQ ID NO:32), a protein with an IgE leader linked to consensus protein HCMV-UL128 (SEQ ID NO:34), a protein with an IgE leader linked to consensus protein HCMV-UL130 (SEQ ID NO:36), a protein with an IgE leader linked to consensus protein HCMV-UL-131A (SEQ ID NO:38), a protein with an IgE leader linked to consensus protein HCMV-UL-83 (pp65) (SEQ ID NO:40). IgE leader used is (SEQ ID NO:62). Embodiments are also provided in which HA tags are linked at the C terminus of the consensus sequence. Accordingly, a protein with an IgE leader linked to consensus protein HCMV-gB with an HA Tag at the C terminal (SEQ ID NO:42), a protein with an IgE leader linked to consensus protein HCMV-gM (SEQ ID NO:44), a protein with an IgE leader linked to consensus protein HCMV-gN (SEQ ID NO:46), a protein with an IgE leader linked to consensus protein HCMV-gH (SEQ ID NO:48), a protein with an IgE leader linked to consensus protein HCMV-gL (SEQ ID NO:50), a protein with an IgE leader linked to consensus protein HCMV-gO (SEQ ID NO:52), a protein with an IgE leader linked to consensus protein HCMV-UL128 (SEQ ID NO:54), a protein with an IgE leader linked to consensus protein HCMV-UL130 (SEQ ID NO:56), a protein with an IgE leader linked to consensus protein HCMV-UL-131A (SEQ TD NO:58), a protein with an IgE leader linked to consensus protein HCMV-UL-83 (pp65) (SEQ ID NO:60) are also provided. In some embodiments, nucleic acid constructs are provided in which two or more herpes virus antigens are expressed as fusion proteins linked to each other by proteolytic cleavage sites. A furin proteolytic cleavage site (SEQ ID NO:63) is an example of a proteolytic cleavage site which may link herpes virus antigens in a fusion protein expressed by a construct.

Proteins may be homologous to any of the protein sequences provided herein for each of the specific consensus antigens. Some embodiments relate to immunogenic proteins that have 95% homology to the consensus protein sequences herein. Some embodiments relate to immunogenic proteins that have 96% homology to the consensus protein sequences herein. Some embodiments relate to immunogenic proteins that have 97% homology to the consensus protein sequences herein. Some embodiments relate to immunogenic proteins that have 95% homolody, or 98% homology in some instances, to the consensus protein sequences herein. Some embodiments relate to immunogenic proteins that have 99% homology to the consensus protein sequences herein.

Fragments of consensus proteins may comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of a consensus protein Immunogenic fragments of any of the protein sequences provided herein for each of the specific consensus antigens may be provided Immunogenic fragments may comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of any of the protein sequences provided herein for each of the specific consensus antigens.

Immunogenic fragments of proteins with amino acid sequences homologous immunogenic fragments of any of the protein sequences provided herein for each of the specific consensus antigens may be provided. Such immunogenic fragments may comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 95% homologous to any of the protein sequences provided herein for each of the specific consensus antigens. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 95% homology, or 98% homology in some instances, to the immunogenic fragments of consensus protein sequences herein. Some embodiments relate to immunogenic fragments that have 99% homology to the immunogenic fragments of consensus protein sequences herein.

3. Genetic Sequences, Constructs and Plasmids

Nucleic acid sequences encoding the SEQ ID NO:2, SEQ ID NO:4, SEQ ID NO:6, SEQ TD NO:8, SEQ TD NO:10, SEQ TD NO:12, SEQ TD NO:14, SEQ TD NO:16, SEQ TD NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, a consensus protein HSV1-gB SEQ TD NO:85, a consensus protein HSV1-gH (N-terminal region up to position 838 of SEQ ID NO:87), a consensus protein HSV1-gL (C-terminal region from position 846 of SEQ ID NO:87), a consensus protein HSV1-gC (N-terminal region up to position 511 of SEQ ID NO:89), a consensus protein HSV1-gD (C-terminal region from position 519 of SEQ ID NO:89), a consensus protein HSV2-gB (SEQ ID NO:91), a consensus protein HSV2-gH (N-terminal region up to position 838 of SEQ ID NO:93), a consensus protein HSV2-gL (C-terminal region from position 846 of SEQ ID NO:93), a consensus protein HSV2-gC (N-terminal region up to position 480 of SEQ ID NO:95), a consensus protein HSV2-gD (C-terminal region from position 488 of SEQ ID NO:95), a consensus protein VZV-gB (SEQ ID NO:97), a consensus protein VZV-gH (N-terminal region up to position 841 of SEQ ID NO:99), a consensus protein VZV-gL (C-terminal region from position 849 of SEQ ID NO:99), a consensus protein VZV-gM (N-terminal region up to position 435 of SEQ ID NO:101), a consensus protein VZV-gN (C-terminal region from position 443 of SEQ ID NO:101), a consensus protein CeHV1-gB (SEQ ID NO:103), a consensus protein CeHV1-gH (N-terminal region up to position 858 of SEQ ID NO:105), a consensus protein CeHV1-gL (C-terminal region from position 866 of SEQ ID NO:105), a consensus protein CeHV1-gC (N-terminal region up to position 467 of SEQ ID NO:107), a consensus protein CeHV1-gD (C-terminal region from position 475 of SEQ ID NO:107), a consensus protein VZV-gE (N-terminal region up to position 623 of SEQ ID NO:109), a consensus protein VZV-gI (C-terminal region from position 631 of SEQ ID NO:109), a consensus protein VZV-gC (SEQ ID NO:111), and a consensus protein VZV-gK (SEQ ID NO:113) as well as homologous protein, immunogenic fragment and immunogenic fragments of homologous proteins can be generated routinely. Thus, nucleic acid molecules that encode immunogenic proteins that have up to 95% homology to a consensus sequence, up to 96% homology to a consensus sequence, up to 96% homology to a consensus sequence, up to 97% homology to a consensus sequence, up to 98% homology to a consensus sequence and up to 99% may be provided. Likewise, nucleic acid sequences encoding the immunogenic fragments set forth herein and the immunogenic fragments of protein homologous to the proteins set forth herein are also provided.

Nucleic acid molecules encoding the consensus amino acid sequences were generated. Vaccines may comprise one or more nucleic acid sequences that encode one or more of the consensus versions of the immunogenic proteins selected from this group of sequences generated to optimize stability and expression in humans. Nucleic acid sequence encoding consensus protein HCMV-gB (SEQ ID NO:1), nucleic acid sequence encoding consensus protein HCMV-gM (SEQ ID NO:3), nucleic acid sequence encoding consensus protein HCMV-gN (SEQ ID NO:5), nucleic acid sequence encoding consensus protein HCMV-gH (SEQ ID NO:7), nucleic acid sequence encoding consensus protein HCMV-gL (SEQ ID NO:9), nucleic acid sequence encoding consensus protein HCMV-gO (SEQ ID NO:11), nucleic acid sequence encoding consensus protein HCMV-UL128 (SEQ ID NO:13), nucleic acid sequence encoding consensus protein HCMV-UL130 (SEQ ID NO:15), nucleic acid sequence encoding consensus protein HCMV-UL-131A (SEQ ID NO:17), nucleic acid sequence encoding consensus protein HCMV-UL-83 (pp65) (SEQ ID NO:19), nucleic acid sequence encoding consensus protein HSV1-gB (SEQ ID NO:86), nucleic acid sequence encoding consensus protein HSV1-gH (N-terminal portion of SEQ ID NO:88, before furin site), nucleic acid sequence encoding consensus protein HSV1-gL (C-terminal portion of SEQ ID NO:88, after furin site), nucleic acid sequence encoding consensus protein HSV1-gC (N-terminal portion of SEQ ID NO:90, prior to furin site), nucleic acid sequence encoding consensus protein HSV1-gD (C-terminal portion of SEQ ID NO:90, after faring site), nucleic acid sequence encoding consensus protein HSV2-gB (SEQ ID NO:92), nucleic acid sequence encoding consensus protein HSV2-gH (N-terminal portion of SEQ ID NO:94, prior to furin site), nucleic acid sequence encoding consensus protein HSV2-gL (C-terminal portion of SEQ ID NO:94, after furin site), nucleic acid sequence encoding consensus protein HSV2-gC (N-terminal portion of SEQ ID NO:96, prior to furin site), nucleic acid sequence encoding consensus protein HSV2-gD (C-terminal portion of SEQ ID NO:96, after furin site), nucleic acid sequence encoding consensus protein VZV-gB (SEQ ID NO:98), nucleic acid sequence encoding consensus protein VZV-gH (N-terminal portion of SEQ ID NO:100, prior to furin site), nucleic acid sequence encoding consensus protein VZV-gL (C-terminal portion of SEQ ID NO:100, after furin site), nucleic acid sequence encoding consensus protein VZV-gM (N-terminal portion of SEQ ID NO:102, prior to furin site), nucleic acid sequence encoding consensus protein VZV-gN (C-terminal portion of SEQ ID NO:102, after furin site), nucleic acid sequence encoding consensus protein CeHV1-gB (SEQ ID NO:104), nucleic acid sequence encoding consensus protein CeHV1-gH (N-terminal portion of SEQ ID NO:106, prior to furin site), nucleic acid sequence encoding consensus protein CeHV1-gL (C-terminal portion of sEQ ID NO:106, after furin site), nucleic acid sequence encoding consensus protein CeHV1-gC (N-terminal portion of SEQ ID NO:108, prior to furin site), nucleic acid sequence encoding consensus protein CeHV1-gD (C-terminal portion of SEQ ID NO:108, after furin site), nucleic acid sequence encoding consensus protein VZV-gE (N-terminal portion of SEQ ID NO:110, prior to furin site), nucleic acid sequence encoding consensus protein VZV-gI (C-terminal portion of SEQ ID NO:110, after furin site), nucleic acid sequence encoding consensus protein VZV-gC (SEQ ID NO:112), and nucleic acid sequence encoding consensus protein VZV-gK (SEQ ID NO:114) are provided herein. In addition, nucleic acid sequences incorporating coding sequence for the IgE leader at the 5' end of the optimized, consensus encoding nucleic acid sequence were generated which encoded proteins having the IgE leader sequence at the N terminus of the consensus amino acid sequence. The nucleic acid sequence encoding IgE leader linked to consensus protein HCMV-gB (SEQ TD NO:21), nucleic acid sequence encoding IgE leader linked to consensus protein HCMV-gM (SEQ ID NO:23), nucleic acid sequence encoding IgE leader linked to consensus protein HCMV-gN (SEQ ID NO:25), nucleic acid sequence encoding IgE leader linked to consensus protein HCMV-gH (SEQ ID NO:27), nucleic acid sequence encoding IgE leader linked to consensus protein HCMV-gL (SEQ ID NO:29), nucleic acid sequence encoding IgE leader linked to consensus protein HCMV-gO (SEQ ID NO:31), nucleic acid sequence encoding IgE leader linked to consensus protein HCMV-UL128 (SEQ ID NO:33), nucleic acid sequence encoding IgE leader linked to consensus protein HCMV-UL130 (SEQ ID NO:35), nucleic acid sequence encoding IgE leader linked to consensus protein HCMV-UL-131A (SEQ ID NO:37), nucleic acid sequence encoding IgE leader linked to consensus protein HCMV-UL-83 (pp65) (SEQ ID NO:39), are provided. The nucleic acid sequence encoding IgE leader (DNA encoding SEQ ID NO:61). The nucleic acid sequence encoding IgE leader linked to consensus protein HCMV-gB with an HA Tag at the C terminus (SEQ ID NO:42), nucleic acid sequence encoding IgE leader linked to consensus protein HCMV-gM with an HA Tag at the C terminus (SEQ ID NO:43), nucleic acid sequence encoding IgE leader linked to consensus protein HCMV-gN with an HA Tag at the C terminus (SEQ ID NO:45), nucleic acid sequence encoding IgE leader linked to consensus protein HCMV-gH with an HA Tag at the C terminus (SEQ ID NO:47), nucleic acid sequence encoding IgE leader linked to consensus protein HCMV-gL with an HA Tag at the C terminus (SEQ ID NO:49), nucleic acid sequence encoding IgE leader linked to consensus protein HCMV-gO with an HA Tag at the C terminus (SEQ ID NO:51), nucleic acid sequence encoding IgE leader linked to consensus protein HCMV-UL128 with an HA Tag at the C terminus (SEQ ID NO:53), nucleic acid sequence encoding IgE leader linked to consensus protein HCMV-UL130 with an HA Tag at the HCMV-C terminus (SEQ ID NO:55), nucleic acid sequence encoding IgE leader linked to consensus protein HCMV-UL-131A with an HA Tag at the C terminus (SEQ ID NO:57), nucleic acid sequence encoding IgE leader linked to consensus protein HCMV-UL-83 (pp65) with an HA Tag at the C terminus (SEQ ID NO:59), are provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to fragments of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:86, nucleic acid sequence encoding consensus protein HSV1-gH (N-terminal portion of SEQ ID NO:88, before furin site), nucleic acid sequence encoding consensus protein HSV1-gL (C-terminal portion of SEQ ID NO:88, after furin site), nucleic acid sequence encoding consensus protein HSV1-gC (N-terminal portion of SEQ ID NO:90, prior to furin site), nucleic acid sequence encoding consensus protein HSV1-gD (C-terminal portion of SEQ ID NO:90, after furing site), SEQ ID NO:92, nucleic acid sequence encoding consensus protein HSV2-gH (N-terminal portion of SEQ ID NO:94, prior to furin site), nucleic acid sequence encoding consensus protein HSV2-gL (C-terminal portion of SEQ ID NO:94, after furin site), nucleic acid sequence encoding consensus protein HSV2-gC (N-terminal portion of SEQ ID NO:96, prior to furin site), nucleic acid sequence encoding consensus protein HSV2-gD (C-terminal portion of SEQ ID NO:96, after furin site), SEQ ID NO:98, nucleic acid sequence encoding consensus protein VZV-gH (N-terminal portion of SEQ ID NO:100, prior to furin site), nucleic acid sequence encoding consensus protein VZV-gL (C-terminal portion of SEQ ID NO:100, after furin site), nucleic acid sequence encoding consensus protein VZV-gM (N-terminal portion of SEQ TD NO:102, prior to furin site), nucleic acid sequence encoding consensus protein VZV-gN (C-terminal portion of SEQ ID NO:102, after furin site), SEQ ID NO:104, nucleic acid sequence encoding consensus protein CeHV1-gH (N-terminal portion of SEQ ID NO:106, prior to furin site), nucleic acid sequence encoding consensus protein CeHV1-gL (C-terminal portion of sEQ ID NO:106, after furin site), nucleic acid sequence encoding consensus protein CeHV1-gC (N-terminal portion of SEQ ID NO:108, prior to furin site), nucleic acid sequence encoding consensus protein CeHV1-gD (C-terminal portion of SEQ ID NO:108, after furin site), nucleic acid sequence encoding consensus protein VZV-gE (N-terminal portion of SEQ ID NO:110, prior to furin site), nucleic acid sequence encoding consensus protein VZV-gI (C-terminal portion of SEQ ID NO:110, after furin site), SEQ ID NO:112, and SEQ ID NO:114. Fragments may at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of any of the nucleotide sequences provided herein for each of the specific consensus antigens. Fragments may be at least 95%, at least 96%, at least 97% at least 98% or at least 99% homologous to fragments of any of the nucleotide sequences provided herein for each of the specific consensus antigens.

Provided herein are genetic constructs that can comprise a nucleic acid sequence that encodes the herpes virus antigen disclosed herein including consensus protein sequences, sequences homologous to consensus protein sequences, fragments of consensus protein sequences and sequences homologous to fragments of consensus protein sequences. The genetic construct can be present in the cell as a functioning extrachromosomal molecule. The genetic construct can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences may make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

In some embodiments, coding sequences for one antigen may be provided on a single vector.

In some embodiments, coding sequences for two or more different antigens may be provided on a single vector. In some embodiments, the coding sequences may have separate promoters controlling expression. In some embodiments, the coding sequences may have a single promoters controlling expression with an IRES sequence separating coding sequence. The presence of the IRES sequence results in the separate translation of the transcription product. In some embodiments, the coding sequences may have a single promoters controlling expression with coding sequence encoding a proteolytic cleavage peptide sequence separating coding sequences of the antigens. A single translation product is produced which is then processed by the protease that recognizes the protease cleavage site to generate separate protein molecules. The protease cleave sites used is typically recognized by a protease endogenously present in the cell where expression occurs. In some embodiments, a separate coding sequence for a protease may be included to provide for the production of the protease needed to process the polyprotein translation product. In some embodiment, vectors comprise coding sequences for one, two, three, four or more HCMV antigens, HSV1 antigens, HSV2 antigens, VZV antigens, or CeHV1 antigens.

In some embodiments, coding sequences for HCMV antigens gM and gN are included on the same vector. In some embodiments, coding sequences for HCMV antigens consensus gM and consensus gN4-c are included on the same vector. In some embodiments, coding sequences for HCMV antigens gM and gN are included on the same vector and are under control of a single promoter. In some embodiments, coding sequences for HCMV antigens consensus gM and consensus gN4-c are included on the same vector and are under control of a single promoter. In some embodiments, coding sequences for HCMV antigens gM and gN are included on the same vector, under control of a single promoter and linked with a coding sequence for a proteolytic cleavage site. In some embodiments, coding sequences for HCMV antigens consensus gM and consensus gN4-c are included on the same vector, are under control of a single promoter and linked with a coding sequence for a proteolytic cleavage site. In some embodiments, coding sequences for HCMV antigens gH and gL are included on the same vector. In some embodiments, coding sequences for HCMV antigens consensus gH and consensus gL are included on the same vector. In some embodiments, coding sequences for HCMV antigens gH and gL are included on the same vector and are under control of a single promoter. In some embodiments, coding sequences for HCMV antigens consensus gH and consensus gL are included on the same vector and are under control of a single promoter. In some embodiments, coding sequences for HCMV antigens gH and gL are included on the same vector, under control of a single promoter and linked with a coding sequence for a proteolytic cleavage site. In some embodiments, coding sequences for HCMV antigens consensus gH and consensus gL are included on the same vector, are under control of a single promoter and linked with a coding sequence for a proteolytic cleavage site.

In some embodiments, coding sequences for HCMV antigens/chaperone proteins UL128, UL130 and UL-131A are included on the same vector. In some embodiments, coding sequences for HCMV antigens/chaperone proteins consensus UL128, consensus UL130 and consensus UL-131A are included on the same vector. In some embodiments, coding sequences for HCMV antigens/chaperone proteins UL128, UL130 and UL-131A are included on the same vector and are under control of a single promoter. In some embodiments, coding sequences for HCMV antigens/chaperone proteins consensus UL128, consensus UL130 and consensus UL-131A are included on the same vector and are under control of a single promoter. In some embodiments, coding sequences for HCMV antigens/chaperone proteins UL128, UL130 and UL-131A are included on the same vector, under control of a single promoter and linked with a coding sequence for a proteolytic cleavage site. In some embodiments, coding sequences for HCMV antigens/chaperone proteins consensus UL128, consensus UL130 and consensus UL-131A are included on the same vector, are under control of a single promoter and linked with a coding sequence for a proteolytic cleavage site.

In some embodiments, coding sequences for HSV1 antigens gH and gL are included on the same vector, and in some cases under the control of a single promoter, and in some cases linked together with a coding sequence for a poteolytic cleavage site, preferably furin cleavage site. In some embodiments, coding sequences for HSV1 antigens gC and gD are included on the same vector, and in some cases under the control of a single promoter, and in some cases linked together with a coding sequence for a poteolytic cleavage site, preferably furin cleavage site. In some embodiments, coding sequences for HSV2 antigens gH and gL are included on the same vector, and in some cases under the control of a single promoter, and in some cases linked together with a coding sequence for a poteolytic cleavage site, preferably furin cleavage site. In some embodiments, coding sequences for HSV2 antigens gC and gD are included on the same vector, and in some cases under the control of a single promoter, and in some cases linked together with a coding sequence for a poteolytic cleavage site, preferably furin cleavage site. In some embodiments, coding sequences for VZV antigens gH and gL are included on the same vector, and in some cases under the control of a single promoter, and in some cases linked together with a coding sequence for a poteolytic cleavage site, preferably furin cleavage site. In some embodiments, coding sequences for VZV antigens gM and gN are included on the same vector, and in some cases under the control of a single promoter, and in some cases linked together with a coding sequence for a poteolytic cleavage site, preferably furin cleavage site. In some embodiments, coding sequences for CeHV1 antigens gH and gL are included on the same vector, and in some cases under the control of a single promoter, and in some cases linked together with a coding sequence for a poteolytic cleavage site, preferably furin cleavage site. In some embodiments, coding sequences for CeHV1 antigens gC and gD are included on the same vector, and in some cases under the control of a single promoter, and in some cases linked together with a coding sequence for a poteolytic cleavage site, preferably furin cleavage site. In some embodiments, coding sequences for VZV antigens gE and gI are included on the same vector, and in some cases under the control of a single promoter, and in some cases linked together with a coding sequence for a poteolytic cleavage site, preferably furin cleavage site.

Coding sequences for any protein disclosed herein may be provided as a single coding sequence on a single. Likewise, coding sequences for any combination of different proteins disclosed herein may be provided on a single vector, either with its own promoter, linked with an IRES sequence or as a single coding sequence of a polyprotein in which the individual proteins are linked with proteolytic cleavage sites.

In each and every instance set forth herein, coding sequences may be optimized for stability and high levels of expression. In some instances, codons are selected to reduce secondary structure formation of the RNA such as that formed due to intramolecular bonding.

The vector can comprise heterologous nucleic acid encoding an antigen and can further comprise an initiation codon, which can be upstream of the antigen coding sequence, and a stop codon, which can be downstream of the antigen coding sequence. The initiation and termination codon can be in frame with the antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the herpes antigen coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus herpes antigen coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant (FIG. 1) with changes such as those included in SEQ ID NO:76. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993. Based upon the sequence of pVAX1 available from Invitrogen, the following mutations were found in the sequence of pVAX1 that was used as the backbone for plasmids 1-6 set forth herein:

C>G 241 in CMV promoter

C>T 1942 backbone, downstream of the bovine growth hormone polyadenylation signal (bGHpolyA)

A>—2876 backbone, downstream of the Kanamycin gene

C>T 3277 in pUC origin of replication (Ori) high copy number mutation (see Nucleic Acid Research 1985)

G>C 3753 in very end of pUC On upstream of RNASeH site

Base pairs 2, 3 and 4 are changed from ACT to CTG in backbone, upstream of CMV promoter. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus herpes antigen coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning an Laboratory Manual, Second Ed., Cold Spring Harbor (1989), which is incorporated fully by reference.

4. Pharmaceutical Compositions

Provided herein are pharmaceutical compositions according to the present invention which comprise about 1 nanogram to about 10 mgs of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mgs. In some embodiments, pharmaceutical compositions according to the present invention comprise about 5 nanograms to about 10 mgs of DNA. In some embodiments, pharmaceutical compositions according to the present invention comprise about 25 nanograms to about 5 mgs of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

Provided herein is a vaccine capable of generating in a mammal an immune response against herpes virus antigens. The vaccine can comprise the genetic construct as discussed above. The vaccine can comprise a plurality of the vectors each directed to one or more herpes virus antigens. The vaccine may comprise one or more nucleic acid sequences that encode one or more consensus herpes virus antigens. When the vaccine comprises more than one consensus herpes virus nucleic acid sequences, all such sequences may be present on a single nucleic acid molecule or each such sequences may be present on a different nucleic acid molecule. Alternatively, vaccines that comprise more than one consensus herpes virus nucleic acid sequences may comprise nucleic acid molecules with a single consensus herpes virus-nucleic acid sequence and nucleic acid molecules with more than one consensus herpes virus nucleic acid sequences. In addition, vaccines comprising one or more consensus herpes virus nucleic acid sequences may further comprise coding sequences for one or more herpes virus antigens.

Vaccines may comprise one or more of the consensus versions of the immunogenic proteins set forth herein and/or vaccines may comprise one or more nucleic acid sequences that encode one or more of the consensus versions of the immunogenic proteins selected from this group. Vaccines may comprise one or more of the consensus versions of the immunogenic proteins set forth herein in combination with other immunogenic herpes virus proteins with sequences other than the consensus sequences disclosed herein including wild type sequences and/or vaccines may comprise one or more nucleic acid sequences that encode one or more of the consensus versions of the immunogenic proteins selected from this group in combination with nucleic acid molecules that encode other immunogenic herpes virus proteins with sequences other than the consensus sequences disclosed herein including wild type sequences.

While not being bound by scientific theory, a vaccine that can be used to elicit an immune response (humoral, cellular, or both) broadly against herpes virus may comprise one or more of the following nucleic acid sequences that encodes one or more herpes virus antigens selected from the group consisting of: a) for HCMV: consensus gB, consensus gM, consensus gN4-c, consensus gH, consensus gL, consensus gO-5, consensus UL128, consensus UL130, consensus UL131a, consensus UL83; b) for HSV1: consensus gB, consensus gH, consensus gL, consensus gC, and consensus gD; c) for HSV2: consensus gB, consensus gH, consensus gL, consensus gC, and consensus gD; d) for CeHV1: consensus gB, consensus gH, consensus gL, consensus gC, and consensus gD; and e) for VZV: consensus gB, consensus gH, consensus gL, consensus gC, and consensus gK, consensus gM, consensus gN, consensus gE, and consensus gI; proteins homologous to any of the consensus herpes antigens, above; fragments of any of the consensus herpes antigens, above; and fragments of proteins homologous to any of the consensus herpes antigens, above. In addition, vaccines comprising any of the above nucleic acid sequences may further comprise one or more nucleic acid sequences encoding one or more proteins selected from the group consisting of: a) for HCMV: gB, gM, gN, gH, gL, gO, UL128, UL130, UL131a, and UL83; b) for HSV1: gB, gH, gL, gC, and gD; c) for HSV2: gB, gH, gL, gC, and gD, d) for CeHV1: gB, gH, gL, gC, and gD; and e) for VZV: gB, gH, gL, gC, gK, gM, gN, gE, and gI. Alternatively, vaccines may comprise one or more protein molecules instead of or in addition to any coding sequence set forth above.

Vaccines may comprise coding sequences for consensus protein gB (SEQ ID NO:2 and/or SEQ ID NO:22 and/or SEQ ID NO:42). Vaccines may comprise coding sequences for consensus protein gB (SEQ ID NO:2 and/or SEQ ID NO:22 and/or SEQ ID NO:42) plus one or more coding sequences for gM, gN, gH, gL, gO, UL128, UL130, UL131a and UL83. Vaccines may comprise coding sequences for consensus protein gB (SEQ ID NO:2 and/or SEQ ID NO:22 and/or SEQ ID NO:42). plus coding sequences for one or more of (SEQ ID NO:4), (SEQ ID NO:6), (SEQ ID NO:8), (SEQ ID NO:10), (SEQ ID NO:12), (SEQ ID NO:14), (SEQ ID NO:16), (SEQ ID NO:18), (SEQ ID NO:20), (SEQ ID NO:24), (SEQ ID NO:26), (SEQ ID NO:28), (SEQ ID NO:30), (SEQ ID NO:32), (SEQ ID NO:34), (SEQ ID NO:36), (SEQ ID NO:38), (SEQ ID NO:40), (SEQ ID NO:44), (SEQ ID NO:46), (SEQ ID NO:48), (SEQ ID NO:50), (SEQ ID NO:52), (SEQ ID NO:54), (SEQ ID NO:56), (SEQ ID NO:58), (SEQ ID NO:60).

Vaccines may comprise specific coding sequences encoding consensus protein gB SEQ ID NO:1 and/or SEQ ID NO:21 and/or SEQ ID NO:41. Vaccines may comprise consensus protein gB coding sequences SEQ ID NO:1 and/or SEQ ID NO:21 and/or SEQ ID NO:41 plus one or more coding sequences for gM, gN, gH, gL, gO, UL128, UL130, UL131a and UL83. Vaccines may comprise gB coding sequences (SEQ ID NO:1 and/or SEQ ID NO:21 and/or SEQ ID NO:41). plus consensus protein coding sequences (SEQ ID NO:3), (SEQ ID NO:5), (SEQ ID NO:7), (SEQ ID NO:9), (SEQ ID NO:11), (SEQ ID NO:13), (SEQ ID NO:15), (SEQ ID NO:17), (SEQ ID NO:19), (SEQ ID NO:23), (SEQ ID NO:25), (SEQ ID NO:27), (SEQ ID NO:29), (SEQ ID NO:31), (SEQ ID NO:33), (SEQ ID NO:35), (SEQ ID NO:37), (SEQ ID NO:39) (SEQ ID NO:43), (SEQ ID NO:45), (SEQ ID NO:47), (SEQ ID NO:49), (SEQ ID NO:51), (SEQ ID NO:53), (SEQ ID NO:55), (SEQ ID NO:57), and (SEQ ID NO:59).

Vaccines may comprise coding sequences for consensus protein gM (SEQ ID NO:4 and/or SEQ ID NO:24 and/or SEQ ID NO:44). Vaccines may comprise coding sequences for consensus protein gM (SEQ ID NO:4 and/or SEQ ID NO:24 and/or SEQ ID NO:44) plus one or more coding sequences for gB, gN, gH, gL, gO, UL128, UL130, UL131a and UL83. Vaccines may comprise coding sequences for consensus protein gM (SEQ TD NO:4 and/or SEQ ID NO:24 and/or SEQ ID NO:44). plus coding sequences for one or more of (SEQ ID NO:2), (SEQ ID NO:6), (SEQ ID NO:8), (SEQ ID NO:10), (SEQ ID NO:12), (SEQ ID NO:14), (SEQ ID NO:16), (SEQ ID NO:18), (SEQ ID NO:20), (SEQ ID NO:22), (SEQ ID NO:26), (SEQ ID NO:28), (SEQ ID NO:30), (SEQ ID NO:32), (SEQ ID NO:34), (SEQ ID NO:36), (SEQ ID NO:38), (SEQ ID NO:40), (SEQ ID NO:42), (SEQ ID NO:46), (SEQ ID NO:48), (SEQ ID NO:50), (SEQ ID NO:52), (SEQ ID NO:54), (SEQ ID NO:56), (SEQ ID NO:58), and (SEQ ID NO:60).

Vaccines may comprise specific coding sequences encoding consensus protein gM SEQ ID NO:3 and/or SEQ ID NO:23 and/or SEQ ID NO:43. Vaccines may comprise consensus protein gM coding sequences SEQ ID NO:3 and/or SEQ ID NO:23 and/or SEQ ID NO:43 plus one or more coding sequences for gB, gN, gH, gL, gO, UL128, UL130, UL131a and UL83. Vaccines may comprise gM coding sequences (SEQ ID NO:3 and/or SEQ ID NO:23 and/or SEQ ID NO:43). plus consensus protein coding sequences (SEQ ID NO:1), (SEQ ID NO:5), (SEQ ID NO:7), (SEQ ID NO:9), (SEQ ID NO:11), (SEQ ID NO:13), (SEQ ID NO:15), (SEQ ID NO:17), (SEQ ID NO:19), (SEQ ID NO:21), (SEQ ID NO:25), (SEQ ID NO:27), (SEQ ID NO:29), (SEQ ID NO:31), (SEQ ID NO:33), (SEQ ID NO:35), (SEQ ID NO:37), (SEQ ID NO:39). SEQ ID NO:41), (SEQ ID NO:45), (SEQ ID NO:47), (SEQ ID NO:49), (SEQ ID NO:51), (SEQ ID NO:53), (SEQ ID NO:55), (SEQ ID NO:57), and (SEQ ID NO:59).

Vaccines may comprise coding sequences for consensus protein gN (SEQ ID NO:6 and/or SEQ ID NO:26 and/or SEQ ID NO:46). Vaccines may comprise coding sequences for consensus protein gN (SEQ ID NO:6 and/or SEQ ID NO:26 and/or SEQ ID NO:46) plus one or more coding sequences for gB, gM, gH, gL, gO, UL128, UL130, UL131a and UL83. Vaccines may comprise coding sequences for consensus protein gN (SEQ ID NO:6 and/or SEQ ID NO:26 and/or SEQ ID NO:46). plus coding sequences for one or more of (SEQ ID NO:2), (SEQ ID NO:4), (SEQ ID NO:8), (SEQ ID NO:10), (SEQ ID NO:12), (SEQ ID NO:14), (SEQ ID NO:16), (SEQ ID NO:18), (SEQ ID NO:20), (SEQ ID NO:22), (SEQ ID NO:24), (SEQ ID NO:28), (SEQ ID NO:30), (SEQ ID NO:32), (SEQ ID NO:34), (SEQ ID NO:36), (SEQ ID NO:38), (SEQ ID NO:40). SEQ ID NO:42), (SEQ ID NO:44), (SEQ ID NO:48), (SEQ ID NO:50), (SEQ ID NO:52), (SEQ ID NO:54), (SEQ ID NO:56), (SEQ ID NO:58), and (SEQ TD NO:60).

Vaccines may comprise specific coding sequences encoding consensus protein gN SEQ ID NO:5 and/or SEQ ID NO:25 and/or SEQ ID NO:45. Vaccines may comprise consensus protein gN coding sequences SEQ ID NO:5 and/or SEQ ID NO:25 and/or SEQ ID NO:45 plus one or more coding sequences for gB, gM, gH, gL, gO, UL128, UL130, UL131a and UL83. Vaccines may comprise gN coding sequences (SEQ ID NO:5 and/or SEQ ID NO:25 and/or SEQ ID NO:45). plus consensus protein coding sequences (SEQ ID NO:1), (SEQ ID NO:3), (SEQ ID NO:7), (SEQ ID NO:9), (SEQ ID NO:11), (SEQ ID NO:13), (SEQ ID NO:15), (SEQ ID NO:17), (SEQ ID NO:19), (SEQ ID NO:21), (SEQ ID NO:23), (SEQ ID NO:27), (SEQ ID NO:29), (SEQ ID NO:31), (SEQ ID NO:33), (SEQ ID NO:35), (SEQ ID NO:37), (SEQ ID NO:39). SEQ ID NO:41), (SEQ ID NO:43), (SEQ ID NO:47), (SEQ ID NO:49), (SEQ ID NO:51), (SEQ ID NO:53), (SEQ ID NO:55), (SEQ ID NO:57), and (SEQ ID NO:59).

Vaccines may comprise coding sequences for consensus protein gH (SEQ ID NO:8 and/or SEQ ID NO:28 and/or SEQ ID NO:48). Vaccines may comprise coding sequences for consensus protein gH (SEQ ID NO:8 and/or SEQ ID NO:28 and/or SEQ ID NO:48) plus one or more coding sequences for gB, gM, gN, gL, gO, UL128, UL130, UL131a and UL83. Vaccines may comprise coding sequences for consensus protein gH (SEQ ID NO:8 and/or SEQ ID NO:28 and/or SEQ ID NO:48). plus coding sequences for one or more of (SEQ ID NO:2), (SEQ ID NO:4), (SEQ ID NO:6), (SEQ ID NO:10), (SEQ ID NO:12), (SEQ ID NO:14), (SEQ ID NO:16), (SEQ ID NO:18), (SEQ ID NO:20), (SEQ ID NO:22), (SEQ ID NO:24), (SEQ ID NO:26), (SEQ ID NO:30), (SEQ ID NO:32), (SEQ ID NO:34), (SEQ ID NO:36), (SEQ ID NO:38), (SEQ ID NO:40), (SEQ ID NO:42), (SEQ ID NO:44), (SEQ ID NO:46), (SEQ ID NO:50), (SEQ ID NO:52), (SEQ ID NO:54), (SEQ ID NO:56), (SEQ ID NO:58), (SEQ ID NO:60).

Vaccines may comprise specific coding sequences encoding consensus protein gH SEQ ID NO:7 and/or SEQ ID NO:27 and/or SEQ ID NO:47. Vaccines may comprise consensus protein gH coding sequences SEQ ID NO:7 and/or SEQ ID NO:27 and/or SEQ ID NO:47 plus one or more coding sequences for gB, gM, gN, gL, gO, UL128, UL130, UL131a and UL83. Vaccines may comprise gH coding sequences (SEQ ID NO:7 and/or SEQ ID NO:27 and/or SEQ ID NO:47) plus consensus protein coding sequences (SEQ ID NO:1), (SEQ ID NO:3), (SEQ TD NO:5), (SEQ ID NO:9), (SEQ TD NO:11), (SEQ ID NO:13), (SEQ ID NO:15), (SEQ ID NO:17), (SEQ ID NO:19), (SEQ ID NO:21), (SEQ ID NO:23), (SEQ ID NO:25), (SEQ ID NO:29), (SEQ ID NO:31), (SEQ ID NO:33), (SEQ ID NO:35), (SEQ ID NO:37), (SEQ ID NO:39), (SEQ ID NO:41), (SEQ ID NO:43), (SEQ ID NO:45), (SEQ ID NO:49), (SEQ ID NO:51), (SEQ ID NO:53), (SEQ ID NO:55), (SEQ ID NO:57), and (SEQ ID NO:59)

Vaccines may comprise coding sequences for consensus protein gL (SEQ ID NO:10 and/or SEQ ID NO:30 and/or SEQ ID NO:50). Vaccines may comprise coding sequences for consensus protein gL (SEQ ID NO:10 and/or SEQ ID NO:30 and/or SEQ ID NO:50) plus one or more coding sequences for gB, gM, gN, gH, gO, UL128, UL130, UL131a and UL83. Vaccines may comprise coding sequences for consensus protein gL (SEQ ID NO:10 and/or SEQ ID NO:30 and/or SEQ ID NO:50) plus coding sequences for one or more of (SEQ ID NO:2), (SEQ ID NO:4), (SEQ ID NO:6), (SEQ ID NO:8), (SEQ ID NO:12), (SEQ ID NO:14), (SEQ ID NO:16), (SEQ ID NO:18), (SEQ ID NO:20), (SEQ ID NO:22), (SEQ ID NO:24), (SEQ ID NO:26), (SEQ ID NO:28), (SEQ ID NO:32), (SEQ ID NO:34), (SEQ ID NO:36), (SEQ ID NO:38), (SEQ ID NO:40), (SEQ ID NO:42), (SEQ ID NO:44), (SEQ ID NO:46), (SEQ ID NO:48), (SEQ ID NO:52), (SEQ ID NO:54), (SEQ ID NO:56), (SEQ ID NO:58), (SEQ ID NO:60).

Vaccines may comprise specific coding sequences encoding consensus protein gL SEQ ID NO:9 and/or SEQ ID NO:29 and/or SEQ ID NO:49. Vaccines may comprise consensus protein gL coding sequences SEQ ID NO:9 and/or SEQ ID NO:29 and/or SEQ ID NO:49 plus one or more coding sequences for gB, gM, gN, gH, gO, UL128, UL130, UL131a and UL83. Vaccines may comprise gL coding sequences (SEQ ID NO:9 and/or SEQ ID NO:29 and/or SEQ ID NO:49) plus consensus protein coding sequences (SEQ ID NO:1), (SEQ ID NO:3), (SEQ ID NO:5), (SEQ ID NO:7), (SEQ ID NO:11), (SEQ ID NO:13), (SEQ ID NO:15), (SEQ ID NO:17), (SEQ ID NO:19), (SEQ ID NO:21), (SEQ ID NO:23), (SEQ ID NO:25), (SEQ ID NO:27), (SEQ ID NO:31), (SEQ ID NO:33), (SEQ ID NO:35), (SEQ ID NO:37), (SEQ ID NO:39), (SEQ ID NO:41), (SEQ ID NO:43), (SEQ ID NO:45), (SEQ ID NO:47), (SEQ ID NO:51), (SEQ ID NO:53), (SEQ ID NO:55), (SEQ ID NO:57), and (SEQ ID NO:59).

Vaccines may comprise coding sequences for consensus protein gO (SEQ TD NO:12 and/or SEQ ID NO:32 and/or SEQ ID NO:52). Vaccines may comprise coding sequences for consensus protein gO (SEQ ID NO:12 and/or SEQ ID NO:32 and/or SEQ ID NO:52) plus one or more coding sequences for gB, gM, gN, gH, gL, UL128, UL130, UL131a and UL83. Vaccines may comprise coding sequences for consensus protein gO (SEQ ID NO:12 and/or SEQ ID NO:32 and/or SEQ ID NO:52) plus coding sequences for one or more of (SEQ ID NO:2), (SEQ ID NO:4), (SEQ ID NO:6), (SEQ ID NO:8), (SEQ ID NO:10), (SEQ ID NO:14), (SEQ ID NO:16), (SEQ ID NO:18), (SEQ ID NO:20), (SEQ ID NO:22), (SEQ ID NO:24), (SEQ ID NO:26), (SEQ ID NO:28), (SEQ ID NO:30), (SEQ ID NO:34), (SEQ ID NO:36), (SEQ ID NO:38), (SEQ ID NO:40) (SEQ ID NO:42), (SEQ ID NO:44), (SEQ ID NO:46), (SEQ ID NO:48), (SEQ ID NO:50), (SEQ ID NO:54), (SEQ ID NO:56), (SEQ ID NO:58), (SEQ ID NO:60).

Vaccines may comprise specific coding sequences encoding consensus protein gO SEQ ID NO:11 and/or SEQ ID NO:31 and/or SEQ ID NO:51. Vaccines may comprise consensus protein gO coding sequences SEQ ID NO:11 and/or SEQ ID NO:31 and/or SEQ ID NO:51 plus one or more coding sequences for gB, gM, gN, gH, gL, UL128, UL130, UL131a and UL83. Vaccines may comprise gO coding sequences (SEQ ID NO:11 and/or SEQ ID NO:31 and/or SEQ ID NO:51) plus consensus protein coding sequences (SEQ ID NO:1), (SEQ ID NO:3), (SEQ ID NO:5), (SEQ ID NO:7), (SEQ ID NO:9), (SEQ ID NO:13), (SEQ ID NO:15), (SEQ ID NO:17), (SEQ ID NO:19), (SEQ ID NO:21), (SEQ ID NO:23), (SEQ ID NO:25), (SEQ ID NO:27), (SEQ ID NO:29), (SEQ ID NO:33), (SEQ ID NO:35), (SEQ ID NO:37), (SEQ ID NO:39), (SEQ ID NO:41), (SEQ ID NO:43), (SEQ ID NO:45), (SEQ ID NO:47), (SEQ ID NO:49), (SEQ ID NO:53), (SEQ ID NO:55), (SEQ ID NO:57), and (SEQ ID NO:59).

Vaccines may comprise coding sequences for consensus protein UL128 (SEQ ID NO:14 and/or SEQ ID NO:34 and/or SEQ ID NO:54). Vaccines may comprise coding sequences for consensus protein UL128 (SEQ ID NO:14 and/or SEQ ID NO:34 and/or SEQ ID NO:54) plus one or more coding sequences for gB, gM, gN, gH, gL, gO, UL130, UL131a and UL83. Vaccines may comprise coding sequences for consensus protein UL128 (SEQ ID NO:14 and/or SEQ ID NO:34 and/or SEQ ID NO:54) plus coding sequences for one or more of (SEQ ID NO:2), (SEQ ID NO:4), (SEQ ID NO:6), (SEQ ID NO:8), (SEQ ID NO:10), (SEQ TD NO:12), (SEQ TD NO:16), (SEQ TD NO:18), (SEQ TD NO:20), (SEQ ID NO:22), (SEQ ID NO:24), (SEQ ID NO:26), (SEQ ID NO:28), (SEQ ID NO:30), (SEQ ID NO:32), (SEQ ID NO:36), (SEQ ID NO:38), (SEQ ID NO:40), (SEQ ID NO:42), (SEQ ID NO:44), (SEQ ID NO:46), (SEQ ID NO:48), (SEQ ID NO:50), (SEQ ID NO:52), (SEQ ID NO:56), (SEQ ID NO:58), (SEQ ID NO:60).

Vaccines may comprise specific coding sequences encoding consensus protein UL128 SEQ ID NO:13 and/or SEQ ID NO:33 and/or SEQ ID NO:53. Vaccines may comprise consensus protein UL128 coding sequences SEQ ID NO:13 and/or SEQ ID NO:33 and/or SEQ ID NO:53 plus one or more coding sequences for gB, gM, gN, gH, gL, gO, UL130, UL131a and UL83. Vaccines may comprise UL128 coding sequences (SEQ ID NO:13 and/or SEQ ID NO:33 and/or SEQ ID NO:53) plus consensus protein coding sequences (SEQ ID NO:1), (SEQ ID NO:3), (SEQ ID NO:5), (SEQ ID NO:7), (SEQ ID NO:9), (SEQ ID NO:11), (SEQ ID NO:15), (SEQ ID NO:17), (SEQ ID NO:19), (SEQ ID NO:21), (SEQ ID NO:23), (SEQ ID NO:25), (SEQ ID NO:27), (SEQ ID NO:29), (SEQ ID NO:31), (SEQ ID NO:35), (SEQ ID NO:37), (SEQ ID NO:39), (SEQ ID NO:41), (SEQ ID NO:43), (SEQ ID NO:45), (SEQ ID NO:47), (SEQ ID NO:49), (SEQ ID NO:51), (SEQ ID NO:55), (SEQ ID NO:57), and (SEQ ID NO:59).

Vaccines may comprise coding sequences for consensus protein UL130 SEQ ID NO:16 and/or SEQ ID NO:36 and/or SEQ ID NO:56). Vaccines may comprise coding sequences for consensus protein UL130 (SEQ ID NO:16 and/or SEQ ID NO:36 and/or SEQ ID NO:56) plus one or more coding sequences for gB, gM, gN, gH, gL, gO, UL128, UL131a and UL83. Vaccines may comprise coding sequences for consensus protein UL130 (SEQ ID NO:16 and/or SEQ ID NO:36 and/or SEQ ID NO:56) plus coding sequences for one or more of (SEQ ID NO:2), (SEQ ID NO:4), (SEQ ID NO:6), (SEQ ID NO:8), (SEQ ID NO:10), (SEQ ID NO:12), (SEQ ID NO:14), (SEQ ID NO:18), (SEQ ID NO:20), (SEQ ID NO:22), (SEQ ID NO:24), (SEQ ID NO:26), (SEQ ID NO:28), (SEQ ID NO:30), (SEQ ID NO:32), (SEQ ID NO:34), (SEQ ID NO:38), (SEQ ID NO:40), (SEQ ID NO:42), (SEQ ID NO:44), (SEQ ID NO:46), (SEQ ID NO:48), (SEQ ID NO:50), (SEQ ID NO:52), (SEQ ID NO:54), (SEQ ID NO:58), (SEQ ID NO:60).

Vaccines may comprise specific coding sequences encoding consensus protein UL130 (SEQ ID NO:15 and/or SEQ ID NO:35 and/or SEQ ID NO:55). Vaccines may comprise consensus protein UL130 coding sequences SEQ TD NO:15 and/or SEQ TD NO:35 and/or SEQ ID NO:55 plus one or more coding sequences for gB, gM, gN, gH, gL, gO, UL128, UL131a and UL83. Vaccines may comprise UL130 coding sequences (SEQ ID NO:15 and/or SEQ ID NO:35 and/or SEQ ID NO:55) plus consensus protein coding sequences (SEQ ID NO:1), (SEQ ID NO:3), (SEQ ID NO:5), (SEQ ID NO:7), (SEQ ID NO:9), (SEQ ID NO:11), (SEQ ID NO:13), (SEQ ID NO:17), (SEQ ID NO:19), (SEQ ID NO:21), (SEQ ID NO:23), (SEQ ID NO:25), (SEQ ID NO:27), (SEQ ID NO:29), (SEQ ID NO:31), (SEQ ID NO:33), (SEQ ID NO:37), (SEQ ID NO:39), (SEQ ID NO:41), (SEQ ID NO:43), (SEQ ID NO:45), (SEQ ID NO:47), (SEQ ID NO:49), (SEQ ID NO:51), (SEQ ID NO:53), (SEQ ID NO:57), and (SEQ ID NO:59).

Vaccines may comprise coding sequences for consensus protein UL131a (SEQ ID NO:18 and/or SEQ ID NO:38 and/or SEQ ID NO:58). Vaccines may comprise coding sequences for consensus protein UL131a (SEQ ID NO:18 and/or SEQ ID NO:38 and/or SEQ ID NO:58) plus one or more coding sequences for gB, gM, gN, gH, gL, gO, UL128, UL130 and UL83. Vaccines may comprise coding sequences for consensus protein UL131a (SEQ ID NO:18 and/or SEQ ID NO:38 and/or SEQ ID NO:58) plus coding sequences for one or more of (SEQ ID NO:2), (SEQ ID NO:4), (SEQ ID NO:6), (SEQ ID NO:8), (SEQ ID NO:10), (SEQ ID NO:12), (SEQ ID NO:14), (SEQ ID NO:16), (SEQ ID NO:20), (SEQ ID NO:22), (SEQ ID NO:24), (SEQ ID NO:26), (SEQ ID NO:28), (SEQ ID NO:30), (SEQ ID NO:32), (SEQ ID NO:34), (SEQ ID NO:36), and (SEQ ID NO:40), (SEQ ID NO:42), (SEQ ID NO:44), (SEQ ID NO:46), (SEQ ID NO:48), (SEQ ID NO:50), (SEQ ID NO:52), (SEQ ID NO:54), (SEQ ID NO:56), and (SEQ ID NO:60).

Vaccines may comprise specific coding sequences encoding consensus protein UL131a SEQ ID NO:17 and/or SEQ ID NO:37 and/or SEQ ID NO:57. Vaccines may comprise consensus protein UL131a coding sequences SEQ ID NO:17 and/or SEQ ID NO:37 and/or SEQ ID NO:57 plus one or more coding sequences for gB, gM, gN, gH, gL, gO, UL128, UL130 and UL83. Vaccines may comprise UL131a coding sequences (SEQ ID NO:17 and/or SEQ ID NO:57 and/or SEQ ID NO:37) plus consensus protein coding sequences (SEQ ID NO:1), (SEQ ID NO:3), (SEQ ID NO:5), (SEQ ID NO:7), (SEQ ID NO:9), (SEQ ID NO:11), (SEQ ID NO:13), (SEQ ID NO:15), (SEQ ID NO:19), (SEQ ID NO:21), (SEQ ID NO:23), (SEQ ID NO:25), (SEQ ID NO:27), (SEQ ID NO:29), (SEQ ID NO:31), (SEQ ID NO:33), (SEQ ID NO:35), (SEQ TD NO:39), (SEQ ID NO:41), (SEQ ID NO:43), (SEQ ID NO:45), (SEQ ID NO:47), (SEQ ID NO:49), (SEQ ID NO:51), (SEQ ID NO:53), (SEQ ID NO:55), and (SEQ ID NO:59).

Vaccines may comprise coding sequences for consensus protein UL83 SEQ ID NO:20 and/or SEQ ID NO:40 and/or SEQ ID NO:6). Vaccines may comprise coding sequences for consensus protein UL83 (SEQ ID NO:20 and/or SEQ ID NO:40 and/or SEQ ID NO:60) plus one or more coding sequences for gB, gM, gN, gH, gL, gO, UL128, UL130 and UL131a. Vaccines may comprise coding sequences for consensus protein UL83 (SEQ ID NO:20 and/or SEQ ID NO:40 and/or SEQ ID NO:60) plus coding sequences for one or more of (SEQ ID NO:2), (SEQ ID NO:4), (SEQ ID NO:6), (SEQ ID NO:8), (SEQ ID NO:10), (SEQ ID NO:12), (SEQ ID NO:14), (SEQ ID NO:16), (SEQ ID NO:18), (SEQ ID NO:22), (SEQ ID NO:24), (SEQ ID NO:26), (SEQ ID NO:28), (SEQ ID NO:30), (SEQ ID NO:32), (SEQ ID NO:34), (SEQ ID NO:36), (SEQ ID NO:38), (SEQ ID NO:42), (SEQ ID NO:44), (SEQ ID NO:46), (SEQ ID NO:48), (SEQ ID NO:50), (SEQ ID NO:52), (SEQ ID NO:54), (SEQ ID NO:56), and (SEQ ID NO:58).

Vaccines may comprise specific coding sequences encoding consensus protein UL83 SEQ ID NO:19 and/or SEQ ID NO:39 and/or SEQ ID NO:59. Vaccines may comprise consensus protein UL83 a coding sequences SEQ ID NO:19 and/or SEQ ID NO:39 and/or SEQ ID NO:59 plus one or more coding sequences for gB, gM, gN, gH, gL, gO, UL128, UL130 and UL131a. Vaccines may comprise UL83 coding sequences (SEQ ID NO:19 and/or SEQ ID NO:39 and/or SEQ ID NO:59) plus consensus protein coding sequences (SEQ ID NO:1), (SEQ ID NO:3), (SEQ ID NO:5), (SEQ ID NO:7), (SEQ ID NO:9), (SEQ ID NO:11), (SEQ ID NO:13), (SEQ ID NO:15), (SEQ ID NO:17), (SEQ ID NO:21), (SEQ ID NO:23), (SEQ ID NO:25), (SEQ ID NO:27), (SEQ ID NO:29), (SEQ ID NO:31), (SEQ ID NO:33), (SEQ ID NO:35), (SEQ ID NO:37), (SEQ ID NO:41), (SEQ ID NO:43), (SEQ ID NO:45), (SEQ ID NO:47), (SEQ ID NO:49), (SEQ ID NO:51), (SEQ ID NO:53), (SEQ ID NO:55), and (SEQ ID NO:57).

Vaccines may comprise specific coding sequences encoding consensus protein HSV1-gB, HSV1-gH, HSV1-gL, HSV-gC, or HSV1-gD, optionally with an IgE leader sequence and/or HA tag. Vaccines may comprise any one of the specific coding sequences encoding a consensus HSV1 protein, plus one or more coding sequences for any one or more of the other HSV1 consensus proteins. Vaccines may comprise a HSV1 coding sequence (DNA sequence) plus a consensus HSV1 coding sequence for any one or more of the other HSV1 coding sequences.

Vaccines may comprise specific coding sequences encoding consensus protein HSV2-gB, HSV2-gH, HSV2-gL, HSV2-gC, or HSV2-gD, optionally with an IgE leader sequence and/or HA tag. Vaccines may comprise any one of the specific coding sequences encoding a consensus HSV2 protein, plus one or more coding sequences for any one or more of the other HSV2 consensus proteins. Vaccines may comprise a HSV2 coding sequence (DNA sequence) plus a consensus HSV2 coding sequence for any one or more of the other HSV2 coding sequences.

Vaccines may comprise specific coding sequences encoding consensus protein CeHV1-gB, CeHV1-gH, CeHV1-gL, CeHV1-gC, or CeHV1-gD, optionally with an IgE leader sequence and/or HA tag. Vaccines may comprise any one of the specific coding sequences encoding a consensus CeHV1 protein, plus one or more coding sequences for any one or more of the other CeHV1 consensus proteins. Vaccines may comprise a CeHV1 coding sequence (DNA sequence) plus a consensus CeHV1 coding sequence for any one or more of the other CeHV1 coding sequences.

Vaccines may comprise specific coding sequences encoding consensus protein VZV-gB, VZV-gH, VZV-gL, VZV-gC, VZV-gK, VZV-gM, VZV-gN, VZV-gE, or VZV-gI, optionally with an IgE leader sequence and/or HA tag. Vaccines may comprise any one of the specific coding sequences encoding a consensus VZV protein, plus one or more coding sequences for any one or more of the other VZV consensus proteins. Vaccines may comprise a VZV coding sequence (DNA sequence) plus a consensus VZV coding sequence for any one or more of the other VZV coding sequences.

Some alternative embodiments include those which comprise nucleic acid sequences encoding immunogenic fragments of one or more herpes virus antigens, one or more proteins homologous to herpes virusantigens, and immunogenic fragments of one or more proteins homologous to herpes virusantigens. Some alternative embodiments include those which comprise one or more herpes virusantigen proteins, immunogenic fragments of one or more herpes virus antigens, one or more proteins homologous to herpes virus antigens, and immunogenic fragments of one or more proteins homologous to herpes virus antigens.

Some embodiments provide methods of generating immune responses against herpes virus proteins comprise administering to an individual one or more compositions which collectively comprise one or more coding sequences or combinations described herein. Some embodiments provide methods of prophylactically vaccinating an individual against herpes virus infection comprise administering one or more compositions which collectively comprise one or more coding sequences or combinations described herein. Some embodiments provide methods of therapeutically vaccinating an individual has been infected with herpes virus comprise administering one or more compositions which collectively comprise one or more coding sequences or combinations described herein.

The vaccine may be a DNA vaccine. The DNA vaccine may comprise a plurality of the same or different plasmids comprising one or more of consensus herpes virus nucleic acid sequences. The DNA vaccine may comprise one or more nucleic acid sequences that encode one or more consensus herpes virus antigens. When the DNA vaccine comprises more than one consensus herpes virus nucleic acid sequences, all such sequences may be present on a single plasmid, or each such sequences may be present on a different plasmids, or some plasmids may comprise a single consensus herpes virus nucleic acid sequences while other plasmids have more than one consensus herpes virus nucleic acid sequences. In addition, DNA vaccines may further comprise one or more consensus coding sequences for one or more herpes virus antigens. Such additional coding sequences may be on the same or different plasmids from each other and from the plasmids comprising one or more of consensus pros DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the herpes virus antigen. The RNA vaccine can be introduced into the cell.

The vaccine can be a recombinant vaccine comprising the genetic construct or antigen described above. The vaccine can also comprise one or more consensus herpes virus antigen in the form of one or more protein subunits, one or more killed viral particles comprising one or more consensus herpes virus antigens, or one or more attenuated viral particles comprising one or more consensus herpes virus antigens. The attenuated vaccine can be attenuated live vaccines, killed vaccines and vaccines that use recombinant vectors to deliver foreign genes that encode one or more consensus herpes virus antigens, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to herpes virus serotypes from particular regions in the world. The vaccine can also be directed against herpes virus serotypes from multiple regions in the world.

The vaccine provided may be used to induce immune responses including therapeutic or prophylactic immune responses. Antibodies and/or killer T cells may be generated which are directed to the consensus herpes virus antigen, and also broadly across multiple subtypes of herpes viruses. Such antibodies and cells may be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, TCAM-1, TCAM-2, TCAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, TRAK, TRAF6, TkB, Inactive NTK, SAP K, SAP-1, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Pat. No. 5,739,118, filed Apr. 1, 1994, which is fully incorporated by reference.

5. Methods of Delivery

Provided herein is a method for delivering the pharmaceutical formulations, preferably vaccines, for providing genetic constructs and proteins of the herpes virus antigen which comprise epitopes that make them particular effective immunogens against which an immune response to herpes virus viral infections can be induced. The method of delivering the vaccine, or vaccination, can be provided to induce a therapeutic and/or prophylactic immune response. The vaccination process can generate in the mammal an immune response against a plurality of herpes virus subtypes. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognized and induces a cellular, humoral, or cellular and humoral response. The delivery of the vaccine can be use to induce or elicit and immune response in mammals against a plurality of herpes viruses, herpes family specific, by administering to the mammals the relevant herpes virus family vaccine as discussed herein.

Upon delivery of the vaccine to the mammal, and thereupon the vector into the cells of the mammal, the transfected cells will express and secrete the corresponding one or more herpes virusantigens. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with a relevant herpes viral strain, the primed immune system will allow for rapid clearing of subsequent herpes viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination Treatments

The pharmaceutical compositions, preferably vaccines, can be administered in combination with one or more herpes virus antigens. The vaccine can be administered in combination with proteins or genes encoding adjuvants, which can include: α-interferon (IFN-α), β-interferon (IFN-β), γ-interferon, IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The herpes virus antigen can be delivered via DNA injection and along with in vivo electroporation.

c. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA® EP system (Inovio Pharmaceuticals, Inc., Blue Bell, Pa.) or Elgen electroporator (Inovio Pharmaceuticals, Inc., Blue Bell, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1 Generating Herpes Antigens and Expression Constructs

A DNA vaccine strategy was employed that focused on glycoproteins, chaperone proteins and matrix proteins of herpes virus family. To increase the potential breadth of immunity elicited by each viral antigen (Ag), phylogenetic diversity was first examined to assess polymorphism and to aid in the production of clinically-relevant consensus amino acid sequences.

Genetic and Statistical Analysis

Phylogenetic and molecular evolutionary analyses were conducted using MEGA version 5 (Tamura, Peterson, Stecher, Nei, and Kumar 2011) to estimate diversity among clinically relevant and publically available herpes target protein sequences used for generating consensus vaccine Ags. Neighbor-joining phylogenetic reconstruction analysis using the bootstrap method with 1,000 bootstrap replications was used to generate bootstrap consensus trees with radiation view. P-distances are shown for HCMV, for example (FIG. 17).

All values are reported as the mean±SEM. Analysis between groups was completed by ANOVA with a post-hoc Dunnett's test to correct for multiple comparisons to one control (HCMV infected). All statistical analysis was carried out using GraphPad Prism (GraphPad Software Inc., La Jolla, Calif.) or the Statistical Package for the Social Sciences (SPSS, Chicago, Ill.).

Strategies for generating the consensus amino acid sequences for each herpes immunogen are outlined, below. In general, consensus sequences from highly conserved herpes proteins were used for vaccine immunogens while consensus sequences from specific, clinically relevant subgroups were used for the highly divergent proteins.

Amino acid sequences of herpes vaccine proteins were generated by taking the consensus of publically available (GenBank) and clinically relevant strains (passaged no more than six times in tissue culture) using Vector NTI software (Invitrogen) for sequence alignment. Some plasmids (VZV gHgL, VZV gEgI, VZV gMgN, HSV1 gHgL, HSV1 gCgD, HSV2 gHgL, HSV2 gCgD, CeHV1 gHgL, CeHV1 gCgD, pCMV-gHgL, pCMV-gMgN, and pCMV-UL) expressed multiple herpes proteins which were separated by a cleavage site (furin site SEQ ID NO:63) for the co-expression of structurally-relevant macromolecules. Genetic optimization of DNA vaccines included codon and RNA optimization for protein expression in humans and all genes were synthesized and subcloned into a modified pVAX1 mammalian expression vector (GeneArt, Regensburg, Germany or GenScript, Piscataway, N.J.).

HCMV Specific Analysis

Figure 17A:
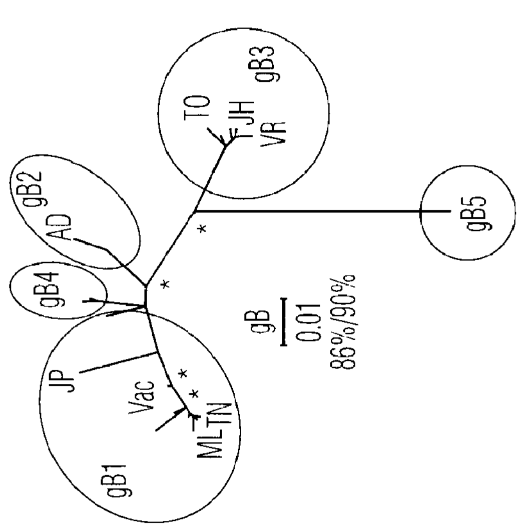
FIG. 17*a-j* shows schematic of phylogenetic trees of HCMV putative vaccine protein immunogens from publically available sources are shown. Amino acid sequences were multiple-aligned with ClustalW and cluster analysis was performed by maximum-likelihood method. The significance of the unrooted phylogenetic trees was verified by bootstrap analysis and significant support values (≥80%; 1,000 bootstrap replicates) are indicated by asterisks at major nodes. Major reported genotypes are illustrated, percentages are amino acid identity positions of all full-length sequences, and reference strains are indicated; AD—AD169, DV—Davis, JH—JHC, JP—JP, ML—Merlin, TO—Toledo, TN—Towne, VR—VR 1814. DNA vaccine-encoded HCMV immunogens are also shown (Vac). Scale bars signify distance of amino acids per site and analyses were conducted using MEGA version 5.

Phylogenetic analysis of the HCMV gB confirmed the presence of four main variants (gB1-gB4) and one nonprototypic variant (gB5) (FIG. 17*a*). Since the gB protein is relatively conserved among clinical and low-passage strains (~86% identical), we chose the consensus of these sequences to represent our DNA vaccine-encoded Ag. The vaccine sequence was phylogenetically closest to the gB1 genotype which has been found in some cases to account for the majority of highly symptomatic individuals in the clinic.

Figure 17B:
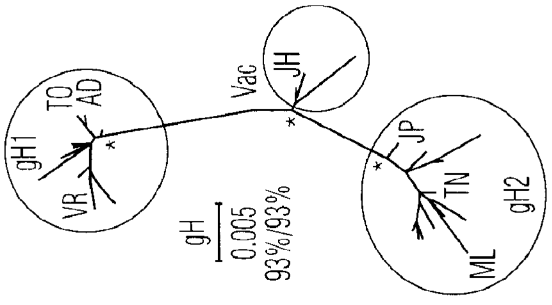
Figure 17C:
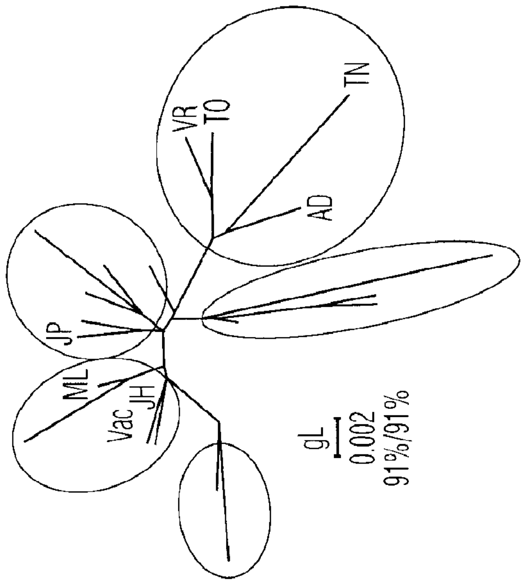
Figure 17D:
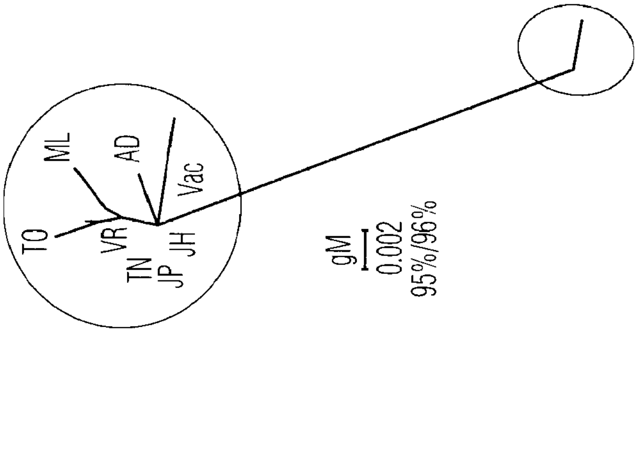
Figure 17E:
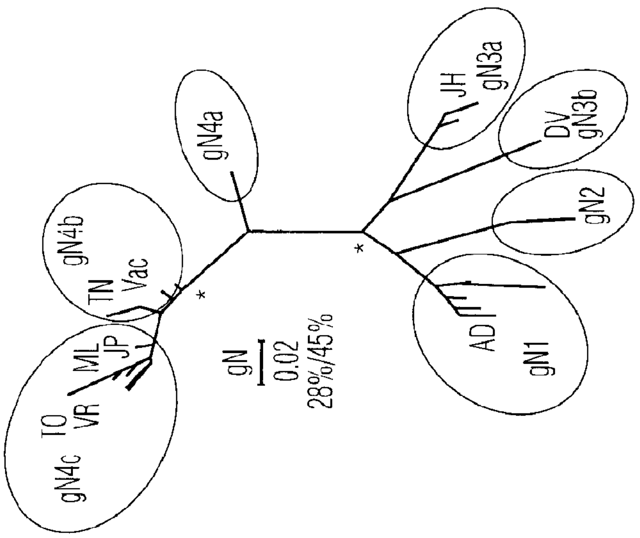
Figure 17F:
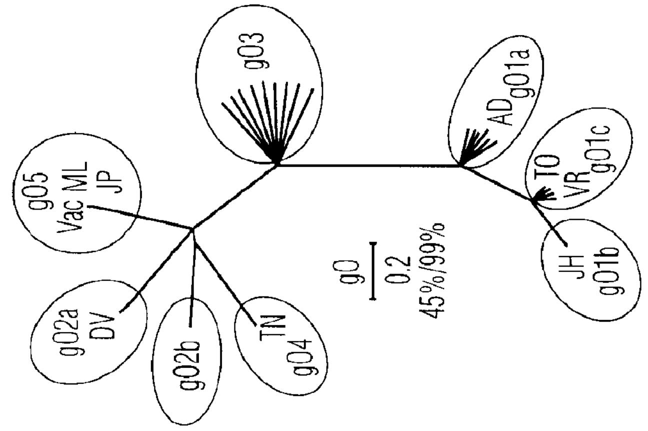

Next, components of the HCMV gCIII fusion complex, gH, gL and gO were developed as candidate immunogens for evaluation as a DNA vaccine. Phylogenetic analysis of gH confirmed the presence of two main genotypes in addition to a possible third group including the newly reported JHC strain that was isolated from a bone marrow transplant patient [Jung, et. Al., *Virus Res.* 2011 June; 158(1-2):298] (FIG. 17*b*). Analysis confirmed a low level of amino acid variation among the gHs (~7%) which may explain why anti-gH MAbs appear broadly reactive. Due to this high level of conservation, the DNA vaccine consensus immunogen fell right between gH1 and gH2 and was closest to the putative third gH group along with the JHC clinical isolate. Phylogenetic analysis of the gL protein, while similarly highly conserved (~91%), was less distinctly grouped (FIG. 17*c*). Upon removal of amino acid sequences of gLs from strains extensively passaged the resultant DNA consensus immunogen fell closest on the tree to the JHC and Merlin clinical isolates and farthest away from the AD169 and Towne lab-adapted strains. The third component of the classically defined gCIII complex is the gO, which is highly glycosylated, and is highly variable at the 5' end. Since gO polymorphism was high (~55%), we chose the consensus sequence of the gO5 genotype group for our target immunogen since this group has been previously described to be genetically linked with the gN-4c genotype, the largest gN-4 variant group and most seroprevalent (FIG. 17*f*). Identity within the gO5 subgroup was ~99% and thus, the consensus Ag was phylogenetically grouped with this subgroup that also included the Merlin and JP clinical isolates.

Novel candidate vaccine immunogens HCMV gM and gN heterodimerize in the ER by both covalent disulfide bonding and noncovalent interaction to form the viral infectivity complex. While the gM is highly conserved among the CMV (~95%), the gN is variable (~45). Due to this relatively high identity among the gM, consensus of all clinically relevant sequences determined our candidate vaccine immunogen (FIG. 17*d*). Conversely, due to the highly modified nature of gN, characterized by almost exclusive O-linked sugars, consensus of the gN-4 subtype was used as vaccine immunogen since this subgroup was reported to be the most prevalent of all clinical isolates in North America, Europe, China, and Australia (FIG. 17*e*). Thus, this sequence was phylogenetically closest to the gN4b subtype, which occurs directly between the gN4a and gN4c groups, all of which constitute the gN4 group.

Figure 17G:
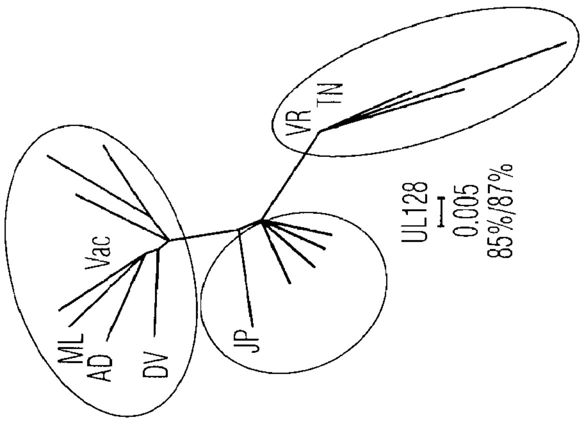
Figure 17H:
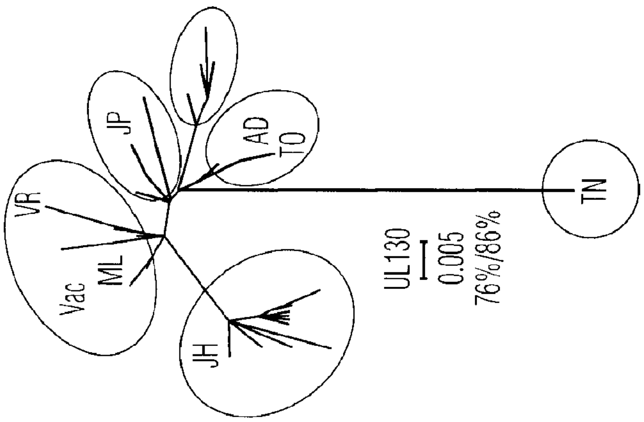
Figure 17I:
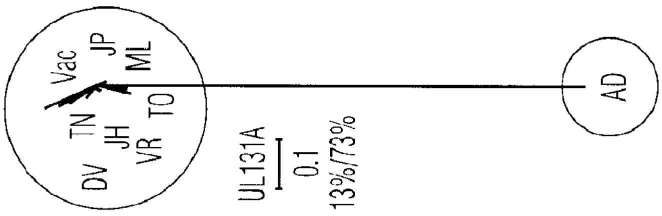
Figure 17J:
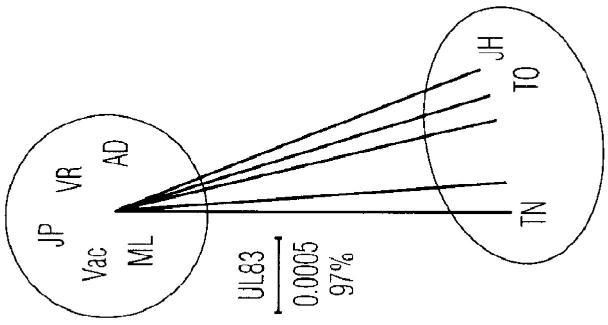

Recently, it has been shown that UL128, UL130, and UL131A can form a pentameric complex with gH and gL, instead of the classically defined association of gH/gL/gO for the gCIII fusion complex. Furthermore, that this complex has been described to elicit potent mAbs. Due to the relatively high level of amino acid conservation upon removal of high-passaged and lab-adapted strains (~87% for UL128, ~86% for UL130, and ~73% for UL131A), consensus sequences were used for each gene for candidate vaccine immunogens (FIG. 17*g*-*i*). The UL128 vaccine sequence was phylogenetically grouped in a group including the Merlin and Davis isolates, as well as the Ad169 strain. However, Both of the UL130 and UL131A sequences were phylogenetically distant from the Towne and AD169 lab strains, respectively, which have lost their ability to infect endothelial cells, epithelial cells, and leukocytes due to deletions or mutations of these genes. And lastly, the UL83 protein (pp65) was chosen due to its current use in recent vaccine strategies as a T cell target. This protein was initially attractive based upon its apparent dominance in the cellular immune response to HCMV since it was recognized by the majority of virus-specific CD8 T cells. This protein is highly conserved among the CMV and was ~97% identical when no accounting for the 3' truncation associated with many published sequences (FIG. 17*j*). Thus, consensus of the UL83 proteins was used for the target vaccine Ag and was phylogenetically similar to the JP, VR1814, Merlin and Ad169 strains, but further from the Towne, Toledo, and JHC strains.

Full-length candidate CMV immunogens were next used to construct plasmid DNA vaccines. Each Ag was genetically optimized for expression in humans, commercially synthesized, and then subcloned into a modified pVAX1 mammalian expression vector. In addition, proteins requiring heterologous interaction for the construction of functional virion surface complexes were encoded in combination within the same DNA vaccine plasmid. Multiple protein-expressing plasmids gHgL, gMgN, and pUL encoded ubiquitous endo-proteolytic furin cleavage sites between immunogens to facilitate post-translational cleavage and modification. In this way, co-expression of structurally and functionally relevant proteins hypothetically facilitates the formation of macromolecular complexes that may better express clinically- and virologically-relevant B cell epitopic determinants. This may be particularly critical in cases where coexpression is required for productive expression; gH requires coexpression of gL for intracellular transport and terminal carbohydrate modifications [Spaete, 1993 #1195] and similarly, gL remains localized in the ER when expressed in the absence of gH.

One plasmid included coding sequences for HCMV-gB, a 907-9 amino acid protein which forms a homodimer and is a type I membrane protein. Another plasmid included coding sequences for HCMV-gM, a 373 amino acid protein linked to coding sequences for HCMV-gN, a 139 amino acid protein. The HCMV-gM and gN proteins form a heterodimer and are involved in infectivity. Another plasmid included coding sequences for HCMV-gH, a 740 amino acid protein linked to coding sequences for gL, a 278 amino acid protein. The HCMV-gH protein and the HCMV-gL protein form a hterotrimer with the HCMV-gO-gCIII complex involved in viral fusion. The HCMV-gH and gL proteins can also form a disulfide-linked heterodimer in the ER. Another plasmid included coding sequences for HCMV-gO, a 472 amino acid protein that forms the aforementioned heterotrimer with the HCMV-gH and gL. Another plasmid encodes coding sequences for HCMV-pUL (UL128), a 140 amino acid protein, linked to coding sequences for HCMV-UL130, a 215 amino acid protein linked to coding sequences for HCMV-UL131A, a 77 amino acid protein. These three proteins serve as chaperones for HCMV-gO. Another plasmid encodes HCMV-gUL83 (pp65); which is a T cell target protein.

In one embodiment, ten coding sequences (SEQ TD NO:1, SEQ TD NO:3, SEQ ID NO:5, SEQ ID NO:7, SEQ ID NO:9, SEQ ID NO:11, SEQ ID NO:13, SEQ ID NO:15, SEQ ID NO:17 and SEQ ID NO:19) for HCMV consensus amino acid sequences (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20) were included on six separate expression vector plasmids. Single gene constructs were provided for gB (plasmid 1), (plasmid 4) gO and gUL83 (modified plasmid 6). Chimeric genes encoding fusion proteins were provided for constructs encoding gM and gN (plasmid 2), gH and gL (plasmid 3), and UL128, UL130 and UL131a (plasmid 5) which are expressed as a single polyprotein. In each instance of a fusion protein, the coding sequences for the different antigens in the polyprotein were linked sequences encoding the furin proteolytic cleavage site (SEQ ID NO:63). The coding sequences for the fusion proteins also included coding sequence for the IgE signal peptide (SEQ ID NO:61) at the N terminal of the polyprotein as well as coding sequences for an HA Tag (SEQ TD NO:62) which is linked at the C terminal of each HCMV antigen in the polyprotein. Following processing at the proteolytic cleavage site(s) of the polyprotein into separate proteins, each protein comprises an HA Tag. The coding sequences for the single antigen constructs each were provided with coding sequences for the IgE signal peptide (SEQ ID NO:61) to be included at the N terminal of each translation product. Coding sequences for gB and gO were each also provided with coding sequences for an HA Tag (SEQ ID NO:62) so that the C terminal of each HCMV antigen protein comprises an HA Tag. Coding sequences for gUL83 in modified plasmid 6 do not contain coding sequences for HA Tags. However, another version of modified plasmid 6 can be constructed to contain coding sequences for an HA Tag (SEQ ID NO:62) so that the C terminal of the HCMV antigen protein comprises an HA Tag.

Each of plasmids 1-6 and modified plasmids 1-6 may be made using the variant pVax1 (FIG. 1, SEQ ID NO:76) disclosed herein.

Figure 2:
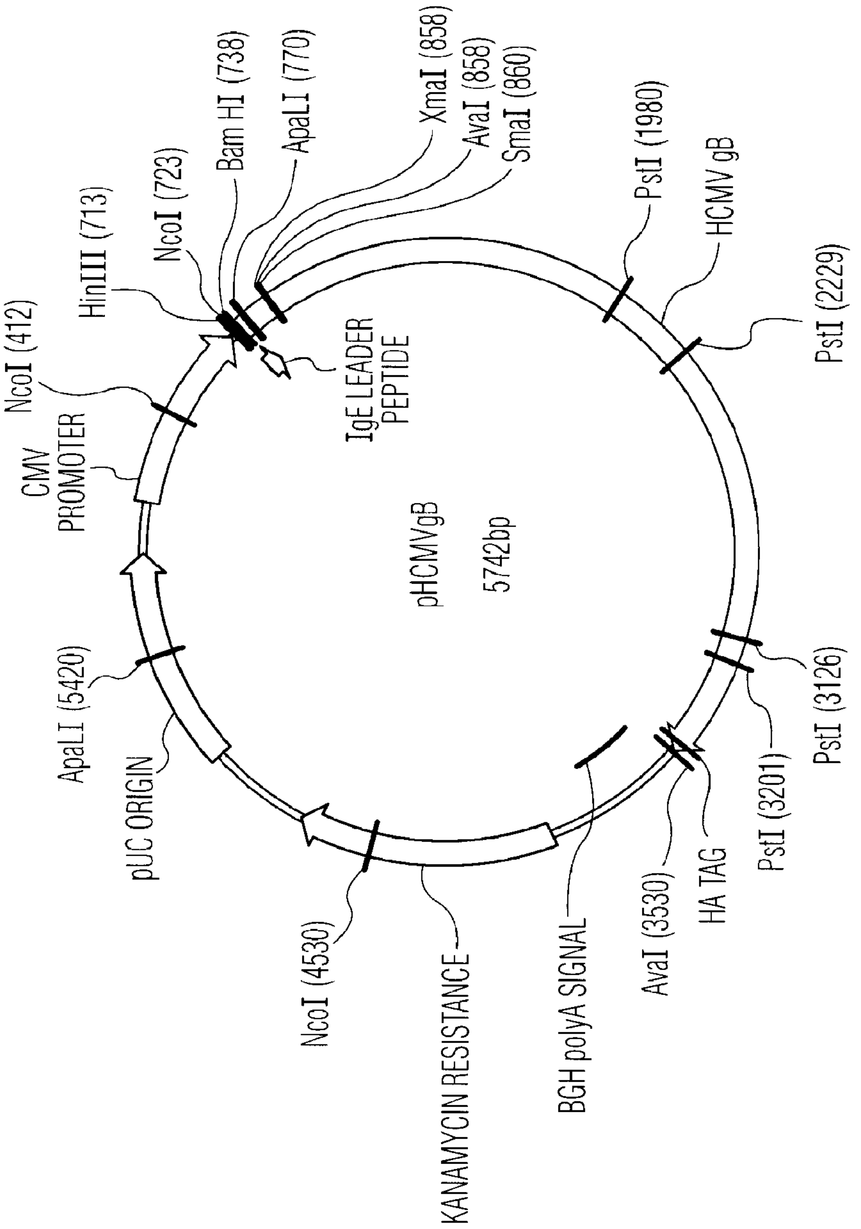
FIG. 2 is a plasmid map of plasmid 1 described in Example 1. Plasmid 1 is also referred to as pHCMVgB or pHCMVgB_pVAX1. The sequence of pHCMVgB_pVAX1 is set forth in SEQ ID NO:77.

Plasmid 1 (FIG. 2) is the variant pVax1 with an insert having regulatory elements operably linked to SEQ IN NO:41, i.e. nucleic acid sequence that encodes IgE leader linked to consensus gB linked to the HA Tag, thus encoding the protein SEQ ID NO:42.

Figure 3:
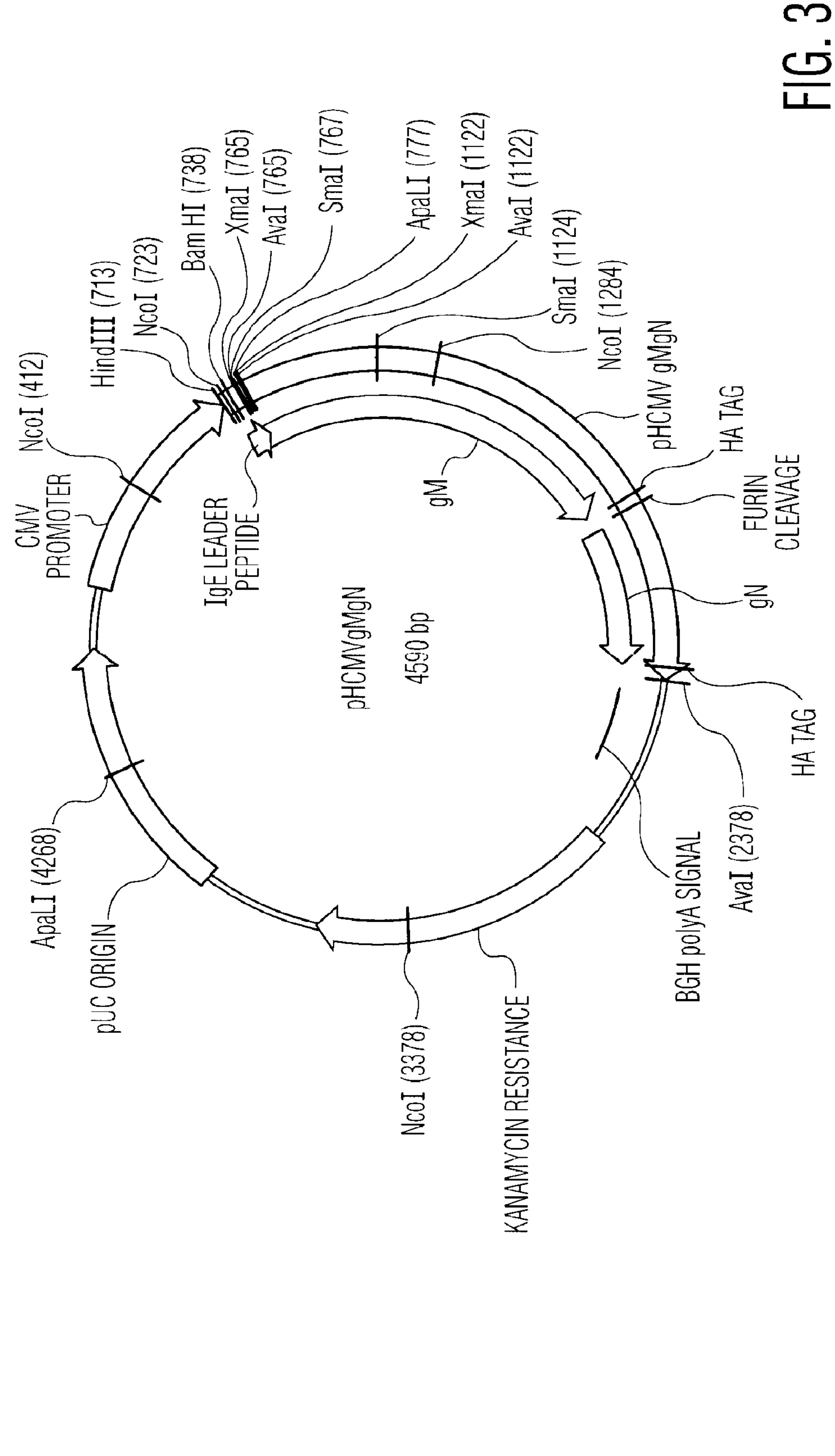
FIG. 3 is a plasmid map of plasmid 2 described in Example 1. Plasmid 2 is also referred to as pHCMVgMgN or pHCMVgMgN_pVAX1. The sequence of pHCMVgMgN_pVAX1 is set forth in SEQ ID NO:78.

Plasmid 2 (FIG. 3) is a variant pVax1 with an insert having regulatory elements operably linked to nucleic acid sequence SEQ ID NO:64 that encodes IgE leader linked to consensus gM linked to the HA tag linked to a furin proteolytic cleavage site linked to nucleic acid sequence that consensus gN4-c linked to an HA Tag, thus encoding the fusion protein SEQ ID NO:65.

Figure 4:
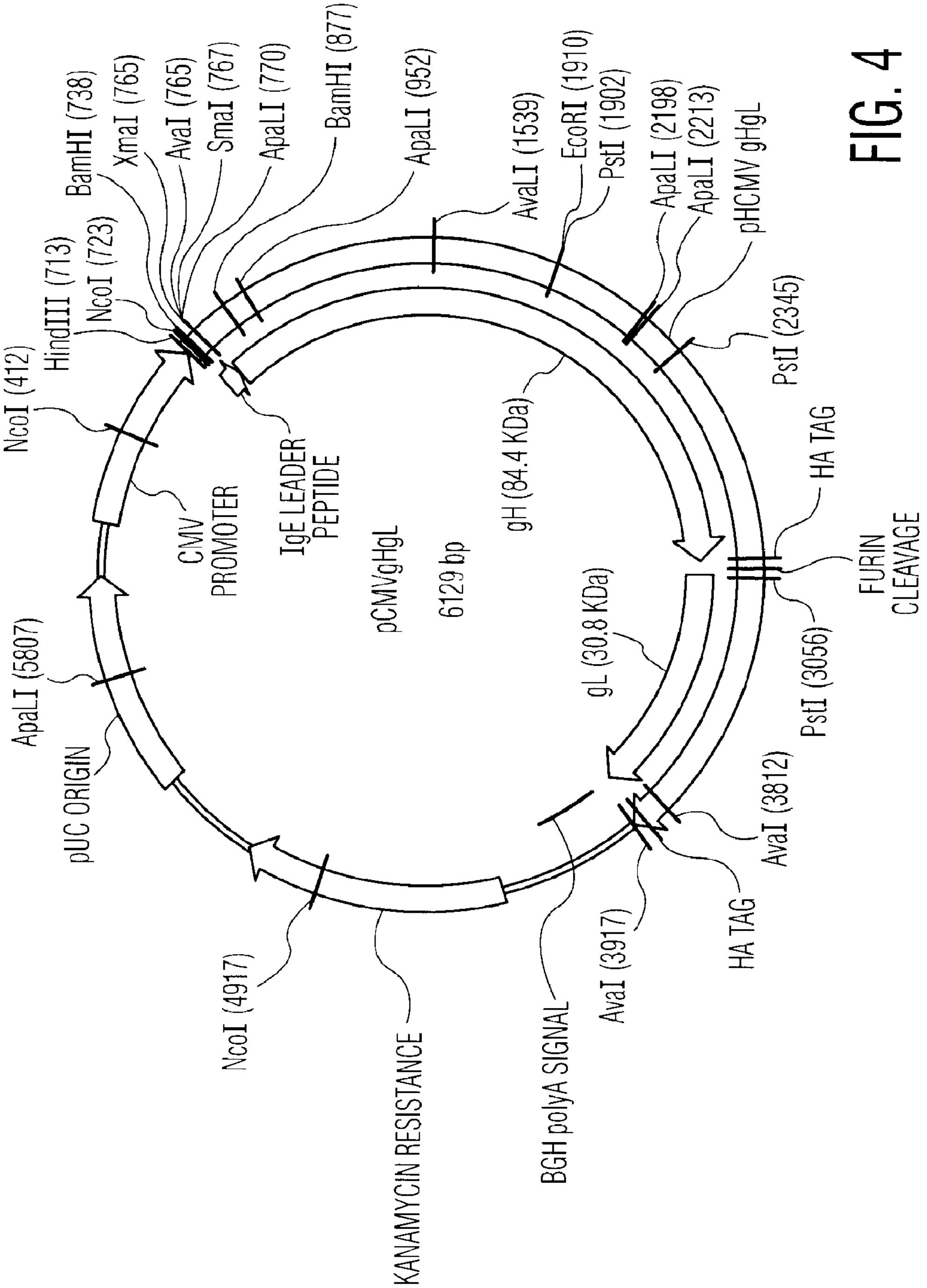
FIG. 4 is a plasmid map of plasmid 3 described in Example 1. Plasmid 3 is also referred to as pHCMVgHgL or pHCMVgHgL_pVAX1. The sequence of pHCMVgHgL_pVAX1 is set forth in SEQ ID NO:79.

Plasmid 3 (FIG. 4) is a variant pVax1 with an insert having regulatory elements operably linked to nucleic acid sequence SEQ ID NO:66 that encodes IgE leader linked to consensus gH linked to the HA tag linked to a furin proteolytic cleavage site linked to nucleic acid sequence that consensus gL linked to an HA Tag, thus encoding the fusion protein SEQ ID NO:67.

Figure 5:
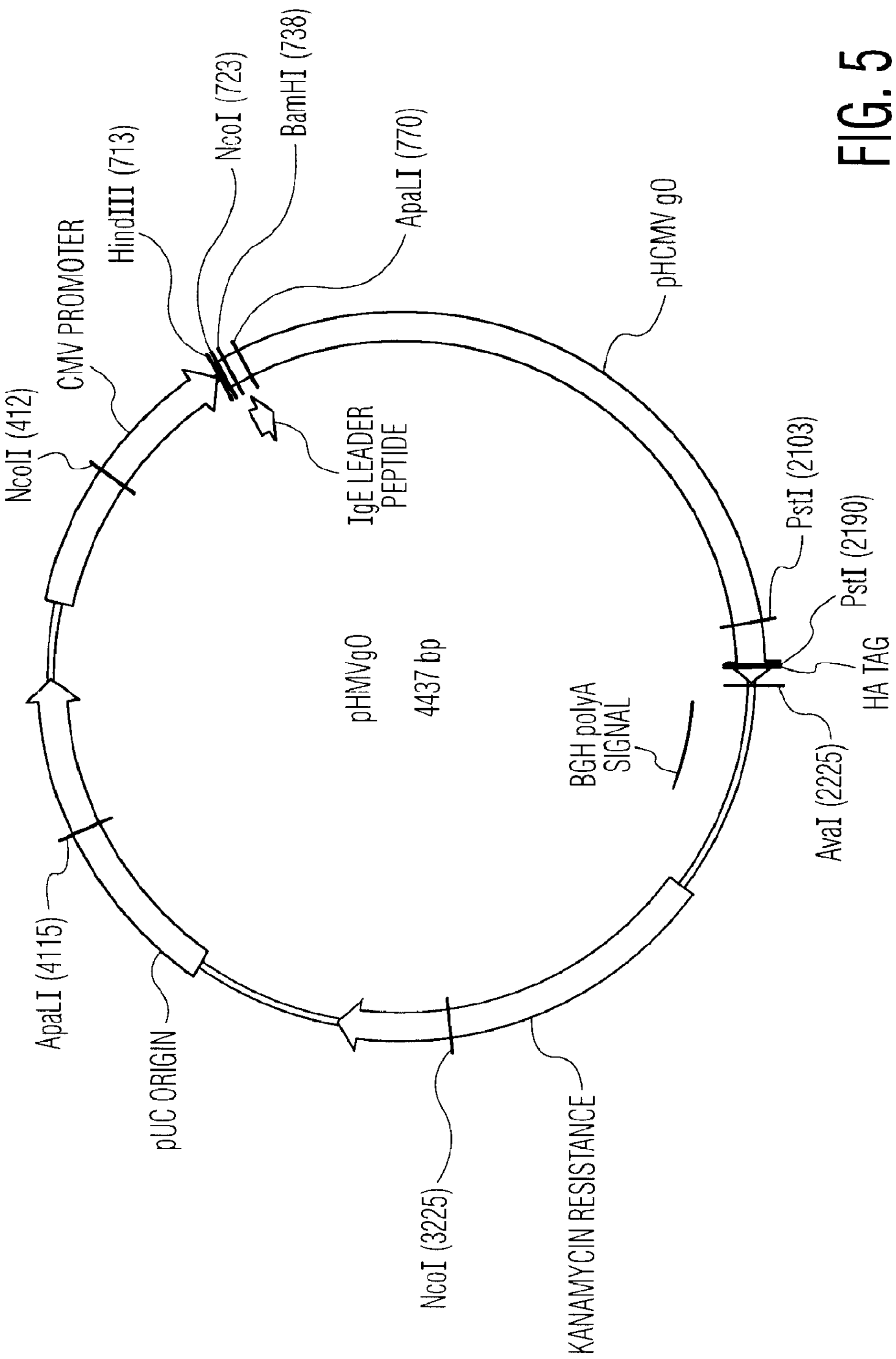
FIG. 5 is a plasmid map of plasmid 4 described in Example 1. Plasmid 4 is also referred to as pHCMVgO or pHCMVgO_pVAX1. The sequence of pHCMVgO_pVAX1 is set forth in SEQ ID NO:80.

Plasmid 4 (FIG. 5) is a variant pVax1 with an insert having regulatory elements operably linked to nucleic acid sequence SEQ ID NO:51 that encodes IgE leader linked to consensus gO-5 linked to and HA tag, thus encoding the protein SEQ ID NO:52.

Figure 6:
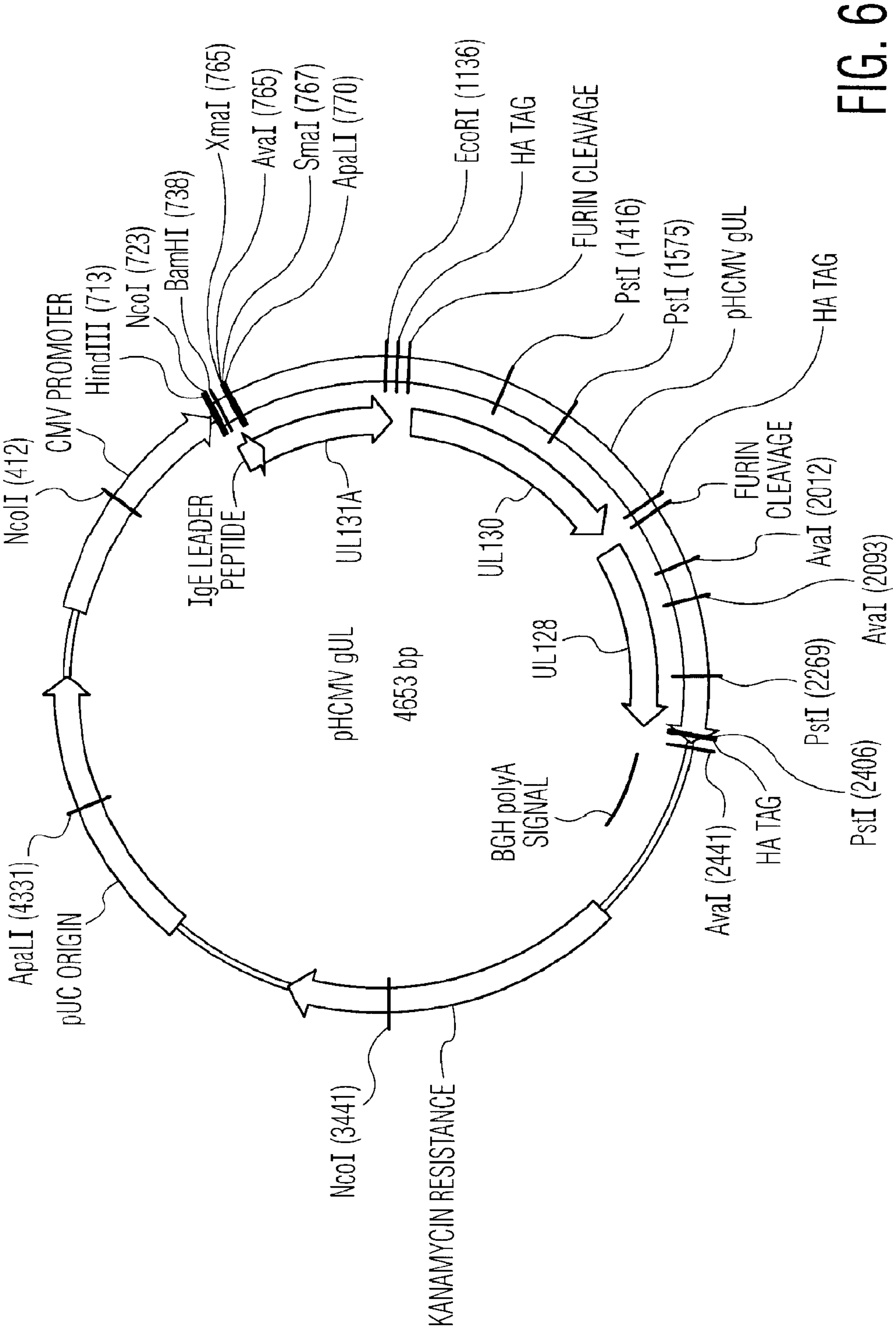
FIG. 6 is a plasmid map of plasmid 5 described in Example 1. Plasmid 5 is also referred to as pHCMVgUL or pHCMVgUL_pVAX1. The sequence of pHCMVgUL_pVAX1 is set forth in SEQ ID NO:81.

Plasmid 5 (FIG. 6) is a variant pVax1 with an insert having regulatory elements operably linked to nucleic acid sequence SEQ ID NO:68 that encodes IgE leader linked to consensus UL131a linked to an HA Tag linked to a furin proteolytic cleavage site linked to consensus UL130 linked to an HA Tag linked to a furin proteolytic cleavage site linked to consensus UL128 linked to an HA Tag, thus encoding the fusion protein SEQ ID NO:69.

Figure 9:
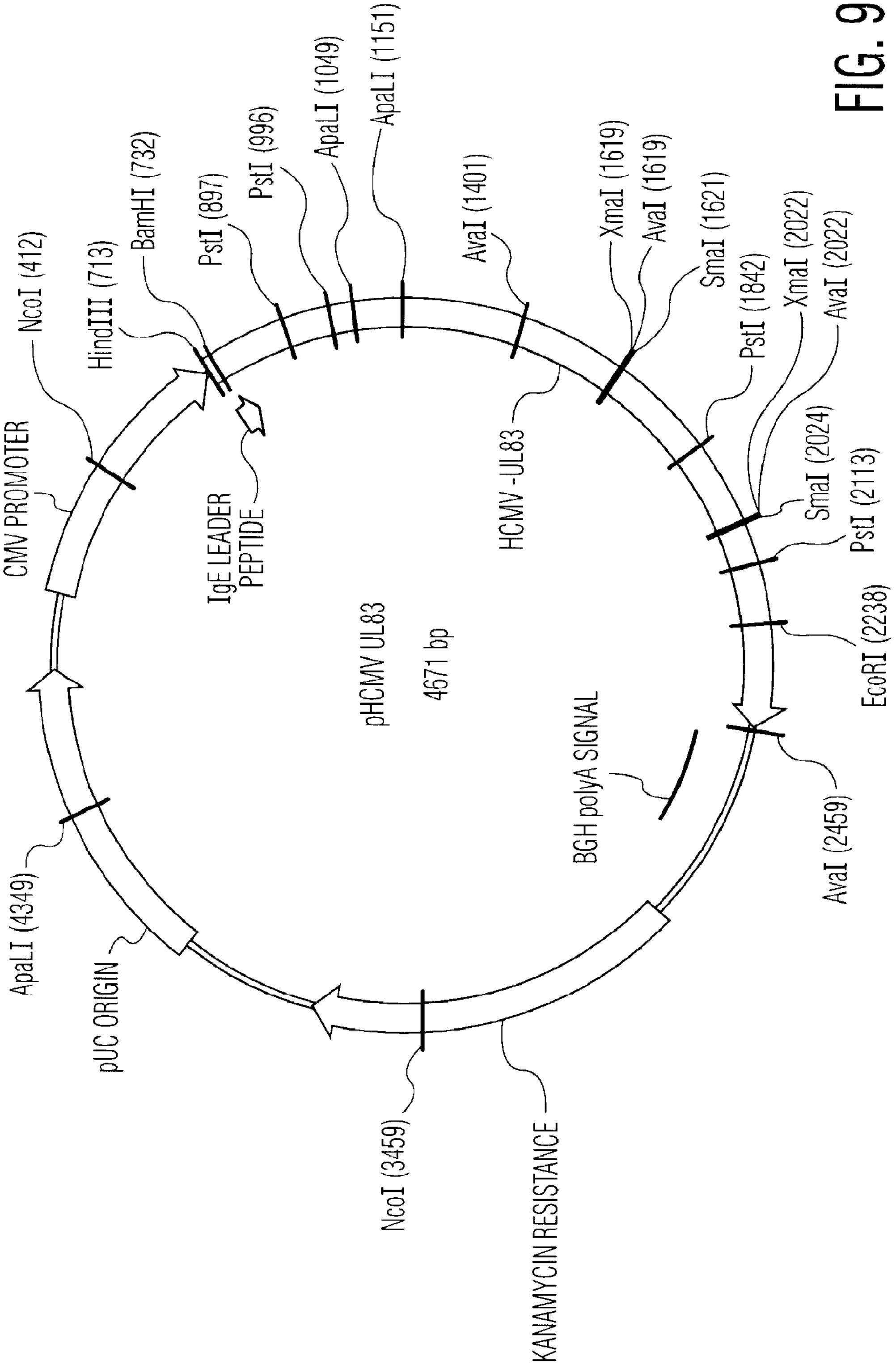
FIG. 9 is a plasmid map of modified plasmid 6 described in Example 1. Modified plasmid 6 is different from plasmid 6 (not shown) in that modified plasmid 6 does not contain coding sequences for HA Tags linked to the coding sequences for HCMV gU83 antigen sequence. Modified plasmid 6 is also referred to as pHCMVgU83 or pHCMV_UL83_pVAX1. The sequence of pHCMV_UL83_pVAX1 is set forth in SEQ ID NO:84.

Modified plasmid 6 (FIG. 9) is a variant pVax1 with an insert having regulatory elements operably linked to SEQ ID NO:39; i.e, nucleic acid sequence that encodes IgE leader linked to consensus UL-83 (pp65), thus encoding the protein SEQ ID NO:40.

Figure 7:
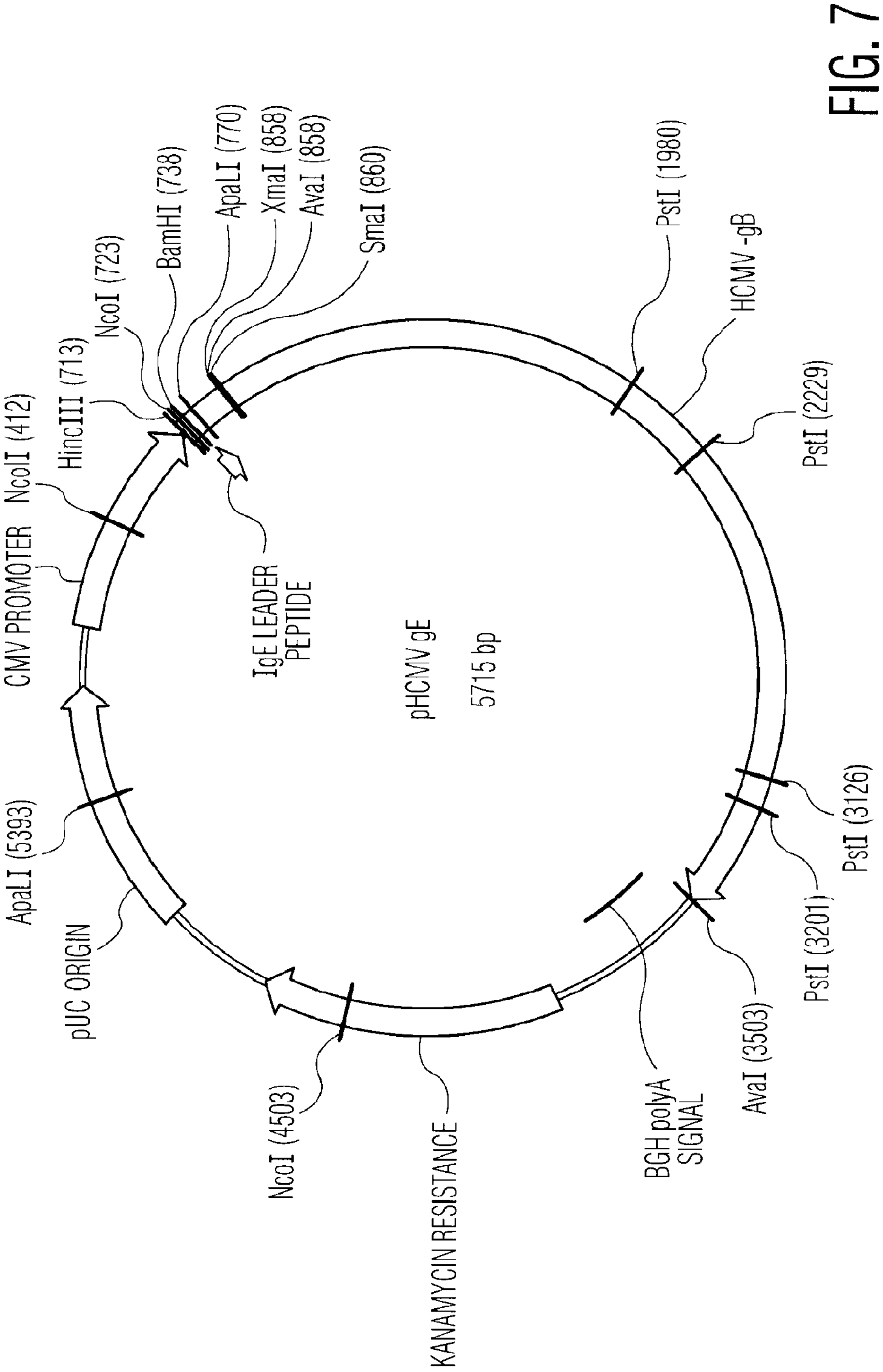
FIG. 7 is a plasmid map of modified plasmid 1 described in Example 1. Modified plasmid 1 is different from plasmid 1 in that modified plasmid 1 does not contain coding sequences for HA Tags linked to the coding sequences for HCMV gB antigen sequence. Modified plasmid 1 is also referred to as pHCMVgB or pHCMV_gB_pVAX1. The sequence of pHCMV_gB_pVAX1 is set forth in SEQ ID NO:82.

Plasmid 6 (FIG. 7) may be used in place of modified plasmid 6 if HA Tags linked to the U83 translation product is desirable. Plasmid 6 may be a variant pVax1 with an insert having regulatory elements operably linked to SEQ ID NO:59; i.e, nucleic acid sequence that encodes IgE leader linked to consensus UL-83 (pp65), thus encoding the protein SEQ ID NO:60.

In some embodiments, plasmids 1-5 may be modified so that the coding sequences for HA Tags are absent.

Modified plasmid 1 (FIG. 7) may be a variant pVax1 described herein with an insert having regulatory elements operably linked to SEQ IN NO:21, i.e. nucleic acid sequence that encodes IgE leader linked to consensus gB, thus encoding the protein SEQ ID NO:22.

Modified plasmid 2 may be a variant pVax1 described herein with an insert having regulatory elements operably linked to nucleic acid sequence SEQ ID NO:70 that encodes IgE leader linked to consensus gM linked to a furin proteolytic cleavage site linked to nucleic acid sequence that consensus gN4-c, thus encoding the fusion protein SEQ ID NO:71.

Figure 8:
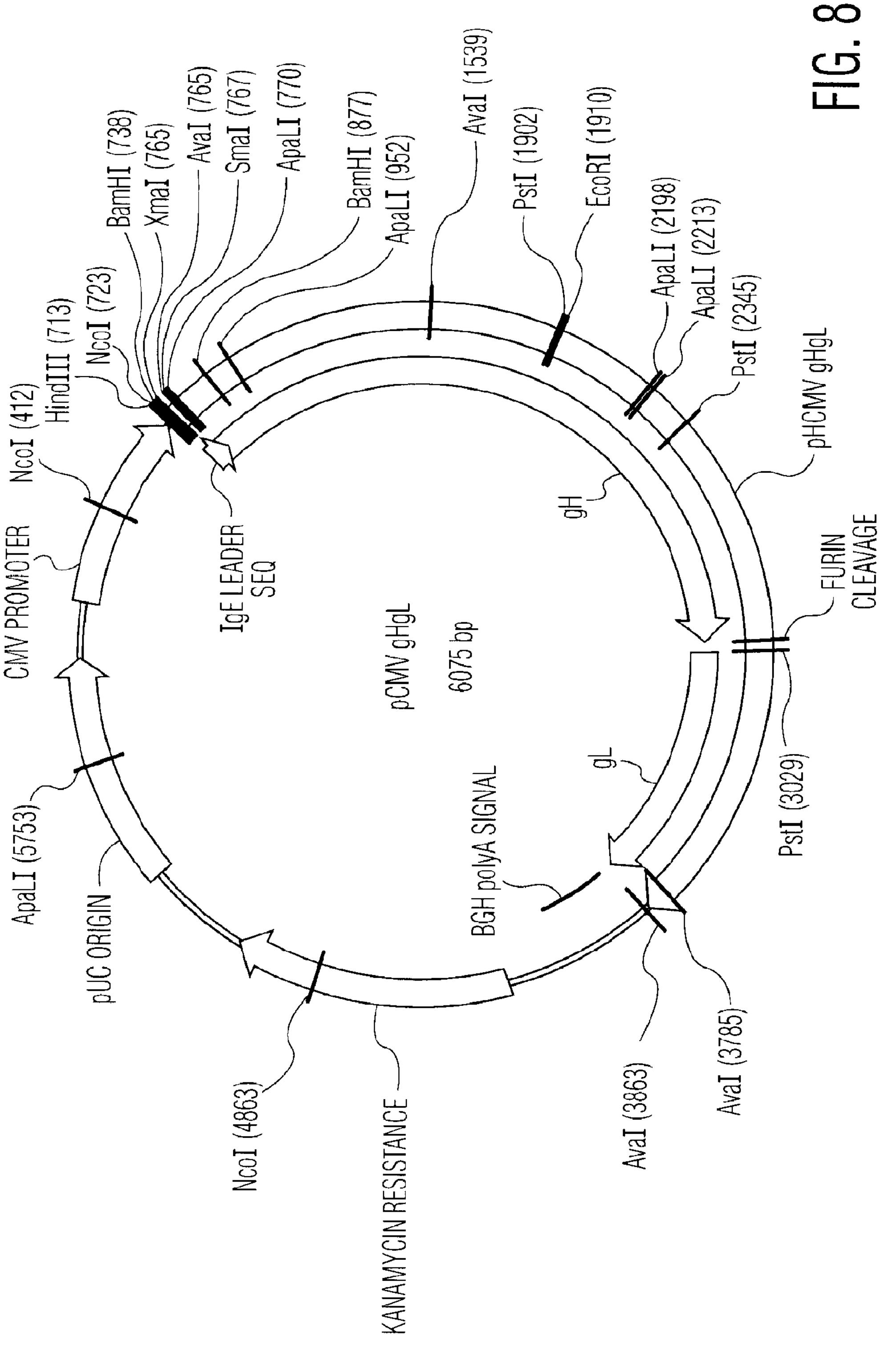
FIG. 8 is a plasmid map of modified plasmid 3 described in Example 1. Modified plasmid 3 is different from plasmid 3 in that modified plasmid 3 does not contain coding sequences for HA Tags linked to the coding sequences for HCMV gH and gL antigen sequences. Modified plasmid 3 is also referred to as pHCMVgHgL or pHCMV_gHgL_pVAX1. The sequence of pHCMV_gHgL_pVAX1 is set forth in SEQ ID NO:83.

Modified plasmid 3 (FIG. 8) may be a variant pVax1 described herein with an insert having regulatory elements operably linked to nucleic acid sequence SEQ ID NO:72 that encodes IgE leader linked to consensus gH linked to a furin proteolytic cleavage site linked to nucleic acid sequence that consensus gL, thus encoding the fusion protein SEQ ID NO:73.

Modified plasmid 4 may be a variant pVax1 described herein with an insert having regulatory elements operably linked to nucleic acid sequence SEQ ID NO:31 that encodes IgE leader linked to consensus gO-5 linked to, thus encoding the protein SEQ ID NO:32.

Modified plasmid 5 may be a variant pVax1 described herein with an insert having regulatory elements operably linked to nucleic acid sequence SEQ ID NO:74 that encodes IgE leader linked to consensus UL131a linked to a furin proteolytic cleavage site linked to consensus UL130 linked to a furin proteolytic cleavage site linked to consensus UL128, thus encoding the fusion protein SEQ TD NO:75.

In some embodiments, a composition comprising these six plasmids is an example of an anti-HCMV vaccine. In some embodiments of an anti-HCMV vaccine, two or more compositions which collectively comprise these six plasmids. Some embodiments provide methods of generating immune responses against HCMV proteins comprise administering to an individual one or more compositions which collectively comprise each of these six plasmids. Some embodiments provide methods of prophylactically vaccinating an individual against HCMV infection comprise administering one or more compositions which collectively comprise each of these six plasmids. Some embodiments provide methods of therapeutically vaccinating an individual has been infected with HCMV comprise administering one or more compositions which collectively comprise each of these six plasmids.

Analysis of other Herpes Viruses:

Similar to HCMV, above, similar strategy was used to identify antigens for HSV1, HSV2, CeHV1, and VZV.

For the herpes viruses from families VZV, CeHV1, HSV1, and HSV2, the following antigens were considered, based on similar criteria used for CMV, above, and consensus antigens were made and cloned into similar vectors as CMV: surface antigens envelope gB, gH, gL, gM, gN, gO, gE, gI, and gK were considered.

Plasmids were constructed for optimizing nascent coexpression of relevant proteins. In total, 21 plasmids were constructed that express HCMV gB, gM/gN, gH/gL, gO, UL128-131, and U183; VZV gHgL, gEgI, gMgN, gB, gC, and gK; HSV1 gB, gHgL, gCgD; HSV2 gB, gHgL, gCgD; and CeHV1 gB, gHgL, and gCgD, in highly-optimized DNA vaccines plasmids were constructed for optimizing nascent coexpression of relevant proteins. In total, 21 plasmids were constructed that express HCMV gB, gM/gN, gH/gL, gO, UL128-131, and U183; VZV gHgL, gEgI, gMgN, gB, gC, and gK; HSV1 gB, gHgL, gCgD; HSV2 gB, gHgL, gCgD; and CeHV1 gB, gHgL, and gCgD in highly-optimized DNA vaccines.

Plasmids 7-21 correspond to each one of the following VZV gHgL, gEgI, gMgN, gB, gC, and gK; HSV1 gB, gHgL, gCgD; HSV2 gB, gHgL, gCgD; and CeHV1 gB, gHgL, and gCgD econding sequences cloned into variant pVax1 (FIG. 1, SEQ TD NO:76) vector disclosed herein. In some embodiments, the pVax1 has an insert having regulatory elements operably linked to the encoding nucleic acid sequence for the herpes antigen which includes an encoding sequence for IgE leader (enocoding amino acid sequence SEQ ID NO:61) linked to the antigen. In some embodiments, plasmids 7-21 may be modified so that the coding sequences for HA Tags (encoding amino acid sequence SEQ ID NO:62) are linked to the N-terminal end of the antigen.

Example 2

In some embodiments, a composition comprising coding sequences for each of: HCMV: gB, gM, gN, gH, gL, gO, UL128, UL130, UL131a, U83, or multiple compositions which collectively comprise coding sequences for each of: gB, gM, gN, gH, gL, gO, UL128, UL130, UL131a, U83 are administered. The composition which comprises coding sequences of each of gB, gM, gN, gH, gL, gO, UL128, UL130, UL131a, U83, or combinations of compositions that collectively comprise coding sequences of each of gB, gM, gN, gH, gL, gO, UL128, UL130, UL131a. In some embodiments, vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, a vaccine comprises each of the coding sequences SEQ ID NO:1, 3, 5, 7, 9, 11, 13, 15, 17 and 19. In some embodiments, a vaccine comprises each of the coding sequences in SEQ ID NO:21, 23, 25, 27, 29, 31, 33, 35, 37 and 39. In some embodiments, a vaccine comprises each of the coding sequences in SEQ ID NO:41, 43, 45, 47, 49, 51, 53, 55, 57 and 59.

Example 3

In some embodiments, a composition comprising coding sequences for nine of: gB, gM, gN, gH, gL, gO, UL128, UL130, UL131a, U83, or multiple compositions which collectively comprise coding sequences for nine of: gB, gM, gN, gH, gL, gO, UL128, UL130, UL131a, U83 are administered. The composition may comprises coding sequences of nine of gB, gM, gN, gH, gL, gO, UL128, UL130, UL131a, U83, or combinations of compositions that collectively comprise coding sequences of nine of gB, gM, gN, gH, gL, gO, UL128, UL130, UL131a, U83. The following combinations 9-1 to 9-10 may be present in such vaccines: 9-1 gB, gM, gN, gH, gL, gO, UL128, UL130, UL131a; 9-2 gB, gM, gN, gH, gL, gO, UL128, UL130, UL83; 9-3 gB, gM, gN, gH, gL, gO, UL128, UL131a, UL83; 9-4 gB, gM, gN, gH, gL, gO, UL130, UL131a, UL83; 9-5 gB, gM, gN, gH, gL, UL128, UL130, UL131a, UL83; 9-6 gB, gM, gN, gH, gO, UL128, UL130, UL131a, UL83; 9-7 gB, gM, gN, gL, gO, UL128, UL130, UL131a, UL83; 9-8 gB, gM, gH, gL, gO, UL128, UL130, UL131a, UL83; 9-9 gB, gN, gH, gL, gO, UL128, UL130, UL131a, UL83; and 9-10 gM, gN, gH, gL, gO, UL128, UL130, UL131a, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 4

In some embodiments, a composition comprising coding sequences for eight of: gB, gM, gN, gH, gL, gO, UL128, UL130, UL131a, U83, or multiple compositions which collectively comprise coding sequences for eight of: gB, gM, gN, gH, gL, gO, UL128, UL130, UL131a, U83 are administered. The composition may comprises coding sequences of eight of gB, gM, gN, gH, gL, gO, UL128, UL130, UL131a, U83, or combinations of compositions that collectively comprise coding sequences of eight of gB, gM, gN, gH, gL, gO, UL128, UL130, UL131a, U83. The following combinations 8-1 to 8-45 may be present in an eight antigen vaccine: 8-1: gB, gM, gN, gH, gL, gO, UL128, UL130; 8-2: gB, gM, gN, gH, gL, gO, UL128, UL131a; 8-3: gB, gM, gN, gH, gL, gO, UL128, UL83; 8-4: gB, gM, gN, gH, gL, gO, UL130, UL131a; 8-5: gB, gM, gN, gH, gL, gO, UL130, UL83; 8-6: gB, gM, gN, gH, gL, gO, UL131a, UL83; 8-7: gB, gM, gN, gH, gL, UL128, UL130, UL131a; 8-8: gB, gM, gN, gH, gL, UL128, UL130, UL83; 8-9: gB, gM, gN, gH, gL, UL128, UL131a, UL83; 8-10: gB, gM, gN, gH, gL, UL130, UL131a, UL83; 8-11: gB, gM, gN, gH, gO, UL128, UL130, UL131a; 8-12: gB, gM, gN, gH, gO, UL128, UL130, UL83; 8-13: gB, gM, gN, gH, gO, UL128, UL131a, UL83; 8-14: gB, gM, gN, gH, gO, UL130, UL131a, UL83; 8-15: gB, gM, gN, gH, UL128, UL130, UL131a, UL83; 8-16: gB, gM, gN, gL, gO, UL128, UL130, UL131a; 8-17: gB, gM, gN, gL, gO, UL128, UL130, UL83; 8-18: gB, gM, gN, gL, gO, UL128, UL131a, UL83; 8-19: gB, gM, gN, gL, gO, UL130, UL131a, UL83; 8-20: gB, gM, gN, gL, UL128, UL130, UL131a, UL83; 8-21: gB, gM, gN, gO, UL128, UL130, UL131a, UL83; 8-22: gB, gM, gH, gL, gO, UL128, UL130, UL131a; 8-23: gB, gM, gH, gL, gO, UL128, UL130, UL83; 8-24: gB, gM, gH, gL, gO, UL128, UL131a, UL83; 8-25: gB, gM, gH, gL, gO, UL130, UL131a, UL83; 8-26: gB, gM, gH, gL, UL128, UL130, UL131a, UL83; 8-27: gB, gM, gH, gO, UL128, UL130, UL131a, UL83; 8-28: gB, gM, gL, gO, UL128, UL130, UL131a, UL83; 8-29: gB, gN, gH, gL, gO, UL128, UL130, UL131a; 8-30: gB, gN, gH, gL, gO, UL128, UL130, UL83; 8-31: gB, gN, gH, gL, gO, UL128, UL131a, UL83; 8-32: gB, gN, gH, gL, gO, UL130, UL131a, UL83; 8-33: gB, gN, gH, gL, UL128, UL130, UL131a, UL83; 8-34: gB, gN, gH, gO, UL128, UL130, UL131a, UL83; 8-35: gB, gN, gL, gO, UL128, UL130, UL131a, UL83; 8-36: gB, gH, gL, gO, UL128, UL130, UL131a, UL83; 8-37: gM, gN, gH, gL, gO, UL128, UL130, UL131a; 7-x: 8-38: gM, gN, gH, gL, gO, UL128, UL130, UL83; 8-39: gM, gN, gH, gL, gO, UL128, UL131a, UL83; 8-40: gM, gN, gH, gL, gO, UL130, UL131a, UL83; 8-41: gM, gN, gH, gL, gL, UL128, UL130, UL131a, UL83; 8-42: gM, gN, gH, gL, gO, UL128, UL130, UL131a, UL83; 8-43: gM, gN, gL, gO, UL128, UL130, UL131a, UL83; 8-44: gM, gH, gL, gO, UL128, UL130, UL131a, UL83; and 8-45: gN, gH, gL, gO, UL128, UL130, UL131a, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 5

In some embodiments, a composition comprising coding sequences for seven of: gB, gM, gN, gH, gL, gO, UL128, UL130, UL131a, U83, or multiple compositions which collectively comprise coding sequences for seven of: gB, gM, gN, gH, gL, gO, UL128, UL130, UL131a, U83 are administered. The composition may comprises coding sequences of seven of gB, gM, gN, gH, gL, gO, UL128, UL130, UL131a, U83, or combinations of compositions that collectively comprise coding sequences of seven of gB, gM, gN, gH, gL, gO, UL128, UL130, UL131a, U83. The following combinations 7-1 to 7-120 may be present in an seven antigen vaccine: 7-1: gB, gM, gN, gH, gL, gO, UL128; 7-2: gB, gM, gN, gH, gL, gO, UL130; 7-3: gB, gM, gN, gH, gL, gO, UL131a; 7-4: gB, gM, gN, gH, gL, gO, UL83; 7-5: gB, gM, gN, gH, gL, UL128, UL130; 7-6: gB, gM, gN, gH, gL, UL128, UL131a; 7-7: gB, gM, gN, gH, gL, UL128, UL83; 7-8: gB, gM, gN, gH, gL, UL130, UL131a; 7-9: gB, gM, gN, gH, gL, UL130, UL83; 7-10: gB, gM, gN, gH, gL, UL131a, UL83; 7-11: gB, gM, gN, gH, gO, UL128, UL130; 7-12: gB, gM, gN, gH, gO, UL128, UL131a; 7-13: gB, gM, gN, gH, gO, UL128, UL83; 7-14: gB, gM, gN, gH, gO, UL130, UL131a; 7-15: gB, gM, gN, gH, gO, UL130, UL83; 7-16: gB, gM, gN, gH, gO, UL131a, UL83; 7-17: gB, gM, gN, gH, UL128, UL130, UL131a; 7-18: gB, gM, gN, gH, UL128, UL130, UL83; 7-19: gB, gM, gN, gH, UL128, UL130, UL131a; 7-20: gB, gM, gN, gH, UL128, UL130, UL83; 7-21: gB, gM, gN, gH, UL128, UL131a, UL83; 7-22: gB, gM, gN, gH, UL130, UL131a, UL83; 7-23: gB, gM, gN, gL, gO, UL128, UL130; 7-24: gB, gM, gN, gL, gO, UL128, UL131a; 7-25: gB, gM, gN, gL, gO, UL128, UL83; 7-26: gB, gM, gN, gL, gO, UL130, UL131a; 7-27: gB, gM, gN, gL, gO, UL130, UL83; 7-28: gB, gM, gN, gL, gO, UL131a, UL83; 7-29: gB, gM, gN, gL, UL128, UL130, UL131a; 7-30: gB, gM, gN, gL, UL128, UL130, UL83; 7-31: gB, gM, gN, gL, UL128, UL130, UL131a; 7-32: gB, gM, gN, gL, UL128, UL130, UL83; 7-33: gB, gM, gN, gL, UL128, UL131a, UL83; 7-34: gB, gM, gN, gL, UL130, UL131a, UL83; 7-35: gB, gM, gN, gO, UL128, UL130, UL131a; 7-36: gB, gM, gN, gO, UL128, UL130, UL83; 7-37: gB, gM, gN, gO, UL128, UL131a, UL83; 7-38: gB, gM, gN, gO, UL130, UL131a, UL83; 7-39: gB, gM, gN, UL128, UL130, UL131a, UL83; 7-40: gB, gM, gH, gL, gO, UL128, UL130; 7-41: gB, gM, gH, gL, gO, UL128, UL131a; 7-42: gB, gM, gH, gL, gO, UL128, UL83; 7-43: gB, gM, gH, gL, gO, UL130, UL131a; 7-44: gB, gM, gH, gL, gO, UL130, UL83; 7-45: gB, gM, gH, gL, gO, UL131a, UL83; 7-46: gB, gM, gH, gO, UL128, UL130, UL131a; 7-47: gB, gM, gH, gO, UL128, UL130, UL83; 7-48: gB, gM, gH, gO, UL128, UL131a, UL83; 7-49: gB, gM, gH, gO, UL130, UL131a, UL83; 7-50: gB, gM, gH, UL128, UL130, UL131a, UL83; 7-51: gB, gM, gL, gO, UL128, UL130, UL131a; 7-52: gB, gM, gL, gO, UL128, UL130, UL83; 7-53: gB, gM, gL, gO, UL128, UL131a, UL83; 7-54: gB, gM, gL, gO, UL130, UL131a, UL83; 7-55: gB, gM, gL, UL128, UL130, UL131a, UL83; 7-56: gB, gM, gO, UL128, UL130, UL131a, UL83; 7-57: gB, gN, gH, gL, gO, UL128, UL130; 7-58: gB, gN, gH, gL, gO, UL128, UL131a; 7-59: gB, gN, gH, gL, gO, UL128, UL83; 7-60: gB, gN, gH, gL, gO, UL130, UL131a; 7-61: gB, gN, gH, gL, gO, UL130, UL83; 7-62: gB, gN, gH, gL, gO, UL131a, UL83; 7-63: gB, gN, gH, gL, UL128, UL130, UL131a; 7-64: gB, gN, gH, gL, UL128, UL130, UL83; 7-65: gB, gN, gH, gL, UL128, UL131a, UL83; 7-66: gB, gN, gH, gL, UL130, UL131a, UL83; 7-67: gB, gN, gH, gO, UL128, UL130, UL131a; 7-68: gB, gN, gH, gO, UL128, UL130, UL83; 7-69: gB, gN, gH, gO, UL128, UL131a, UL83; 7-70: gB, gN, gH, gO, UL130, UL131a, UL83; 7-71: gB, gN, gH, UL128, UL130, UL131a, UL83; 7-72: gB, gN, gL, gO, UL128, UL130, UL131a; 7-73: gB, gN, gL, gO, UL128, UL130, UL83; 7-74: gB, gN, gL, gO, UL128, UL131a, UL83; 7-75: gB, gN, gL, gO, UL130, UL131a, UL83; 7-76: gB, gN, gL, UL128, UL130, UL131a, UL83; 7-77: gB, gN, gO, UL128, UL130, UL131a, UL83; 7-78: gB, gH, gL, gO, UL128, UL130, UL131a; 7-79: gB, gH, gL, gO, UL128, UL130, UL83; 7-80: gB, gH, gL, gO, UL128, UL131a, UL83; 7-81: gB, gH, gL, gO, UL130, UL131a, UL83; 7-82 gB, gH, gL, UL128, UL130, UL131a, UL83; 7-83: gB, gH, gO, UL128, UL130, UL131a, UL83; 7-84: gB, gL, gO, UL128, UL130, UL131a, UL83; 7-85: gM, gN, gH, gL, gO, UL128, UL130; 7-86: gM, gN, gH, gL, gO, UL128, UL131a; 7-87: gM, gN, gH, gL, gO, UL128, UL83; 7-88: gM, gN, gH, gL, gO, UL130, UL131a; 7-89: gM, gN, gH, gL, gO, UL130, UL83; 7-90: gM, gN, gH, gL, gO, UL131a, UL83; 7-91: gM, gN, gH, gL, gL, UL128, UL130, UL131a; 7-92: gM, gN, gH, gL, gL, UL128, UL130, UL83; 7-93: gM, gN, gH, gL, gL, UL128, UL131a, UL83; 7-94: gM, gN, gH, gL, gL, UL130, UL131a, UL83; 7-95: gM, gN, gH, gL, gO, UL128, UL130, UL131a; 7-96: gM, gN, gH, gL, gO, UL128, UL130, UL83; 7-97: gM, gN, gH, gL, gO, UL128, UL131a, UL83; 7-98: gM, gN, gH, gL, gO, UL130, UL131a, UL83; 7-99: gM, gN, gH, gL, UL128, UL130, UL131a, UL83; 7-100: gM, gN, gL, gO, UL128, UL130, UL131a; 7-101: gM, gN, gL, gO, UL128, UL130, UL83; 7-102: gM, gN, gL, gO, UL128, UL131a, UL83; 7-103: gM, gN, gL, gO, UL130, UL131a, UL83; 7-104: gM, gN, gL, UL128, UL130, UL131a, UL83; 7-105: gM, gN, gO, UL128, UL130, UL131a, UL83; 7-106: gM, gH, gL, gO, UL128, UL130, UL131a; 7-107: gM, gH, gL, gO, UL128, UL130, UL83; 7-108: gM, gH, gL, gO, UL128, UL131a, UL83; 7-109: gM, gH, gL, gO, UL130, UL131a, UL83; 7-110: gM, gH, gL, UL128, UL130, UL131a, UL83; 7-111: gM, gH, gO, UL128, UL130, UL131a, UL83; 7-112: gM, gL, gO, UL128, UL130, UL131a, UL83; 7-113: gN, gH, gL, gO, UL128, UL130, UL131a; 7-114: gN, gH, gL, gO, UL128, UL130, UL83; 7-115: gN, gH, gL, gO, UL128, UL131a, UL83; 7-116: gN, gH, gL, gO, UL130, UL131a, UL83; 7-117: gN, gH, gL, UL128, UL130, UL131a, UL83; 7-118: gN, gH, gO, UL128, UL130, UL131a, UL83; 7-119: gN, gL, gO, UL128, UL130, UL131a, UL83; 7-120: gH, gL, gO, UL128, UL130, UL131a, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 6

In some embodiments, a composition comprising coding sequences for six of: gB, gM, gN, gH, gL, gO, UL128, UL130, UL131a, U83, or multiple compositions which collectively comprise coding sequences for six of: gB, gM, gN, gH, gL, gO, UL128, UL130, UL131a, U83 are administered. The composition may comprises coding sequences of six of gB, gM, gN, gH, gL, gO, UL128, UL130, UL131a, U83, or combinations of compositions that collectively comprise coding sequences of six of gB, gM, gN, gH, gL, gO, UL128, UL130, UL131a, U83. The following combinations 6-1 to 6-210 may be present in an seven antigen vaccine: 6-1: gB, gM, gN, gH, gL, gO; 6-2: gB, gM, gN, gH, gL, UL128; 6-3: gB, gM, gN, gH, gL, UL130; 6-4: gB, gM, gN, gH, gL, UL131a; 6-5: gB, gM, gN, gH, gL, UL83; 6-6: gB, gM, gN, gH, gO, UL128; 6-7: gB, gM, gN, gH, gO, UL130; 6-8: gB, gM, gN, gH, gO, UL131a; 6-9: gB, gM, gN, gH, gO, UL83; 6-10: gB, gM, gN, gH, UL128, UL130; 6-11: gB, gM, gN, gH, UL128, UL131a; 6-12: gB, gM, gN, gH, UL128, UL83; 6-13: gB, gM, gN, gH, UL130, UL131a; 6-14: gB, gM, gN, gH, UL130, UL83; 6-15: gB, gM, gN, gH, UL131a, UL83; 6-16: gB, gM, gN, gL, gO, UL128; 6-17: gB, gM, gN, gL, gO, UL130; 6-18: gB, gM, gN, gL, gO, UL131a; 6-19: gB, gM, gN, gL, gO, UL83; 6-20: gB, gM, gN, gL, UL128, UL130; 6-21: gB, gM, gN, gL, UL128, UL131a; 6-22: gB, gM, gN, gL, UL128, UL83; 6-23: gB, gM, gN, gL, UL130, UL131a; 6-24: gB, gM, gN, gL, UL130, UL83; 6-25: gB, gM, gN, gL, UL131a, UL83; 6-26: gB, gM, gN, gO, UL128, UL130; 6-27: gB, gM, gN, gO, UL128, UL131a; 6-28: gB, gM, gN, gO, UL128, UL83; 6-29: gB, gM, gN, gO, UL130, UL131a; 6-30: gB, gM, gN, gO, UL130, UL83; 6-31: gB, gM, gN, gO, UL131a, UL83; 6-32: gB, gM, gN, UL128, UL130, UL131a; 6-33: gB, gM, gN, UL128, UL130, UL83; 6-34: gB, gM, gN, UL128, UL131a, UL83; 6-35: gB, gM, gN, UL130, UL131a, UL83; 6-36: gB, gM, gH, gL, gO, UL128; 6-37: gB, gM, gH, gL, gO, UL130; 6-38: gB, gM, gH, gL, gO, UL131a; 6-39: gB, gM, gH, gL, gO, UL83; 6-40: gB, gM, gH, gL, UL128, UL130; 6-41: gB, gM, gH, gL, UL128, UL131a; 6-42: gB, gM, gH, gL, UL128, UL83; 6-43: gB, gM, gH, gL, UL130, UL131a; 6-44: gB, gM, gH, gL, UL130, UL83; 6-45: gB, gM, gH, gL, UL131a, UL83; 6-46: gB, gM, gH, gO, UL128, UL130; 6-47: gB, gM, gH, gO, UL128, UL131a; 6-48: gB, gM, gH, gO, UL128, UL83; 6-49: gB, gM, gH, gO, UL130, UL131a; 6-50: gB, gM, gH, gO, UL130, UL83; 6-51: gB, gM, gH, gO, UL131a, UL83; 6-52: gB, gM, gH, UL128, UL130, UL131a; 6-53: gB, gM, gH, UL128, UL130, UL83; 6-54: gB, gM, gH, UL128, UL131a, UL83; 6-55: gB, gM, gH, UL130, UL131a, UL83; 6-56: gB, gM, gL, gO, UL128, UL130; 6-57: gB, gM, gL, gO, UL128, UL131a; 6-58: gB, gM, gL, gO, UL128, UL83; 6-59: gB, gM, gL, gO, UL130, UL131a; 6-60: gB, gM, gL, gO, UL130, UL83; 6-61: gB, gM, gL, gO, UL131a, UL83; 6-62: gB, gM, gL, UL128, UL130, UL131a; 6-63: gB, gM, gL, UL128, UL130, UL83; 6-64: gB, gM, gL, UL128, UL131a, UL83; 6-65: gB, gM, gL, UL130, UL131a, UL83; 6-66: gB, gM, gO, UL128, UL130, UL131a; 6-67: gB, gM, gO, UL128, UL130, UL83; 6-68: gB, gM, gO, UL128, UL131a, UL83; 6-69: gB, gM, gO, UL130, UL131a, UL83; 6-70: gB, gM, UL128, UL130, UL131a, UL83; 6-71: gB, gN, gH, gL, gO, UL128; 6-72:

gB, gN, gH, gL, gO, UL130; 6-73: gB, gN, gH, gL, gO, UL131a; 6-74: gB, gN, gH, gL, gO, UL83; 6-75: gB, gN, gH, gL, UL128, UL130; 6-76: gB, gN, gH, gL, UL128, UL131a; 6-77: gB, gN, gH, gL, UL128, UL83; 6-78: gB, gN, gH, gL, UL130, UL131a; 6-79: gB, gN, gH, gL, UL130, UL83; 6-80: gB, gN, gH, gL, UL131a, UL83; 6-81: gB, gN, gH, gO, UL128, UL130; 6-82: gB, gN, gH, gO, UL128, UL131a; 6-83: gB, gN, gH, gO, UL128, UL83; 6-84: gB, gN, gH, gO, UL130, UL131a; 6-85: gB, gN, gH, gO, UL130, UL83; 6-86: gB, gN, gH, gO, UL131a, UL83; 6-87: gB, gN, gH, UL128, UL130, UL131a; 6-88: gB, gN, gH, UL128, UL130, UL83; 6-89: gB, gN, gH, UL128, UL131a, UL83; 6-90: gB, gN, gH, UL130, UL131a, UL83; 6-91: gB, gN, gL, gO, UL128, UL130; 6-92: gB, gN, gL, gO, UL128, UL131a; 6-93: gB, gN, gL, gO, UL128, UL83; 6-94: gB, gN, gL, gO, UL130, UL131a; 6-95: gB, gN, gL, gO, UL130, UL83; 6-96 gB, gN, gL, gO, UL131a, UL83; 6-97: gB, gN, gL, UL128, UL130, UL131a; 6-98: gB, gN, gL, UL128, UL130, UL83; 6-99: gB, gN, gL, UL128, UL131a, UL83; 6-100: gB, gN, gL, UL130, UL131a, UL83; 6-101: gB, gN, gO, UL128, UL130, UL131a; 6-102: gB, gN, gO, UL128, UL130, UL83; 6-103: gB, gN, gO, UL128, UL131a, UL83; 6-104: gB, gN, gO, UL130, UL131a, UL83; 6-105: gB, gN, UL128, UL130, UL131a, UL83; 6-106: gB, gH, gL, gO, UL128, UL130; 6-107: gB, gH, gL, gO, UL128, UL131a; 6-108: gB, gH, gL, gO, UL128, UL83; 6-109: gB, gH, gL, gO, UL130, UL131a; 6-110: gB, gH, gL, gO, UL130, UL83; 6-111: gB, gH, gL, gO, UL131a, UL83; 6-112: gB, gH, gL, UL128, UL130, UL131a; 6-113: gB, gH, gL, UL128, UL130, UL83; 6-114: gB, gH, gL, UL128, UL131a, UL83; 6-115: gB, gH, gL, UL130, UL131a, UL83; 6-116: gB, gH, gO, UL128, UL130, UL131a; 6-117: gB, gH, gO, UL128, UL130, UL83; 6-118: gB, gH, gO, UL128, UL131a, UL83; 6-119: gB, gH, gO, UL130, UL131a, UL83; 6-120: gB, gH, UL128, UL130, UL131a, UL83; 6-121: gB, gL, gO, UL128, UL130, UL131a; 6-122: gB, gL, gO, UL128, UL130, UL83; 6-123: gB, gL, gO, UL128, UL131a, UL83; 6-124: gB, gL, gO, UL130, UL131a, UL83; 6-125: gB, gL, UL128, UL130, UL131a, UL83; 6-126: gB, gO, UL128, UL130, UL131a, UL83; 6-127: gM, gN, gH, gL, gO, UL128; 6-128: gM, gN, gH, gL, gO, UL130; 6-129: gM, gN, gH, gL, gO, UL131a; 6-130: gM, gN, gH, gL, gO, UL83; 6-131: gM, gN, gH, gL, UL128, UL130; 6-132: gM, gN, gH, gL, UL128, UL131a; 6-133: gM, gN, gH, gL, UL128, UL83; 6-134: gM, gN, gH, gL, UL130, UL131a; 6-135: gM, gN, gH, gL, UL130, UL83; 6-136: gM, gN, gH, gL, UL131a, UL83; 6-137: gM, gN, gH, gO, UL128, UL130; 6-138: gM, gN, gH, gO, UL128, UL131a; 6-139: gM, gN, gH, gO, UL128, UL83; 6-140: gM, gN, gH, gO, UL130, UL131a; 6-141: gM, gN, gH, gO, UL130, UL83; 6-142: gM, gN, gH, gO, UL131a, UL83; 6-143: gM, gN, gH, UL128, UL130, UL131a; 6-144: gM, gN, gH, UL128, UL130, UL83; 6-145: gM, gN, gH, UL128, UL131a, UL83; 6-146: gM, gN, gH, UL130, UL131a, UL83; 6-147: gM, gN, gL, gO, UL128, UL130; 6-148: gM, gN, gL, gO, UL128, UL131a; 6-149: gM, gN, gL, gO, UL128, UL83; 6-150: gM, gN, gL, gO, UL130, UL131a; 6-151: gM, gN, gL, gO, UL130, UL83; 6-152: gM, gN, gL, gO, UL131a, UL83; 6-153: gM, gN, gL, UL128, UL130, UL131a; 6-154: gM, gN, gL, UL128, UL130, UL83; 6-155: gM, gN, gL, UL128, UL131a, UL83; 6-156: gM, gN, gL, UL130, UL131a, UL83; 6-157: gM, gN, gO, UL128, UL130, UL131a; 6-158: gM, gN, gO, UL128, UL130, UL83; 6-159: gM, gN, gO, UL128, UL131a, UL83; 6-160: gM, gN, gO, UL130, UL131a, UL83; 6-161: gM, gN, UL128, UL130, UL131a, UL83; 6-162: gM, gH, gL, gO, UL128, UL130; 6-163: gM, gH, gL, gO, UL128, UL131a; 6-164: gM, gH, gL, gO, UL128, UL83; 6-165: gM, gH, gL, gO, UL130, UL131a; 6-166: gM, gH, gL, gO, UL130, UL83; 6-167: gM, gH, gL, gO, UL131a, UL83; 6-168: gM, gH, gL, UL128, UL130, UL131a; 6-169: gM, gH, gL, UL128, UL130, UL83; 6-170: gM, gH, gL, UL128, UL131a, UL83; 6-171: gM, gH, gL, UL130, UL131a, UL83; 6-172: gM, gH, gO, UL128, UL130, UL131a; 6-173: gM, gH, gO, UL128, UL130, UL83; 6-174: gM, gH, gO, UL128, UL131a, UL83; 6-175: gM, gH, gO, UL130, UL131a, UL83; 6-176: gM, gH, UL128, UL130, UL131a, UL83; 6-177: gM, gL, gO, UL128, UL130, UL131a; 6-178: gM, gL, gO, UL128, UL130, UL83; 6-179: gM, gL, gO, UL128, UL131a, UL83; 6-180: gM, gL, gO, UL130, UL131a, UL83; 6-181: gM, gL, UL128, UL130, UL131a, UL83; 6-182: gM, gO, UL128, UL130, UL131a, UL83; 6-183: gN, gH, gL, gO, UL128, UL130; 6-184: gN, gH, gL, gO, UL128, UL131a; 6-185: gN, gH, gL, gO, UL128, UL83; 6-186: gN, gH, gL, gO, UL130, UL131a; 6-187: gN, gH, gL, gO, UL130, UL83; 6-188: gN, gH, gL, gO, UL131a, UL83; 6-189: gN, gH, gL, UL128, UL130, UL131a; 6-190: gN, gH, gL, UL128, UL130, UL83; 6-191: gN, gH, gL, UL128, UL131a, UL83; 6-192: gN, gH, gL, UL130, UL131a, UL83; 6-193: gN, gH, gO, UL128, UL130, UL131a; 6-194: gN, gH, gO, UL128, UL130, UL83; 6-195: gN, gH, gO, UL128, UL131a, UL83; 6-196: gN, gH, gO, UL130, UL131a, UL83; 6-197: gN, gH, UL128, UL130, UL131a, UL83; 6-198: gN, gL, gO, UL128, UL130, UL131a; 6-199: gN, gL, gO, UL128, UL130, UL83; 6-200: gN, gL, gO, UL128, UL131a, UL83; 6-201: gN, gL, gO, UL130, UL131a, UL83; 6-202 gN, gL, UL128, UL130, UL131a, UL83; 6-203: gN, gO, UL128, UL130, UL131a, UL83; 6-204: gH, gL, gO, UL128, UL130, UL131a; 6-205: gH, gL, gO, UL128, UL130, UL83; 6-206: gH, gL, gO, UL128, UL131a, UL83; 6-207: gH, gL, gO, UL130, UL131a, UL83; 6-208: gH, gL, UL128, UL130, UL131a, UL83; 6-209: gH, gO, UL128, UL130, UL131a, UL83; and 6-210: gL, gO, UL128, UL130, UL131a, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 7

In some embodiments, a composition comprising coding sequences for five of: gB, gM, gN, gH, gL, gO, UL128, UL130, UL131a, U83, or multiple compositions which collectively comprise coding sequences for five of: gB, gM, gN, gH, gL, gO, UL128, UL130, UL131a, U83 are administered. The composition which comprises coding sequences of five of gB, gM, gN, gH, gL, gO, UL128, UL130, UL131a, U83, or combinations of compositions that collectively comprise coding sequences of five of gB, gM, gN, gH, gL, gO, UL128, UL130, UL131a, U83 are referred to as “five antigen vaccines”. The following combinations 5-1 to 5-252 may be present in an five antigen vaccine: 5-1: gB, gM, gN, gH, gL; 5-2: gB, gM, gN, gH, gO; 5-3: gB, gM, gN, gH, UL128; 5-4: gB, gM, gN, gH, UL130; 5-5: gB, gM, gN, gH, UL131a; 5-6: gB, gM, gN, gH, UL83; 5-7: gB, gM, gN, gL, gO; 5-8: gB, gM, gN, gL, UL128; 5-9: gB, gM, gN, gL, UL130; 5-10: gB, gM, gN, gL, UL131a; 5-11: gB, gM, gN, gL, UL83; 5-12: gB, gM, gN, gO, UL128; 5-13: gB, gM, gN, gO, UL130; 5-14: gB, gM, gN, gO, UL131a; 5-15: gB, gM, gN, gO, UL83; 5-16: gB, gM, gN, UL128, UL130; 5-17: gB, gM, gN, UL128, UL131a; 5-18: gB, gM, gN, UL128, UL83; 5-19: gB, gM, gN, UL130, UL131a; 5-20: gB, gM, gN, UL130, UL83; 5-21: gB, gM, gN, UL131A, UL83; 5-22: gB, gM, gH, gL, gO; 5-23: gB, gM, gH, gL, UL128; 5-24: gB, gM, gH, gL, UL130; 5-25: gB, gM, gH, gL, UL131a; 5-26: gB, gM, gH, gL, UL83; 5-27: gB, gM, gH, gO, UL128; 5-28: gB, gM, gH, gO, UL130; 5-29: gB, gM, gH, gO, UL131a; 5-30: gB, gM, gH, gO, UL83; 5-31: gB, gM, gH, UL128, UL130; 5-32: gB, gM, gH, UL128, UL131a; 5-33: gB, gM, gH, UL128, UL83; 5-34: gB, gM, gH, UL130, UL131a; 5-35: gB, gM, gH, UL130, UL83; 5-36: gB, gM, gH, UL131A, UL83; 5-37: gB, gM, gL, gO, UL128; 5-38: gB, gM, gL, gO, UL130; 5-39: gB, gM, gL, gO, UL131a; 5-40: gB, gM, gL, gO, UL83; 5-41: gB, gM, gL, UL128, UL130; 5-42: gB, gM, gL, UL128, UL131a; 5-43: gB, gM, gL, UL128, UL83; 5-44: gB, gM, gL, UL130, UL131a; 5-45: gB, gM, gL, UL130, UL83; 5-46: gB, gM, gL, UL131A, UL83; 5-47: gB, gM, gO, UL128, UL130; 5-48: gB, gM, gO, UL128, UL131a; 5-49: gB, gM, gO, UL128, UL83; 5-50: gB, gM, gO, UL130, UL131a; 5-51: gB, gM, gO, UL130, UL83; 5-52: gB, gM, gO, UL131A, UL83; 5-53: gB, gM, UL128, UL130, UL131a; 5-54: gB, gM, UL128, UL130, UL83; 5-55: gB, gM, UL128, UL131A, UL83; 5-56: gB, gM, UL130, UL131A, UL83; 5-57: gB, gN, gH, gL, gO; 5-58: gB, gN, gH, gL, UL128; 5-59: gB, gN, gH, gL, UL130; 5-60: gB, gN, gH, gL, UL131a; 5-61: gB, gN, gH, gL, UL83; 5-62: gB, gN, gH, gO, UL128; 5-63: gB, gN, gH, gO, UL130; 5-64: gB, gN, gH, gO, UL131a; 5-65: gB, gN, gH, gO, UL83; 5-66: gB, gN, gH, UL128, UL130; 5-67: gB, gN, gH, UL128, UL131a; 5-68: gB, gN, gH, UL128, UL83; 5-69: gB, gN, gH, UL130, UL131a; 5-70: gB, gN, gH, UL130, UL83; 5-71: gB, gN, gH, UL131A, UL83; 5-72: gB, gN, gL, gO, UL128; 5-73: gB, gN, gL, gO, UL130; 5-74: gB, gN, gL, gO, UL131a; 5-75: gB, gN, gL, gO, UL83; 5-76: gB, gN, gL, UL128, UL130; 5-77: gB, gN, gL, UL128, UL131a; 5-78: gB, gN, gL, UL128, UL83; 5-79: gB, gN, gL, UL130, UL131a; 5-80: gB, gN, gL, UL130, UL83; 5-81: gB, gN, gL, UL131A, UL83; 5-82: gB, gN, gO, UL128, UL130; 5-83: gB, gN, gO, UL128, UL131a; 5-84: gB, gN, gO, UL128, UL83; 5-85: gB, gN, gO, UL130, UL131a; 5-86: gB, gN, gO, UL130, UL83; 5-87: gB, gN, gO, UL131A, UL83; 5-88: gB, gN, UL128, UL130, UL131a; 5-89: gB, gN, UL128, UL130, UL83; 5-90: gB, gN, UL128, UL131A, UL83; 5-91: gB, gN, UL130, UL131A, UL83; 5-92: gB, gH, gL, gO, UL128; 5-93: gB, gH, gL, gO, UL130; 5-94: gB, gH, gL, gO, UL131a; 5-95: gB, gH, gL, gO, UL83; 5-96: gB, gH, gL, UL128, UL130; 5-97: gB, gH, gL, UL128, UL131a; 5-98: gB, gH, gL, UL128, UL83; 5-99: gB, gH, gL, UL130, UL131a; 5-100: gB, gH, gL, UL130, UL83; 5-101: gB, gH, gL, UL131A, UL83; 5-102: gB, gH, gO, UL128, UL130; 5-103: gB, gH, gO, UL128, UL131a; 5-104: gB, gH, gO, UL128, UL83; 5-105: gB, gH, gO, UL130, UL131a; 5-106: gB, gH, gO, UL130, UL83; 5-107: gB, gH, gO, UL131A, UL83; 5-108: gB, gH, UL128, UL130, UL131a; 5-109: gB, gH, UL128, UL130, UL83; 5-110: gB, gH, UL128, UL131A, UL83; 5-111: gB, gH, UL130, UL131A, UL83; 5-112: gB, gL, gO, UL128, UL130; 5-113: gB, gL, gO, UL128, UL131a; 5-114: gB, gL, gO, UL128, UL83; 5-115: gB, gL, gO, UL130, UL131a; 5-116: gB, gL, gO, UL130, UL83; 5-117: gB, gL, gO, UL131A, UL83; 5-118: gB, gL, UL128, UL130, UL131a; 5-119: gB, gL, UL128, UL130, UL83; 5-120: gB, gL, UL128, UL131A, UL83; 5-121: gB, gL, UL130, UL131A, UL83; 5-122: gB, gO, UL128, UL130, UL131a; 5-123: gB, gO, UL128, UL130, UL83; 5-124: gB, gO, UL128, UL131A, UL83; 5-125: gB, gO, UL130, UL131A, UL83; 5-126: gB, UL128, UL130, UL131A, UL83; 5-127: gM, gN, gH, gL, gO; 5-128: gM, gN, gH, gL, UL128; 5-129: gM, gN, gH, gL, UL130; 5-130: gM, gN, gH, gL, UL131a; 5-131: gM, gN, gH, gL, UL83; 5-132: gM, gN, gH, gO, UL128; 5-133: gM, gN, gH, gO, UL130; 5-134: gM, gN, gH, gO, UL131a; 5-135: gM, gN, gH, gO, UL83; 5-136: gM, gN, gH, UL128, UL130; 5-137: gM, gN, gH, UL128, UL131a; 5-138: gM, gN, gH, UL128, UL83; 5-139: gM, gN, gH, UL130, UL131a; 5-140: gM, gN, gH, UL130, UL83; 5-141: gM, gN, gH, UL131A, UL83; 5-142: gM, gN, gL, gO, UL128; 5-143: gM, gN, gL, gO, UL130; 5-144: gM, gN, gL, gO, UL131a; 5-145: gM, gN, gL, gO, UL83; 5-146: gM, gN, gL, UL128, UL130; 5-147: gM, gN, gL, UL128, UL131a; 5-148: gM, gN, gL, UL128, UL83; 5-149: gM, gN, gL, UL130, UL131a; 5-150: gM, gN, gL, UL130, UL83; 5-151: gM, gN, gL, UL131A, UL83; 5-152: gM, gN, gO, UL128, UL130; 5-153: gM, gN, gO, UL128, UL131a; 5-154: gM, gN, gO, UL128, UL83; 5-155: gM, gN, gO, UL130, UL131a; 5-156: gM, gN, gO, UL130, UL83; 5-157: gM, gN, gO, UL131A, UL83; 5-158: gM, gN, UL128, UL130, UL131a; 5-159: gM, gN, UL128, UL130, UL83; 5-160: gM, gN, UL128, UL131A, UL83; 5-161: gM, gN, UL130, UL131A, UL83; 5-162: gM, gH, gL, gO, UL128; 5-163: gM, gH, gL, gO, UL130; 5-164: gM, gH, gL, gO, UL131a; 5-165: gM, gH, gL, gO, UL83; 5-166: gM, gH, gL, UL128, UL130; 5-167: gM, gH, gL, UL128, UL131a; 5-168: gM, gH, gL, UL128, UL83; 5-169: gM, gH, gL, UL130, UL131a; 5-170: gM, gH, gL, UL130, UL83; 5-171: gM, gH, gL, UL131A, UL83; 5-172: gM, gH, gO, UL128, UL130; 5-173: gM, gH, gO, UL128, UL131a; 5-174: gM, gH, gO, UL128, UL83; 5-175: gM, gH, gO, UL130, UL131a; 5-176: gM, gH, gO, UL130, UL83; 5-177: gM, gH, gO, UL131A, UL83; 5-178: gM, gH, UL128, UL130, UL131a; 5-179: gM, gH, UL128, UL130, UL83; 5-180: gM, gH, UL128, UL131A, UL83; 5-181: gM, gH, UL130, UL131A, UL83; 5-182: gM, gL, gO, UL128, UL130; 5-183: gM, gL, gO, UL128, UL131a; 5-184: gM, gL, gO, UL128, UL83; 5-185: gM, gL, gO, UL130, UL131a; 5-186: gM, gL, gO, UL130, UL83; 5-187: gM, gL, gO, UL131A, UL83; 5-188: gM, gL, UL128, UL130, UL131a; 5-189: gM, gL, UL128, UL130, UL83; 5-190: gM, gL, UL128, UL131A, UL83; 5-191: gM, gL, UL130, UL131A, UL83; 5-192: gM, gO, UL128, UL130, UL131a; 5-193: gM, gO, UL128, UL130, UL83; 5-194: gM, gO, UL128, UL131A, UL83; 5-195: gM, gO, UL130, UL131A, UL83; 5-196: gM, UL128, UL130, UL131A, UL83; 5-197: gN, gH, gL, gO, UL128; 5-198: gN, gH, gL, gO, UL130; 5-199: gN, gH, gL, gO, UL131a; 5-200: gN, gH, gL, gO, UL83; 5-201: gN, gH, gL, UL128, UL130; 5-202: gN, gH, gL, UL128, UL131a; 5-203: gN, gH, gL, UL128, UL83; 5-204: gN, gH, gL, UL130, UL131a; 5-205: gN, gH, gL, UL130, UL83; 5-206: gN, gH, gL, UL131A, UL83; 5-207: gN, gH, gO, UL128, UL130; 5-208: gN, gH, gO, UL128, UL131a; 5-209: gN, gH, gO, UL128, UL83; 5-210: gN, gH, gO, UL130, UL131a; 5-211: gN, gH, gO, UL130, UL83; 5-212: gN, gH, gO, UL131A, UL83; 5-213: gN, gH, UL128, UL130, UL131a; 5-214: gN, gH, UL128, UL130, UL83; 5-215: gN, gH, UL128, UL131A, UL83; 5-216: gN, gH, UL130, UL131A, UL83; 5-217: gN, gL, gO, UL128, UL130; 5-218: gN, gL, gO, UL128, UL131a; 5-219: gN, gL, gO, UL128, UL83; 5-220: gN, gL, gO, UL130, UL131a; 5-221: gN, gL, gO, UL130, UL83; 5-222: gN, gL, gO, UL131A, UL83; 5-223: gN, gL, UL128, UL130, UL131a; 5-224: gN, gL, UL128, UL130, UL83; 5-225: gN, gL, UL128, UL131A, UL83; 5-226: gN, gL, UL130, UL131A, UL83; 5-227: gN, gO, UL128, UL130, UL131a; 5-228: gN, gO, UL128, UL130, UL83; 5-229: gN, gO, UL128, UL131A, UL83; 5-230: gN, gO, UL130, UL131A, UL83; 5-231: gN, UL128, UL130, UL131A, UL83; 5-232: gH, gL, gO, UL128, UL130; 5-233: gH, gL, gO, UL128, UL131a; 5-234: gH, gL, gO, UL128, UL83; 5-235: gH, gL, gO, UL130, UL131a; 5-236: gH, gL, gO, UL130, UL83; 5-237: gH, gL, gO, UL131A, UL83; 5-238: gH, gL, UL128, UL130, UL131a; 5-239: gH, gL, UL128, UL130, UL83; 5-240: gH, gL, UL128, UL131A, UL83; 5-241: gH, gL, UL130, UL131A, UL83; 5-242: gH, gO, UL128, UL130, UL131a; 5-243: gH, gO, UL128, UL130, UL83; 5-244: gH, gO, UL128, UL131A, UL83; 5-245: gH, gO, UL130, UL131A, UL83; 5-246: gH, UL128, UL130, UL131A, UL83; 5-247: gL, gO, UL128, UL130, UL131a; 5-248: gL, gO, UL128, UL130, UL83; 5-249: gL, gO, UL128, UL131A, UL83; 5-250: gL, gO, UL130, UL131A, UL83; 5-251: gL, UL128, UL130, UL131A, UL83; and 5-252: gO, UL128, UL130, UL131A, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 8

In some embodiments, a composition comprising coding sequences for four of: gB, gM, gN, gH, gL, gO, UL128, UL130, UL131a, U83, or multiple compositions which collectively comprise coding sequences for four of: gB, gM, gN, gH, gL, gO, UL128, UL130, UL131a, U83 are administered. The composition may comprises coding sequences of four of gB, gM, gN, gH, gL, gO, UL128, UL130, UL131a, U83, or combinations of compositions that collectively comprise coding sequences of four of gB, gM, gN, gH, gL, gO, UL128, UL130, UL131a, U83. The following combinations 4-1 to 4-210 may be present in a four antigen vaccine: 4-1: gB, gM, gN, gH; 4-2: gB, gM, gN, gL; 4-3: gB, gM, gN, gO; 4-4: gB, gM, gN, U128; 4-5: gB, gM, gN, U130; 4-6: gB, gM, gN, U131a; 4-7: gB, gM, gN, U83; 4-8: gB, gM, gH, gL; 4-9: gB, gM, gH, gO; 4-10: gB, gM, gH, U128; 4-11: gB, gM, gH, U130; 4-12: gB, gM, gH, U131A; 4-13: gB, gM, gH, U83; 4-14: gB, gM, gL, gO; 4-15: gB, gM, gL, U128; 4-16: gB, gM, gL, U130; 4-17: gB, gM, gL, U131A; 4-18: gB, gM, gL, U83; 4-19: gB, gM, gO, U128; 4-20: gB, gM, gO, U130; 4-21: gB, gM, gO, U131A; 4-22: gB, gM, gO, U83; 4-23: gB, gM, U128; U130; 4-24: gB, gM, U128; U131A; 4-25: gB, gM, U128; U83; 4-26: gB, gM, U130; U131A; 4-27: gB, gM, U130; U83; 4-28: gB, gM, U131A; U83; 4-29: gB, gN, gH, gL; 4-31: gB, gN, gH, gO; 4-32: gB, gN, gH, U128; 4-33: gB, gN, gH, U130; 4-34: gB, gN, gH, U131A; 4-35: gB, gN, gH, U83; 4-36: gB, gN, gL, gO; 4-37: gB, gN, gL, U128; 4-38: gB, gN, gL, U130; 4-39: gB, gN, gL, U131A; 4-40: gB, gN, gL, U83; 4-41: gB, gN, gO, U128; 4-42: gB, gN, gO, U130; 4-43: gB, gN, gO, U131A; 4-44: gB, gN, gO, U83; 4-45: gB, gN, U128; U130; 4-46: gB, gN, U128; U131A; 4-47: gB, gN, U128; U83; 4-48: gB, gN, U130; U131A; 4-49: gB, gN, U130; U83; 4-50: gB, gN, U131A; U83; 4-51: gB, gH, gL, gO; 4-52: gB, gH, gL, U128; 4-53: gB, gH, gL, U130; 4-54: gB, gH, gL, U131A; 4-55: gB, gH, gL, U83; 4-56: gB, gH, gO, U128; 4-57: gB, gH, gO, U130; 4-58: gB, gH, gO, U131A; 4-59: gB, gH, gO, U83; 4-60: gB, gH, U128; U130; 4-61: gB, gH, U128; U131A; 4-62: gB, gH, U128; U83; 4-63: gB, gH, U130; U131A; 4-64: gB, gH, U130; U83; 4-65: gB, gH, U131A; U83; 4-66: gB, gL, gO, U128; 4-67: gB, gL, gO, U130; 4-68: gB, gL, gO, U131A; 4-69: gB, gL, gO, U83; 4-70: gB, gL, U128; U130; 4-71: gB, gL, U128; U131A; 4-72: gB, gL, U128; U83; 4-73: gB, gL, U130; U131A; 4-74: gB, gL, U130; U83; 4-75: gB, gL, U131A; U83; 4-76: gB, gO, U128; U130; 4-77: gB, gO, U128; U131A; 4-78: gB, gO, U128; U83; 4-79: gB, gO, U130; U131A; 4-80: gB, gO, U130; U83; 4-81: gB, gO, U131A; U83; 4-82: gB, U128; U130; U131A; 4-83: gB, U128; U130; U83; 4-84: gB, U128; U131A; U83; 4-85: gB, U130; U131A; U83; 4-86: gM, gN, gH, gL; 4-87: gM, gN, gH, gO; 4-88: gM, gN, gH, U128; 4-89: gM, gN, gH, U130; 4-90: gM, gN, gH, U131A; 4-91: gM, gN, gH, U83; 4-92: gM, gN, gL, gO; 4-93: gM, gN, gL, U128; 4-94: gM, gN, gL, U130; 4-95: gM, gN, gL, U131A; 4-96: gM, gN, gL, U83; 4-97: gM, gN, gO, U128; 4-98: gM, gN, gO, U130; 4-99: gM, gN, gO, U131A; 4-100: gM, gN, gO, U83; 4-101: gM, gN, U128; U130; 4-102: gM, gN, U128; U131A; 4-103: gM, gN, U128; U83; 4-104: gM, gN, 0130; U131A; 4-105: gM, gN, 0130; U83; 4-106: gM, gN, U131A; U83; 4-107: gM, gH, gL, gO; 4-108: gM, gH, gL, U128; 4-109: gM, gH, gL, U130; 4-110: gM, gH, gL, U131A; 4-111: gM, gH, gL, U83; 4-112: gM, gH, gO, U128; 4-113: gM, gH, gO, U130; 4-114: gM, gH, gO, U131A; 4-115: gM, gH, gO, U83; 4-116: gM, gH, U128; U130; 4-117: gM, gH, U128; U131A; 4-118: gM, gH, U128; U83; 4-119: gM, gH, U130; U131A; 4-120: gM, gH, U130; U83; 4-121: gM, gH, U131A; U83; 4-122: gM, gL, gO, U128; 4-123: gM, gL, gO, U130; 4-124: gM, gL, gO, U131A; 4-125: gM, gL, gO, U83; 4-126: gM, gL, U128; U130; 4-127: gM, gL, U128; U131A; 4-128: gM, gL, U128; U83; 4-129: gM, gL, U130; U131A; 4-130: gM, gL, U130; U83; 4-131: gM, gL, U131A; U83; 4-132: gM, gO, U128; U130; 4-133: gM, gO, U128; U131A; 4-134: gM, gO, U128; U83; 4-135: gM, gO, U130; U131A; 4-136: gM, gO, U130; U83; 4-137: gM, gO, U131A; U83; 4-138: gM, U128; U130; U131A; 4-139: gM, U128; U130; U83; 4-140: gM, U128; U131A; U83; 4-141: gM, U130; U131A; U83; 4-142: gN, gH, gL, gO; 4-143: gN, gH, gL, U128; 4-144: gN, gH, gL, U130; 4-145: gN, gH, gL, U131A; 4-146: gN, gH, gL, U83; 4-147: gN, gH, gO, U128; 4-148: gN, gH, gO, U130; 4-149: gN, gH, gO, U131A; 4-150: gN, gH, gO, U83; 4-151: gN, gH, U128; U130; 4-152: gN, gH, U128; U131A; 4-153: gN, gH, U128; U83; 4-154: gN, gH, U130; U131A; 4-155: gN, gH, U130; U83; 4-156: gN, gH, U131A; U83; 4-157: gN, gL, gO, U128; 4-158: gN, gL, gO, U130; 4-159: gN, gL, gO, U131A; 4-160: gN, gL, gO, U83; 4-161: gN, gL, U128; U130; 4-162: gN, gL, U128; U131A; 4-163: gN, gL, U128; U83; 4-164: gN, gL, U130; U131A; 4-165: gN, gL, U130; U83; 4-166: gN, gL, U131A; U83; 4-167: gN, gO, U128; U130; 4-168: gN, gO, U128; U131A; 4-169: gN, gO, U128; U83; 4-170: gN, gO, U130; U131A; 4-171: gN, gO, U130; U83; 4-172: gN, gO, U131A; U83; 4-173: gN, U128; U130; U131A; 4-174: gN, U128; U130; U83; 4-175: gN, U128; U131A; U83; 4-176: gN, U130; U131A; U83; 4-177: gH, gL, gO, U128; 4-178: gH, gL, gO, U130; 4-179: gH, gL, gO, U131A; 4-180: gH, gL, gO, U83; 4-181: gH, gL, U128; U130; 4-182: gH, gL, U128; U131A; 4-183: gH, gL, U128; U83; 4-184: gH, gL, U130; U131A; 4-185: gH, gL, 0130;

U83; 4-186: gH, gL, U131A; U83; 4-187: gH, gO, U128; U130; 4-188: gH, gO, U128; U131A; 4-189: gH, gO, U128; U83; 4-190: gH, gO, U130; U131A; 4-191: gH, gO, U130; U83; 4-192: gH, gO, U131A; U83; 4-193: gH, U128; U130; U131A; 4-194: gH, U128; U130; U83; 4-195: gH, U128; U131A; U83; 4-196: gH, U130; U131A; U83; 4-197: gL, gO, U128; U130; 4-198: gL, gO, U128; U131A; 4-199: gL, gO, 0128; U83; 4-200: gL, gO, 0130; U131A; 4-201: gL, gO, U130; U83; 4-202: gL, gO, U131A; U83; 4-202: gL, U128; U130; U131A; 4-203: gL, U128; U130; U83; 4-204: gL, U128; U131A; U83; 4-205: gL, U130; U131A; U83; 4-206: gO, U128; U130; U131A; 4-207: gO, U128; U130; U83; 4-208: gO, U128; U131A; U83; 4-209: gO, U130; U131A; U83; and 4-210: U128; U130; U131A; U83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 9

In some embodiments, a composition comprising coding sequences for three of: gB, gM, gN, gH, gL, gO, UL128, UL130, UL131a, U83, or multiple compositions which collectively comprise coding sequences for three of: gB, gM, gN, gH, gL, gO, UL128, UL130, UL131a, U83 are administered. The composition which comprises coding sequences of three of gB, gM, gN, gH, gL, gO, UL128, UL130, UL131a, U83, or combinations of compositions that collectively comprise coding sequences of three of gB, gM, gN, gH, gL, gO, UL128, UL130, UL131a, U83 are referred to as "three antigen vaccines". The following combinations 3-1 to 3-120 may be present in a three antigen vaccine: 3-1: gB, gM, gN; 3-2: gB, gM, gH; 3-3: gB, gM, gL; 3-4: gB, gM, gO; 3-5: gB, gM, UL128; 3-6: gB, gM, UL130; 3-7: gB, gM, UL131A; 3-8: gB, gM, UL83; 3-9: gB, gN, gH; 3-10: gB, gN, gL; 3-11: gB, gN, gO; 3-12: gB, gN, UL128; 3-13: gB, gN, UL130; 3-14: gB, gN, UL131A; 3-15: gB, gN, UL83; 3-16: gB, gH, gL; 3-17: gB, gH, gO; 3-18: gB, gH, UL128; 3-19: gB, gH, UL130; 3-20: gB, gH, UL131A; 3-21: gB, gH, UL83; 3-22: gB, gL, gO; 3-23: gB, gL, UL128; 3-24: gB, gL, UL130; 3-25: gB, gL, UL131A; 3-26: gB, gL, UL83; 3-27: gB, gO, UL128; 3-28: gB, gO, UL130; 3-29: gB, gO, UL131A; 3-30: gB, gO, UL83; 3-31: gB, UL128, UL130; 3-32: gB, UL128, UL131A; 3-33: gB, UL128, UL83; 3-34: gB, UL130, UL131A; 3-35: gB, UL130, UL83; 3-36: gB, UL131A, UL83; 3-37: gM, gN, gH; 3-38: gM, gN, gL; 3-39: gM, gN, gO; 3-40: gM, gN, UL128; 3-41: gM, gN, UL130; 3-42: gM, gN, UL131A; 3-43: gM, gN, UL83; 3-44: gM, gH, gL; 3-45: gM, gH, gO; 3-46: gM, gH, UL128; 3-47: gM, gH, UL130; 3-48: gM, gH, UL131A; 3-49: gM, gH, UL83; 3-50: gM, gL, gO; 3-51: gM, gL, UL128; 3-52: gM, gL, UL130; 3-53: gM, gL, UL131A; 3-54: gM, gL, UL83; 3-55: gM, gO, UL128; 3-56: gM, gO, UL130; 3-57: gM, gO, UL131A; 3-58: gM, gO, UL83; 3-59: gM, UL128, UL130; 3-60: gM, UL128, UL131A; 3-61: gM, UL128, UL83; 3-62: gM, UL130, UL131A; 3-63: gM, UL130, UL83; 3-64: gM, UL131A, UL83; 3-65: gN, gH, gL; 3-66: gN, gH, gO; 3-67: gN, gH, UL128; 3-68: gN, gH, UL130; 3-69: gN, gH, UL131A; 3-70: gN, gH, UL83; 3-71: gN, gL, gO; 3-72: gN, gL, UL128; 3-73: gN, gL, UL130; 3-74: gN, gL, UL131A; 3-75: gN, gL, UL83; 3-76: gN, gO, UL128; 3-77: gN, gO, UL130; 3-78: gN, gO, UL131A; 3-79: gN, gO, UL83; 3-80: gN, UL128, UL130; 3-81: gN, UL128, UL131A; 3-82: gN, UL128, UL83; 3-83: gN, UL130, UL131A; 3-84: gN, UL130, UL83; 3-85: gN, UL131A, UL83; 3-86: gH, gL, gO; 3-87: gH, gL, UL128; 3-88: gH, gL, UL130; 3-89: gH, gL, UL131A; 3-90: gH, gL, UL83; 3-91: gH, gO, UL128; 3-92: gH, gO, UL130; 3-93: gH, gO, UL131A; 3-94: gH, gO, UL83; 3-95: gH, UL128, UL130; 3-96: gH, UL128, UL131A; 3-97: gH, UL128, UL83; 3-98: gH, UL130, UL131A; 3-99: gH, UL130, UL83; 3-100: gH, UL131A, UL83; 3-101: gL, gO, UL128; 3-102: gL, gO, UL130; 3-103: gL, gO, UL131A; 3-104: gL, gO, UL83; 3-105: gL, UL128, UL130; 3-106: gL, UL128, UL131A; 3-107: gL, UL128, UL83; 3-108: gL, UL130, UL131A; 3-109: gL, UL130, UL83; 3-110: gL, UL131A, UL83; 3-111: gO, UL128, UL130; 3-112: gO, UL128, UL131A; 3-113: gO, UL128, UL83; 3-114: gO, UL130, UL131A; 3-115: gO, UL130, UL83; 3-116: gO, UL131A, UL83; 3-117: UL128, UL130, UL131A; 3-118: UL128, UL130, UL83; 3-119: UL128, UL131A, UL83; and 3-120: UL130, UL131A, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 10

In some embodiments, a composition comprising coding sequences for two of: gB, gM, gN, gH, gL, gO, UL128, UL130, UL131a, U83, or multiple compositions which collectively comprise coding sequences for two of: gB, gM, gN, gH, gL, gO, UL128, UL130, UL131a, U83 are administered. The composition may comprises coding sequences of two of gB, gM, gN, gH, gL, gO, UL128, UL130, UL131a, U83, or combinations of compositions that collectively comprise coding sequences of two of gB, gM, gN, gH, gL, gO, UL128, UL130, UL131a, U83. There are 45 subsets (2-1 to 2-45) having 2 antigens from the set of HCMV antigens consisting of: gB, gM, gN, gH, gL, gO, UL128, U130, UL131a and UL83. The following combinations 2-1 to 2-45 may be present in a two antigen vaccine: 2-1 gB, gM, 2-2 gB, gN, 2-3 gB, gH, 2-4 gB, gL, 2-5 gB, gO, 2-6 gB, UL128, 2-7 gB, UL130, 2-8 gB, UL131a, 2-9 gB, UL83, 2-10 gM, gN, 2-11 gM, gH, 2-12 gM, gL, 2-13 gM, gO, 2-14 gM, UL128, 2-15 gM, UL130, 2-16 gM, UL131a, 2-17 gM, UL83, 2-18 gN, gH, 2-19 gN, gL, 2-20 gN, gO, 2-21 gN, UL128, 2-22 gN, UL130, 2-23 gN, UL131a, 2-24 gN, UL83 2-25 gH, gL, 2-26 gH, gO, 2-27 gH, UL128, 2-28 gH, UL130, 2-29 gH, UL131a, 2-30 gH, UL83 2-31 gL, gO, 2-32 gL, UL128, 2-33 gL, UL130, 2-34 gL, UL131a, 2-35 gL, UL83 2-36 gO, UL128, 2-37 gO, UL130, 2-38 gO, UL131a, 2-39 gO, UL83 2-40 UL128, UL130, 2-41 UL128, UL131a, 2-42 UL128, UL83 2-43 UL130, UL131a, 2-44 UL130, UL83, and 2-45 UL131a, UL83. In some embodiments, these vaccines comprise one or more of the coding sequences encoding each of gB, gM, gN, gH, gL, gO, UL128, UL130, UL131a that have sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, one or more of the coding sequences is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, one or more of the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 11

In some embodiments, a composition comprising coding sequence for one of: gB, gM, gN, gH, gL, gO, UL128, UL130, UL131a, and UL83 is administered. The following combinations 1-1 to 1-10 may be present in a one antigen vaccine: 1-1 gB, 1-2 gM, 1-3 gN, 1-4 gH, 1-5 gL, 1-6 gO, 1-7 UL128, 1-8 UL130, 1-9 UL131a and 1-10 U83. In some embodiments, these vaccines comprise one of the coding sequences encoding gB, gM, gN, gH, gL, gO, UL128, UL130, UL131a that has a sequences selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, the coding sequence is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59. In some embodiments, the coding sequences in a vaccine is selected from the group consisting of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57 and 59.

Example 12

In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein one or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein two or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein three or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein four or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein five or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein six or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein seven or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein eight or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein nine or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60. In some embodiments, vaccines comprise coding sequences encoding coding sequences for one, two, three, four, five, six, seven, eight, nine or ten antigens selected from the group consisting of each of gB, gM, gN, gH, gL, gO, UL128, UL130, UL131a wherein ten or more of said sequences is selected from the group consisting of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58 and 60.

Example 13

HCMV Antigen Expression

Following construction, protein expression was confirmed by immunoblotting. 293T cells were transfected with each plasmid or empty pVAX vector (negative control) and samples were harvested 48 h later and analyzed by Western immunoblotting (photo not shown). The presence of a ~66 kDa protein was detected in the cell lysates of pHCMV-NPtransfected 293T cells using anti-HA tag Abs (data not shown) and NP-specific polyclonal serum (data not shown), while control pVAX empty vector-transfected lysates were negative for Ag expression. Samples were normalized for total protein by Bradford protein assay and contained equivalent amounts of globular tubulin protein. Furthermore, pHCMV-NP-transfected 293T cells were reactive with serum from HCMV immune and pHCMV-NP immunized mice (n=5), but not from pVAX immunized (n=5) animals (data not shown); hyper-immune serum pooled from mice immunized five times with pHCMV-NP reacted with 16.6% of pHCMV-NP-transfected cells on average as compared with 8.1% from HCMV immune animals and 0.7% from pVAX-transfected mice (data not shown). Non-specific binding was not detected as the positive sera did not react with pVAX-transfected 293T cells. Furthermore, Western immunoblotting confirmed host-cell proteolytic cleavage of the three fusion proteins segregated by Turin cleavage sites into independent Ags gM, gN, gH, gL, UL128, UL130, and UL131A.

Western Blot Analysis

Expression of the plasmid DNA-encoded vaccine proteins was verified by Western immunoblotting. 293T cells ($1\times10^6$ cells) were transfected using the Fugene transfection method (Roche, Indianapolis, Ind.). Forty-eight hours post-transfection, proteins were isolated using cell lysis buffer, fractionated on SDS-PAGE (12%), and transferred to nitrocellulose using iBlot Dry Blotting System (Invitrogen, CA, USA) Immunodetection was performed using SNAP i.d. Protein Detection System (Millipore, Mass., USA) with specific mouse antiserum (pooled from individual groups of mice immunized 4-6 times using the respective plasmid DNA construct) and the expressed proteins were visualized with horseradish peroxidase-conjugated goat anti-mouse IgG using an ECL detection system (Amersham Pharmacia Biotech, Piscataway, N.J.).

Altogether, transfection of 293T cells using the each of the plasmid DNA constructs was sufficient for the production of the consensus immunogens in vitro that was specifically reactive with Abs generated from repeat immunization of mice.

Epitope Mapping

Figure 10:
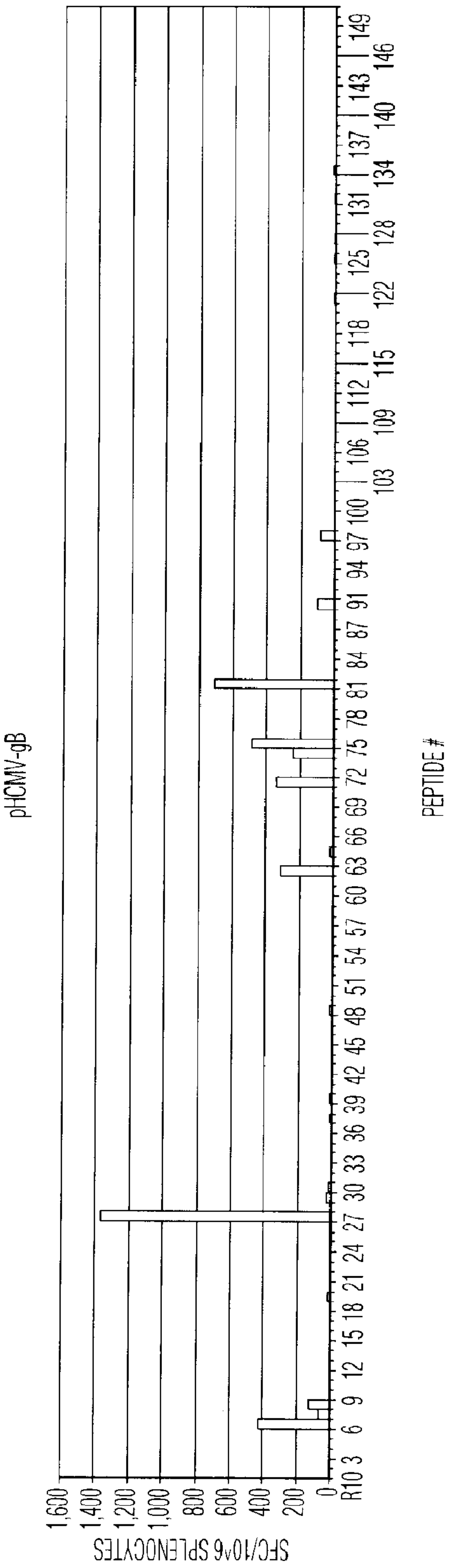
FIG. 10 shows data from experiments identifying immunodominant epitopes of HCMV-gB using plasmid 1.

Data was generated to identify immunodominant epitopes of HCMV-gB using splenocytes from animal vaccinated with plasmid 1 and a series of overlapping peptides of HCMV-gB. ELISpot data is shown in FIG. 10.

Figure 11:
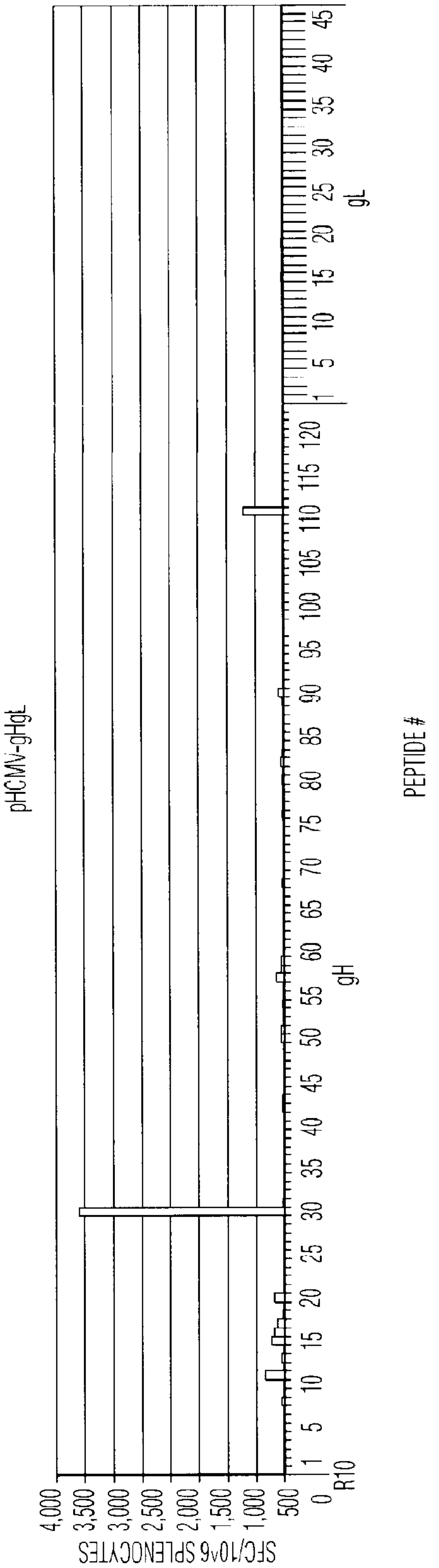
FIG. 11 shows data from experiments identifying immunodominant epitopes of HCMV-gH and HCMV-gL using plasmid 3.

Data was generated to identify immunodominant epitopes of HCMV-gH and HCMV-gL using splenocytes from animal vaccinated with plasmid 3 and a series of overlapping peptides of HCMV-gH and HCMV-gL. ELISpot data is shown in FIG. 11.

Figure 12:
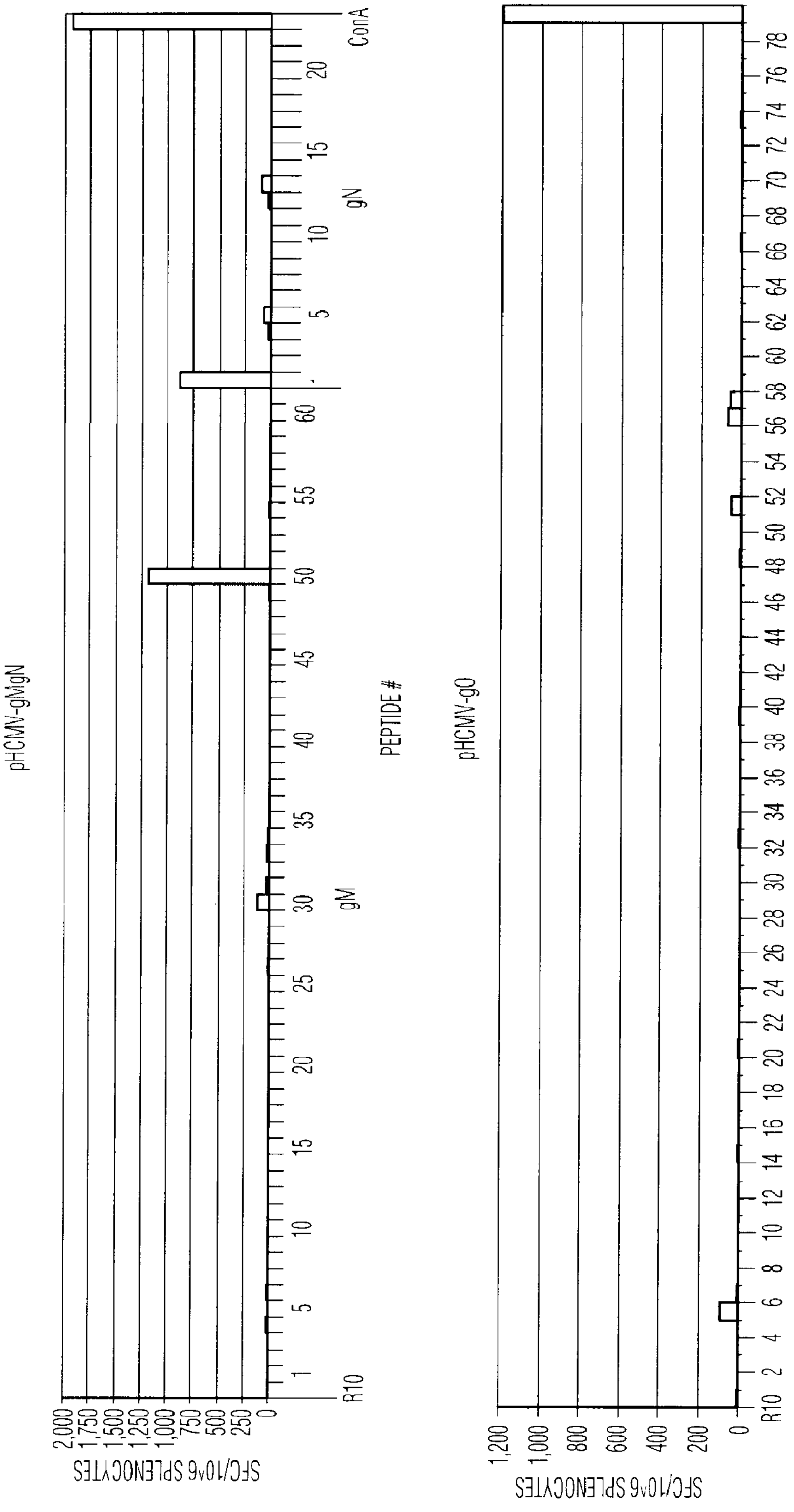
FIG. 12 shows data from experiments identifying immunodominant epitopes of HCMV-gM and HCMV-gN using plasmid 2 and of HMCV-gO using plasmid 4.

Data was generated to identify immunodominant epitopes of HCMV-gM and HCMV-gN using splenocytes from animal vaccinated with plasmid 2 and a series of overlapping peptides of HCMV-gM and HCMV-gN. Data was generated to identify immunodominant epitopes of HCMV-gO using splenocytes from animal vaccinated with plasmid 4 and a series of overlapping peptides of HCMV-gO. ELISpot data is shown in FIG. 12.

Figure 13:
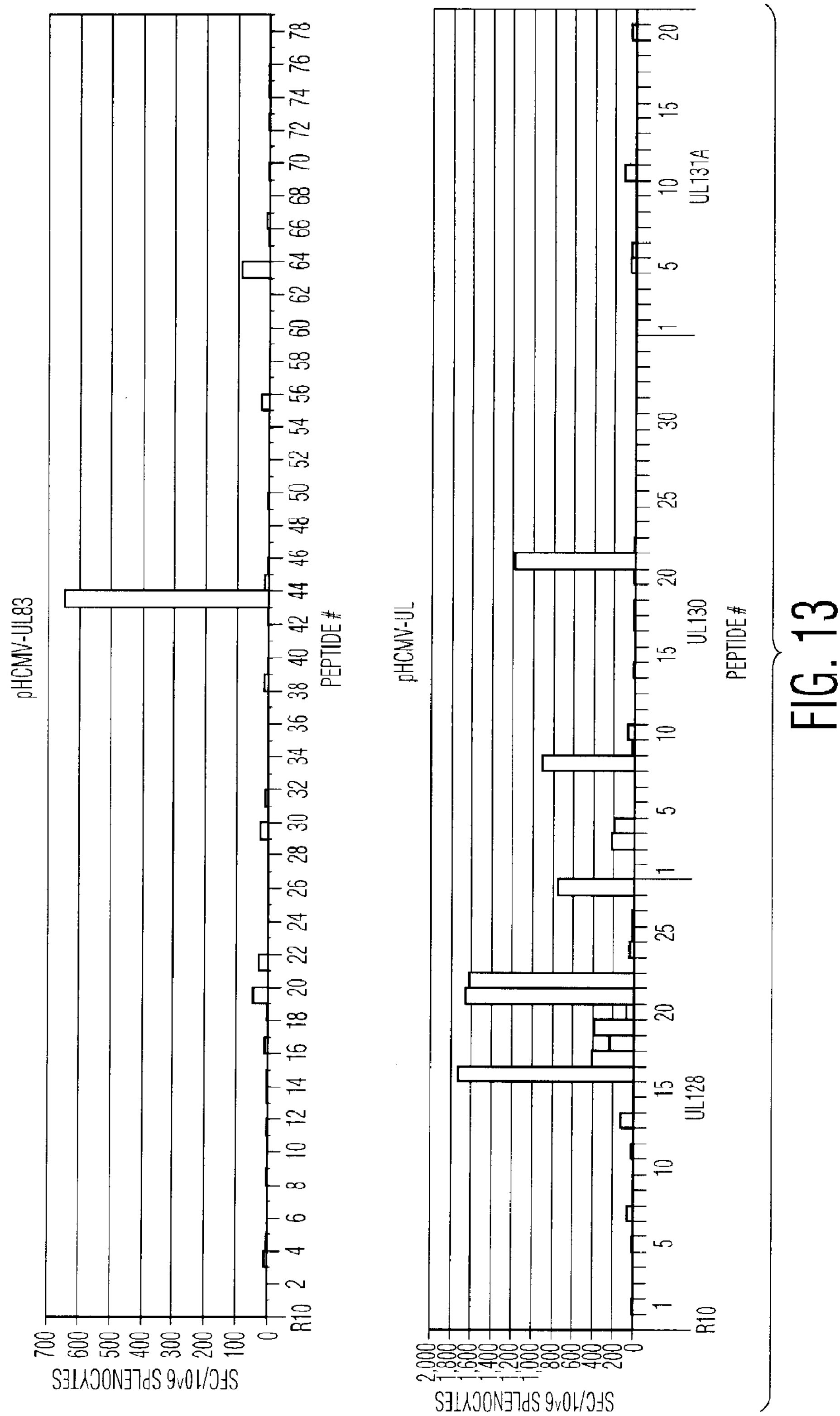
FIG. 13 shows data from experiments identifying immunodominant epitopes of HCMV-UL83 using modified plasmid 6 and HCMV-UL131A, HCMV-UL130, and HCMV-UL128 using plasmid 5.

Data was generated to identify immunodominant epitopes of HCMV-UL131A, HCMV-UL130 and HCMV-UL128 using splenocytes from animal vaccinated with plasmid 5 and a series of overlapping peptides of HCMV-UL131A, HCMV-UL130 and HCMV-UL128. Data was generated to identify immunodominant epitopes of HCMV-UL83 using splenocytes from animal vaccinated with plasmid 6 and a series of overlapping peptides of HCMV-UL83. ELTSpot data is shown in FIG. 13.

Figure 18A:
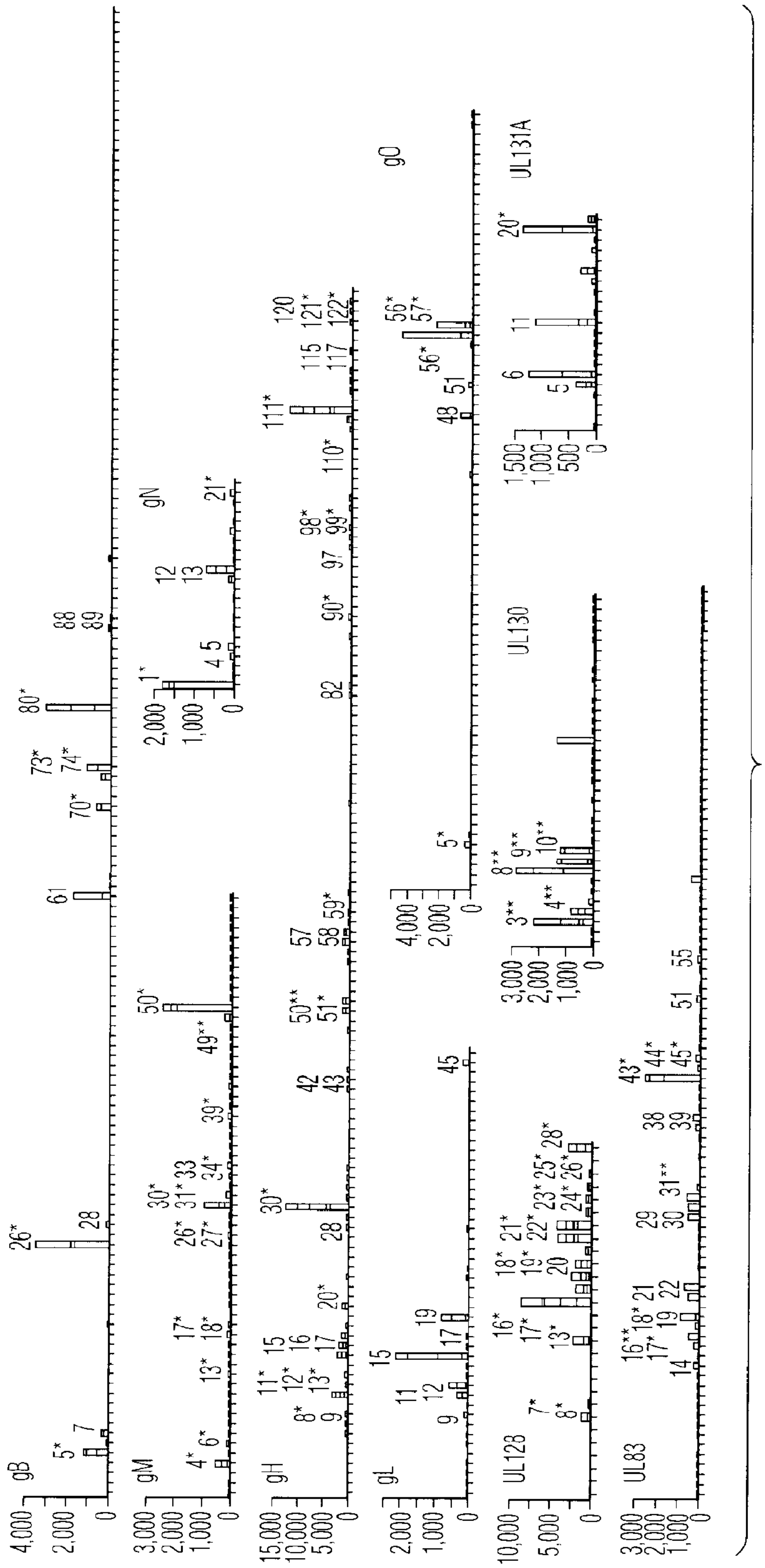
FIG. 18*a-d* shows graphs and images that depict nascent co-expression of structurally-relevant HCMV immunogens induces robust immunity, including a) a graph of HCMV: gB, gM, gN, gH, gL, gO, UL128, UL130, UL131A, and UL83 domains showing immunicity (see also FIGS. 10-13 for different graphical display of same data); b) images showing character of immune response; c) images for HCMV: UL83, gO, gB, gMgN, UL, and gHgL, and d) percent CD44+ IFNg+ T cells for HCMV: UL83, gO, gB, gMgN, UL, and gHgL.

Sec also FIG. 18*a* for epitope anaylsis.

Example 14

HCMV Plasmid Immunization and Mice

Adult female C57BL/6 (H-$2^b$) mice 6-8 weeks of age were purchased from The Jackson Laboratory (Bar Harbor, Me.) and were cared for in accordance with Institutional Animal Care and Use Committee-approved protocols at the University Pennsylvania School of Medicine Animal Facility. Mice were immunized with the indicated doses of plasmid DNA by i.m. injection into the anterior tibialis muscle followed by in vivo electroporation (EP) using the CELLECTRA® adaptive constant current EP Minimally Invasive Device (MID) (Inovio Pharmaceuticals, Blue Bell, Pa.) as described previously [Khan, 2005 #727; Shedlock, 2011 #1097]. A total of four 0.1 Amp constant current square-wave pulses were delivered as two sets of two pulses through a triangular 3-electrode array consisting of 26-gauge solid stainless steel electrodes. Each pulse was 52 milliseconds in length with a 1 second delay between the individual pulses with three seconds between the sets of pulses.

Figure 16A:
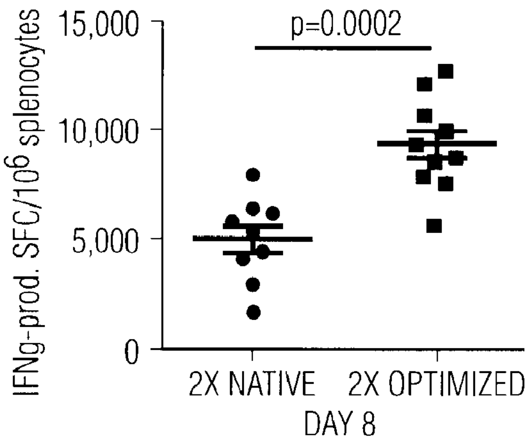
FIG. 16*a-e* shows graphs that show (a) two groups of mice were immunized twice with 35 μg of pHCMV-NP in which the genetic sequences differed, derived from the virus (Native) or optimized for expression in mice (Optimized), but the encoded amino acids were identical. Splenocytes were harvested 8 days after the second immunization and NP-specific T cells were assessed by ELISPOT. (b) Mice were immunized twice with pHCMV-NP, either with or without EP, pVAX with EP (n=10), or with $2\times10^5$ PFU HCMV i.p. (n=5). Mice were challenged with $20LD_{50}$ HCMV i.c. 8 weeks after the second immunization or HCMV acute infection and survival data are shown. (c) Mice were immunized one, two, three or four times with or without EP, pVAX four times with EP, or HCMV acute infected. NP-specific IgG responses were evaluated 7 days following each immunization, or 60 days post-HCMV infection, and data are shown. (d) Mice were immunized twice with either 35 μg pHCMV-NP with EP or 45 μg of pHCMV-GP with EP, and viral protein-specific T cell immunity was assessed 8 days later. (e) Mice were given a single injection of 35 μg of pHCMV-NP with EP or 45 μg of pHCMV-GP with EP, pVAX with EP (n=10), or with $2\times10^5$ PFU HCMV i.p. (n=5) and were later challenged with $20LD_{50}$ HCMV i.c. 8 weeks after the vaccination or infection. Survival data for each group of mice are shown.

The native, virus-derived DNA sequence of the HCMV NP protein ('Native' or non-optimized) was compared with a gene that was optimized for its host species for immunogenicity in the DNA vaccination of mice (FIG. 16*a*). Mice (n=10) were immunized twice with 35 μg of either the 'Native' or 'Optimized' gene subcloned into a modified mammalian DNA expression vector and delivered with EP, and T cell immunity was assessed 8 days later. NP-specific T cells were 2-fold greater (p=0.0001) in mice immunized with the 'Optimized' construct thus demonstrating that species-specific gene optimization can enhance DNA vaccine-induced T cell immunity.

Figure 16B:
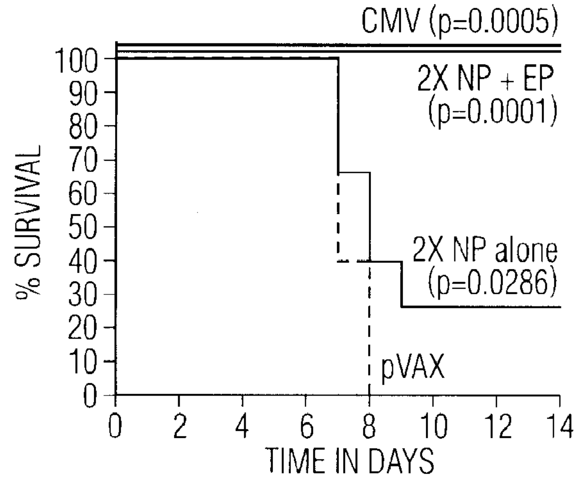
Figure 16C:
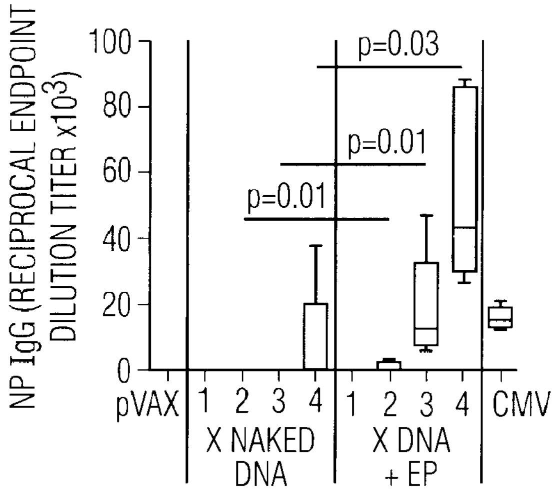
Figure 16D:
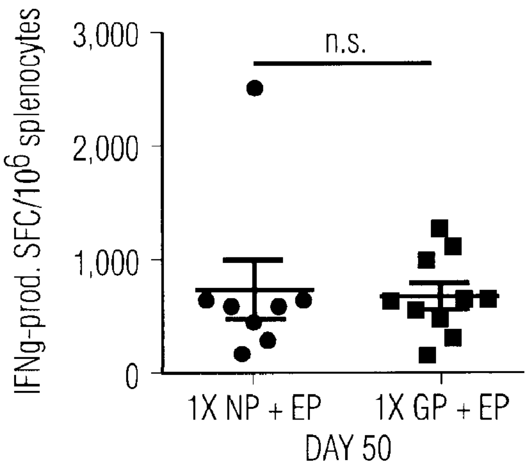
Figure 16E:
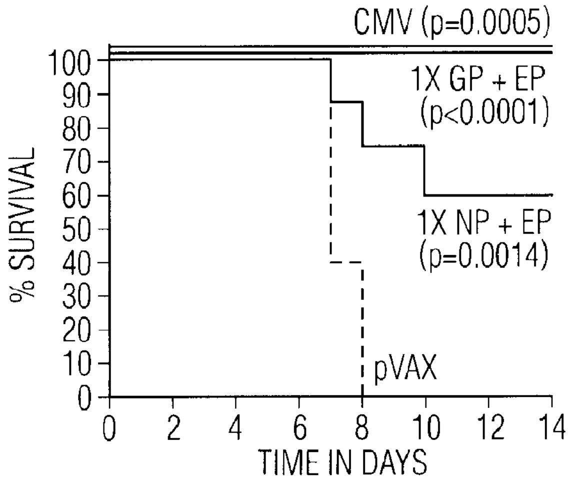

The contribution of in vivo EP delivery to the elicitation of T and B cell immunity was also assessed. The 'Optimized' version of the HCMV NP DNA vaccine was administered to mice (n=5-10/group) similarly as above, but delivered either with or without EP, and protective efficacy was assessed with lethal challenge (FIG. 16*b*). While both vaccines elicited protective efficacy when compared with the control vector, EP delivery during DNA vaccination was completely protective versus only 60% protection without. These data show a significant contribution by EP delivery to the generation of T cells that mediate protective efficacy against lethal challenge. For evaluation of EP contribution to the generation of B cells, animals were immunized (n=5/group) several times and Ab production was compared 7 days after each injection with that from wild type HCMV infection (FIG. 16*c*). While animals immunized with DNA alone yielded NP-specific Abs only after a total of 4 immunizations, those that received vaccine delivered with EP exhibited Abs after the second administration. Furthermore, Ab responses in the EP-immunized mice surpassed those in mice following wild type HCMV infection, which demonstrated that EP delivery is a potent technology for enhancing DNA vaccine-induced immunity.

DNA Vaccination Induces Robust T and B Cell Immunity

A summary of DNA vaccine data is shown in FIG. 15. These data show that highly effective immune responses induced by vaccines exemplified herein were observed. The HCMV-gHgL data show the construct as an outstanding vaccine target with superior efficacy, providing high neutralizing titers and CTL epitopes. Such a construct can be delivered as a DNA vaccine or used as a component of other vaccine platforms. Similarly, the HCMV: UL131A, UL130, and UL138 complex immunogen possesses both CTL activity as well as neutralization activity supporting its importance as a novel vaccine target. The data also shows that the designed HCV-gMgN is established for vaccine production, that HCMV-gO is established for protection and that the importance of multiantigen approach is established as a viable example.

Figure 18B:
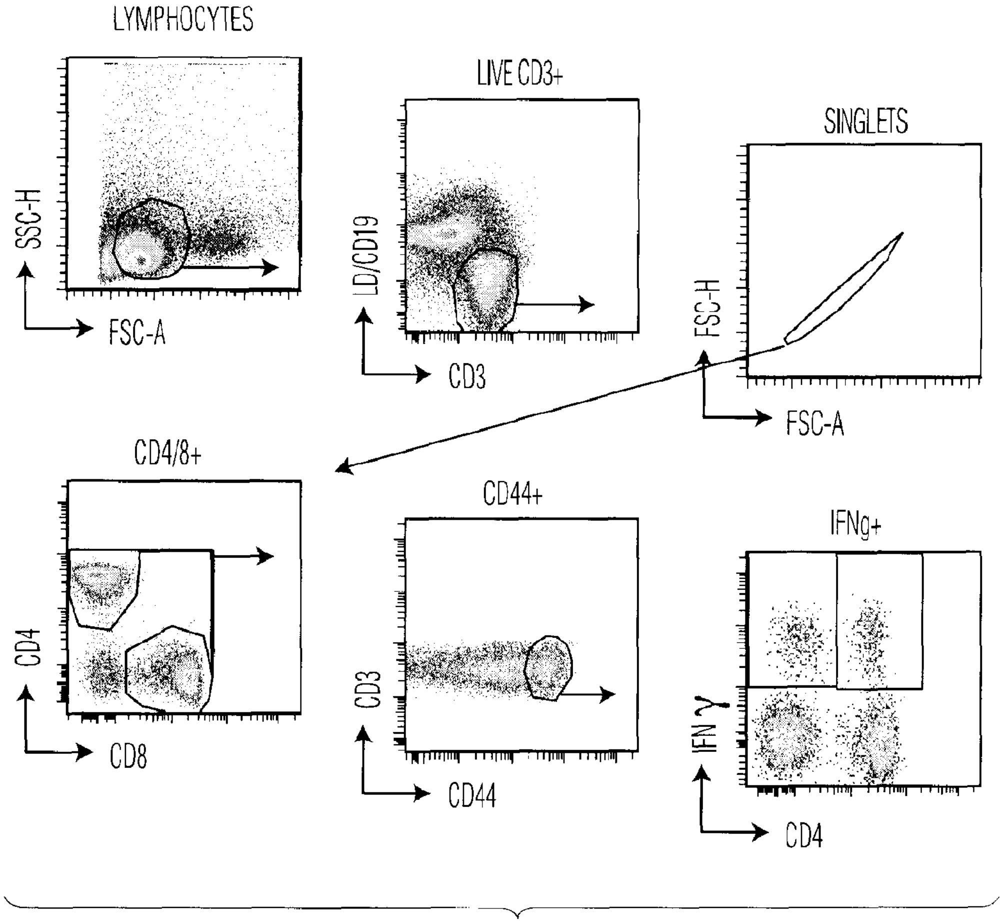
Figure 18C:
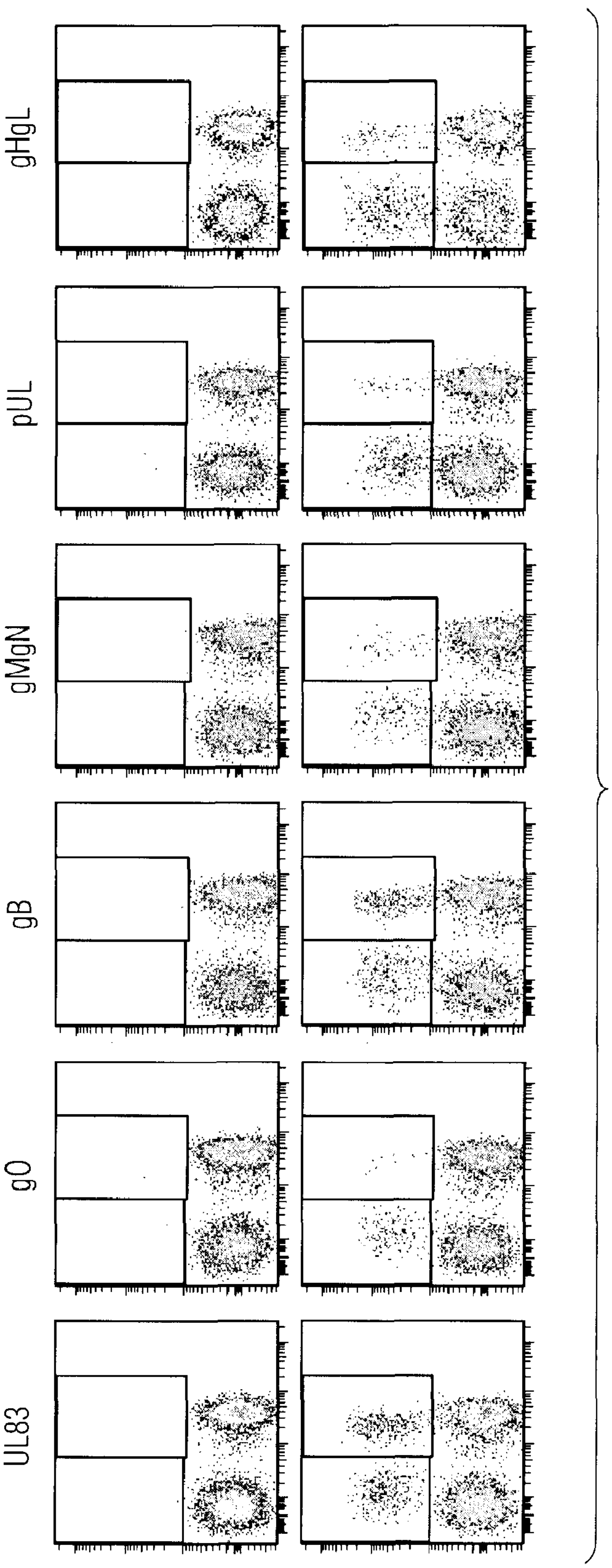
Figure 18D:
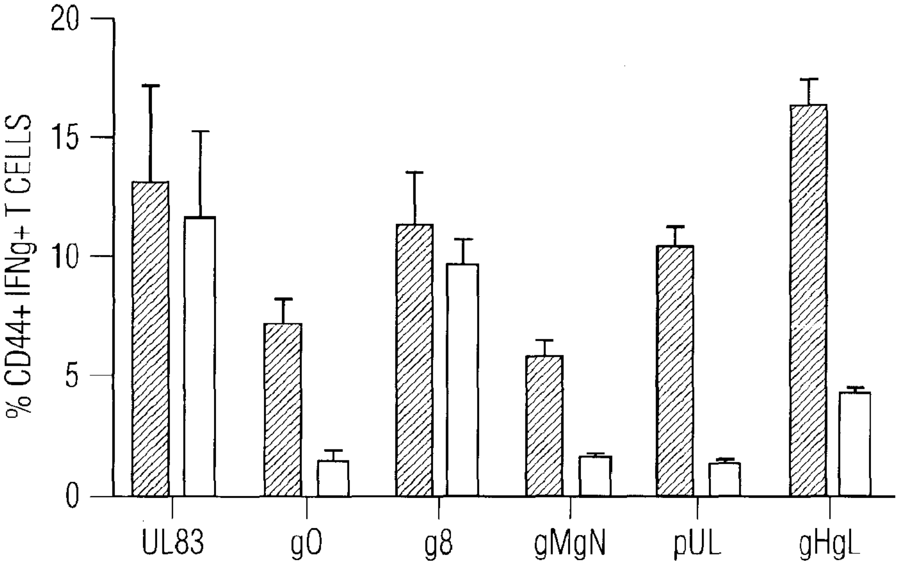

For evaluation of plasmid DNA immunogenicity, mice (n=4-6/group) were immunized twice with 45 μg of each respective plasmid vaccine, two weeks between injections and immediately followed by EP. Mice were sacked 7-8 days following the second immunization and ELISPOT and FACS was performed to assess T cell immunity. Immunization with the novel gHgL vaccine resulted in the highest level of T cell immunity (~>10,000 IFNγ-producing cells per million splenocytes) followed by pUL (~8,000 cells). Moreover, the breadth of the epitopic responses for each vaccine was assessed and showed that DNA vaccination with a combination of optimization strategies generated a diversity of T cell epitopes. Altogether, these data show that all six HCMV DNA vaccine constructs were immunogenic in mice following immunization in combination with in vivo EP and yielded measurable immunogen-specific T cell responses; and T cell immunogenicity was ranked as follows: gHgL>pUL>UL83>gB>gMgN>gO (see FIGS. 18*b-d*).

Figure 19A:
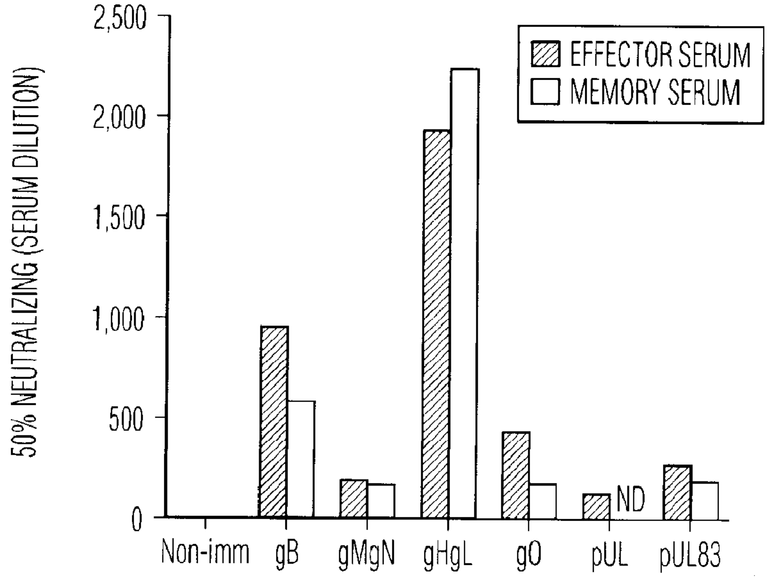
FIG. 19*a-b* shows graphs that neutralization data for: a) 50% neutralization levels for HCMV: gB, gMgN, gHgL, gO, UL, and UL83, and b) 50% neutralization levels for CMV only, seropositive serum, and HCMV-gHgL immunized serum.
Figure 19B:
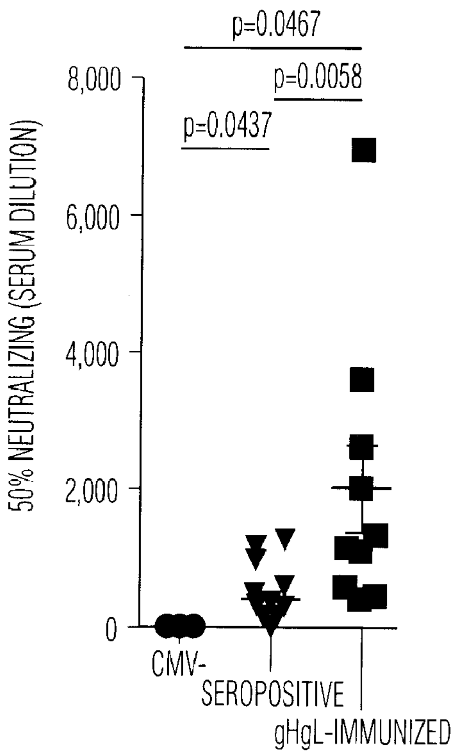

Serum samples were collected and pooled from each group of mice (n=5) 7-10 days following each of five to six immunizations (spaced two weeks apart), and then pooled thereafter up to 1 month following the final immunization. Furthermore, serum was collected 6 months following each of the final immunizations (a time point considered to be clinically relevant for long-term Ab responses) and tested along with the pooled-effector sera for the capacity for neutralization of infection with the AD169-EGFP virus into life extended human foreskin fibroblast cells. Data confirmed a neutralization capacity for gB immunized animals which supports previous data demonstrating its ability to elicit nAbs and protect in some challenge models. See FIGS. 19*a-b*. However, immunization with the novel gHgL DNA vaccine generated nAb responses that were ~2-4-fold greater than gB immunization. Interestingly, neither of these levels of neutralization ability was achieved by any other immunogen, including the gMgN, gO, UL128-131A, nor the UL83. However, this is not entirely unexpected for the UL128-131A plasmid since the AD169 vector is known to contain a sizable mutation/deletion in the 131A protein. Lastly, neutralization levels were relatively stable for each immunogen comparing effector and memory serum collected 6 months following the final immunization. Thus, these data demonstrate that DNA vaccination in combination with EP generated robust B cell responses. Altogether, data herein show that the DNA plasmids were immunogenic in mice and generated robust T and B cell responses.

Immunity to the HCMV gB alone has been demonstrated to completely protective in guinea pigs, but has limited efficacy in the clinic. Thus, we next set out to determine whether their combination with the gB DNA vaccine would enhance HCMV-specific immunity. Mice (n=5/group) were given several doses of the gB plasmid alone, gB+gHgL, or gB+gHgL+pUL, and T and B cell immunity was assessed. Indeed, trivalent formulation of these plasmids induced the highest level of both T and B cell responses. Thus, these data demonstrate that vaccine-induced CMV-specific immunity can be increased by immunization with multi-valent plasmid DNA formulations.

Sero-Reactivity to gH/gL Correlates with Virus Neutralization

FIG. 19 shows graphs that neutralization data for: a) 50% neutralization levels for HCMV: gB, gMgN, gHgL, gO, UL, and UL83, and b) 50% neutralization levels for CMV only, seropositive serum, and HCMV-gHgL immunized serum.

Splenocyte Isolation and ELISpot Assay

Mice were sacrificed 8 days following the final immunization with plasmid DNA and the spleens were harvested and placed in RPMI 1640 medium (Mediatech Inc., Manassas, Va.) supplemented with 10% FBS, 1×Anti-anti (Invitrogen), and 1×β-ME (Invitrogen). Splenocytes were isolated by mechanical disruption of the spleen using a Stomacher machine (Seward Laboratory Systems Inc., Bohemia, N.Y.), and the resulting product was filtered using a 40 μm cell strainer (BD Falcon). The cells were treated for 5 min with ACK lysis buffer (Lonza, Switzerland) for lysis of RBCs and then the splenocytes were washed in PBS and then resuspended in complete RPMI medium.

An IFNγ ELISPOT assay was conducted. Briefly, ELISPOT 96-well plates (Millipore, Billerica, Mass.) were coated with anti-mouse IFN-γ capture antibody and incubated for 24 h at 4° C. (R&D Systems, Minneapolis, Minn.). The following day, plates were washed with PBS and then blocked for 2 h with blocking buffer (1% BSA and 5% sucrose in PBS). One to two-hundred thousand splenocytes per well and in triplicate from each animal were stimulated overnight at 37° C. in 5% CO, and in the presence of RPMI 1640 (negative control), Concanavalin A (Con A; positive control), or with individual (individual peptides overlapping complete vaccine proteins were used for the Single Peptide Analysis (SPA) as indicated) or pooled 15-mer peptides as indicated (GenScript). After approximately 18-20 h of stimulation, the cells were washed in PBS and incubated for 24 h at 4° C. with biotinylated anti-mouse IFN-γ mAb (R&D Systems, Minneapolis, Minn.). The plates were washed in PBS, and streptavidin-alkaline phosphatase (MabTech, Sweden) was added to each well and incubated for 2 h at room temperature. The plates were washed again in PBS, BCIP/NBT Plus substrate (MabTech) was added to each well for 15-30 min, and then the plate was rinsed with distilled water and dried at room temperature. Spots were counted with an automated ELISPOT reader (Cellular Technology Ltd., Shaker Heights, Ohio).

Moreover, splenocytes from immunized mice were stimulated with individual peptides (15-mers overlapping by 11 amino acids and spanning the entire lengths of their respective DNA vaccine-encoded Ags) to also assess the breadth of the epitopic response and data are displayed in FIGS. 10-13 and FIG. 18*a*. To better visualize positive T-cell responses for the identification of epitope-containing peptides, ELISpot data from each animal were stacked in bar graph form and expressed as the SUM of the IFNγ+ response per group. Epitope-comprising peptides were considered positive only if they stimulated at least 10 spots on average with an 80% or higher response rate.

Immunization with any of the six HCMV DNA plasmid vaccines were observed to stimulated a diversity of measurable T-cell epitopes; HCMV-gB induced X epitopes, HCMV-gMgN-X, HCMV-gHgL-X, HCMV-gO-C, HCMV-pUL-X, and HCMV-UL83-X. Additionally, immunodominant epitopes were observed in all mice (#5:$GP_{25-39}$ in H-$2^b$ mice and #27:$GP_{151-171}$ in H-$2^d$ mice) and pEBOS (#4:$GP_{19-33}$ in H-$2^b$ mice and #41:$GP_{241-255}$ in H-$2^d$ mice), while pEBOZ stimulated them only in the H-$2^d$ mice (#24:$_{139-153}$, #30:$_{175-189}$, and #66:$_{391-405}$). See FIGS. 10-13 and FIG. 18*a*. Moreover, data for epitope-containing peptides are further characterized in Table 1 in which predicted epitope sequences are displayed and T cell responses were confirmed and de-convoluted by flow cytometry. Total DNA vaccine-induced IFNγ+ responses are reported and are the SUM of the average responses per positively identified epitope—see Table 1 (below)

TABLE 1

| | | | | | | | | Best con. % rank ($H-2^b$) | | |
|---|---|---|---|---|---|---|---|---|---|---|
| Plasmid | CMV | [a] PEP | | | ELISPOT | | FACS | CD8+ | (s0.6) | CD4+ (S28) |
| Vaccine | ag | # | AA# | Peptide Sequence | AVE | ±SEM | T cell | Db | Kb | I-ab |
| pHCMV-gB | gB | 5 | 25-39 | SSSTRGTSATHSHHS | 388 | 140 | 8+ | | | 14.6 |
| | | 7 | 37-51 | HHSSHTTSAAHSRSG | 37 | 35 | 4+ | | | 18.4 |
| | | 26 | 151-165 | RRSYAYIHTTYLLGS | 1,105 | 472 | 8+ | 0.1 | 0.2 | 13.5 |
| | | 28 | 163-177 | LGSNTEYVAPPMWEI | 30 | 16 | 4+ | | | 4.0 |
| | | 51 | 361-375 | AEDSYHFSSAKMTAT | 577 | 430 | 4+ | | 0.1 | 1.2 |
| | | 70 | 415-429 | KYGNVSVFETTGGLV | 183 | 89 | 8+ | | 0.4 | |
| | | 73* | 433-447 | QKIKQKSLVELERLA | 95 | 73 | 8+ | | | |
| | | 74 | 439-453 | SLVELERLANRSSLN | 360 | 146 | 8+ | | | |
| | | 80 | 475-489 | SVHNLVYAQLQFTYD | 1,045 | 169 | 8+ | | 0.2 | |
| | | 88 | 523-537 | INPSAILSAIYNKPI | 53 | 31 | 4+ | | | 20.7 |
| | | 89 | 529-543 | LSAIYNKPIAARFMG | 18 | 13 | 4+ | 0.3 | | 2.5 |
| pHCMV-gHgL | gH | 8 | 43-57 | LNTYGRPIRFLRENT | 38 | 33 | 8+ | | | |
| | | 9 | 49-63 | PIRFLRENTTQCTYN | 26 | 15 | 4+ | | | |
| | | 11 | 61-75 | TYNSSLRNSTVVREN | 776 | 141 | 8+ | 0.1 | | 24.5 |
| | | 12 | 67-81 | RNSTVVRENAISFNF | 72 | 46 | 8+ | | | |
| | | 13 | 73-87 | RENAISFNFFQSYNQ | 94 | 28 | 8+ | 0.1 | 0.1 | |
| | | 15 | 85-99 | YNQYYVFHMPRCLFA | 559 | 231 | 4+ | | | 3.5 |
| | | 16 | 91-105 | FHMPRCLFAGPLAEQ | 419 | 199 | 4+ | | | 6.9 |
| | | 17 | 97-111 | LFAGPLAEQFLNQVD | 261 | 139 | 4+ | | | 25.5 |
| | | 20 | 115-129 | TLERYQQRLNTYALV | 153 | 36 | 8+ | 0.6 | | |
| | | 28 | 163-177 | SIPHVWMPPQTTPHG | 20 | 5 | 4+ | | | 1.2 |
| | | 30 | 175-189 | PHGWKESHTTSGLHR | 2,942 | 81 | 8+ | | | 25.0 |
| | | 42 | 247-261 | MLLIFGHLPRVLFKA | 78 | 58 | 4+ | 0.6 | 0.3 | 27.6 |
| | | 43 | 253-267 | HLPRVLFKAPYQRDN | 24 | 9 | 4+ | | | 26.8 |
| | | 50 | 295-309 | DPDFLDAALDFNYLD | 331 | 187 | 8+/4+ | | 0.5 | |
| | | 51* | 301-315 | AALDFNYLDLSALLR | 307 | 181 | 8+ | | 0.5 | 16.1 |
| | | 57 | 337-351 | RTVEMAFAYALALFA | 340 | 190 | 4+ | | 0.4 | 1.6 |
| | | 58 | 343-357 | FAYALALFAAARQEE | 265 | 157 | 4+ | 0.4 | | 5.2 |
| | | 59 | 349-363 | LFAAARQEEAGAEVS | 27 | 17 | 8+ | | | 12.9 |
| | | 82 | 487-501 | EIFIVETGLCSLAEL | 64 | 31 | 4+ | | | |
| | | 90 | 535-549 | RLTRLFPDATVPATV | 81 | 32 | 8+ | | | 6.5 |
| | | 97 | 577-591 | ESFSALTVSEHVSYV | 51 | 21 | 4+ | | | 15.9 |
| | | 98* | 583-597 | TVSEHVSYVVTNQYL | 10 | 5 | 8+ | | | |
| | | 99 | 589-603 | SYVVTNQYLIKGISY | 17 | 4 | 8+ | 0.1 | | |
| | | 110* | 655-669 | LLEYDDTQGVINIMY | 191 | 83 | 8+ | | | |
| | | 111 | 661-675 | TQGVINIMYMHDSDD | 2,864 | 136 | 8+ | 0.4 | | |
| | | 115 | 685-699 | EVVVSSPRTHYLMLL | 22 | 14 | 4+ | | | 13.1 |
| | | 117 | 697-711 | MLLKNGTVLEVTDVV | 58 | 23 | 4+ | 0.4 | | |
| | | 120 | 715-729 | TDSRLLMMSVYALSA | 14 | 4 | 4+ | | | |
| | | 121 | 721-735 | MMSVYALSAIIGIYL | 32 | 16 | 8+ | | | 7.4 |
| | | 122 | 727-741 | LSAIIGIYLLYRMLK | 13 | 9 | 8+ | 0.5 | 0.2 | |
| | gL | 9 | 49-63 | ELTRRCLLGEVFQGD | 25 | 15 | 4+ | | | |
| | | 11 | 61-75 | QGDKYESWLRPLVNV | 76 | 41 | 4+ | | | 17.4 |
| | | 12 | 67-81 | SWLRPLVNVTGRDGP | 128 | 64 | 4+ | | | |
| | | 15 | 85-99 | LIRYRPVTPEAANSV | 483 | 220 | 4+ | | | 0.1 |
| | | 17 | 97-111 | NSVLLDEAFLDTLAL | 16 | 11 | 4+ | | | |
| | | 19 | 109-123 | LALLYNNPDQLRALL | 186 | 87 | 4+ | | | 19.8 |
| | | 45 | 265-279 | PAHSRYGPQAVDAR | 41 | 24 | 4+ | | | 14.2 |
| pHCMV-UL83 | UL83 | 14 | 79-93 | HTYFTGSEVENVSVN | 130 | 74 | 4+ | | | 11.4 |
| | | 16 | 91-105 | SVNVHNPTGRSICPS | 106 | 46 | 8+/4+ | | | |
| | | 17 | 97-111 | PTGRSICPSQEPMSI | 161 | 127 | 8+ | 0.6 | | |
| | | 18* | 103-117 | CPSQEPMSIYVYALP | 39 | 28 | 8+ | | 0.3 | |
| | | 19 | 109-123 | MSIYVYALPLKMLNI | 427 | 196 | 4+ | 0.3 | 0.1 | 0.4 |
| | | 21 | 121-135 | LNIPSINVHHYPSAA | 192 | 132 | 4+ | | | 16.9 |
| | | 22 | 127-141 | NVHHYPSAAERKHRH | 277 | 178 | 4+ | | | 15.2 |
| | | 29 | 169-183 | TRQQNQWKEPDVYYT | 192 | 115 | 4+ | | | |
| | | 30 | 175-189 | WKEPDVYYTSAFVFP | 216 | 117 | 4+ | | 0.6 | 23.1 |
| | | 31 | 181-195 | YYTEAFVFPTKDVAL | 338 | 161 | 8+/4+ | 0.6 | 0.5 | 4.8 |
| | | 38 | 223-237 | YVKVYLESFCEDVPS | 87 | 50 | 4+ | | | |
| | | 39 | 229-243 | ESFCEDVPSGKLFMH | 117 | 62 | 4+ | | | |
| | | 43 | 253-267 | DLTMTRNPQPEMRPH | 994 | 468 | 8+ | 0.5 | | |
| | | 44* | 259-273 | NPQPFMRPHERNGFT | 190 | 177 | 8+ | | | |
| | | 45 | 265-279 | RPHERNGFTVLCPKN | 150 | 97 | 8+ | | | |
| | | 51 | 301-315 | HFGLLCFKSIPGLSI | 45 | 22 | 4+ | | | 27.0 |
| | | 55 | 325-339 | QIFLEVQAIRETVEL | 34 | 8 | 4+ | | | |

TABLE 1-continued

| Plasmid Vaccine | CMV ag | [a] PEP # | AA# | Peptide Sequence | ELISPOT AVE | ELISPOT ±SEM | FACS T cell | Best con. % rank (H-$2^b$) CD8+ Db | (s0.6) Kb | CD4+ (S28) I-ab |
|---|---|---|---|---|---|---|---|---|---|---|
| pHCMV-UL | UL128 | 7 | 37-51 | NHPPERCYDFKMCNR | 172 | 107 | 8+ | | | |
| | | 8* | 43-57 | CYDFKMCNRFTVALR | 12 | 5 | 8+ | 0.1 | | |
| | | 13 | 73-87 | IRGIVTTMTHSLTRQ | 350 | 199 | 8+ | | | |
| | | 16 | 91-105 | NKLTSCNYNPLYLEA | 1,650 | 230 | 8+ | 0.2 | 0.2 | |
| | | 17* | 97-111 | NYNPLYLEADGRIRC | 454 | 58 | 8+ | | | |
| | | 18 | 103-117 | LEADGRIRCGKVNDK | 443 | 163 | 8+ | | | |
| | | 19 | 109-123 | IRCGKVNDKAQYLLG | 303 | 133 | 8+ | | | |
| | | 20 | 115-129 | NDKAQYLLGAAGSVP | 100 | 52 | 4+ | | | 9.7 |
| | | 21* | 121-135 | LLGAAGSVPYRWINL | 731 | 208 | 8+ | | 0.2 | 24.4 |
| | | 22 | 127-141 | SVPYRWINLEYDKIT | 739 | 202 | 8+ | | 0.2 | |
| | | 23* | 133-147 | INLEYDKITRIVGLD | 65 | 36 | 8+ | | | |
| | | 24 | 139-153 | KITRIVGLDQYLESV | 89 | 50 | 8+ | | | |
| | | 25 | 145-159 | GLDQYLESVKKHKRL | 56 | 32 | 8+ | | | |
| | | 26 | 151-165 | ESVKKHKRLDVCRAK | 11 | 4 | 8+ | | | |
| | | 28 | 163-171 | RAKMGYMLQ | 498 | 206 | 8+ | | | |
| | UL130 | 3 | 13-27 | LLLCAVWATPCLASP | 332 | 146 | 8+/4+ | | | 4.6 |
| | | 4 | 19-33 | WATPCLASPWSTLTA | 104 | 33 | 8+/4+ | | | 22.9 |
| | | 8 | 43-57 | KLTYSKPHDAATFYC | 465 | 169 | 8+/4+ | | | 15.1 |
| | | 9* | 49-63 | PHDAATFYCPFLYPS | 237 | 185 | 8+/4+ | 0.2 | | |
| | | 10 | 55-69 | FYCPFLYPSPPRSPL | 222 | 179 | 8+/4+ | 0.6 | | 0.6 |
| | UL131A | 5 | 25-39 | AEKNDYYRVPHYWDA | 61 | 34 | 4+ | | | |
| | | 6 | 31-45 | YRVPHYWDACSRALP | 223 | 130 | 4+ | | | 16.2 |
| | | 11 | 61-75 | LNYHYDASHGLDNFD | 429 | 220 | 4+ | | | 12.1 |
| | | 20 | 115-129 | PHARSLEFSVRLFAN | 255 | 145 | 8+ | | 0.6 | |
| pHCMV-gMgN | gM | 4 | 19-33 | VFMVLTFVNYSVHLV | 153 | 39 | 8+ | | 0.2 | 22.2 |
| | | 6 | 31-46 | HLVLSNFPHLGYPCV | 31 | 7 | 8+ | 0.5 | 0.4 | 21.7 |
| | | 13 | 73-87 | DSVQLVCYAVFMQLV | 22 | 8 | 8+ | | | |
| | | 17 | 97-111 | VCWIKISMRKDKGMS | 23 | 11 | 8+ | 0.3 | | |
| | | 18* | 103-117 | SMRKDKGMSLNQSTR | 15 | 3 | 8+ | | | |
| | | 26* | 151-165 | GMIAFMAAVHFFCLT | 14 | 4 | 8+ | | 0.3 | 26.2 |
| | | 27 | 157-171 | AAVHFFCLTIFNVSM | 21 | 10 | 8+ | 0.1 | | |
| | | 30 | 175-189 | YRSYKRSLFFFSRLH | 258 | 93 | 8+ | 0.1 | 0.1 | |
| | | 31* | 181-196 | SLFFFSRLHPKLKGT | 57 | 8 | 8+ | 0.1 | 0.1 | 24.4 |
| | | 33 | 193-207 | KGTVQFRTLIVLNLE | 14 | 8 | 4+ | | 0.3 | 17.7 |
| | | 34 | 199-213 | RTLIVNLVEVALGFN | 28 | 12 | 8+ | 0.4 | | |
| | | 39 | 229-243 | FFVRTFHMVLAVFVV | 32 | 15 | 8+ | | | |
| | | 49 | 289-303 | TFLSNEYRTFISWSF | 83 | 38 | 8+/4+ | | | |
| | | 50 | 295-309 | YRTGISWSFGMLFFI | 627 | 441 | 8+ | 0.1 | 0.1 | |
| | gN | 1 | 1-15 | MEWNTLVLGLLVLSV | 472 | 343 | 8+ | | | |
| | | 4 | 19-33 | SNNTSTASTPSPSSS | 33 | 11 | 4+ | | | 2.7 |
| | | 5 | 25-30 | ASTPSPSSSTHTSTT | 67 | 36 | 4+ | | | 16.0 |
| | | 12 | 67-81 | STTHDPNVMRPHAHN | 46 | 14 | 4+ | | | 25.0 |
| | | 13 | 73-87 | NVMRPHAHNDFYKAH | 182 | 48 | 4+ | | | |
| | | 21 | 121-135 | RHCCFQNFTATTTKG | 24 | 10 | 8+ | | | 8.6 |
| pHCMV-gO | gO | 5 | 25-39 | LLSLINCNVLVNSKG | 65 | 47 | 8+ | 0.1 | | |
| | | 48 | 283-297 | PYLSYTTSTAFNVTT | 101 | 65 | 4+ | | | 2.4 |
| | | 51 | 301-315 | YSATAAVTRVATSTT | 43 | 8 | 4+ | | | 12.9 |
| | | 55 | 325-339 | KSIMATQLRDLATWV | 14 | 10 | 8+ | | | |
| | | 56 | 331-345 | QLRDLATWVYTTLRY | 784 | 317 | 8+ | | 0.2 | |
| | | 57* | 337-351 | TWVYTTLRYRNEPFC | 394 | 156 | 8+ | | | |

[a] Epitope-containing peptides were identified by IFNγ ELISPOT (≥10 spots AND ≥ 80% response rate)
All peptides identified by ELISPOT were confirmed by FACS (≥3-5 × $10^4$ CD3+ cells were acquired)
Responding T cells for each epitope-containing peptide were characterized by FACS (expression of CD4 and/or CD8 by CD3+/CD44+/IFNγ+ cells).
Predicted CD8+ epitopes are underlined (best consensus % rank by IEDB) Contigious peptide with shared and/or partial epitope as confirmed by ELISPOT (*)
No H-2b epitopes reported herein have been described (IEBS 70% BLAST)

Regarding fragment of HCMV antigens, preferably the fragments will have the following domains for each of the following HCMV antigens:

HCMV-gB: amino acid region 25-39 (peptide #5); amino acid region 151-165 (peptide #26); amino acid region 151-165 (peptide #26); amino acid region 361-375 (peptide #5=61); amino acid region 439-453 (peptide #74); and/or amino acid region 475-489 (peptide #80);

HCMV-gH: amino acid region 61-75 (peptide #11); amino acid region 85-99 (peptide #15); amino acid region 91-105 (peptide #15); amino acid region 175-189 (peptide #30); amino acid region 661-675 (peptide #111);

HCMV-gL: amino acid region 85-99 (peptide #15);

HCMV-UL83: amino acid region 109-123 (peptide #19); amino acid region 253-267 (peptide #43);

HCMV-UL128: amino acid region 91-105 (peptide #16); amino acid region 97-111 (peptide #17); amino acid region 103-117 (peptide #18); amino acid region 121-135 (peptide #21); amino acid region 127-141 (peptide #22); amino acid region 163-171 (peptide #28);

HCMV-UL130: amino acid region 13-27 (peptide #3); amino acid region 43-57 (peptide #8);

HCMV-UL131A: amino acid region 61-75 (peptide #11);

HCMV-gM: amino acid region 175-189 (peptide #30); amino acid region 295-309 (peptide #50);

HCMV-gN: amino acid region 1-15 (peptide #1); and

HCMV-gO: amino acid region 331-345 (peptide #56); amino acid region 337-351 (peptide #57).

ELISA

To determine sera Ab titers against HCMV gB, gH or gL, Nunc-Immuno MaxiSorp plates (Nunc, Rochester, N.Y.) were coated overnight at 4° C. with recombinant protein (GenScript) at the indicated amounts or BSA (control) diluted in PBS. The next day, plates were washed with PBS, 0.05% Tween 20 (PBS-T), blocked for 1 h with 10% BSA/PBS-T, and incubated overnight at 4° C. with serial dilutions of serum from either human patients or immunized animals. Plates were then washed six times and bound IgG was detected using either goat anti-human IgG (Southern Biotech) or goat-anti mouse IgG (Santa Cruz, Santa Cruz, Calif.), both at a dilution of 1:5,000. Bound enzyme was detected by SigmaFAST™ O-phenylenediamine dihydrochloride (OPD; Sigma-Aldrich), and the optical density was determined at 450 nm on a Biotek (Winooski, Vt.) EL312e reader. The reciprocal endpoint titer was reported as the 10% of maximum OD calculated by curve fitting using the sigmoidal dose-response model with a variable slope in GraphPad Prism (GraphPad Software Inc., La Jolla, Calif.).

Neutralization Assay

Figure 14:
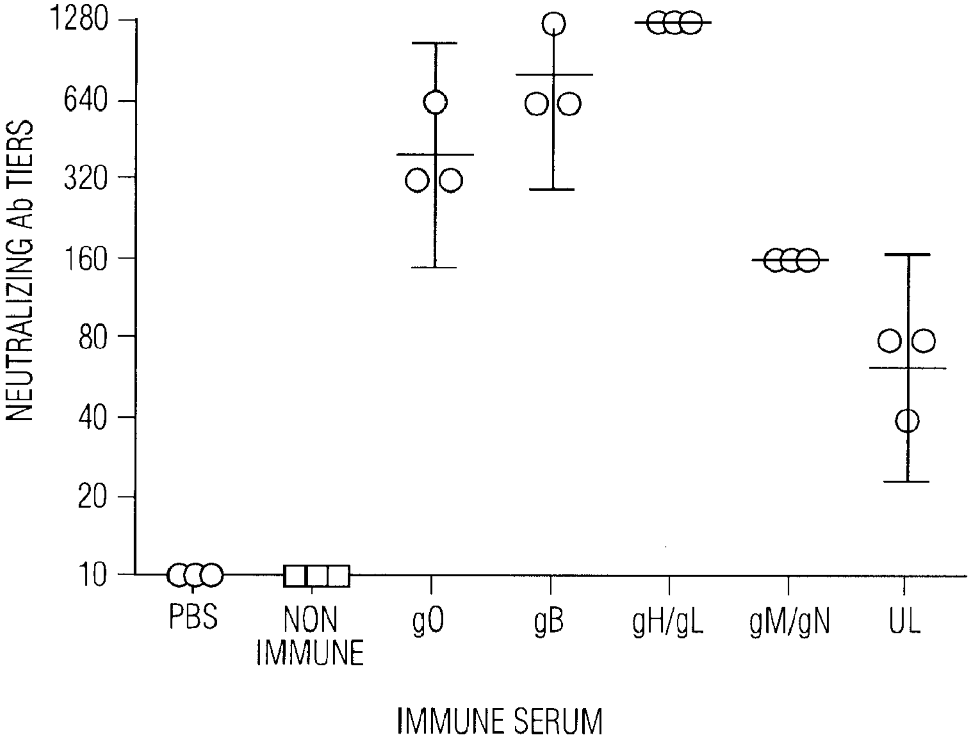
FIG. 14 shows neutralizing antibody titers of mouse serum from mice immunized with HCMV proteins. The data is expressed as a geometric mean of 3 values with 95% CI. Life-extended HFF (human foreskin fibroblasts) cells were used.

Serum samples were collected and pooled from each group of mice (n=5) 7-10 days following each of five to six immunizations (spaced two weeks apart), and then pooled thereafter up to 1 month following the final immunization. Furthermore, serum was collected 6 months following each of the final immunizations (a time point considered to be clinically relevant for long-term Ab responses) and tested along with the pooled-effector sera for the capacity for neutralization of infection with the relevant. Data confirmed a neutralization capacity for gB immunized animals which supports previous data demonstrating its ability to elicit nAbs and protect in some challenge models. However, immunization with the novel gHgL DNA vaccine generated nAb responses that were ~2-4-fold greater than gB immunization. Neutralizing antibody titers were measured using mouse serum from mice immunized with HCMV proteins and life-extended HFF (human foreskin fibroblasts) cells. The data is expressed as a geometric mean of 3 values with 95% CI. The data are shown in FIG. 14.

Interestingly, neither of these levels of neutralization ability was achieved by any other immunogen, including the gMgN, gO, UL128-131A, nor the UL83. Lastly, neutralization levels were relatively stable for each immunogen comparing effector and memory serum collected 6 months following the final immunization. Thus, these data demonstrate that DNA vaccination in combination with EP generated robust B cell responses. Altogether, data herein show that the DNA plasmids were immunogenic in mice and generated robust T and B cell responses.

Immunity to the HCMV gB alone has been demonstrated to completely protective in guinea pigs, but has limited efficacy in the clinic. Thus, we next set out to determine whether their combination with the gB DNA vaccine would enhance HCMV-specific immunity. Mice (n=5/group) were given several doses of the gB plasmid alone, gB+gHgL, or gB+gHgL+pUL, and T and B cell immunity was assessed. Indeed, trivalent formulation of these plasmids induced the highest level of both T and B cell responses. Thus, these data demonstrate that vaccine-induced CMV-specific immunity can be increased by immunization with multi-valent plasmid DNA formulations.

Example 15 a) HSV1 Antigen and Expression in 293T Cells

Using the same strategy as provided in Example 1, above, and the above example related to HCMV, HSV1 antigens were selected and nucleic acid constructs were made. HSV1 antigens selected based on the foregoing are: gB, gH, gL, gC, and gD. Furthermore, combinations as discussed herein were made, including HSV1-gHgL and HSV1-gCgD.

HSV1 gB, gC, and gD were found to be expressed on the surface of transfected cells, showing effective translation, translocation, presentation by cell; moreover, the combined antigens gCgD were found to co-express (data not shown). This was evidenced by MHC class I binding with the aforementioned antigens in serum (1:200 dilution) of animals immunized with the antigens, versus no antigen binding with serum from control (vector only).

Immuization with the same plasmids, above, was found to induce robust antibodies in vivo (data not shown).

b) HSV2 Antigen Expression in 293T Cells

Using the same strategy as provided in Example 1, above, and the above example related to HCMV, HSV2 antigens were selected and nucleic acid constructs were made. HSV2 antigens selected based on the foregoing are: gB, gH, gL, gC, and gD. Furthermore, combinations as discussed herein were made, including HSV2-gHgL and HSV2-gCgD.

HSV2 gB, gC, gD, gH and gL were found to be expressed on the surface of transfected cells, showing effective translation, translocation, presentation by cell; moreover, the combined antigens gCgD and gHgL were found to co-express (data not shown). This was evidenced by MHC class I binding with the aforementioned antigens in serum (1:200 dilution) of animals immunized with the antigens, versus no antigen binding with serum from control (vector only).

c) CeHV1 Antigen Expression in 293T Cells

Using the same strategy as provided in Example 1, above, and the above example related to HCMV, CeHV1 antigens were selected and nucleic acid constructs were made. CeHV1 antigens selected based on the foregoing are: gB, gH, gL, gC, and gD. Furthermore, combinations as discussed herein were made, including CeHV1-gHgL and CeHV1-gCgD.

CeHV1 gB, gC, and gD were found to be expressed on the surface of transfected cells, showing effective translation, translocation, presentation by cell; moreover, the combined antigens gCgD were found to co-express (data not shown). This was evidenced by MHC class I binding with the aforementioned antigens in serum (1:200 dilution) of animals immunized with the antigens, versus no antigen binding with serum from control (vector only).

Immuization with the same plasmids, above, was found to induce robust antibodies in vivo (data not shown).

d) VZV Antigen Expression in 293T Cells

Using the same strategy as provided in Example 1, above, and the above example related to HCMV, VZV antigens were selected and nucleic acid constructs were made. VZV antigens selected based on the foregoing are: gB, gH, gL, gC, gK, gM, gN, gE, and gI. Furthermore, combinations as discussed herein were made, including VZV-gHgL, VZV-gM,gN, and VZV-gEgI.

VZV gB, gH, gL, gC, gK, gM, gN, gE, and gI will be analyzed, as above, for expression on the surface of transfected cells, including combined antigens gHgL, gM,gN, and gEgI. This will evidenced by MHC class T binding with the aforementioned antigens in serum (1:200 dilution) of animals immunized with the antigens, versus no antigen binding being detected with serum from control (vector only).

Immuization with the same plasmids, above, will likely find induction of robust antibodies in vivo (data not shown).

Example 16 Neutralizing Antibody Data

Figure 20A:
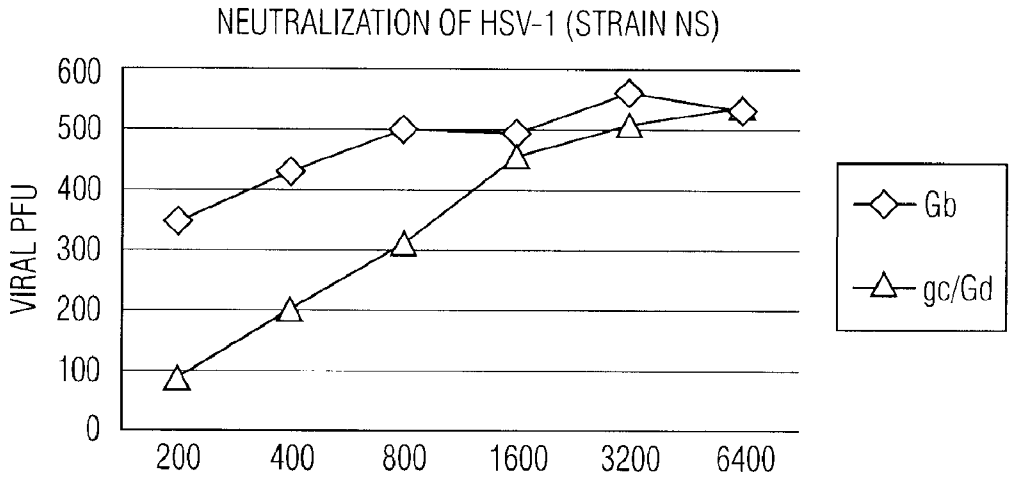
FIG. 20*a-b* shows graphs that depict neutralization levels for a) neutralization against HSV-1 (strain NS) by HSV1-gB and HSV1-gCgD immunized serum; and b) neutralization against HSV-2 (strain MS) by HSV2-gB and HSV2-gCgD immunized serum.
Figure 20B:
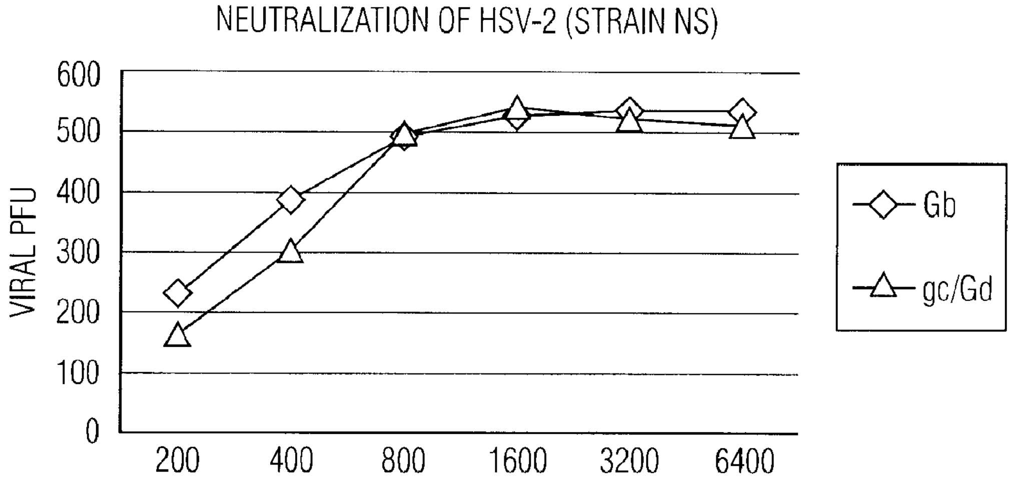

Immunization with either of the plasmids alone exhibited neutralizing activity using Vero cells: for HSV1 either HSV1-gB or HSV1-gCgD, and for HSV2, either HSV2-gB or HSV2-gCgD. The HSV1 plasmids neutralized an HSV1 clinical virus HSV-1 strain NS, and the HSV2 plasmids neutralized an HSV2 clinical virus HSV2 strain MS. See FIGS. 20*a* and 20*b*. A combination of multiple herpes virus family-specific plasmids, further multi-valency will likely further increase the level of neutralization of such herpes virus.

Example 17 HSV1

Permutations of the five listed HSV1 antigens in combinations of 2, 3 4 and 5 may include the following. Two antigens: HSV1-gB, HSV1-gH; HSV1-gB, HSV1-gL; HSV1-gB, HSV1-gC; HSV1-gB, HSV1-gD; HSV1-gH, HSV1-gL; HSV1-gH, HSV1-gC; HSV1-gH, HSV1-gD; HSV1-gL, HSV1-gC; and HSV1-gL, HSV1-gD. Three antigens: HSV1-gB, HSV1-gH, HSV1-gL; HSV1-gB, HSV1-gH, HSV1-gC; HSV1-gB, HSV1-gH, HSV1-gD; HSV1-gB, HSV1-gL, HSV1-gC; HSV1-gB, HSV1-gL, HSV1-gD; HSV1-gB, HSV1-gC, HSV1-gD; HSV1-gH, HSV1-gL, HSV1-gC; HSV1-gH, HSV1-gL, HSV1-gD; and HSV1-gL, HSV1-gC, HSV1-gD. Four antigens: HSV1-gB, HSV1-gH, HSV1-gL, HSV1-gC; HSV1-gB, HSV1-gH, HSV1-gL, HSV1-gD; HSV1-gB, HSV1-gL, HSV1-gC, HSV1-gD; HSV1-gH, HSV1-gL, HSV1-gC, HSV1-gD; and HSV1-gB, HSV1-gH, HSV1-gC, HSV1-gD. Five antigens: HSV1-gB, HSV1-gH, HSV1-gL, HSV1-gC, HSV1-gD.

The permutations may be present on multiple plasmids. Examples of two antigens on one plasmid include: HSV1-gB, HSV1-gH; HSV1-gB, HSV1-gL; HSV1-gB, HSV1-gC; HSV1-gB, HSV1-gD; HSV1-gH, HSV1-gL; HSV1-gH, HSV1-gC; HSV1-gH, HSV1-gD; HSV1-gL, HSV1-gC, HSV1-gL, HSV1-gD. Examples of two antigens on two plasmids include: HSV1-gB, and HSV1-gH; HSV1-gB, and HSV1-gL; HSV1-gB, and HSV1-gC; HSV1-gB, and HSV1-gD; HSV1-gH, and HSV1-gL; HSV1-gH, and HSV1-gC; HSV1-gH, and HSV1-gD; HSV1-gL, and HSV1-gC; and HSV1-gL, and HSV1-gD. Examples of three antigens on one plasmid include: HSV1-gB, HSV1-gH, HSV1-gL; HSV1-gB, HSV1-gH, HSV1-gC; HSV1-gB, HSV1-gH, HSV1-gD; HSV1-gB, HSV1-gL, HSV1-gC; HSV1-gB, HSV1-gL, HSV1-gD; HSV1-gB, HSV1-gC, HSV1-gD; HSV1-gH, HSV1-gL, HSV1-gC; HSV1-gH, HSV1-gL, HSV1-gD; HSV1-gL, HSV1-gC, HSV1-gD. Examples of three antigens on two plasmids include: HSV1-gB, HSV1-gH, and HSV1-gL; HSV1-gB, HSV1-gH, and HSV1-gC; HSV1-gB, HSV1-gH, and HSV1-gD; HSV1-gB, HSV1-gL, and HSV1-gC; HSV1-gB, HSV1-gL, and HSV1-gD; HSV1-gB, HSV1-gC, and HSV1-gD; HSV1-gH, HSV1-gL, and HSV1-gC; HSV1-gH, HSV1-gL, and HSV1-gD; HSV1-gL, HSV1-gC, and HSV1-gD; HSV1-gB, HSV1-gL, and HSV1-gH; HSV1-gB, HSV1-gC, and HSV1-gH; HSV1-gB, HSV1-gD, and HSV1-gH; HSV1-gB, HSV1-gC, and HSV1-gL; HSV1-gB, HSV1-gD, and HSV1-gL; HSV1-gB, HSV1-gD, and HSV1-gC; HSV1-gH, HSV1-gC, and HSV1-gL; HSV1-gH, HSV1-gD, and HSV1-gL; HSV1-gL, HSV1-gD, and HSV1-gC; HSV1-gH, HSV1-gL, and HSV1-gB; HSV1-gH, HSV1-gC, and HSV1-gB; HSV1-gH, HSV1-gD, and HSV1-gB; HSV1-gL, HSV1-gC, and HSV1-gB; HSV1-gL, HSV1-gD, and HSV1-gB; HSV1-gC, HSV1-gD, and HSV1-gB; HSV1-gL, HSV1-gC, and HSV1-gH; HSV1-gL, HSV1-gD, and HSV1-gH; HSV1-gC, HSV1-gD, and HSV1-gL. Examples of three antigens on three plasmids include: HSV1-gB, and HSV1-gH, and HSV1-gL; HSV1-gB, and HSV1-gH, and HSV1-gC; HSV1-gB, and HSV1-gH, and HSV1-gD; HSV1-gB, and HSV1-gL, and HSV1-gC; HSV1-gB, and HSV1-gL, and HSV1-gD; HSV1-gB, and HSV1-gC, and HSV1-gD; HSV1-gH, and HSV1-gL, and HSV1-gC; HSV1-gH, and HSV1-gL, and HSV1-gD; HSV1-gL, and HSV1-gC, and HSV1-gD. Examples of four antigens on one plasmid include: HSV1-gB, HSV1-gH, HSV1-gL, HSV1-gC; HSV1-gB, HSV1-gH, HSV1-gL, HSV1-gD; HSV1-gB, HSV1-gL, HSV1-gC, HSV1-gD; HSV1-gH, HSV1-gL, HSV1-gC, HSV1-gD; HSV1-gB, HSV1-gH, HSV1-gC, HSV1-gD. Examples of four antigens on two plasmids include: HSV1-gB, and HSV1-gH, HSV1-gL, HSV1-gC; HSV1-gB, and HSV1-gH, HSV1-gL, HSV1-gD; HSV1-gB, and HSV1-gL, HSV1-gC, HSV1-gD; HSV1-gH, and HSV1-gL, HSV1-gC, HSV1-gD; HSV1-gB, and HSV1-gH, HSV1-gC, HSV1-gD; HSV1-gB, HSV1-gH, and HSV1-gL, HSV1-gC; HSV1-gB, HSV1-gH, and HSV1-gL, HSV1-gD; HSV1-gB, HSV1-gL, and HSV1-gC, HSV1-gD; HSV1-gH, HSV1-gL, and HSV1-gC, HSV1-gD; HSV1-gB, HSV1-gH, and HSV1-gC, HSV1-gD; HSV1-gB, HSV1-gH, HSV1-gL, and HSV1-gC; HSV1-gB, HSV1-gH, HSV1-gL, and HSV1-gD; HSV1-gB, HSV1-gL, HSV1-gC, and HSV1-gD; HSV1-gH, HSV1-gL, HSV1-gC, and HSV1-gD; HSV1-gB, HSV1-gH, HSV1-gC, and HSV1-gD; HSV1-gH, and HSV1-gB, HSV1-gL, HSV1-gC; HSV1-gH, and HSV1-gB, HSV1-gL, HSV1-gD; HSV1-gL, and HSV1-gB, HSV1-gC, HSV1-gD; HSV1-gL, and HSV1-gH, HSV1-gC, HSV1-gD; HSV1-gH, and HSV1-gB, HSV1-gC, HSV1-gD; HSV1-gH, HSV1-gB, HSV1-gL, and HSV1-gC; HSV1-gH, HSV1-gB, HSV1-gL, and HSV1-gD; HSV1-gL, HSV1-gB, HSV1-gC, and HSV1-gD; HSV1-gL, HSV1-gH, HSV1-gC, and HSV1-gD; HSV1-gH, HSV1-gB, HSV1-gC, and HSV1-gD; HSV1-gL, and HSV1-gB, HSV1-gH, HSV1-gC; HSV1-gL, and HSV1-gB, HSV1-gH, HSV1-gD; HSV1-gC, and HSV1-gB, HSV1-gL, HSV1-gD; HSV1-gC, and HSV1-gH, HSV1-gL, HSV1-gD; HSV1-gC, and HSV1-gB, HSV1-gH, HSV1-gD; HSV1-gL, HSV1-gB, and HSV1-gH, HSV1-gC; HSV1-gL, HSV1-gB, and HSV1-gH, HSV1-gD; HSV1-gC, HSV1-gB, and HSV1-gL, HSV1-gD; HSV1-gC, HSV1-gH, and HSV1-gL, HSV1-gD; HSV1-gC, HSV1-gB, and HSV1-gH, HSV1-gD; Examples of four antigens on three plasmids include: HSV1-gB, and HSV1-gH, and HSV1-gL, HSV1-gC; HSV1-gB, and HSV1-gH, and HSV1-gL, HSV1-gD; HSV1-gB, and HSV1-gL, and HSV1-gC, HSV1-gD; HSV1-gH, and HSV1-gL, and HSV1-gC, HSV1-gD; HSV1-gB, and HSV1-gH, and HSV1-gC, HSV1-gD; HSV1-gB, and HSV1-gH, HSV1-gL, and HSV1-gC, HSV1-gB, and HSV1-gH, HSV1-gL, and HSV1-gD, HSV1-gB, and HSV1-gL, HSV1-gC, and HSV1-gD; HSV1-gH, and HSV1-gL, HSV1-gC, and HSV1-gD, HSV1-gB, and HSV1-gH, HSV1-gC, and HSV1-gD, HSV1-gB HSV1-gC, and HSV1-gH, and HSV1-gL; HSV1-gB, HSV1-gD, and HSV1-gH, and HSV1-gL; HSV1-gB HSV1-gD, and HSV1-gL, and HSV1-gC; HSV1-gH HSV1-gD, and HSV1-gL, and HSV1-gC; HSV1-gB HSV1-gD, and HSV1-gH, and HSV1-gC. Examples of four antigens on four plasmids include: HSV1-gB, HSV1-gH, HSV1-gL, HSV1-gC. Examples of four antigens on five plasmids include: HSV1-gB, HSV1-gH, HSV1-gL, HSV1-gC, HSV1-gD. Experiments detecting localization and intracellular antigen transport showed that as in the case of HCMV, the co-expression of gH and gL in a cell resulted in a transport to the cell surface which does not occur when either protein is expressed in the absence of the other.

Example 18 HSV2

Permutations of the five listed HSV2 antigens in combinations of 2, 3 4 and 5 may include the following. Two antigens: HSV2-gB, HSV2-gH; HSV2-gB, HSV2-gL; HSV2-gB, HSV2-gC; HSV2-gB, HSV2-gD; HSV2-gH, HSV2-gL; HSV2-gH, HSV2-gC; HSV2-gH, HSV2-gD; HSV2-gL, HSV2-gC; and HSV2-gL, HSV2-gD. Three antigens: HSV2-gB, HSV2-gH, HSV2-gL; HSV2-gB, HSV2-gH, HSV2-gC; HSV2-gB, HSV2-gH, HSV2-gD; HSV2-gB, HSV2-gL, HSV2-gC; HSV2-gB, HSV2-gL, HSV2-gD; HSV2-gB, HSV2-gC, HSV2-gD; HSV2-gH, HSV2-gL, HSV2-gC; HSV2-gH, HSV2-gL, HSV2-gD; and HSV2-gL, HSV2-gC, HSV2-gD. Four antigens: HSV2-gB, HSV2-gH, HSV2-gL, HSV2-gC; HSV2-gB, HSV2-gH, HSV2-gL, HSV2-gD; HSV2-gB, HSV2-gL, HSV2-gC, HSV2-gD; HSV2-gH, HSV2-gL, HSV2-gC, HSV2-gD; and HSV2-gB, HSV2-gH, HSV2-gC, HSV2-gD. Five antigens: HSV2-gB, HSV2-gH, HSV2-gL, HSV2-gC, HSV2-gD.

The permutations may be present on multiple plasmids. Examples of two antigens on one plasmid include: HSV2-gB, HSV2-gH; HSV2-gB, HSV2-gL; HSV2-gB, HSV2-gC; HSV2-gB, HSV2-gD; HSV2-gH, HSV2-gL; HSV2-gH, HSV2-gC; HSV2-gH, HSV2-gD; HSV2-gL, HSV2-gC, HSV2-gL, HSV2-gD. Examples of two antigens on two plasmids include: HSV2-gB, and HSV2-gH; HSV2-gB, and HSV2-gL; HSV2-gB, and HSV2-gC; HSV2-gB, and HSV2-gD; HSV2-gH, and HSV2-gL; HSV2-gH, and HSV2-gC; HSV2-gH, and HSV2-gD; HSV2-gL, and HSV2-gC; and HSV2-gL, and HSV2-gD. Examples of three antigens on one plasmid include: HSV2-gB, HSV2-gH, HSV2-gL; HSV2-gB, HSV2-gH, HSV2-gC; HSV2-gB, HSV2-gH, HSV2-gD; HSV2-gB, HSV2-gL, HSV2-gC; HSV2-gB, HSV2-gL, HSV2-gD; HSV2-gB, HSV2-gC, HSV2-gD; HSV2-gH, HSV2-gL, HSV2-gC; HSV2-gH, HSV2-gL, HSV2-gD; HSV2-gL, HSV2-gC, HSV2-gD. Examples of three antigens on two plasmids include: HSV2-gB, HSV2-gH, and HSV2-gL; HSV2-gB, HSV2-gH, and HSV2-gC; HSV2-gB, HSV2-gH, and HSV2-gD; HSV2-gB, HSV2-gL, and HSV2-gC; HSV2-gB, HSV2-gL, and HSV2-gD; HSV2-gB, HSV2-gC, and HSV2-gD; HSV2-gH, HSV2-gL, and HSV2-gC; HSV2-gH, HSV2-gL, and HSV2-gD; HSV2-gL, HSV2-gC, and HSV2-gD; HSV2-gB, HSV2-gL, and HSV2-gH; HSV2-gB, HSV2-gC, and HSV2-gH; HSV2-gB, HSV2-gD, and HSV2-gH; HSV2-gB, HSV2-gC, and HSV2-gL; HSV2-gB, HSV2-gD, and HSV2-gL; HSV2-gB, HSV2-gD, and HSV2-gC; HSV2-gH, HSV2-gC, and HSV2-gL; HSV2-gH, HSV2-gD, and HSV2-gL; HSV2-gL, HSV2-gD, and HSV2-gC; HSV2-gH, HSV2-gL, and HSV2-gB; HSV2-gH, HSV2-gC, and HSV2-gB; HSV2-gH, HSV2-gD, and HSV2-gB; HSV2-gL, HSV2-gC, and HSV2-gB; HSV2-gL, HSV2-gD, and HSV2-gB; HSV2-gC, HSV2-gD, and HSV2-gB; HSV2-gL, HSV2-gC, and HSV2-gH; HSV2-gL, HSV2-gD, and HSV2-gH; HSV2-gC, HSV2-gD, and HSV2-gL. Examples of three antigens on three plasmids include: HSV2-gB, and HSV2-gH, and HSV2-gL; HSV2-gB, and HSV2-gH, and HSV2-gC; HSV2-gB, and HSV2-gH, and HSV2-gD; HSV2-gB, and HSV2-gL, and HSV2-gC; HSV2-gB, and HSV2-gL, and HSV2-gD; HSV2-gB, and HSV2-gC, and HSV2-gD; HSV2-gH, and HSV2-gL, and HSV2-gC; HSV2-gH, and HSV2-gL, and HSV2-gD; HSV2-gL, and HSV2-gC, and HSV2-gD. Examples of four antigens on one plasmid include: HSV2-gB, HSV2-gH, HSV2-gL, HSV2-gC; HSV2-gB, HSV2-gH, HSV2-gL, HSV2-gD; HSV2-gB, HSV2-gL, HSV2-gC, HSV2-gD; HSV2-gH, HSV2-gL, HSV2-gC, HSV2-gD; HSV2-gB, HSV2-gH, HSV2-gC, HSV2-gD. Examples of four antigens on two plasmids include: HSV2-gB, and HSV2-gH, HSV2-gL, HSV2-gC; HSV2-gB, and HSV2-gH, HSV2-gL, HSV2-gD; HSV2-gB, and HSV2-gL, HSV2-gC, HSV2-gD; HSV2-gH, and HSV2-gL, HSV2-gC, HSV2-gD; HSV2-gB, and HSV2-gH, HSV2-gC, HSV2-gD; HSV2-gB, HSV2-gH, and HSV2-gL, HSV2-gC;

HSV2-gB, HSV2-gH, and HSV2-gL, HSV2-gD; HSV2-gB, HSV2-gL, and HSV2-gC, HSV2-gD; HSV2-gH, HSV2-gL, and HSV2-gC, HSV2-gD; HSV2-gB, HSV2-gH, and HSV2-gC, HSV2-gD; HSV2-gB, HSV2-gH, HSV2-gL, and HSV2-gC; HSV2-gB, HSV2-gH, HSV2-gL, and HSV2-gD; HSV2-gB, HSV2-gL, HSV2-gC, and HSV2-gD; HSV2-gH, HSV2-gL, HSV2-gC, and HSV2-gD; HSV2-gB, HSV2-gH, HSV2-gC, and HSV2-gD; HSV2-gH, and HSV2-gB, HSV2-gL, HSV2-gC; HSV2-gH, and HSV2-gB, HSV2-gL, HSV2-gD; HSV2-gL, and HSV2-gB, HSV2-gC, HSV2-gD; HSV2-gL, and HSV2-gH, HSV2-gC, HSV2-gD; HSV2-gH, and HSV2-gB, HSV2-gC, HSV2-gD; HSV2-gH, HSV2-gB, HSV2-gL, and HSV2-gC; HSV2-gH, HSV2-gB, HSV2-gL, and HSV2-gD; HSV2-gL, HSV2-gB, HSV2-gC, and HSV2-gD; HSV2-gL, HSV2-gH, HSV2-gC, and HSV2-gD; HSV2-gH, HSV2-gB, HSV2-gC, and HSV2-gD; HSV2-gL, and HSV2-gB, HSV2-gH, HSV2-gC; HSV2-gL, and HSV2-gB, HSV2-gH, HSV2-gD; HSV2-gC, and HSV2-gB, HSV2-gL, HSV2-gD; HSV2-gC, and HSV2-gH, HSV2-gL, HSV2-gD; HSV2-gC, and HSV2-gB, HSV2-gH, HSV2-gD; HSV2-gL, HSV2-gB, and HSV2-gH, HSV2-gC; HSV2-gL, HSV2-gB, and HSV2-gH, HSV2-gD; HSV2-gC, HSV2-gB, and HSV2-gL, HSV2-gD; HSV2-gC, HSV2-gH, and HSV2-gL, HSV2-gD; HSV2-gC, HSV2-gB, and HSV2-gH, HSV2-gD; Examples of four antigens on three plasmids include: HSV2-gB, and HSV2-gH, and HSV2-gL, HSV2-gC; HSV2-gB, and HSV2-gH, and HSV2-gL, HSV2-gD; HSV2-gB, and HSV2-gL, and HSV2-gC, HSV2-gD; HSV2-gH, and HSV2-gL, and HSV2-gC, HSV2-gD; HSV2-gB, and HSV2-gH, and HSV2-gC, HSV2-gD; HSV2-gB, and HSV2-gH, HSV2-gL, and HSV2-gC, HSV2-gB, and HSV2-gH, HSV2-gL, and HSV2-gD, HSV2-gB, and HSV2-gL, HSV2-gC, and HSV2-gD; HSV2-gH, and HSV2-gL, HSV2-gC, and HSV2-gD, HSV2-gB, and HSV2-gH, HSV2-gC, and HSV2-gD, HSV2-gB HSV2-gC, and HSV2-gH, and HSV2-gL; HSV2-gB, HSV2-gD, and HSV2-gH, and HSV2-gL; HSV2-gB HSV2-gD, and HSV2-gL, and HSV2-gC; HSV2-gH HSV2-gD, and HSV2-gL, and HSV2-gC; HSV2-gB HSV2-gD, and HSV2-gH, and HSV2-gC. Examples of four antigens on four plasmids include: HSV2-gB, HSV2-gH, HSV2-gL, HSV2-gC. Examples of four antigens on five plasmids include: HSV2-gB, HSV2-gH, HSV2-gL, HSV2-gC, HSV2-gD.

Example 19 VZV

Permutations of the five listed VZV antigens in combinations of 2, 3 4 and 5 may include the following. Two antigens: VZV-gB, VZV-gH; VZV-gB, VZV-gL; VZV-gB, VZV-gM; VZV-gB, VZV-gN; VZV-gH, VZV-gL; VZV-gH, VZV-gM; VZV-gH, VZV-gN; VZV-gL, VZV-gM; and VZV-gL, VZV-gN. Three antigens: VZV-gB, VZV-gH, VZV-gL; VZV-gB, VZV-gH, VZV-gM; VZV-gB, VZV-gH, VZV-gN; VZV-gB, VZV-gL, VZV-gM; VZV-gB, VZV-gL, VZV-gN; VZV-gB, VZV-gM, VZV-gN; VZV-gH, VZV-gL, VZV-gM; VZV-gH, VZV-gL, VZV-gN; and VZV-gL, VZV-gM, VZV-gN. Four antigens: VZV-gB, VZV-gH, VZV-gL, VZV-gM; VZV-gB, VZV-gH, VZV-gL, VZV-gN; VZV-gB, VZV-gL, VZV-gM, VZV-gN; VZV-gH, VZV-gL, VZV-gM, VZV-gN; and VZV-gB, VZV-gH, VZV-gM, VZV-gN. Five antigens: VZV-gB, VZV-gH, VZV-gL, VZV-gM, VZV-gN.

The permutations may be present on multiple plasmids. Examples of two antigens on one plasmid include: VZV-gB, VZV-gH; VZV-gB, VZV-gL; VZV-gB, VZV-gM; VZV-gB, VZV-gN; VZV-gH, VZV-gL; VZV-gH, VZV-gM; VZV-gH, VZV-gN; VZV-gL, VZV-gM, VZV-gL, VZV-gN. Examples of two antigens on two plasmids include: VZV-gB, and VZV-gH; VZV-gB, and VZV-gL; VZV-gB, and VZV-gM; VZV-gB, and VZV-gN; VZV-gH, and VZV-gL; VZV-gH, and VZV-gM; VZV-gH, and VZV-gN; VZV-gL, and VZV-gM; and VZV-gL, and VZV-gN. Examples of three antigens on one plasmid include: VZV-gB, VZV-gH, VZV-gL; VZV-gB, VZV-gH, VZV-gM; VZV-gB, VZV-gH, VZV-gN; VZV-gB, VZV-gL, VZV-gM; VZV-gB, VZV-gL, VZV-gN; VZV-gB, VZV-gM, VZV-gN; VZV-gH, VZV-gL, VZV-gM; VZV-gH, VZV-gL, VZV-gN; VZV-gL, VZV-gM, VZV-gN. Examples of three antigens on two plasmids include: VZV-gB, VZV-gH, and VZV-gL; VZV-gB, VZV-gH, and VZV-gM; VZV-gB, VZV-gH, and VZV-gN; VZV-gB, VZV-gL, and VZV-gM; VZV-gB, VZV-gL, and VZV-gN; VZV-gB, VZV-gM, and VZV-gN; VZV-gH, VZV-gL, and VZV-gM; VZV-gH, VZV-gL, and VZV-gN; VZV-gL, VZV-gM, and VZV-gN; VZV-gB, VZV-gL, and VZV-gH; VZV-gB, VZV-gM, and VZV-gH; VZV-gB, VZV-gN, and VZV-gH; VZV-gB, VZV-gM, and VZV-gL; VZV-gB, VZV-gN, and VZV-gL; VZV-gB, VZV-gN, and VZV-gM; VZV-gH, VZV-gM, and VZV-gL; VZV-gH, VZV-gN, and VZV-gL; VZV-gL, VZV-gN, and VZV-gM; VZV-gH, VZV-gL, and VZV-gB; VZV-gH, VZV-gM, and VZV-gB; VZV-gH, VZV-gN, and VZV-gB; VZV-gL, VZV-gM, and VZV-gB; VZV-gL, VZV-gN, and VZV-gB; VZV-gM, VZV-gN, and VZV-gB; VZV-gL, VZV-gM, and VZV-gH; VZV-gL, VZV-gN, and VZV-gH; VZV-gM, VZV-gN, and VZV-gL. Examples of three antigens on three plasmids include: VZV-gB, and VZV-gH, and VZV-gL; VZV-gB, and VZV-gH, and VZV-gM; VZV-gB, and VZV-gH, and VZV-gN; VZV-gB, and VZV-gL, and VZV-gM; VZV-gB, and VZV-gL, and VZV-gN; VZV-gB, and VZV-gM, and VZV-gN; VZV-gH, and VZV-gL, and VZV-gM; VZV-gH, and VZV-gL, and VZV-gN; VZV-gL, and VZV-gM, and VZV-gN. Examples of four antigens on one plasmid include: VZV-gB, VZV-gH, VZV-gL, VZV-gM; VZV-gB, VZV-gH, VZV-gL, VZV-gN; VZV-gB, VZV-gL, VZV-gM, VZV-gN; VZV-gH, VZV-gL, VZV-gM, VZV-gN; VZV-gB, VZV-gH, VZV-gM, VZV-gN. Examples of four antigens on two plasmids include: VZV-gB, and VZV-gH, VZV-gL, VZV-gM; VZV-gB, and VZV-gH, VZV-gL, VZV-gN; VZV-gB, and VZV-gL, VZV-gM, VZV-gN; VZV-gH, and VZV-gL, VZV-gM, VZV-gN; VZV-gB, and VZV-gH, VZV-gM, VZV-gN; VZV-gB, VZV-gH, and VZV-gL, VZV-gM; VZV-gB, VZV-gH, and VZV-gL, VZV-gN; VZV-gB, VZV-gL, and VZV-gM, VZV-gN; VZV-gH, VZV-gL, and VZV-gM, VZV-gN; VZV-gB, VZV-gH, and VZV-gM, VZV-gN; VZV-gB, VZV-gH, VZV-gL, and VZV-gM; VZV-gB, VZV-gH, VZV-gL, and VZV-gN; VZV-gB, VZV-gL, VZV-gM, and VZV-gN; VZV-gH, VZV-gL, VZV-gM, and VZV-gN; VZV-gB, VZV-gH, VZV-gM, and VZV-gN; VZV-gH, and VZV-gB, VZV-gL, VZV-gM; VZV-gH, and VZV-gB, VZV-gL, VZV-gN; VZV-gL, and VZV-gB, VZV-gM, VZV-gN; VZV-gL, and VZV-gH, VZV-gM, VZV-gN; VZV-gH, and VZV-gB, VZV-gM, VZV-gN; VZV-gH, VZV-gB, VZV-gL, and VZV-gM; VZV-gH, VZV-gB, VZV-gL, and VZV-gN; VZV-gL, VZV-gB, VZV-gM, and VZV-gN; VZV-gL, VZV-gH, VZV-gM, and VZV-gN; VZV-gH, VZV-gB, VZV-gM, and VZV-gN; VZV-gL, and VZV-gB, VZV-gH, VZV-gM; VZV-gL, and VZV-gB, VZV-gH, VZV-gN; VZV-gM, and VZV-gB, VZV-gL, VZV-gN; VZV-gM, and VZV-gH, VZV-gL, VZV-gN; VZV-gM, and VZV-gB, VZV-gH, VZV-gN; VZV-gL, VZV-gB, and VZV-gH, VZV-gM; VZV-gL, VZV-gB, and VZV-gH, VZV-gN; VZV-gM, VZV-gB, and VZV-gL, VZV-gN; VZV-gM, VZV-gH, and VZV-gL, VZV-gN; VZV-gM, VZV-gB, and VZV-gH, VZV-gN; Examples of four antigens on three plasmids include: VZV-gB, and VZV-gH, and VZV-gL, VZV-gM; VZV-gB, and VZV-gH, and VZV-gL, VZV-gN; VZV-gB, and VZV-gL, and VZV-gM, VZV-gN; VZV-gH, and VZV-gL, and VZV-gM, VZV-gN; VZV-gB, and VZV-gH, and VZV-gM, VZV-gN; VZV-gB, and VZV-gH, VZV-gL, and VZV-gM, VZV-gB, and VZV-gH, VZV-gL, and VZV-gN, VZV-gB, and VZV-gL, VZV-gM, and VZV-gN; VZV-gH, and VZV-gL, VZV-gM, and VZV-gN, VZV-gB, and VZV-gH, VZV-gM, and VZV-gN, VZV-gB VZV-gM, and VZV-gH, and VZV-gL; VZV-gB, VZV-gN, and VZV-gH, and VZV-gL; VZV-gB VZV-gN, and VZV-gL, and VZV-gM; VZV-gH VZV-gN, and VZV-gL, and VZV-gM; VZV-gB VZV-gN, and VZV-gH, and VZV-gM. Examples of four antigens on four plasmids include: VZV-gB, VZV-gH, VZV-gL, VZV-gM. Examples of four antigens on five plasmids include: VZV-gB, VZV-gH, VZV-gL, VZV-gM, VZV-gN.

The invention claimed is:

1. A nucleic acid molecule comprising a coding sequence for a herpes virus antigen encoding one or more proteins selected from the group consisting of:

a protein comprising VZV-gH (N-terminal region up to position 841 of SEQ ID NO:99);

a protein comprising VZV-gL (C-terminal region from position 849 of SEQ ID NO:99);

a protein comprising VZV-gE (N-terminal region up to position 623 of SEQ ID NO:109);

a protein comprising VZV-gI (C-terminal region from position 631 of SEQ ID NO:109); and a protein comprising SEQ ID NO:111.

2. The nucleic acid molecule of claim 1, wherein the nucleic acid molecule further comprises an additional nucleotide sequence that encodes a different herpes virus antigen selected from the group consisting of: HCMV gB, HCMV gM, HCMV gN, HCMV gH, HCMV gL, HCMV gO, HCMV-UL131a, HCMV-UL130, HCMV-UL128, HCMV-UL83, HSV1-gB, HSV1-gH, HSV1-gL, HSV1-gC, HSV1-gD, HSV2-gB, HSV2-gH, HSV2-gL, HSV2-gC, HSV2-gD, VZV-gB, VZV-gH, VZV-gL, VZV-gM, VZV-gN, VZV-gE, VZV-gI, VZV-gC, VZV-gK, CeHV1-gB, CeHV1-gH, CeHV1-gL, CeHV1-gC, and CeHV1-gD.

3. A nucleic acid molecule comprising a coding sequence for a herpes virus antigen selected from the group consisting of:

a nucleotide sequence comprising SEQ ID NO:98; a nucleotide sequence that is at least 95% homologous to SEQ ID NO:98;

a nucleotide sequence comprising nucleotides 13-2535 of SEQ ID NO:100, encoding VZV-gH; a nucleotide sequence that is at least 95% homologous to nucleotides 13-2535 of SEQ ID NO:100, encoding VZV-gH;

a nucleotide sequence comprising nucleotides 2557-3033 of SEQ ID NO:100, encoding VZV-gL; a nucleotide sequence that is at least 95% homologous to nucleotides 2557-3033 of SEQ ID NO:100, encoding VZV-gL;

a nucleotide sequence comprising nucleotides 13-1317 of SEQ ID NO:102, encoding VZV-gM; a nucleotide sequence that is at least 95% homologous to nucleotides 13-1317 of SEQ ID NO:102, encoding VZV-gM;

a nucleotide sequence comprising nucleotides 1339-1599 of SEQ ID NO:102, encoding VZV-gN; a nucleotide sequence that is at least 95% homologous to nucleotides 1339-1599 of SEQ ID NO:102, encoding VZV-gN;

a nucleotide sequence comprising nucleotides 13-1881 of SEQ ID NO:110, encoding VZV-gE; a nucleotide sequence that is at least 95% homologous to nucleotides 13-1881 of SEQ ID NO:110, encoding VZV-gE;

a nucleotide sequence comprising nucleotides 1903-2964 of SEQ ID NO:110, encoding VZV-gI; a nucleotide sequence that is at least 95% homologous to nucleotides 1903-2964 of SEQ ID NO:110, encoding VZV-gI;

a nucleotide sequence comprising SEQ ID NO:112; a nucleotide sequence that is at least 95% homologous to SEQ ID NO:112;

a nucleotide sequence comprising SEQ ID NO:114; and a nucleotide sequence that is at least 95% homologous to SEQ ID NO:114.

4. The nucleic acid molecule of claim 3, comprising one or more nucleotide sequences selected from the group consisting of: SEQ ID NO:98; a nucleotide sequence comprising nucleotides 13-2535 of SEQ ID NO:100, encoding VZV-gH; a nucleotide sequence comprising nucleotides 2557-3033 of SEQ ID NO:100, encoding VZV-gL; a nucleotide sequence comprising nucleotides 13-1317 of SEQ ID NO:102, encoding VZV-gM; a nucleotide sequence comprising nucleotides 1339-1599 of SEQ ID NO:102, encoding VZV-gN a nucleotide sequence comprising nucleotides 13-1881 of SEQ ID NO:110, encoding VZV-gE; a nucleotide sequence comprising nucleotides 1903-2964 of SEQ ID NO:110, encoding VZV-gI; SEQ ID NO:112; and SEQ ID NO:114.

5. The nucleic acid molecule of claim 4, wherein the nucleic acid molecule is a DNA plasmid.

6. The nucleic acid molecule of claim 3, wherein the nucleic acid molecule further comprises an additional nucleotide sequence that encodes a different herpes virus antigen selected from the group consisting of: HCMV gB, HCMV gM, HCMV gN, HCMV gH, HCMV gL, HCMV gO, HCMV-UL131a, HCMV-UL130, HCMV-UL128, HCMV-UL83, HSV1-gB, HSV1-gH, HSV1-gL, HSV1-gC, HSV1-gD, HSV2-gB, HSV2-gH, HSV2-gL, HSV2-gC, HSV2-gD, VZV-gB, VZV-gH, VZV-gL, VZV-gM, VZV-gN, VZV-gE, VZV-gI, VZV-gC, VZV-gK, CeHV1-gB, CeHV1-gH, CeHV1-gL, CeHV1-gC, and CeHV1-gD.

7. The nucleic acid molecule of claim 6, wherein the nucleic acid molecule comprises a coding sequence for a VZV antigen, and wherein the additional nucleotide sequence encodes a herpes virus antigen selected from VZV-gB, VZV-gH, VZV-gL, VZV-gM, VZV-gN, VZV-gE, VZV-gI, VZV-gC, or VZV-gK.

8. The nucleic acid molecule of claim 3, wherein the nucleic acid molecule is a plasmid.

9. The nucleic acid molecule of claim 3, wherein the nucleic acid molecule is an expression vector, and the coding sequence is operably linked to regulatory elements.

10. The nucleic acid molecule of claim 3, wherein the nucleic acid molecule is incorporated into a viral particle.

11. A composition comprising one or more nucleic acid molecules of claim 3.

12. A method of inducing an immune response against a herpes virus antigen comprising administering a nucleic acid molecule of claim 3 to an individual.

13. A method of protecting an individual from herpes virus infection comprising administering a nucleic acid molecule of claim 3 to an individual.

14. A method of protecting an individual who has been diagnosed with herpes virus infection comprising administering a nucleic acid molecule of claim 3 to an individual.

15. A protein selected from the group consisting of:

a protein comprising VZV-gH (N-terminal region up to position 841 of SEQ ID NO:99);

a protein comprising VZV-gL (C-terminal region from position 849 of SEQ ID NO:99);

a protein comprising VZV-gE (N-terminal region up to position 623 of SEQ ID NO:109);

a protein comprising VZV-gI (C-terminal region from position 631 of SEQ ID NO:109); and a protein comprising SEQ ID NO:111.

16. A method of inducing an immune response against a herpes virus infection comprising delivering to an individual a protein of claim 15.

17. A method of treating an individual who has been diagnosed with herpes virus infection comprising delivering to said individual a protein of claim 15.

18. The nucleic acid molecule of claim 1, wherein the nucleic acid molecule is a plasmid.

19. The nucleic acid molecule of claim 1, wherein the nucleic acid molecule is an expression vector, and the coding sequences encoding said one or more proteins are operably linked to regulatory elements.

20. A composition comprising a nucleic acid molecule of claim 1.

* * * * *

SEQUENCE LISTING

```
<160> NUMBER OF SEQ ID NOS: 114

<210> SEQ ID NO 1
<211> LENGTH: 2724
<212> TYPE: DNA
<213> ORGANISM: Artificial Sequence
<220> FEATURE:
<223> OTHER INFORMATION: gB consensus nucleic acid sequence
<220> FEATURE:
<221> NAME/KEY: misc_feature
<222> LOCATION: (1)..(3)
<223> OTHER INFORMATION: n is a, c, g, or t
```

-continued

<400> SEQUENCE: 1

```
nnngagagca gaatctggtg cctggtcgtg tgcgtgaacc tgtgcatcgt gtgcctggga     60
gccgccgtgt ccagcagcag cacccggggc acaagcgcca cacacagcca ccacagcagc    120
cacaccacca gcgccgccca cagccggagc ggaagcgtga gcagccagcg ggtgaccagc    180
agcgaggccg tgtcccaccg ggccaacgag acaatctaca acaccaccct gaagtacggc    240
gacgtcgtgg gagtgaacac caccaagtac ccctacagag tgtgcagcat ggcccagggc    300
accgacctga tcagattcga gcggaacatc gtgtgtacca gcatgaagcc catcaacgag    360
gacctggacg agggcatcat ggtggtgtac aagagaaaca tcgtggccca caccttcaaa    420
gtgcgggtgt accagaaggt gctgaccttc cggcggagct acgcctacat ccacaccacc    480
tacctgctgg gcagcaacac cgagtacgtg gcccctccca tgtgggagat ccaccacatc    540
aacagccaca gccagtgcta cagcagctac agccgcgtga tcgccggcac cgtgttcgtg    600
gcctaccacc gggacagcta cgagaacaag accatgcagc tgatgcccga cgactacagc    660
aacacccaca gcaccagata cgtgaccgtg aaggaccagt ggcacagccg gggaagcacc    720
tggctgtaca gagagacatg caacctgaac tgcatggtca ccatcaccac cgccagaagc    780
aagtaccctt accacttctt cgccaccagc accggcgacg tggtggacat cagccccttc    840
tacaacggca ccaaccggaa cgccagctac ttcggcgaga acgccgacaa gttcttcatc    900
ttccccaact acaccatcgt gtccgacttc ggcagaccca acagcgcccc tgagacacac    960
cggctggtgg cctttctgga acgggccgac agcgtgatca gctgggacat ccaggacgag   1020
aagaacgtga cctgccagct gaccttctgg gaggctagcg agcggaccat cagaagcgag   1080
gccgaggaca gctaccactt cagcagcgcc aagatgaccg ccaccttcct gagcaagaaa   1140
caggaagtga acatgagcga cagcgccctg gactgcgtgc gggatgaggc catcaacaag   1200
ctgcagcaga tcttcaacac cagctacaac cagacctacg agaagtatgg caacgtgtcc   1260
gtgttcgaga caacaggcgg cctggtggtg ttctggcagg gcatcaagca gaagtccctg   1320
gtcgagctgg aacggctggc caacagaagc agcctgaacc tgacccaccg gaccaagcgg   1380
agcaccgacg gcaacaatac cacccacctg agcaacatgg aaagcgtcca caacctggtg   1440
tacgcccagc tgcagttcac ctacgacacc ctgcggggct acatcaaccg ggccctggcc   1500
cagatcgccg aggcttggtg tgtggaccag cggcggaccc tggaagtgtt caaagagctg   1560
agcaagatca accccagcgc catcctgagc gccatctaca acaagcctat cgccgccaga   1620
ttcatgggcg acgtgctggg cctggccagc tgcgtgacca tcaaccagac cagcgtgaag   1680
gtgctgcggg acatgaacgt gaaagaaagc cccggcagat gctactccag acccgtggtc   1740
atcttcaact tcgccaacag ctcctacgtg cagtacggcc agctgggcga ggacaacgag   1800
atcctgctgg gaaaccaccg gaccgaggaa tgccagctgc ccagcctgaa gatctttatc   1860
gccggcaaca gcgcctacga gtatgtggac tacctgttca agcggatgat cgacctgagc   1920
agcatcagca ccgtggacag catgatcgcc ctggacatcg acccccctgga aaacaccgac   1980
ttccgggtgc tggaactgta cagccagaaa gagctgcgga gcagcaacgt gttcgacctg   2040
gaagagatca tgcgcgagtt caacagctac aagcagcgcg tgaaatacgt cgaggacaag   2100
gtggtggacc ccctgccccc ctacctgaag ggcctggacg acctgatgag cggcctggga   2160
gctgctggca aggccgtggg agtggccatt ggagctgtgg gcggagccgt ggccagcgtg   2220
gtggaaggcg tggccacctt tctgaagaac cccttcggcg ccttcaccat catcctggtg   2280
gctatcgccg tcgtgatcat cacctacctg atctacaccc ggcagcggcg gctgtgtacc   2340
```

```
cagcctctgc agaacctgtt cccctacctg gtgtccgccg acggcaccac cgtgacaagc   2400

ggctccacca aggacaccag cctgcaggcc ccacccagct acgaggaatc cgtgtacaac   2460

agcggccgga agggcccagg ccctcctagc tctgacgcct ctacagccgc cccaccctac   2520

accaacgagc aggcctacca gatgctgctg gccctggcta gactggacgc cgagcagaga   2580

gcccagcaga acggaaccga cagcctggat ggccagaccg gcacccagga caagggccag   2640

aagcccaacc tgctggaccg gctgcggcac agaaagaacg gctaccggca cctgaaggac   2700

agcgacgaag aggaaaacgt gtga                                          2724
```

```
<210> SEQ ID NO 2
<211> LENGTH: 907
<212> TYPE: PRT
<213> ORGANISM: Artificial Sequence
<220> FEATURE:
<223> OTHER INFORMATION: gB consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Ser Gln Arg Val Thr Ser Ser Glu Ala Val
    50                  55                  60

Ser His Arg Ala Asn Glu Thr Ile Tyr Asn Thr Thr Leu Lys Tyr Gly
65                  70                  75                  80

Asp Val Val Gly Val Asn Thr Thr Lys Tyr Pro Tyr Arg Val Cys Ser
                85                  90                  95

Met Ala Gln Gly Thr Asp Leu Ile Arg Phe Glu Arg Asn Ile Val Cys
            100                 105                 110

Thr Ser Met Lys Pro Ile Asn Glu Asp Leu Asp Glu Gly Ile Met Val
        115                 120                 125

Val Tyr Lys Arg Asn Ile Val Ala His Thr Phe Lys Val Arg Val Tyr
    130                 135                 140

Gln Lys Val Leu Thr Phe Arg Arg Ser Tyr Ala Tyr Ile His Thr Thr
145                 150                 155                 160

Tyr Leu Leu Gly Ser Asn Thr Glu Tyr Val Ala Pro Pro Met Trp Glu
                165                 170                 175

Ile His His Ile Asn Ser His Ser Gln Cys Tyr Ser Ser Tyr Ser Arg
            180                 185                 190

Val Ile Ala Gly Thr Val Phe Val Ala Tyr His Arg Asp Ser Tyr Glu
        195                 200                 205

Asn Lys Thr Met Gln Leu Met Pro Asp Asp Tyr Ser Asn Thr His Ser
    210                 215                 220

Thr Arg Tyr Val Thr Val Lys Asp Gln Trp His Ser Arg Gly Ser Thr
225                 230                 235                 240

Trp Leu Tyr Arg Glu Thr Cys Asn Leu Asn Cys Met Val Thr Ile Thr
                245                 250                 255

Thr Ala Arg Ser Lys Tyr Pro Tyr His Phe Phe Ala Thr Ser Thr Gly
            260                 265                 270
```

-continued

```
Asp Val Val Asp Ile Ser Pro Phe Tyr Asn Gly Thr Asn Arg Asn Ala
        275                 280                 285

Ser Tyr Phe Gly Glu Asn Ala Asp Lys Phe Phe Ile Phe Pro Asn Tyr
    290                 295                 300

Thr Ile Val Ser Asp Phe Gly Arg Pro Asn Ser Ala Leu Glu Thr His
305                 310                 315                 320

Arg Leu Val Ala Phe Leu Glu Arg Ala Asp Ser Val Ile Ser Trp Asp
                325                 330                 335

Ile Gln Asp Glu Lys Asn Val Thr Cys Gln Leu Thr Phe Trp Glu Ala
            340                 345                 350

Ser Glu Arg Thr Ile Arg Ser Glu Ala Glu Asp Ser Tyr His Phe Ser
        355                 360                 365

Ser Ala Lys Met Thr Ala Thr Phe Leu Ser Lys Lys Gln Glu Val Asn
    370                 375                 380

Met Ser Asp Ser Ala Leu Asp Cys Val Arg Asp Glu Ala Ile Asn Lys
385                 390                 395                 400

Leu Gln Gln Ile Phe Asn Thr Ser Tyr Asn Gln Thr Tyr Glu Lys Tyr
                405                 410                 415

Gly Asn Val Ser Val Phe Glu Thr Thr Gly Gly Leu Val Val Phe Trp
            420                 425                 430

Gln Gly Ile Lys Gln Lys Ser Leu Val Glu Leu Glu Arg Leu Ala Asn
        435                 440                 445

Arg Ser Ser Leu Asn Leu Thr His Arg Thr Lys Arg Ser Thr Asp Gly
    450                 455                 460

Asn Asn Thr Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685
```

```
Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905


<210> SEQ ID NO 3
<211> LENGTH: 1119
<212> TYPE: DNA
<213> ORGANISM: Artificial Sequence
<220> FEATURE:
<223> OTHER INFORMATION: gM consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 3

nnngcaccca gccacgtgga caaagtgaac acccggactt ggagcgccag catcgtgttc      60

atggtgctga ccttcgtgaa tgtgtccgtc cacctggtgc tgagcaactt cccccacctg     120

ggctacccct gcgtgtacta ccacgtggtg gacttcgagc ggctgaacat gagcgcctac     180

aacgtgatgc atctgcacac ccccatgctg tttctggaca gcgtgcagct cgtgtgctac     240

gccgtgttta tgcagctggt gttcctggcc gtgaccatct actacctcgt gtgctggatc     300

aagatttcta tgcggaagga caagggcatg agcctgaacc agagcacccg ggacatcagc     360

tacatgggcg acagcctgac cgccttcctg ttcatcctga gcatggacac cttccagctg     420

ttcaccctga ccatgagctt ccggctgccc agcatgatcg cctttatggc cgccgtccac     480

ttcttctgtc tgaccatctt caacgtgtcc atggtcaccc agtacagaag ctacaagcgg     540

agcctgttct tcttcagtcg gctgcacccc aagctgaagg gcaccgtcca gttccggacc     600

ctgatcgtga acctggtgga agtggccctg ggcttcaaca ccaccgtggt ggctatggct     660

ctgtgctacg gcttcggcaa caacttcttc gtgcggacag gccacatggt gctggccgtg     720
```

```
ttcgtggtgt acgccattat cagcatcatc tactttctgc tgatcgaggc cgtgttcttc    780

cagtacgtga aggtgcagtt cggctaccac ctgggcgcct ttttcggcct gtgcggcctg    840

atctacccca tcgtgcagta cgacaccttc ctgagcaacg agtaccggac cggcatcagc    900

tggtccttcg gcatgctgtt cttcatctgg gccatgttca ccacctgtcg ggccgtgcgg    960

tacttcagag gcagaggcag cggctccgtg aagtaccagg ccctggccac agccagcggc   1020

gaagaagtgg ccgccctgag ccaccacgac agcctggaaa gcagacggct gagagaggaa   1080

gaggacgacg acgacgatga ggacttcgag gacgcctga                          1119
```

```
<210> SEQ ID NO 4
<211> LENGTH: 372
<212> TYPE: PRT
<213> ORGANISM: Artificial Sequence
<220> FEATURE:
<223> OTHER INFORMATION: gM consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270
```

```
Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Ala Leu Ser His His Asp Ser Leu
            340                 345                 350

Glu Ser Arg Arg Leu Arg Glu Glu Glu Asp Asp Asp Asp Asp Glu Asp
        355                 360                 365

Phe Glu Asp Ala
    370


<210> SEQ ID NO 5
<211> LENGTH: 411
<212> TYPE: DNA
<213> ORGANISM: Artificial Sequence
<220> FEATURE:
<223> OTHER INFORMATION: gN consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 5

nnngagtgga acaccctggt gctgggtctg ctggtgctgt ctgtggccgc cagcagcaac     60

aacaccagca ctgccagcac ccccagccct agcagcagca cccacacctc caccaccgtg    120

aaggccacca ccaccgccac cacaagcacc acaacagcca ccagcaccac ctcttccacc    180

accagcacaa agcccggcag caccactcac gaccccaacg tgatgaggcc ccacgcccac    240

aacgacttct acaaggccca ctgcaccagc catatgtacg agctgagcct gagcagcttc    300

gccgcctggt ggaccatgct gaacgccctg atcctgatgg gcgccttctg catcgtgctg    360

cggcactgct gcttccagaa cttcaccgcc acaaccacca agggctactg a             411


<210> SEQ ID NO 6
<211> LENGTH: 136
<212> TYPE: PRT
<213> ORGANISM: Artificial Sequence
<220> FEATURE:
<223> OTHER INFORMATION: gN consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 6

Xaa Glu Trp Asn Thr Leu Val Leu Gly Leu Leu Val Leu Ser Val Ala
1               5                   10                  15

Ala Ser Ser Asn Asn Thr Ser Thr Ala Ser Thr Pro Ser Pro Ser Ser
            20                  25                  30

Ser Thr His Thr Ser Thr Thr Val Lys Ala Thr Thr Thr Ala Thr Thr
        35                  40                  45

Ser Thr Thr Thr Ala Thr Ser Thr Thr Ser Ser Thr Thr Ser Thr Lys
    50                  55                  60

Pro Gly Ser Thr Thr His Asp Pro Asn Val Met Arg Pro His Ala His
65                  70                  75                  80
```

```
Asn Asp Phe Tyr Lys Ala His Cys Thr Ser His Met Tyr Glu Leu Ser
                85                  90                  95

Leu Ser Ser Phe Ala Ala Trp Trp Thr Met Leu Asn Ala Leu Ile Leu
            100                 105                 110

Met Gly Ala Phe Cys Ile Val Leu Arg His Cys Cys Phe Gln Asn Phe
        115                 120                 125

Thr Ala Thr Thr Thr Lys Gly Tyr
    130                 135


<210> SEQ ID NO 7
<211> LENGTH: 2232
<212> TYPE: DNA
<213> ORGANISM: Artificial Sequence
<220> FEATURE:
<223> OTHER INFORMATION: gH consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 7

nnncgacccg gcctgcccag ctacctgacc gtgttcgccg tgtacctgct gagccatctg     60

cccagccaga gatacggcgc cgatgccgcc tctgaggccc tggatcctca cgccttccat    120

ctgctgctga acacctacgg cagacctatc cggttcctgc gcgagaacac cacccagtgc    180

acctacaaca gcagcctgcg gaacagcacc gtcgtgcgcg agaatgctat cagcttcaac    240

ttcttccaga gctacaacca gtactacgtg ttccacatgc cccggtgcct gttcgccgga    300

cctctggccg agcagttcct gaaccaggtg gacctgaccg agacactgga aagataccag    360

cagcggctga atacctacgc cctggtgtcc aaggacctgg ccagctaccg gtccttcagc    420

cagcagctga aggctcagga cagcctgggc gagcagccta ccaccgtgcc ccctccaatc    480

gacctgagca tcccccacgt gtggatgccc ccccagacca cacctcacgg ctggaaagag    540

agccacacca ccagcggcct gcacagaccc cacttcaacc agacctgcat tctgttcgac    600

ggccacgacc tgctgttcag caccgtgacc ccctgcctgc accagggctt ctacctgatc    660

gacgagctga gatacgtgaa gatcaccctg accgaggatt tcttcgtggt caccgtgtcc    720

atcgacgacg acacccccat gctgctgatc ttcggccatc tgcctcgggt gctgttcaag    780

gcccccctacc agcgggacaa cttcatcctg cggcagaccg agaagcacga gctgctggtg    840

ctggtcaaga aggaccagct gaaccggcac tcctacctga aggaccccga cttcctggac    900

gccgccctgg acttcaacta cctggacctg agcgccctgc tgagaaacag cttccacaga    960

tacgccgtgg acgtgctgaa gtccggccgg tgccagatgc tggacagacg gaccgtggaa   1020

atggccttcg cctatgccct ggccctgttt gccgccgctc ggcaggaaga ggctggcgct   1080

gaagtgtccg tgcccagagc cctggacaga caggccgctc tgctgcagat ccaggaattc   1140

atgatcacct gtctgagcca gacccccccct cggaccaccc tgctgctgta ccctaccgcc   1200

gtggatctgg ccaagcgggc cctgtggacc cccaaccaga tcaccgacat cacaagcctc   1260

gtgcggctgg tgtacatcct gagcaagcag aaccagcagc acctgatccc ccagtgggcc   1320

ctgagacaga tcgccgactt cgccctgaag ctgcacaaga cccacctggc tagctttctg   1380

agcgccttcg ctaggcagga actgtacctg atgggcagcc tggtgcactc catgctggtg   1440

cacaccaccg agaggcggga aatcttcatc gtggaaaccg gcctgtgcag cctggccgag   1500

ctgagccact tcacccagct gctggcccac ccccaccacg agtacctgag cgacctgtac   1560

accccctgca gctctagcgg cagacgggat cacagcctgg aacggctgac ccggctgttc   1620
```

cccgatgcca cagtgcctgc cactgtgcca gccgccctgt ccatcctgtc caccatgcag 1680
cccagcaccc tggaaacctt ccccgacctg ttctgcctgc ccctgggcga gagcttcagc 1740
gccctgacag tgtccgagca cgtgtcctac gtggtcacca accagtacct gatcaagggc 1800
atcagctacc ccgtgtccac caccgtcgtg ggccagagcc tgatcatcac ccagaccgac 1860
agccagacca agtgcgagct gacccggaac atgcacacca cacacagcat cactgccgcc 1920
ctgaacatca gcctggaaaa ctgcgccttc tgccagtctg ccctgctgga atacgacgat 1980
acccagggcg tgatcaacat catgtacatg cacgacagcg acgacgtgct gttcgccctg 2040
gacccctaca acgaggtggt ggtgtccagc cccccggaccc actacctgat gctgctgaag 2100
aacggcaccg tgctggaagt gaccgacgtg gtggtggacg ccaccgacag cagactgctg 2160
atgatgagcg tgtacgccct gagcgccatc atcggcatct acctgctgta ccggatgctg 2220
aaaacctgct ga 2232

<210> SEQ ID NO 8
<211> LENGTH: 743
<212> TYPE: PRT
<213> ORGANISM: Artificial Sequence
<220> FEATURE:
<223> OTHER INFORMATION: gH consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

Xaa Arg Pro Gly Leu Pro Ser Tyr Leu Thr Val Phe Ala Val Tyr Leu
1 5 10 15

Leu Ser His Leu Pro Ser Gln Arg Tyr Gly Ala Asp Ala Ala Ser Glu
20 25 30

Ala Leu Asp Pro His Ala Phe His Leu Leu Leu Asn Thr Tyr Gly Arg
35 40 45

Pro Ile Arg Phe Leu Arg Glu Asn Thr Thr Gln Cys Thr Tyr Asn Ser
50 55 60

Ser Leu Arg Asn Ser Thr Val Val Arg Glu Asn Ala Ile Ser Phe Asn
65 70 75 80

Phe Phe Gln Ser Tyr Asn Gln Tyr Tyr Val Phe His Met Pro Arg Cys
85 90 95

Leu Phe Ala Gly Pro Leu Ala Glu Gln Phe Leu Asn Gln Val Asp Leu
100 105 110

Thr Glu Thr Leu Glu Arg Tyr Gln Gln Arg Leu Asn Thr Tyr Ala Leu
115 120 125

Val Ser Lys Asp Leu Ala Ser Tyr Arg Ser Phe Ser Gln Gln Leu Lys
130 135 140

Ala Gln Asp Ser Leu Gly Glu Gln Pro Thr Thr Val Pro Pro Pro Ile
145 150 155 160

Asp Leu Ser Ile Pro His Val Trp Met Pro Pro Gln Thr Thr Pro His
165 170 175

Gly Trp Lys Glu Ser His Thr Thr Ser Gly Leu His Arg Pro His Phe
180 185 190

Asn Gln Thr Cys Ile Leu Phe Asp Gly His Asp Leu Leu Phe Ser Thr
195 200 205

Val Thr Pro Cys Leu His Gln Gly Phe Tyr Leu Ile Asp Glu Leu Arg
210 215 220

-continued

```
Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
            260                 265                 270

Thr Glu Lys His Glu Leu Leu Val Leu Val Lys Lys Asp Gln Leu Asn
        275                 280                 285

Arg His Ser Tyr Leu Lys Asp Pro Asp Phe Leu Asp Ala Ala Leu Asp
    290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335

Arg Thr Val Glu Met Ala Phe Ala Tyr Ala Leu Ala Leu Phe Ala Ala
            340                 345                 350

Ala Arg Gln Glu Glu Ala Gly Ala Glu Val Ser Val Pro Arg Ala Leu
        355                 360                 365

Asp Arg Gln Ala Ala Leu Leu Gln Ile Gln Glu Phe Met Ile Thr Cys
    370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asn Gln Ile Thr Asp
                405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
        435                 440                 445

Leu Lys Leu His Lys Thr His Leu Ala Ser Phe Leu Ser Ala Phe Ala
    450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
        515                 520                 525

Arg Asp His Ser Leu Glu Arg Leu Thr Arg Leu Phe Pro Asp Ala Thr
    530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
        595                 600                 605

Val Val Gly Gln Ser Leu Ile Ile Thr Gln Thr Asp Ser Gln Thr Lys
    610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
```

-continued

```
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Leu Lys Asn Gly Thr Val
    690                 695                 700

Leu Glu Val Thr Asp Val Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740


<210> SEQ ID NO 9
<211> LENGTH: 837
<212> TYPE: DNA
<213> ORGANISM: Artificial Sequence
<220> FEATURE:
<223> OTHER INFORMATION: gL consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 9

nnntgcaggc ggcccgactg cggcttcagc ttcagccctg gccccgtgat cctgctgtgg     60

tgctgcctgc tgctgcccat cgtgtcctct gccgccgtgt ctgtggcccc tacagccgcc    120

gagaaggtgc cagccgagtg ccctgagctg accagacggt gtctgctggg cgaggtgttc    180

cagggcgata agtacgagag ctggctgcgg cccctggtca acgtgaccgg cagagatggc    240

cccctgagcc agctgatccg gtacagaccc gtgacccctg aggccgccaa cagcgtgctg    300

ctggacgaag cctttctgga cacactggcc ctgctgtaca acaaccccga ccagctgcgg    360

gccctgctga cactgctgag cagcgatacc gcccccagat ggatgaccgt gatgcggggc    420

tacagcgagt gcggcgacgg atctcccgcc gtgtacacct gtgtggacga cctgtgccgg    480

ggctacgacc tgaccagact gagctacggc cggtccatct tcacagagca cgtgctgggc    540

ttcgagctgg tgccccccag cctgttcaat gtggtggtgg ccatccggaa cgaggccacc    600

cggaccaaca gagcagtgcg gctgcctgtg tccaccgctg ctgctccaga gggcatcacc    660

ctgttctacg gcctgtacaa cgccgtgaaa gagttctgcc tgagacacca gctggacccc    720

cccctgctgc ggcacctgga caagtactac gccggcctgc ctcccgagct gaagcagacc    780

agagtgaacc tgcccgccca cagcagatac ggccctcagg ccgtggacgc cagatga       837


<210> SEQ ID NO 10
<211> LENGTH: 278
<212> TYPE: PRT
<213> ORGANISM: Artificial Sequence
<220> FEATURE:
<223> OTHER INFORMATION: gL consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 10

Xaa Cys Arg Arg Pro Asp Cys Gly Phe Ser Phe Ser Pro Gly Pro Val
1               5                   10                  15
```

-continued

```
Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275
```

<210> SEQ ID NO 11
<211> LENGTH: 1419
<212> TYPE: DNA
<213> ORGANISM: Artificial Sequence
<220> FEATURE:
<223> OTHER INFORMATION: gO consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 11

```
nnnggcaaga aagaaatgat catggtcaag ggcatcccca agatcatgct gctgatcagc      60

atcacctttc tgctgctgag cctgatcaac tgcaacgtgc tggtcaacag caagggcaca     120

cggcggagct ggccctacac cgtgctgagc taccggggca aagagatcct gaagaagcag     180

aaagaggaca tcctgaagcg gctgatgagc accagcagcg acggctaccg gttcctgatg     240

taccccagcc agcagaaatt ccacgccatc gtgatcagca tggacaagtt cccccaggac     300

tacatcctgg ccggacccat ccggaacgac agcatcaccc acatgtggtt cgacttctac     360

agcacccagc tgcggaagcc cgccaaatac gtgtacagcg agtacaacca caccgcccac     420
```

aagatcaccc tgcggcctcc cccttgcggc accgtgccca gcatgaactg cctgagcgag 480
atgctgaacg tgtccaagcg gaacgacacc ggcgagaagg gctgcggcaa cttcaccacc 540
ttcaacccca tgttcttcaa cgtgccccgg tggaacacca agctgtacat cggcagcaac 600
aaagtgaacg tggacagcca gaccatctac tttctgggcc tgaccgccct gctgctgcgc 660
tacgcccaga gaaactgcac ccggtccttc tacctggtca acgccatgag ccggaacctg 720
ttccgggtgc ccaagtacat caacggcacc aagctgaaga acaccatgcg gaagctgaag 780
cggaagcagg ccctggtcaa agagcagccc cagaagaaga acaagaagtc ccagagcacc 840 accacccct acctgagcta caccaccagc accgccttca acgtgaccac caacgtgacc 900
tacagcgcca cagccgccgt gaccagagtg gccacctcca ccaccggcta ccggcccgac 960
agcaacttca tgaagtccat catggccacc cagctgaggg acctggccac ctgggtgtac 1020
accaccctgc ggtacagaaa cgagcccttc tgcaagcccg accggaacag aaccgccgtg 1080
tccgagttca tgaagaatac ccacgtgctg atccgcaacg agacacccta caccatctac 1140
ggcaccctgg acatgagcag cctgtactac aacgagacaa tgagcgtcga gaacgagaca 1200
gccagcgaca acaacgaaac cacccccacc agccccagca cccggttcca gcggaccttc 1260
atcgaccccc tgtgggacta cctggacagc ctgctgttcc tggacaagat ccggaacttc 1320
agcctgcagc tgcccgccta cggcaacctg acccccccctg aacacagaag ggccgccaac 1380
ctgagcaccc tgaacagcct gtggtggtgg ctgcagtga 1419

<210> SEQ ID NO 12
<211> LENGTH: 472
<212> TYPE: PRT
<213> ORGANISM: Artificial Sequence
<220> FEATURE:
<223> OTHER INFORMATION: gO consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 12

Xaa Gly Lys Lys Glu Met Ile Met Val Lys Gly Ile Pro Lys Ile Met
1 5 10 15

Leu Leu Ile Ser Ile Thr Phe Leu Leu Leu Ser Leu Ile Asn Cys Asn
20 25 30

Val Leu Val Asn Ser Lys Gly Thr Arg Arg Ser Trp Pro Tyr Thr Val
35 40 45

Leu Ser Tyr Arg Gly Lys Glu Ile Leu Lys Lys Gln Lys Glu Asp Ile
50 55 60

Leu Lys Arg Leu Met Ser Thr Ser Ser Asp Gly Tyr Arg Phe Leu Met
65 70 75 80

Tyr Pro Ser Gln Gln Lys Phe His Ala Ile Val Ile Ser Met Asp Lys
85 90 95

Phe Pro Gln Asp Tyr Ile Leu Ala Gly Pro Ile Arg Asn Asp Ser Ile
100 105 110

Thr His Met Trp Phe Asp Phe Tyr Ser Thr Gln Leu Arg Lys Pro Ala
115 120 125

Lys Tyr Val Tyr Ser Glu Tyr Asn His Thr Ala His Lys Ile Thr Leu
130 135 140

Arg Pro Pro Pro Cys Gly Thr Val Pro Ser Met Asn Cys Leu Ser Glu
145 150 155 160

Met Leu Asn Val Ser Lys Arg Asn Asp Thr Gly Glu Lys Gly Cys Gly

```
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270

Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
            340                 345                 350

Pro Asp Arg Asn Arg Thr Ala Val Ser Glu Phe Met Lys Asn Thr His
        355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
            420                 425                 430

Phe Leu Asp Lys Ile Arg Asn Phe Ser Leu Gln Leu Pro Ala Tyr Gly
        435                 440                 445

Asn Leu Thr Pro Pro Glu His Arg Arg Ala Ala Asn Leu Ser Thr Leu
    450                 455                 460

Asn Ser Leu Trp Trp Trp Leu Gln
465                 470
```

<210> SEQ ID NO 13
<211> LENGTH: 516
<212> TYPE: DNA
<213> ORGANISM: Artificial Sequence
<220> FEATURE:
<223> OTHER INFORMATION: UL128 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 13

```
nnnagcccca aggatctgac ccctttcctg accgccctgt ggctgctcct gggccacagc      60

agagtgccta gagtgcgggc cgaggaatgc tgcgagttca tcaacgtgaa ccacccccccc    120

gagcggtgct acgacttcaa gatgtgcaac cggttcaccg tggctctgag atgccccgac    180
```

```
ggcgaagtgt gctacagccc cgagaaaacc gccgagatcc ggggcatcgt gaccaccatg    240

acccacagcc tgaccagaca ggtggtgcat aacaagctga ccagttgcaa ctacaacccc    300

ctgtacctgg aagccgacgg ccggatcaga tgcggcaaag tgaacgacaa ggcccagtac    360

ctgctgggcg ctgcaggcag tgtgccctac agatggatca acctggaata cgacaagatc    420

acccggatcg tgggcctgga ccagtacctg gaaagcgtga agaagcacaa gcggctggac    480

gtgtgccggg ccaagatggg ctacatgctg cagtga                              516
```

<210> SEQ ID NO 14
<211> LENGTH: 171
<212> TYPE: PRT
<213> ORGANISM: Artificial Sequence
<220> FEATURE:
<223> OTHER INFORMATION: UL128 consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

```
Xaa Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 15
<211> LENGTH: 646
<212> TYPE: DNA
<213> ORGANISM: Artificial Sequence
<220> FEATURE:
<223> OTHER INFORMATION: UL130 consensus amino acid sequence
<220> FEATURE:
<221> NAME/KEY: misc_feature
<222> LOCATION: (1)..(3)
<223> OTHER INFORMATION: n is a, c, g, or t

<400> SEQUENCE: 15

```
nnngctgcgg ctgctgctgc ggcaccactt ccactgcctg ctgctgtgtg ccgtgtgggc     60

cacccccttgt ctggccagcc cttggagcac cctgaccgcc aaccagaacc ctagcccccc    120

ctggtccaag ctgacctaca gcaagcccca cgacgccgct accttctact gcccattcct    180
```

-continued

```
gtaccccagc cctcccagaa gccccctgca gttcagcggc ttccagcggg tgtccaccgg    240

ccctgagtgc cggaacgaga cactgtacct gctgtacaac cgcgagggcc agaccctggt    300

ggaacggtct agcacctggg tcaagaaagt gatctggtat ctgagcggcc ggaaccagac    360

catcctgcag cggatgcctc ggaccgccag caagcctagc gacggcaacg tgcagatcag    420

cgtggaagat gccaaaatct tcggcgccca catggtgccc aagcagacca agctgctgag    480

attcgtggtc aacgacggca ccagatacca gatgtgcgtg atgaagctgg aaagctgggc    540

ccacgtgttc cgggactaca gcgtgtcatt ccaggtccga ctgaccttca ccgaggccaa    600

caaccagacc tacaccttct gcacccaccc caacctgatc gtctga                   646
```

```
<210> SEQ ID NO 16
<211> LENGTH: 214
<212> TYPE: PRT
<213> ORGANISM: Artificial Sequence
<220> FEATURE:
<223> OTHER INFORMATION: UL130 consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210


<210> SEQ ID NO 17
<211> LENGTH: 390
<212> TYPE: DNA
<213> ORGANISM: Artificial Sequence
<220> FEATURE:
<223> OTHER INFORMATION: UL131a consensus nucleic acid sequence
```

<220> FEATURE:
<221> NAME/KEY: misc_feature
<222> LOCATION: (1)..(3)
<223> OTHER INFORMATION: n is a, c, g, or t

<400> SEQUENCE: 17
nnnagactgt gcagagtgtg gctgagcgtg tgcctgtgcg ccgtggtgct gggccagtgc 60
cagagagaga cagccgagaa gaacgactac taccgggtgc cccactactg ggacgcctgc 120
tctagagccc tgcccgacca gacccggtac aaatacgtgg aacagctggt ggacctgacc 180
ctgaactacc actacgacgc cagccacggc ctggacaact tcgacgtgct gaagcggatc 240
aacgtgaccg aggtgtccct gctgatcagc gacttccggc ggcagaacag aagaggcggc 300
accaacaagc ggactacctt caacgccgct ggcagcctgg cccctcacgc cagatccctg 360
gaattcagcg tgcggctgtt cgccaactga 390

<210> SEQ ID NO 18
<211> LENGTH: 129
<212> TYPE: PRT
<213> ORGANISM: Artificial Sequence
<220> FEATURE:
<223> OTHER INFORMATION: UL131a consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 18

Xaa Arg Leu Cys Arg Val Trp Leu Ser Val Cys Leu Cys Ala Val Val
1 5 10 15

Leu Gly Gln Cys Gln Arg Glu Thr Ala Glu Lys Asn Asp Tyr Tyr Arg
20 25 30

Val Pro His Tyr Trp Asp Ala Cys Ser Arg Ala Leu Pro Asp Gln Thr
35 40 45

Arg Tyr Lys Tyr Val Glu Gln Leu Val Asp Leu Thr Leu Asn Tyr His
50 55 60

Tyr Asp Ala Ser His Gly Leu Asp Asn Phe Asp Val Leu Lys Arg Ile
65 70 75 80

Asn Val Thr Glu Val Ser Leu Leu Ile Ser Asp Phe Arg Arg Gln Asn
85 90 95

Arg Arg Gly Gly Thr Asn Lys Arg Thr Thr Phe Asn Ala Ala Gly Ser
100 105 110

Leu Ala Pro His Ala Arg Ser Leu Glu Phe Ser Val Arg Leu Phe Ala
115 120 125

Asn

<210> SEQ ID NO 19
<211> LENGTH: 1687
<212> TYPE: DNA
<213> ORGANISM: Artificial Sequence
<220> FEATURE:
<223> OTHER INFORMATION: UL83 consensus nucleic acid sequence
<220> FEATURE:
<221> NAME/KEY: misc_feature
<222> LOCATION: (1)..(3)
<223> OTHER INFORMATION: n is a, c, g, or t

<400> SEQUENCE: 19
nnntgagagt cgcgggcgga gatgccctga aatgatcagc gtgctgggcc caatttccgg 60
gcatgtgctg aaggccgtct tctcccgcgg agacaccccc gtgctgcctc acgagacaag 120

-continued

```
actgctgcag actggcatcc atgtgagggt ctcccagcca tctctgattc tggtgtctca    180

gtacacccca gatagtacac cctgccacag aggggacaac cagctgcagg tgcagcatac    240

ctacttcacc ggatcagagg tcgaaaatgt gagcgtcaac gtgcacaatc ccacaggcag    300

gagtatctgt ccttcacagg agccaatgag catctacgtg tacgccctgc ccctgaaaat    360

gctgaacatc cctagcatta atgtgcacca ttacccctcc gccgctgaac gaaagcaccg    420

gcatctgcct gtggcagatg ccgtcatcca tgcttcaggc aaacagatgt ggcaggcacg    480

actgaccgtg agcggactgg catggacacg acagcagaac cagtggaagg agccagacgt    540

gtactatact agcgccttcg tgttccccac caaagacgtg gccctgcgac acgtggtctg    600

cgcacatgag ctggtgtgct ctatggaaaa tactcgggcc accaagatgc aggtcattgg    660

cgatcagtac gtcaaagtgt atctggagtc cttttgtgaa gacgtgccct ctgggaagct    720

gttcatgcac gtgaccctgg gaagcgatgt cgaggaagac ctgactatga cccggaaccc    780

acagcccttt atgagacctc acgagaggaa cggcttcact gtgctgtgcc caaagaatat    840

gatcattaag cccgggaaaa tctctcatat tatgctggat gtggccttta caagtcacga    900

gcatttcgga ctgctgtgcc ccaaaagcat ccctgggctg tcaattagcg gaaacctgct    960

gatgaatggc cagcagatct ttctggaagt gcaggccatt cgagagaccg tcgaactgcg   1020

acagtacgac ccagtggcag ccctgttctt tttcgatatc gacctgctgc tgcagagagg   1080

ccctcagtat agtgagcacc caacattcac ttcacagtac aggattcagg ggaagctgga   1140

gtatcggcac acttgggata gacatgacga aggagctgca cagggcgacg atgacgtgtg   1200

gacctccggc tctgatagtg acgaggaact ggtgaccaca gagcgaaaaa ctccccgggt   1260

gaccggagga ggagctatgg caggagcatc aaccagcgcc ggacgaaaga gaaaaagcgc   1320

cagcagcgcc acagcatgca ctgcaggcgt gatgacaagg gggcgcctga aggcagaatc   1380

cacagtcgcc cctgaggaag atactgacga ggattctgac aacgaaatcc acaatccagc   1440

cgtgttcacc tggccacctt ggcaggcagg aattctggct cgcaatctgg tccctatggt   1500

ggccactgtc cagggacaga acctgaagta ccaggagttt ttctgggatg ctaatgacat   1560

ctatcggatt ttcgcagagc tggaaggcgt gtggcagcca gcagctcagc caaaaaggcg   1620

ccgacacaga caggacgcac tgcctggacc atgtatcgcc tccaccccaa agaaacatag   1680

gggctga                                                             1687
```

<210> SEQ ID NO 20
<211> LENGTH: 561
<212> TYPE: PRT
<213> ORGANISM: Artificial Sequence
<220> FEATURE:
<223> OTHER INFORMATION: UL83 consensus amino acid sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 20

```
Xaa Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60
```

-continued

```
Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480
```

```
Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly
```

<210> SEQ ID NO 21
<211> LENGTH: 2775
<212> TYPE: DNA
<213> ORGANISM: Artificial Sequence
<220> FEATURE:
<223> OTHER INFORMATION: IgE leader + gB consensus nucleic acid sequence

<400> SEQUENCE: 21

```
atggactgga cctggatcct gttcctggtg gccgctgcca cacgggtgca cagcgagagc     60

agaatctggt gcctggtcgt gtgcgtgaac ctgtgcatcg tgtgcctggg agccgccgtg    120

tccagcagca gcacccgggg cacaagcgcc acacacagcc accacagcag ccacaccacc    180

agcgccgccc acagccggag cggaagcgtg agcagccagc gggtgaccag cagcgaggcc    240

gtgtcccacc gggccaacga gacaatctac aacaccaccc tgaagtacgg cgacgtcgtg    300

ggagtgaaca ccaccaagta cccctacaga gtgtgcagca tggcccaggg caccgacctg    360

atcagattcg agcggaacat cgtgtgtacc agcatgaagc ccatcaacga ggacctggac    420

gagggcatca tggtggtgta caagagaaac atcgtggccc acaccttcaa agtgcgggtg    480

taccagaagg tgctgacctt ccggcggagc tacgcctaca tccacaccac ctacctgctg    540

ggcagcaaca ccgagtacgt ggcccctccc atgtgggaga tccaccacat caacagccac    600

agccagtgct acagcagcta cagccgcgtg atcgccggca ccgtgttcgt ggcctaccac    660

cgggacagct acgagaacaa gaccatgcag ctgatgcccg acgactacag caacacccac    720

agcaccagat acgtgaccgt gaaggaccag tggcacagcc ggggaagcac ctggctgtac    780

agagagacat gcaacctgaa ctgcatggtc accatcacca ccgccagaag caagtaccct    840

taccacttct tcgccaccag caccggcgac gtggtggaca tcagcccctt ctacaacggc    900

accaaccgga acgccagcta cttcggcgag aacgccgaca agttcttcat cttccccaac    960

tacaccatcg tgtccgactt cggcagaccc aacagcgccc ctgagacaca ccggctggtg   1020

gcctttctgg aacgggccga cagcgtgatc agctgggaca tccaggacga gaagaacgtg   1080

acctgccagc tgaccttctg ggaggctagc gagcggacca tcagaagcga ggccgaggac   1140

agctaccact tcagcagcgc caagatgacc gccaccttcc tgagcaagaa acaggaagtg   1200

aacatgagcg acagcgccct ggactgcgtg cgggatgagg ccatcaacaa gctgcagcag   1260

atcttcaaca ccagctacaa ccagacctac gagaagtatg gcaacgtgtc cgtgttcgag   1320

acaacaggcg gcctggtggt gttctggcag ggcatcaagc agaagtccct ggtcgagctg   1380

gaacggctgg ccaacagaag cagcctgaac ctgacccacc ggaccaagcg gagcaccgac   1440

ggcaacaata ccacccacct gagcaacatg gaaagcgtcc acaacctggt gtacgcccag   1500

ctgcagttca cctacgacac cctgcggggc tacatcaacc gggccctggc ccagatcgcc   1560
```

```
gaggcttggt gtgtggacca gcggcggacc ctggaagtgt tcaaagagct gagcaagatc   1620

aaccccagcg ccatcctgag cgccatctac aacaagccta tcgccgccag attcatgggc   1680

gacgtgctgg gcctggccag ctgcgtgacc atcaaccaga ccagcgtgaa ggtgctgcgg   1740

gacatgaacg tgaaagaaag ccccggcaga tgctactcca gacccgtggt catcttcaac   1800

ttcgccaaca gctcctacgt gcagtacggc cagctgggcg aggacaacga gatcctgctg   1860

ggaaaccacc ggaccgagga atgccagctg cccagcctga agatctttat cgccggcaac   1920

agcgcctacg agtatgtgga ctacctgttc aagcggatga tcgacctgag cagcatcagc   1980

accgtggaca gcatgatcgc cctggacatc gaccccctgg aaaacaccga cttccgggtg   2040

ctggaactgt acagccagaa agagctgcgg agcagcaacg tgttcgacct ggaagagatc   2100

atgcgcgagt tcaacagcta caagcagcgc gtgaaatacg tcgaggacaa ggtggtggac   2160

cccctgcccc cctacctgaa gggcctggac gacctgatga gcggcctggg agctgctggc   2220

aaggccgtgg gagtggccat tggagctgtg ggcggagccg tggccagcgt ggtggaaggc   2280

gtggccacct ttctgaagaa ccccttcggc gccttcacca tcatcctggt ggctatcgcc   2340

gtcgtgatca tcacctacct gatctacacc cggcagcggc ggctgtgtac ccagcctctg   2400

cagaacctgt tcccctacct ggtgtccgcc gacggcacca ccgtgacaag cggctccacc   2460

aaggacacca gcctgcaggc cccacccagc tacgaggaat ccgtgtacaa cagcggccgg   2520

aagggcccag gccctcctag ctctgacgcc tctacagccg ccccacccta caccaacgag   2580

caggcctacc agatgctgct ggccctggct agactggacg ccgagcagag agcccagcag   2640

aacggaaccg acagcctgga tggccagacc ggcacccagg acaagggcca gaagcccaac   2700

ctgctggacc ggctgcggca cagaaagaac ggctaccggc acctgaagga cagcgacgaa   2760

gaggaaaacg tgtga                                                    2775
```

<210> SEQ ID NO 22
<211> LENGTH: 924
<212> TYPE: PRT
<213> ORGANISM: Artificial Sequence
<220> FEATURE:
<223> OTHER INFORMATION: IgE leader + gB consensus amino acid sequence

<400> SEQUENCE: 22

```
Met Asp Trp Thr Trp Ile Leu Phe Leu Val Ala Ala Ala Thr Arg Val
1               5                   10                  15

His Ser Glu Ser Arg Ile Trp Cys Leu Val Val Cys Val Asn Leu Cys
            20                  25                  30

Ile Val Cys Leu Gly Ala Ala Val Ser Ser Ser Ser Thr Arg Gly Thr
        35                  40                  45

Ser Ala Thr His Ser His His Ser Ser His Thr Thr Ser Ala Ala His
    50                  55                  60

Ser Arg Ser Gly Ser Val Ser Ser Gln Arg Val Thr Ser Ser Glu Ala
65                  70                  75                  80

Val Ser His Arg Ala Asn Glu Thr Ile Tyr Asn Thr Thr Leu Lys Tyr
                85                  90                  95

Gly Asp Val Val Gly Val Asn Thr Thr Lys Tyr Pro Tyr Arg Val Cys
            100                 105                 110

Ser Met Ala Gln Gly Thr Asp Leu Ile Arg Phe Glu Arg Asn Ile Val
        115                 120                 125

Cys Thr Ser Met Lys Pro Ile Asn Glu Asp Leu Asp Glu Gly Ile Met
    130                 135                 140
```

-continued

```
Val Val Tyr Lys Arg Asn Ile Val Ala His Thr Phe Lys Val Arg Val
145                 150                 155                 160

Tyr Gln Lys Val Leu Thr Phe Arg Arg Ser Tyr Ala Tyr Ile His Thr
                165                 170                 175

Thr Tyr Leu Leu Gly Ser Asn Thr Glu Tyr Val Ala Pro Pro Met Trp
            180                 185                 190

Glu Ile His His Ile Asn Ser His Ser Gln Cys Tyr Ser Ser Tyr Ser
        195                 200                 205

Arg Val Ile Ala Gly Thr Val Phe Val Ala Tyr His Arg Asp Ser Tyr
    210                 215                 220

Glu Asn Lys Thr Met Gln Leu Met Pro Asp Asp Tyr Ser Asn Thr His
225                 230                 235                 240

Ser Thr Arg Tyr Val Thr Val Lys Asp Gln Trp His Ser Arg Gly Ser
                245                 250                 255

Thr Trp Leu Tyr Arg Glu Thr Cys Asn Leu Asn Cys Met Val Thr Ile
            260                 265                 270

Thr Thr Ala Arg Ser Lys Tyr Pro Tyr His Phe Phe Ala Thr Ser Thr
        275                 280                 285

Gly Asp Val Val Asp Ile Ser Pro Phe Tyr Asn Gly Thr Asn Arg Asn
    290                 295                 300

Ala Ser Tyr Phe Gly Glu Asn Ala Asp Lys Phe Phe Ile Phe Pro Asn
305                 310                 315                 320

Tyr Thr Ile Val Ser Asp Phe Gly Arg Pro Asn Ser Ala Leu Glu Thr
                325                 330                 335

His Arg Leu Val Ala Phe Leu Glu Arg Ala Asp Ser Val Ile Ser Trp
            340                 345                 350

Asp Ile Gln Asp Glu Lys Asn Val Thr Cys Gln Leu Thr Phe Trp Glu
        355                 360                 365

Ala Ser Glu Arg Thr Ile Arg Ser Glu Ala Glu Asp Ser Tyr His Phe
    370                 375                 380

Ser Ser Ala Lys Met Thr Ala Thr Phe Leu Ser Lys Lys Gln Glu Val
385                 390                 395                 400

Asn Met Ser Asp Ser Ala Leu Asp Cys Val Arg Asp Glu Ala Ile Asn
                405                 410                 415

Lys Leu Gln Gln Ile Phe Asn Thr Ser Tyr Asn Gln Thr Tyr Glu Lys
            420                 425                 430

Tyr Gly Asn Val Ser Val Phe Glu Thr Thr Gly Gly Leu Val Val Phe
        435                 440                 445

Trp Gln Gly Ile Lys Gln Lys Ser Leu Val Glu Leu Glu Arg Leu Ala
    450                 455                 460

Asn Arg Ser Ser Leu Asn Leu Thr His Arg Thr Lys Arg Ser Thr Asp
465                 470                 475                 480

Gly Asn Asn Thr Thr His Leu Ser Asn Met Glu Ser Val His Asn Leu
                485                 490                 495

Val Tyr Ala Gln Leu Gln Phe Thr Tyr Asp Thr Leu Arg Gly Tyr Ile
            500                 505                 510

Asn Arg Ala Leu Ala Gln Ile Ala Glu Ala Trp Cys Val Asp Gln Arg
        515                 520                 525

Arg Thr Leu Glu Val Phe Lys Glu Leu Ser Lys Ile Asn Pro Ser Ala
    530                 535                 540

Ile Leu Ser Ala Ile Tyr Asn Lys Pro Ile Ala Ala Arg Phe Met Gly
545                 550                 555                 560

Asp Val Leu Gly Leu Ala Ser Cys Val Thr Ile Asn Gln Thr Ser Val
```

-continued

```
                565                 570                 575

Lys Val Leu Arg Asp Met Asn Val Lys Glu Ser Pro Gly Arg Cys Tyr
            580                 585                 590

Ser Arg Pro Val Val Ile Phe Asn Phe Ala Asn Ser Ser Tyr Val Gln
        595                 600                 605

Tyr Gly Gln Leu Gly Glu Asp Asn Glu Ile Leu Leu Gly Asn His Arg
    610                 615                 620

Thr Glu Glu Cys Gln Leu Pro Ser Leu Lys Ile Phe Ile Ala Gly Asn
625                 630                 635                 640

Ser Ala Tyr Glu Tyr Val Asp Tyr Leu Phe Lys Arg Met Ile Asp Leu
                645                 650                 655

Ser Ser Ile Ser Thr Val Asp Ser Met Ile Ala Leu Asp Ile Asp Pro
            660                 665                 670

Leu Glu Asn Thr Asp Phe Arg Val Leu Glu Leu Tyr Ser Gln Lys Glu
        675                 680                 685

Leu Arg Ser Ser Asn Val Phe Asp Leu Glu Glu Ile Met Arg Glu Phe
    690                 695                 700

Asn Ser Tyr Lys Gln Arg Val Lys Tyr Val Glu Asp Lys Val Val Asp
705                 710                 715                 720

Pro Leu Pro Pro Tyr Leu Lys Gly Leu Asp Asp Leu Met Ser Gly Leu
                725                 730                 735

Gly Ala Ala Gly Lys Ala Val Gly Val Ala Ile Gly Ala Val Gly Gly
            740                 745                 750

Ala Val Ala Ser Val Val Glu Gly Val Ala Thr Phe Leu Lys Asn Pro
        755                 760                 765

Phe Gly Ala Phe Thr Ile Ile Leu Val Ala Ile Ala Val Val Ile Ile
    770                 775                 780

Thr Tyr Leu Ile Tyr Thr Arg Gln Arg Arg Leu Cys Thr Gln Pro Leu
785                 790                 795                 800

Gln Asn Leu Phe Pro Tyr Leu Val Ser Ala Asp Gly Thr Thr Val Thr
                805                 810                 815

Ser Gly Ser Thr Lys Asp Thr Ser Leu Gln Ala Pro Pro Ser Tyr Glu
            820                 825                 830

Glu Ser Val Tyr Asn Ser Gly Arg Lys Gly Pro Gly Pro Pro Ser Ser
        835                 840                 845

Asp Ala Ser Thr Ala Ala Pro Pro Tyr Thr Asn Glu Gln Ala Tyr Gln
    850                 855                 860

Met Leu Leu Ala Leu Ala Arg Leu Asp Ala Glu Gln Arg Ala Gln Gln
865                 870                 875                 880

Asn Gly Thr Asp Ser Leu Asp Gly Gln Thr Gly Thr Gln Asp Lys Gly
                885                 890                 895

Gln Lys Pro Asn Leu Leu Asp Arg Leu Arg His Arg Lys Asn Gly Tyr
            900                 905                 910

Arg His Leu Lys Asp Ser Asp Glu Glu Glu Asn Val
        915                 920
```

<210> SEQ ID NO 23
<211> LENGTH: 1170
<212> TYPE: DNA
<213> ORGANISM: Artificial Sequence
<220> FEATURE:
<223> OTHER INFORMATION: IgE leader + gM consensus nucleic acid sequence

<400> SEQUENCE: 23

```
atggattgga cctggatcct gttcctggtg gccgctgcta cccgggtcca cagtgcaccc     60
```

```
agccacgtgg acaaagtgaa cacccggact tggagcgcca gcatcgtgtt catggtgctg    120

accttcgtga atgtgtccgt ccacctggtg ctgagcaact tcccccacct gggctacccc    180

tgcgtgtact accacgtggt ggacttcgag cggctgaaca tgagcgccta caacgtgatg    240

catctgcaca cccccatgct gtttctggac agcgtgcagc tcgtgtgcta cgccgtgttt    300

atgcagctgg tgttcctggc cgtgaccatc tactacctcg tgtgctggat caagatttct    360

atgcggaagg acaagggcat gagcctgaac cagagcaccc gggacatcag ctacatgggc    420

gacagcctga ccgccttcct gttcatcctg agcatggaca ccttccagct gttcaccctg    480

accatgagct tccggctgcc cagcatgatc gcctttatgg ccgccgtcca cttcttctgt    540

ctgaccatct tcaacgtgtc catggtcacc cagtacagaa gctacaagcg gagcctgttc    600

ttcttcagtc ggctgcaccc caagctgaag ggcaccgtcc agttccggac cctgatcgtg    660

aacctggtgg aagtggccct gggcttcaac accaccgtgg tggctatggc tctgtgctac    720

ggcttcggca acaacttctt cgtgcggaca ggccacatgg tgctggccgt gttcgtggtg    780

tacgccatta tcagcatcat ctactttctg ctgatcgagg ccgtgttctt ccagtacgtg    840

aaggtgcagt tcggctacca cctgggcgcc tttttcggcc tgtgcggcct gatctacccc    900

atcgtgcagt acgacacctt cctgagcaac gagtaccgga ccggcatcag ctggtccttc    960

ggcatgctgt tcttcatctg ggccatgttc accacctgtc gggccgtgcg gtacttcaga   1020

ggcagaggca gcggctccgt gaagtaccag gccctggcca cagccagcgg cgaagaagtg   1080

gccgccctga gccaccacga cagcctggaa agcagacggc tgagagagga agaggacgac   1140

gacgacgatg aggacttcga ggacgcctga                                    1170
```

<210> SEQ ID NO 24
<211> LENGTH: 389
<212> TYPE: PRT
<213> ORGANISM: Artificial Sequence
<220> FEATURE:
<223> OTHER INFORMATION: IgE leader + gM consensus amino acid sequence

<400> SEQUENCE: 24

```
Met Asp Trp Thr Trp Ile Leu Phe Leu Val Ala Ala Ala Thr Arg Val
1               5                   10                  15

His Ser Ala Pro Ser His Val Asp Lys Val Asn Thr Arg Thr Trp Ser
            20                  25                  30

Ala Ser Ile Val Phe Met Val Leu Thr Phe Val Asn Val Ser Val His
        35                  40                  45

Leu Val Leu Ser Asn Phe Pro His Leu Gly Tyr Pro Cys Val Tyr Tyr
    50                  55                  60

His Val Val Asp Phe Glu Arg Leu Asn Met Ser Ala Tyr Asn Val Met
65                  70                  75                  80

His Leu His Thr Pro Met Leu Phe Leu Asp Ser Val Gln Leu Val Cys
                85                  90                  95

Tyr Ala Val Phe Met Gln Leu Val Phe Leu Ala Val Thr Ile Tyr Tyr
            100                 105                 110

Leu Val Cys Trp Ile Lys Ile Ser Met Arg Lys Asp Lys Gly Met Ser
        115                 120                 125

Leu Asn Gln Ser Thr Arg Asp Ile Ser Tyr Met Gly Asp Ser Leu Thr
    130                 135                 140

Ala Phe Leu Phe Ile Leu Ser Met Asp Thr Phe Gln Leu Phe Thr Leu
145                 150                 155                 160
```

```
Thr Met Ser Phe Arg Leu Pro Ser Met Ile Ala Phe Met Ala Ala Val
                165                 170                 175

His Phe Phe Cys Leu Thr Ile Phe Asn Val Ser Met Val Thr Gln Tyr
            180                 185                 190

Arg Ser Tyr Lys Arg Ser Leu Phe Phe Phe Ser Arg Leu His Pro Lys
        195                 200                 205

Leu Lys Gly Thr Val Gln Phe Arg Thr Leu Ile Val Asn Leu Val Glu
    210                 215                 220

Val Ala Leu Gly Phe Asn Thr Thr Val Val Ala Met Ala Leu Cys Tyr
225                 230                 235                 240

Gly Phe Gly Asn Asn Phe Phe Val Arg Thr Gly His Met Val Leu Ala
                245                 250                 255

Val Phe Val Val Tyr Ala Ile Ile Ser Ile Ile Tyr Phe Leu Leu Ile
            260                 265                 270

Glu Ala Val Phe Phe Gln Tyr Val Lys Val Gln Phe Gly Tyr His Leu
        275                 280                 285

Gly Ala Phe Phe Gly Leu Cys Gly Leu Ile Tyr Pro Ile Val Gln Tyr
    290                 295                 300

Asp Thr Phe Leu Ser Asn Glu Tyr Arg Thr Gly Ile Ser Trp Ser Phe
305                 310                 315                 320

Gly Met Leu Phe Phe Ile Trp Ala Met Phe Thr Thr Cys Arg Ala Val
                325                 330                 335

Arg Tyr Phe Arg Gly Arg Gly Ser Gly Ser Val Lys Tyr Gln Ala Leu
            340                 345                 350

Ala Thr Ala Ser Gly Glu Glu Val Ala Ala Leu Ser His His Asp Ser
        355                 360                 365

Leu Glu Ser Arg Arg Leu Arg Glu Glu Glu Asp Asp Asp Asp Asp Glu
    370                 375                 380

Asp Phe Glu Asp Ala
385
```

<210> SEQ ID NO 25
<211> LENGTH: 462
<212> TYPE: DNA
<213> ORGANISM: Artificial Sequence
<220> FEATURE:
<223> OTHER INFORMATION: IgE leader + gN consensus nucleic acid sequence

<400> SEQUENCE: 25

```
atggattgga cctggatcct gttcctggtg gccgctgcta cccgggtcca cagtgagtgg     60

aacaccctgg tgctgggtct gctggtgctg tctgtggccg ccagcagcaa caacaccagc    120

actgccagca cccccagccc tagcagcagc acccacacct ccaccaccgt gaaggccacc    180

accaccgcca ccacaagcac cacaacagcc accagcacca cctcttccac caccagcaca    240

aagcccggca gcaccactca cgaccccaac gtgatgaggc cccacgccca caacgacttc    300

tacaaggccc actgcaccag ccatatgtac gagctgagcc tgagcagctt cgccgcctgg    360

tggaccatgc tgaacgccct gatcctgatg ggcgccttct gcatcgtgct gcggcactgc    420

tgcttccaga acttcaccgc cacaaccacc aagggctact ga                       462
```

<210> SEQ ID NO 26
<211> LENGTH: 153
<212> TYPE: PRT
<213> ORGANISM: Artificial Sequence
<220> FEATURE:
<223> OTHER INFORMATION: IgE leader + gN consensus amino acid sequence

<400> SEQUENCE: 26

```
Met Asp Trp Thr Trp Ile Leu Phe Leu Val Ala Ala Ala Thr Arg Val
1               5                   10                  15

His Ser Glu Trp Asn Thr Leu Val Leu Gly Leu Leu Val Leu Ser Val
            20                  25                  30

Ala Ala Ser Ser Asn Asn Thr Ser Thr Ala Ser Thr Pro Ser Pro Ser
        35                  40                  45

Ser Ser Thr His Thr Ser Thr Thr Val Lys Ala Thr Thr Thr Ala Thr
    50                  55                  60

Thr Ser Thr Thr Thr Ala Thr Ser Thr Thr Ser Ser Thr Thr Ser Thr
65                  70                  75                  80

Lys Pro Gly Ser Thr Thr His Asp Pro Asn Val Met Arg Pro His Ala
                85                  90                  95

His Asn Asp Phe Tyr Lys Ala His Cys Thr Ser His Met Tyr Glu Leu
            100                 105                 110

Ser Leu Ser Ser Phe Ala Ala Trp Trp Thr Met Leu Asn Ala Leu Ile
        115                 120                 125

Leu Met Gly Ala Phe Cys Ile Val Leu Arg His Cys Cys Phe Gln Asn
    130                 135                 140

Phe Thr Ala Thr Thr Thr Lys Gly Tyr
145                 150
```

<210> SEQ ID NO 27
<211> LENGTH: 2283
<212> TYPE: DNA
<213> ORGANISM: Artificial Sequence
<220> FEATURE:
<223> OTHER INFORMATION: IgE leader + gH consensus nucleic acid sequence

<400> SEQUENCE: 27

```
atggactgga cctggatcct gttcctggtg gccgctgcta cccgggtgca cagtcgaccc     60
ggcctgccca gctacctgac cgtgttcgcc gtgtacctgc tgagccatct gcccagccag    120
agatacggcg ccgatgccgc ctctgaggcc ctggatcctc acgccttcca tctgctgctg    180
aacacctacg gcagacctat ccggttcctg cgcgagaaca ccacccagtg cacctacaac    240
agcagcctgc ggaacagcac cgtcgtgcgc gagaatgcta tcagcttcaa cttcttccag    300
agctacaacc agtactacgt gttccacatg ccccggtgcc tgttcgccgg acctctggcc    360
gagcagttcc tgaaccaggt ggacctgacc gagacactgg aaagatacca gcagcggctg    420
aatacctacg ccctggtgtc caaggacctg gccagctacc ggtccttcag ccagcagctg    480
aaggctcagg acagcctggg cgagcagcct accaccgtgc cccctccaat cgacctgagc    540
atcccccacg tgtggatgcc cccccagacc acacctcacg gctggaaaga gagccacacc    600
accagcggcc tgcacagacc ccacttcaac cagacctgca ttctgttcga cggccacgac    660
ctgctgttca gcaccgtgac cccctgcctg caccagggct tctacctgat cgacgagctg    720
agatacgtga agatcaccct gaccgaggat ttcttcgtgg tcaccgtgtc catcgacgac    780
gacaccccca tgctgctgat cttcggccat ctgcctcggg tgctgttcaa ggccccctac    840
cagcgggaca acttcatcct gcggcagacc gagaagcacg agctgctggt gctggtcaag    900
aaggaccagc tgaaccggca ctcctacctg aaggaccccg acttcctgga cgccgccctg    960
gacttcaact acctggacct gagcgccctg ctgagaaaca gcttccacag atacgccgtg   1020
gacgtgctga agtccggccg gtgccagatg ctggacagac ggaccgtgga aatggccttc   1080
gcctatgccc tggccctgtt tgccgccgct cggcaggaag aggctggcgc tgaagtgtcc   1140
```

```
gtgcccagag ccctggacag acaggccgct ctgctgcaga tccaggaatt catgatcacc   1200

tgtctgagcc agaccccccc tcggaccacc ctgctgctgt accctaccgc cgtggatctg   1260

gccaagcggg ccctgtggac ccccaaccag atcaccgaca tcacaagcct cgtgcggctg   1320

gtgtacatcc tgagcaagca gaaccagcag cacctgatcc cccagtgggc cctgagacag   1380

atcgccgact tcgccctgaa gctgcacaag acccacctgg ctagctttct gagcgccttc   1440

gctaggcagg aactgtacct gatgggcagc ctggtgcact ccatgctggt gcacaccacc   1500

gagaggcggg aaatcttcat cgtggaaacc ggcctgtgca gcctggccga gctgagccac   1560

ttcacccagc tgctggccca cccccaccac gagtacctga gcgacctgta cacccccctgc   1620

agctctagcg gcagacggga tcacagcctg gaacggctga cccggctgtt ccccgatgcc   1680

acagtgcctg ccactgtgcc agccgccctg tccatcctgt ccaccatgca gcccagcacc   1740

ctggaaacct tccccgacct gttctgcctg cccctgggcg agagcttcag cgccctgaca   1800

gtgtccgagc acgtgtccta cgtggtcacc aaccagtacc tgatcaaggg catcagctac   1860

cccgtgtcca ccaccgtcgt gggccagagc ctgatcatca cccagaccga cagccagacc   1920

aagtgcgagc tgacccggaa catgcacacc acacacagca tcactgccgc cctgaacatc   1980

agcctggaaa actgcgcctt ctgccagtct gccctgctgg aatacgacga tacccagggc   2040

gtgatcaaca tcatgtacat gcacgacagc gacgacgtgc tgttcgccct ggacccctac   2100

aacgaggtgg tggtgtccag cccccggacc cactacctga tgctgctgaa gaacggcacc   2160

gtgctggaag tgaccgacgt ggtggtggac gccaccgaca gcagactgct gatgatgagc   2220

gtgtacgccc tgagcgccat catcggcatc tacctgctgt accggatgct gaaaacctgc   2280

tga                                                                 2283
```

<210> SEQ ID NO 28
<211> LENGTH: 760
<212> TYPE: PRT
<213> ORGANISM: Artificial Sequence
<220> FEATURE:
<223> OTHER INFORMATION: IgE leader + gH consensus amino acid sequence

<400> SEQUENCE: 28

```
Met Asp Trp Thr Trp Ile Leu Phe Leu Val Ala Ala Ala Thr Arg Val
1               5                   10                  15

His Ser Arg Pro Gly Leu Pro Ser Tyr Leu Thr Val Phe Ala Val Tyr
            20                  25                  30

Leu Leu Ser His Leu Pro Ser Gln Arg Tyr Gly Ala Asp Ala Ala Ser
        35                  40                  45

Glu Ala Leu Asp Pro His Ala Phe His Leu Leu Leu Asn Thr Tyr Gly
    50                  55                  60

Arg Pro Ile Arg Phe Leu Arg Glu Asn Thr Thr Gln Cys Thr Tyr Asn
65                  70                  75                  80

Ser Ser Leu Arg Asn Ser Thr Val Val Arg Glu Asn Ala Ile Ser Phe
                85                  90                  95

Asn Phe Phe Gln Ser Tyr Asn Gln Tyr Tyr Val Phe His Met Pro Arg
            100                 105                 110

Cys Leu Phe Ala Gly Pro Leu Ala Glu Gln Phe Leu Asn Gln Val Asp
        115                 120                 125

Leu Thr Glu Thr Leu Glu Arg Tyr Gln Gln Arg Leu Asn Thr Tyr Ala
    130                 135                 140

Leu Val Ser Lys Asp Leu Ala Ser Tyr Arg Ser Phe Ser Gln Gln Leu
```

-continued

```
145                 150                 155                 160

Lys Ala Gln Asp Ser Leu Gly Glu Gln Pro Thr Thr Val Pro Pro Pro
                165                 170                 175

Ile Asp Leu Ser Ile Pro His Val Trp Met Pro Pro Gln Thr Thr Pro
            180                 185                 190

His Gly Trp Lys Glu Ser His Thr Thr Ser Gly Leu His Arg Pro His
        195                 200                 205

Phe Asn Gln Thr Cys Ile Leu Phe Asp Gly His Asp Leu Leu Phe Ser
    210                 215                 220

Thr Val Thr Pro Cys Leu His Gln Gly Phe Tyr Leu Ile Asp Glu Leu
225                 230                 235                 240

Arg Tyr Val Lys Ile Thr Leu Thr Glu Asp Phe Phe Val Val Thr Val
                245                 250                 255

Ser Ile Asp Asp Asp Thr Pro Met Leu Leu Ile Phe Gly His Leu Pro
            260                 265                 270

Arg Val Leu Phe Lys Ala Pro Tyr Gln Arg Asp Asn Phe Ile Leu Arg
        275                 280                 285

Gln Thr Glu Lys His Glu Leu Leu Val Leu Val Lys Lys Asp Gln Leu
    290                 295                 300

Asn Arg His Ser Tyr Leu Lys Asp Pro Asp Phe Leu Asp Ala Ala Leu
305                 310                 315                 320

Asp Phe Asn Tyr Leu Asp Leu Ser Ala Leu Leu Arg Asn Ser Phe His
                325                 330                 335

Arg Tyr Ala Val Asp Val Leu Lys Ser Gly Arg Cys Gln Met Leu Asp
            340                 345                 350

Arg Arg Thr Val Glu Met Ala Phe Ala Tyr Ala Leu Ala Leu Phe Ala
        355                 360                 365

Ala Ala Arg Gln Glu Glu Ala Gly Ala Glu Val Ser Val Pro Arg Ala
    370                 375                 380

Leu Asp Arg Gln Ala Ala Leu Leu Gln Ile Gln Glu Phe Met Ile Thr
385                 390                 395                 400

Cys Leu Ser Gln Thr Pro Pro Arg Thr Thr Leu Leu Leu Tyr Pro Thr
                405                 410                 415

Ala Val Asp Leu Ala Lys Arg Ala Leu Trp Thr Pro Asn Gln Ile Thr
            420                 425                 430

Asp Ile Thr Ser Leu Val Arg Leu Val Tyr Ile Leu Ser Lys Gln Asn
        435                 440                 445

Gln Gln His Leu Ile Pro Gln Trp Ala Leu Arg Gln Ile Ala Asp Phe
    450                 455                 460

Ala Leu Lys Leu His Lys Thr His Leu Ala Ser Phe Leu Ser Ala Phe
465                 470                 475                 480

Ala Arg Gln Glu Leu Tyr Leu Met Gly Ser Leu Val His Ser Met Leu
                485                 490                 495

Val His Thr Thr Glu Arg Arg Glu Ile Phe Ile Val Glu Thr Gly Leu
            500                 505                 510

Cys Ser Leu Ala Glu Leu Ser His Phe Thr Gln Leu Leu Ala His Pro
        515                 520                 525

His His Glu Tyr Leu Ser Asp Leu Tyr Thr Pro Cys Ser Ser Ser Gly
    530                 535                 540

Arg Arg Asp His Ser Leu Glu Arg Leu Thr Arg Leu Phe Pro Asp Ala
545                 550                 555                 560

Thr Val Pro Ala Thr Val Pro Ala Ala Leu Ser Ile Leu Ser Thr Met
                565                 570                 575
```

Gln Pro Ser Thr Leu Glu Thr Phe Pro Asp Leu Phe Cys Leu Pro Leu
580 585 590

Gly Glu Ser Phe Ser Ala Leu Thr Val Ser Glu His Val Ser Tyr Val
595 600 605

Val Thr Asn Gln Tyr Leu Ile Lys Gly Ile Ser Tyr Pro Val Ser Thr
610 615 620

Thr Val Val Gly Gln Ser Leu Ile Ile Thr Gln Thr Asp Ser Gln Thr
625 630 635 640

Lys Cys Glu Leu Thr Arg Asn Met His Thr Thr His Ser Ile Thr Ala
645 650 655

Ala Leu Asn Ile Ser Leu Glu Asn Cys Ala Phe Cys Gln Ser Ala Leu
660 665 670

Leu Glu Tyr Asp Asp Thr Gln Gly Val Ile Asn Ile Met Tyr Met His
675 680 685

Asp Ser Asp Asp Val Leu Phe Ala Leu Asp Pro Tyr Asn Glu Val Val
690 695 700

Val Ser Ser Pro Arg Thr His Tyr Leu Met Leu Leu Lys Asn Gly Thr
705 710 715 720

Val Leu Glu Val Thr Asp Val Val Val Asp Ala Thr Asp Ser Arg Leu
725 730 735

Leu Met Met Ser Val Tyr Ala Leu Ser Ala Ile Ile Gly Ile Tyr Leu
740 745 750

Leu Tyr Arg Met Leu Lys Thr Cys
755 760

<210> SEQ ID NO 29
<211> LENGTH: 888
<212> TYPE: DNA
<213> ORGANISM: Artificial Sequence
<220> FEATURE:
<223> OTHER INFORMATION: IgE leader + gL consensus nucleic acid sequence

<400> SEQUENCE: 29
atggattgga cctggatcct gtttctggtg gccgctgcaa caagggtcca ctcttgcagg 60
cggcccgact gcggcttcag cttcagccct ggccccgtga tcctgctgtg gtgctgcctg 120
ctgctgccca tcgtgtcctc tgccgccgtg tctgtggccc ctacagccgc cgagaaggtg 180
ccagccgagt gccctgagct gaccagacgg tgtctgctgg gcgaggtgtt ccagggcgat 240
aagtacgaga gctggctgcg gcccctggtc aacgtgaccg gcagagatgg ccccctgagc 300
cagctgatcc ggtacagacc cgtgacccct gaggccgcca acagcgtgct gctggacgaa 360
gcctttctgg acacactggc cctgctgtac aacaaccccg accagctgcg ggccctgctg 420
acactgctga gcagcgatac cgcccccaga tggatgaccg tgatgcgggg ctacagcgag 480
tgcggcgacg gatctcccgc cgtgtacacc tgtgtggacg acctgtgccg gggctacgac 540
ctgaccagac tgagctacgg ccggtccatc ttcacagagc acgtgctggg cttcgagctg 600
gtgcccccca gcctgttcaa tgtggtggtg gccatccgga acgaggccac ccggaccaac 660
agagcagtgc ggctgcctgt gtccaccgct gctgctccag agggcatcac cctgttctac 720
ggcctgtaca acgccgtgaa agagttctgc ctgagacacc agctggaccc cccctgctg 780 cggcacctgg acaagtacta cgccggcctg cctcccgagc tgaagcagac cagagtgaac 840
ctgcccgccc acagcagata cggccctcag gccgtggacg ccagatga 888

<210> SEQ ID NO 30

<211> LENGTH: 295
<212> TYPE: PRT
<213> ORGANISM: Artificial Sequence
<220> FEATURE:
<223> OTHER INFORMATION: IgE leader + gL consensus amino acid sequence

<400> SEQUENCE: 30

Met Asp Trp Thr Trp Ile Leu Phe Leu Val Ala Ala Ala Thr Arg Val
1 5 10 15

His Ser Cys Arg Arg Pro Asp Cys Gly Phe Ser Phe Ser Pro Gly Pro
20 25 30

Val Ile Leu Leu Trp Cys Cys Leu Leu Leu Pro Ile Val Ser Ser Ala
35 40 45

Ala Val Ser Val Ala Pro Thr Ala Ala Glu Lys Val Pro Ala Glu Cys
50 55 60

Pro Glu Leu Thr Arg Arg Cys Leu Leu Gly Glu Val Phe Gln Gly Asp
65 70 75 80

Lys Tyr Glu Ser Trp Leu Arg Pro Leu Val Asn Val Thr Gly Arg Asp
85 90 95

Gly Pro Leu Ser Gln Leu Ile Arg Tyr Arg Pro Val Thr Pro Glu Ala
100 105 110

Ala Asn Ser Val Leu Leu Asp Glu Ala Phe Leu Asp Thr Leu Ala Leu
115 120 125

Leu Tyr Asn Asn Pro Asp Gln Leu Arg Ala Leu Leu Thr Leu Leu Ser
130 135 140

Ser Asp Thr Ala Pro Arg Trp Met Thr Val Met Arg Gly Tyr Ser Glu
145 150 155 160

Cys Gly Asp Gly Ser Pro Ala Val Tyr Thr Cys Val Asp Asp Leu Cys
165 170 175

Arg Gly Tyr Asp Leu Thr Arg Leu Ser Tyr Gly Arg Ser Ile Phe Thr
180 185 190

Glu His Val Leu Gly Phe Glu Leu Val Pro Pro Ser Leu Phe Asn Val
195 200 205

Val Val Ala Ile Arg Asn Glu Ala Thr Arg Thr Asn Arg Ala Val Arg
210 215 220

Leu Pro Val Ser Thr Ala Ala Ala Pro Glu Gly Ile Thr Leu Phe Tyr
225 230 235 240

Gly Leu Tyr Asn Ala Val Lys Glu Phe Cys Leu Arg His Gln Leu Asp
245 250 255

Pro Pro Leu Leu Arg His Leu Asp Lys Tyr Tyr Ala Gly Leu Pro Pro
260 265 270

Glu Leu Lys Gln Thr Arg Val Asn Leu Pro Ala His Ser Arg Tyr Gly
275 280 285

Pro Gln Ala Val Asp Ala Arg
290 295

<210> SEQ ID NO 31
<211> LENGTH: 1470
<212> TYPE: DNA
<213> ORGANISM: Artificial Sequence
<220> FEATURE:
<223> OTHER INFORMATION: IgE leader + gO consensus nucleic acid sequence

<400> SEQUENCE: 31
atggactgga cctggatcct gttcctggtc gccgctgcaa ctagagtgca cagcggcaag 60
aaagaaatga tcatggtcaa gggcatcccc aagatcatgc tgctgatcag catcaccttt 120

-continued

```
ctgctgctga gcctgatcaa ctgcaacgtg ctggtcaaca gcaagggcac acggcggagc    180

tggccctaca ccgtgctgag ctaccggggc aaagagatcc tgaagaagca gaaagaggac    240

atcctgaagc ggctgatgag caccagcagc gacggctacc ggttcctgat gtaccccagc    300

cagcagaaat tccacgccat cgtgatcagc atggacaagt tcccccagga ctacatcctg    360

gccggaccca tccggaacga cagcatcacc cacatgtggt tcgacttcta cagcacccag    420

ctgcggaagc ccgccaaata cgtgtacagc gagtacaacc acaccgccca caagatcacc    480

ctgcggcctc ccccttgcgg caccgtgccc agcatgaact gcctgagcga gatgctgaac    540

gtgtccaagc ggaacgacac cggcgagaag ggctgcggca acttcaccac cttcaacccc    600

atgttcttca acgtgccccg gtggaacacc aagctgtaca tcggcagcaa caaagtgaac    660

gtggacagcc agaccatcta ctttctgggc ctgaccgccc tgctgctgcg ctacgcccag    720

agaaactgca cccggtcctt ctacctggtc aacgccatga gccggaacct gttccgggtg    780

cccaagtaca tcaacggcac caagctgaag aacaccatgc ggaagctgaa gcggaagcag    840

gccctggtca aagagcagcc ccagaagaag aacaagaagt cccagagcac caccaccccc    900

tacctgagct acaccaccag caccgccttc aacgtgacca ccaacgtgac ctacagcgcc    960

acagccgccg tgaccagagt ggccacctcc accaccggct accggcccga cagcaacttc   1020

atgaagtcca tcatggccac ccagctgagg gacctggcca cctgggtgta caccaccctg   1080

cggtacagaa acgagccctt ctgcaagccc gaccggaaca gaaccgccgt gtccgagttc   1140

atgaagaata cccacgtgct gatccgcaac gagacaccct acaccatcta cggcaccctg   1200

gacatgagca gcctgtacta caacgagaca atgagcgtcg agaacgagac agccagcgac   1260

aacaacgaaa ccacccccac cagccccagc acccggttcc agcggacctt catcgacccc   1320

ctgtgggact acctggacag cctgctgttc ctggacaaga tccggaactt cagcctgcag   1380

ctgcccgcct acggcaacct gacccccccct gaacacagaa gggccgccaa cctgagcacc   1440

ctgaacagcc tgtggtggtg gctgcagtga                                     1470
```

<210> SEQ ID NO 32
<211> LENGTH: 489
<212> TYPE: PRT
<213> ORGANISM: Artificial Sequence
<220> FEATURE:
<223> OTHER INFORMATION: IgE leader + gO consensus amino acid sequence

<400> SEQUENCE: 32

```
Met Asp Trp Thr Trp Ile Leu Phe Leu Val Ala Ala Ala Thr Arg Val
1               5                   10                  15

His Ser Gly Lys Lys Glu Met Ile Met Val Lys Gly Ile Pro Lys Ile
            20                  25                  30

Met Leu Leu Ile Ser Ile Thr Phe Leu Leu Leu Ser Leu Ile Asn Cys
        35                  40                  45

Asn Val Leu Val Asn Ser Lys Gly Thr Arg Arg Ser Trp Pro Tyr Thr
    50                  55                  60

Val Leu Ser Tyr Arg Gly Lys Glu Ile Leu Lys Lys Gln Lys Glu Asp
65                  70                  75                  80

Ile Leu Lys Arg Leu Met Ser Thr Ser Ser Asp Gly Tyr Arg Phe Leu
                85                  90                  95

Met Tyr Pro Ser Gln Gln Lys Phe His Ala Ile Val Ile Ser Met Asp
            100                 105                 110

Lys Phe Pro Gln Asp Tyr Ile Leu Ala Gly Pro Ile Arg Asn Asp Ser
        115                 120                 125
```

```
Ile Thr His Met Trp Phe Asp Phe Tyr Ser Thr Gln Leu Arg Lys Pro
    130                 135                 140

Ala Lys Tyr Val Tyr Ser Glu Tyr Asn His Thr Ala His Lys Ile Thr
145                 150                 155                 160

Leu Arg Pro Pro Pro Cys Gly Thr Val Pro Ser Met Asn Cys Leu Ser
                165                 170                 175

Glu Met Leu Asn Val Ser Lys Arg Asn Asp Thr Gly Glu Lys Gly Cys
            180                 185                 190

Gly Asn Phe Thr Thr Phe Asn Pro Met Phe Phe Asn Val Pro Arg Trp
        195                 200                 205

Asn Thr Lys Leu Tyr Ile Gly Ser Asn Lys Val Asn Val Asp Ser Gln
    210                 215                 220

Thr Ile Tyr Phe Leu Gly Leu Thr Ala Leu Leu Leu Arg Tyr Ala Gln
225                 230                 235                 240

Arg Asn Cys Thr Arg Ser Phe Tyr Leu Val Asn Ala Met Ser Arg Asn
                245                 250                 255

Leu Phe Arg Val Pro Lys Tyr Ile Asn Gly Thr Lys Leu Lys Asn Thr
            260                 265                 270

Met Arg Lys Leu Lys Arg Lys Gln Ala Leu Val Lys Glu Gln Pro Gln
        275                 280                 285

Lys Lys Asn Lys Lys Ser Gln Ser Thr Thr Thr Pro Tyr Leu Ser Tyr
    290                 295                 300

Thr Thr Ser Thr Ala Phe Asn Val Thr Thr Asn Val Thr Tyr Ser Ala
305                 310                 315                 320

Thr Ala Ala Val Thr Arg Val Ala Thr Ser Thr Thr Gly Tyr Arg Pro
                325                 330                 335

Asp Ser Asn Phe Met Lys Ser Ile Met Ala Thr Gln Leu Arg Asp Leu
            340                 345                 350

Ala Thr Trp Val Tyr Thr Thr Leu Arg Tyr Arg Asn Glu Pro Phe Cys
        355                 360                 365

Lys Pro Asp Arg Asn Arg Thr Ala Val Ser Glu Phe Met Lys Asn Thr
    370                 375                 380

His Val Leu Ile Arg Asn Glu Thr Pro Tyr Thr Ile Tyr Gly Thr Leu
385                 390                 395                 400

Asp Met Ser Ser Leu Tyr Tyr Asn Glu Thr Met Ser Val Glu Asn Glu
                405                 410                 415

Thr Ala Ser Asp Asn Asn Glu Thr Thr Pro Thr Ser Pro Ser Thr Arg
            420                 425                 430

Phe Gln Arg Thr Phe Ile Asp Pro Leu Trp Asp Tyr Leu Asp Ser Leu
        435                 440                 445

Leu Phe Leu Asp Lys Ile Arg Asn Phe Ser Leu Gln Leu Pro Ala Tyr
    450                 455                 460

Gly Asn Leu Thr Pro Pro Glu His Arg Arg Ala Ala Asn Leu Ser Thr
465                 470                 475                 480

Leu Asn Ser Leu Trp Trp Trp Leu Gln
                485
```

<210> SEQ ID NO 33
<211> LENGTH: 567
<212> TYPE: DNA
<213> ORGANISM: Artificial Sequence
<220> FEATURE:
<223> OTHER INFORMATION: IgE leader + UL128 consensus nucleic acid sequence

<400> SEQUENCE: 33

```
atggattgga cctggatcct gtttctggtg gccgctgcaa caagggtcca ctctagcccc     60

aaggatctga cccctttcct gaccgccctg tggctgctcc tgggccacag cagagtgcct    120

agagtgcggg ccgaggaatg ctgcgagttc atcaacgtga accacccccc cgagcggtgc    180

tacgacttca agatgtgcaa ccggttcacc gtggctctga gatgccccga cggcgaagtg    240

tgctacagcc ccgagaaaac cgccgagatc cggggcatcg tgaccaccat gacccacagc    300

ctgaccagac aggtggtgca taacaagctg accagttgca actacaaccc cctgtacctg    360

gaagccgacg gccggatcag atgcggcaaa gtgaacgaca aggcccagta cctgctgggc    420

gctgcaggca gtgtgcccta cagatggatc aacctggaat acgacaagat cacccggatc    480

gtgggcctgg accagtacct ggaaagcgtg aagaagcaca agcggctgga cgtgtgccgg    540

gccaagatgg gctacatgct gcagtga                                        567
```

<210> SEQ ID NO 34
<211> LENGTH: 188
<212> TYPE: PRT
<213> ORGANISM: Artificial Sequence
<220> FEATURE:
<223> OTHER INFORMATION: IgE leader + UL128 consensus amino acid
      sequence

<400> SEQUENCE: 34

```
Met Asp Trp Thr Trp Ile Leu Phe Leu Val Ala Ala Ala Thr Arg Val
1               5                   10                  15

His Ser Ser Pro Lys Asp Leu Thr Pro Phe Leu Thr Ala Leu Trp Leu
            20                  25                  30

Leu Leu Gly His Ser Arg Val Pro Arg Val Arg Ala Glu Glu Cys Cys
        35                  40                  45

Glu Phe Ile Asn Val Asn His Pro Pro Glu Arg Cys Tyr Asp Phe Lys
    50                  55                  60

Met Cys Asn Arg Phe Thr Val Ala Leu Arg Cys Pro Asp Gly Glu Val
65                  70                  75                  80

Cys Tyr Ser Pro Glu Lys Thr Ala Glu Ile Arg Gly Ile Val Thr Thr
                85                  90                  95

Met Thr His Ser Leu Thr Arg Gln Val Val His Asn Lys Leu Thr Ser
            100                 105                 110

Cys Asn Tyr Asn Pro Leu Tyr Leu Glu Ala Asp Gly Arg Ile Arg Cys
        115                 120                 125

Gly Lys Val Asn Asp Lys Ala Gln Tyr Leu Leu Gly Ala Ala Gly Ser
    130                 135                 140

Val Pro Tyr Arg Trp Ile Asn Leu Glu Tyr Asp Lys Ile Thr Arg Ile
145                 150                 155                 160

Val Gly Leu Asp Gln Tyr Leu Glu Ser Val Lys Lys His Lys Arg Leu
                165                 170                 175

Asp Val Cys Arg Ala Lys Met Gly Tyr Met Leu Gln
            180                 185
```

<210> SEQ ID NO 35
<211> LENGTH: 696
<212> TYPE: DNA
<213> ORGANISM: Artificial Sequence
<220> FEATURE:
<223> OTHER INFORMATION: IgE leader + UL130 consensus nucleic acid
      sequence

<400> SEQUENCE: 35

```
atggactgga cctggatcct gttcctggtc gccgctgcta cccgggtgca cagcctgcgg     60

ctgctgctgc ggcaccactt ccactgcctg ctgctgtgtg ccgtgtgggc cacccccttgt   120

ctggccagcc cttggagcac cctgaccgcc aaccagaacc ctagcccccc ctggtccaag    180

ctgacctaca gcaagcccca cgacgccgct accttctact gcccattcct gtaccccagc    240

cctcccagaa gccccctgca gttcagcggc ttccagcggg tgtccaccgg ccctgagtgc    300

cggaacgaga cactgtacct gctgtacaac cgcgagggcc agaccctggt ggaacggtct    360

agcacctggg tcaagaaagt gatctggtat ctgagcggcc ggaaccagac catcctgcag    420

cggatgcctc ggaccgccag caagcctagc gacggcaacg tgcagatcag cgtggaagat    480

gccaaaatct tcggcgccca catggtgccc aagcagacca agctgctgag attcgtggtc    540

aacgacggca ccagatacca gatgtgcgtg atgaagctgg aaagctgggc ccacgtgttc    600

cgggactaca gcgtgtcatt ccaggtccga ctgaccttca ccgaggccaa caaccagacc    660

tacaccttct gcacccaccc caacctgatc gtctga                              696
```

```
<210> SEQ ID NO 36
<211> LENGTH: 231
<212> TYPE: PRT
<213> ORGANISM: Artificial Sequence
<220> FEATURE:
<223> OTHER INFORMATION: IgE leader + UL130 consensus amino acid
      sequence

<400> SEQUENCE: 36

Met Asp Trp Thr Trp Ile Leu Phe Leu Val Ala Ala Ala Thr Arg Val
1               5                   10                  15

His Ser Leu Arg Leu Leu Leu Arg His His Phe His Cys Leu Leu Leu
            20                  25                  30

Cys Ala Val Trp Ala Thr Pro Cys Leu Ala Ser Pro Trp Ser Thr Leu
        35                  40                  45

Thr Ala Asn Gln Asn Pro Ser Pro Pro Trp Ser Lys Leu Thr Tyr Ser
    50                  55                  60

Lys Pro His Asp Ala Ala Thr Phe Tyr Cys Pro Phe Leu Tyr Pro Ser
65                  70                  75                  80

Pro Pro Arg Ser Pro Leu Gln Phe Ser Gly Phe Gln Arg Val Ser Thr
                85                  90                  95

Gly Pro Glu Cys Arg Asn Glu Thr Leu Tyr Leu Leu Tyr Asn Arg Glu
            100                 105                 110

Gly Gln Thr Leu Val Glu Arg Ser Ser Thr Trp Val Lys Lys Val Ile
        115                 120                 125

Trp Tyr Leu Ser Gly Arg Asn Gln Thr Ile Leu Gln Arg Met Pro Arg
    130                 135                 140

Thr Ala Ser Lys Pro Ser Asp Gly Asn Val Gln Ile Ser Val Glu Asp
145                 150                 155                 160

Ala Lys Ile Phe Gly Ala His Met Val Pro Lys Gln Thr Lys Leu Leu
                165                 170                 175

Arg Phe Val Val Asn Asp Gly Thr Arg Tyr Gln Met Cys Val Met Lys
            180                 185                 190

Leu Glu Ser Trp Ala His Val Phe Arg Asp Tyr Ser Val Ser Phe Gln
        195                 200                 205

Val Arg Leu Thr Phe Thr Glu Ala Asn Asn Gln Thr Tyr Thr Phe Cys
    210                 215                 220

Thr His Pro Asn Leu Ile Val
```

225 230

<210> SEQ ID NO 37
<211> LENGTH: 438
<212> TYPE: DNA
<213> ORGANISM: Artificial Sequence
<220> FEATURE:
<223> OTHER INFORMATION: IgE leader + UL131a consensus nucleic acid sequence

<400> SEQUENCE: 37
atggactgga cctggatcct gttcctggtc gccgctgcta cccgggtgca cagcagactg 60
tgcagagtgt ggctgagcgt gtgcctgtgc gccgtggtgc tgggccagtg ccagagagag 120
acagccgaga agaacgacta ctaccgggtg ccccactact gggacgcctg ctctagagcc 180
ctgcccgacc agacccggta caaatacgtg gaacagctgg tggacctgac cctgaactac 240
cactacgacg ccagccacgg cctggacaac ttcgacgtgc tgaagcggat caacgtgacc 300
gaggtgtccc tgctgatcag cgacttccgg cggcagaaca gaagaggcgg caccaacaag 360
cggactacct tcaacgccgc tggcagcctg gcccctcacg ccagatccct ggaattcagc 420
gtgcggctgt tcgccaac 438

<210> SEQ ID NO 38
<211> LENGTH: 146
<212> TYPE: PRT
<213> ORGANISM: Artificial Sequence
<220> FEATURE:
<223> OTHER INFORMATION: IgE leader + UL131a consensus amino acid sequence

<400> SEQUENCE: 38

Met Asp Trp Thr Trp Ile Leu Phe Leu Val Ala Ala Ala Thr Arg Val
1 5 10 15

His Ser Arg Leu Cys Arg Val Trp Leu Ser Val Cys Leu Cys Ala Val
20 25 30

Val Leu Gly Gln Cys Gln Arg Glu Thr Ala Glu Lys Asn Asp Tyr Tyr
35 40 45

Arg Val Pro His Tyr Trp Asp Ala Cys Ser Arg Ala Leu Pro Asp Gln
50 55 60

Thr Arg Tyr Lys Tyr Val Glu Gln Leu Val Asp Leu Thr Leu Asn Tyr
65 70 75 80

His Tyr Asp Ala Ser His Gly Leu Asp Asn Phe Asp Val Leu Lys Arg
85 90 95

Ile Asn Val Thr Glu Val Ser Leu Leu Ile Ser Asp Phe Arg Arg Gln
100 105 110

Asn Arg Arg Gly Gly Thr Asn Lys Arg Thr Thr Phe Asn Ala Ala Gly
115 120 125

Ser Leu Ala Pro His Ala Arg Ser Leu Glu Phe Ser Val Arg Leu Phe
130 135 140

Ala Asn
145

<210> SEQ ID NO 39
<211> LENGTH: 1737
<212> TYPE: DNA
<213> ORGANISM: Artificial Sequence
<220> FEATURE:
<223> OTHER INFORMATION: IgE leader + UL83 consensus nucleic acid sequence

<400> SEQUENCE: 39

```
atggattgga cctggatcct gtttctggtg gccgctgcaa caagggtcca ctctgagagt      60
cgcgggcgga gatgccctga aatgatcagc gtgctgggcc caatttccgg gcatgtgctg     120
aaggccgtct tctcccgcgg agacaccccc gtgctgcctc acgagacaag actgctgcag     180
actggcatcc atgtgagggt ctcccagcca tctctgattc tggtgtctca gtacacccca     240
gatagtacac cctgccacag aggggacaac cagctgcagg tgcagcatac ctacttcacc     300
ggatcagagg tcgaaaatgt gagcgtcaac gtgcacaatc ccacaggcag gagtatctgt     360
ccttcacagg agccaatgag catctacgtg tacgccctgc cctgaaaat gctgaacatc      420
cctagcatta atgtgcacca ttacccctcc gccgctgaac gaaagcaccg gcatctgcct     480
gtggcagatg ccgtcatcca tgcttcaggc aaacagatgt ggcaggcacg actgaccgtg     540
agcggactgg catggacacg acagcagaac cagtggaagg agccagacgt gtactatact     600
agcgccttcg tgttccccac caaagacgtg gccctgcgac acgtggtctg cgcacatgag     660
ctggtgtgct ctatggaaaa tactcgggcc accaagatgc aggtcattgg cgatcagtac     720
gtcaaagtgt atctggagtc cttttgtgaa gacgtgccct ctgggaagct gttcatgcac     780
gtgaccctgg gaagcgatgt cgaggaagac ctgactatga cccggaaccc acagcccttt     840
atgagacctc acgagaggaa cggcttcact gtgctgtgcc caaagaatat gatcattaag     900
cccgggaaaa tctctcatat tatgctggat gtggccttta caagtcacga gcatttcgga     960
ctgctgtgcc ccaaaagcat ccctgggctg tcaattagcg gaaacctgct gatgaatggc    1020
cagcagatct ttctggaagt gcaggccatt cgagagaccg tcgaactgcg acagtacgac    1080
ccagtggcag ccctgttctt tttcgatatc gacctgctgc tgcagagagg ccctcagtat    1140
agtgagcacc caacattcac ttcacagtac aggattcagg ggaagctgga gtatcggcac    1200
acttgggata gacatgacga aggagctgca cagggcgacg atgacgtgtg gacctccggc    1260
tctgatagtg acgaggaact ggtgaccaca gagcgaaaaa ctccccgggt gaccggagga    1320
ggagctatgg caggagcatc aaccagcgcc ggacgaaaga gaaaaagcgc cagcagcgcc    1380
acagcatgca ctgcaggcgt gatgacaagg gggcgcctga aggcagaatc cacagtcgcc    1440
cctgaggaag atactgacga ggattctgac aacgaaatcc acaatccagc cgtgttcacc    1500
tggccacctt ggcaggcagg aattctggct cgcaatctgg tccctatggt ggccactgtc    1560
cagggacaga acctgaagta ccaggagttt ttctgggatg ctaatgacat ctatcggatt    1620
ttcgcagagc tggaaggcgt gtggcagcca gcagctcagc caaaaaggcg ccgacacaga    1680
caggacgcac tgcctggacc atgtatcgcc tccaccccaa agaaacatag ggctga        1737
```

<210> SEQ ID NO 40
<211> LENGTH: 578
<212> TYPE: PRT
<213> ORGANISM: Artificial Sequence
<220> FEATURE:
<223> OTHER INFORMATION: IgE leader + UL83 consensus amino acid sequence

<400> SEQUENCE: 40

```
Met Asp Trp Thr Trp Ile Leu Phe Leu Val Ala Ala Ala Thr Arg Val
1               5                   10                  15

His Ser Glu Ser Arg Gly Arg Arg Cys Pro Glu Met Ile Ser Val Leu
            20                  25                  30

Gly Pro Ile Ser Gly His Val Leu Lys Ala Val Phe Ser Arg Gly Asp
        35                  40                  45
```

-continued

```
Thr Pro Val Leu Pro His Glu Thr Arg Leu Leu Gln Thr Gly Ile His
    50                  55                  60

Val Arg Val Ser Gln Pro Ser Leu Ile Leu Val Ser Gln Tyr Thr Pro
65                  70                  75                  80

Asp Ser Thr Pro Cys His Arg Gly Asp Asn Gln Leu Gln Val Gln His
                85                  90                  95

Thr Tyr Phe Thr Gly Ser Glu Val Glu Asn Val Ser Val Asn Val His
            100                 105                 110

Asn Pro Thr Gly Arg Ser Ile Cys Pro Ser Gln Glu Pro Met Ser Ile
        115                 120                 125

Tyr Val Tyr Ala Leu Pro Leu Lys Met Leu Asn Ile Pro Ser Ile Asn
    130                 135                 140

Val His His Tyr Pro Ser Ala Ala Glu Arg Lys His Arg His Leu Pro
145                 150                 155                 160

Val Ala Asp Ala Val Ile His Ala Ser Gly Lys Gln Met Trp Gln Ala
                165                 170                 175

Arg Leu Thr Val Ser Gly Leu Ala Trp Thr Arg Gln Gln Asn Gln Trp
            180                 185                 190

Lys Glu Pro Asp Val Tyr Tyr Thr Ser Ala Phe Val Phe Pro Thr Lys
        195                 200                 205

Asp Val Ala Leu Arg His Val Val Cys Ala His Glu Leu Val Cys Ser
    210                 215                 220

Met Glu Asn Thr Arg Ala Thr Lys Met Gln Val Ile Gly Asp Gln Tyr
225                 230                 235                 240

Val Lys Val Tyr Leu Glu Ser Phe Cys Glu Asp Val Pro Ser Gly Lys
                245                 250                 255

Leu Phe Met His Val Thr Leu Gly Ser Asp Val Glu Glu Asp Leu Thr
            260                 265                 270

Met Thr Arg Asn Pro Gln Pro Phe Met Arg Pro His Glu Arg Asn Gly
        275                 280                 285

Phe Thr Val Leu Cys Pro Lys Asn Met Ile Ile Lys Pro Gly Lys Ile
    290                 295                 300

Ser His Ile Met Leu Asp Val Ala Phe Thr Ser His Glu His Phe Gly
305                 310                 315                 320

Leu Leu Cys Pro Lys Ser Ile Pro Gly Leu Ser Ile Ser Gly Asn Leu
                325                 330                 335

Leu Met Asn Gly Gln Gln Ile Phe Leu Glu Val Gln Ala Ile Arg Glu
            340                 345                 350

Thr Val Glu Leu Arg Gln Tyr Asp Pro Val Ala Ala Leu Phe Phe Phe
        355                 360                 365

Asp Ile Asp Leu Leu Leu Gln Arg Gly Pro Gln Tyr Ser Glu His Pro
    370                 375                 380

Thr Phe Thr Ser Gln Tyr Arg Ile Gln Gly Lys Leu Glu Tyr Arg His
385                 390                 395                 400

Thr Trp Asp Arg His Asp Glu Gly Ala Ala Gln Gly Asp Asp Asp Val
                405                 410                 415

Trp Thr Ser Gly Ser Asp Ser Asp Glu Glu Leu Val Thr Thr Glu Arg
            420                 425                 430

Lys Thr Pro Arg Val Thr Gly Gly Gly Ala Met Ala Gly Ala Ser Thr
        435                 440                 445

Ser Ala Gly Arg Lys Arg Lys Ser Ala Ser Ser Ala Thr Ala Cys Thr
    450                 455                 460

Ala Gly Val Met Thr Arg Gly Arg Leu Lys Ala Glu Ser Thr Val Ala
```

-continued 465 470 475 480

Pro Glu Glu Asp Thr Asp Glu Asp Ser Asp Asn Glu Ile His Asn Pro
485 490 495

Ala Val Phe Thr Trp Pro Pro Trp Gln Ala Gly Ile Leu Ala Arg Asn
500 505 510

Leu Val Pro Met Val Ala Thr Val Gln Gly Gln Asn Leu Lys Tyr Gln
515 520 525

Glu Phe Phe Trp Asp Ala Asn Asp Ile Tyr Arg Ile Phe Ala Glu Leu
530 535 540

Glu Gly Val Trp Gln Pro Ala Ala Gln Pro Lys Arg Arg Arg His Arg
545 550 555 560

Gln Asp Ala Leu Pro Gly Pro Cys Ile Ala Ser Thr Pro Lys Lys His
565 570 575

Arg Gly

<210> SEQ ID NO 41
<211> LENGTH: 2802
<212> TYPE: DNA
<213> ORGANISM: Artificial Sequence
<220> FEATURE:
<223> OTHER INFORMATION: IgE leader + gB consensus + HA Tag nucleic acid sequence

<400> SEQUENCE: 41
atggactgga cctggatcct gttcctggtg gccgctgcca cacgggtgca cagcgagagc 60
agaatctggt gcctggtcgt gtgcgtgaac ctgtgcatcg tgtgcctggg agccgccgtg 120
tccagcagca gcacccgggg cacaagcgcc acacacagcc accacagcag ccacaccacc 180
agcgccgccc acagccggag cggaagcgtg agcagccagc gggtgaccag cagcgaggcc 240
gtgtcccacc gggccaacga gacaatctac aacaccaccc tgaagtacgg cgacgtcgtg 300
ggagtgaaca ccaccaagta cccctacaga gtgtgcagca tggcccaggg caccgacctg 360
atcagattcg agcggaacat cgtgtgtacc agcatgaagc ccatcaacga ggacctggac 420
gagggcatca tggtggtgta caagagaaac atcgtggccc acaccttcaa agtgcgggtg 480
taccagaagg tgctgacctt ccggcggagc tacgcctaca tccacaccac ctacctgctg 540
ggcagcaaca ccgagtacgt ggcccctccc atgtgggaga tccaccacat caacagccac 600
agccagtgct acagcagcta cagccgcgtg atcgccggca ccgtgttcgt ggcctaccac 660
cgggacagct acgagaacaa gaccatgcag ctgatgcccg acgactacag caacacccac 720
agcaccagat acgtgaccgt gaaggaccag tggcacagcc ggggaagcac ctggctgtac 780
agagagacat gcaacctgaa ctgcatggtc accatcacca ccgccagaag caagtaccct 840
taccacttct tcgccaccag caccggcgac gtggtggaca tcagcccctt ctacaacggc 900
accaaccgga acgccagcta cttcggcgag aacgccgaca agttcttcat cttccccaac 960
tacaccatcg tgtccgactt cggcagaccc aacagcgccc ctgagacaca ccggctggtg 1020
gcctttctgg aacgggccga cagcgtgatc agctgggaca tccaggacga gaagaacgtg 1080
acctgccagc tgaccttctg ggaggctagc gagcggacca tcagaagcga ggccgaggac 1140
agctaccact tcagcagcgc caagatgacc gccaccttcc tgagcaagaa acaggaagtg 1200
aacatgagcg acagcgccct ggactgcgtg cgggatgagg ccatcaacaa gctgcagcag 1260
atcttcaaca ccagctacaa ccagacctac gagaagtatg gcaacgtgtc cgtgttcgag 1320
acaacaggcg gcctggtggt gttctggcag ggcatcaagc agaagtccct ggtcgagctg 1380

-continued

```
gaacggctgg ccaacagaag cagcctgaac ctgacccacc ggaccaagcg gagcaccgac   1440

ggcaacaata ccacccacct gagcaacatg gaaagcgtcc acaacctggt gtacgcccag   1500

ctgcagttca cctacgacac cctgcggggc tacatcaacc gggccctggc ccagatcgcc   1560

gaggcttggt gtgtggacca gcggcggacc ctggaagtgt tcaaagagct gagcaagatc   1620

aaccccagcg ccatcctgag cgccatctac aacaagccta tcgccgccag attcatgggc   1680

gacgtgctgg gcctggccag ctgcgtgacc atcaaccaga ccagcgtgaa ggtgctgcgg   1740

gacatgaacg tgaaagaaag ccccggcaga tgctactcca gacccgtggt catcttcaac   1800

ttcgccaaca gctcctacgt gcagtacggc cagctgggcg aggacaacga gatcctgctg   1860

ggaaaccacc ggaccgagga atgccagctg cccagcctga agatctttat cgccggcaac   1920

agcgcctacg agtatgtgga ctacctgttc aagcggatga tcgacctgag cagcatcagc   1980

accgtggaca gcatgatcgc cctggacatc gacccctgg aaaacaccga cttccgggtg   2040

ctggaactgt acagccagaa agagctgcgg agcagcaacg tgttcgacct ggaagagatc   2100

atgcgcgagt tcaacagcta caagcagcgc gtgaaatacg tcgaggacaa ggtggtggac   2160

cccctgcccc cctacctgaa gggcctggac gacctgatga gcggcctggg agctgctggc   2220

aaggccgtgg gagtggccat tggagctgtg ggcggagccg tggccagcgt ggtggaaggc   2280

gtggccacct ttctgaagaa ccccttcggc gccttcacca tcatcctggt ggctatcgcc   2340

gtcgtgatca tcacctacct gatctacacc cggcagcggc ggctgtgtac ccagcctctg   2400

cagaacctgt tcccctacct ggtgtccgcc gacggcacca ccgtgacaag cggctccacc   2460

aaggacacca gcctgcaggc ccccacccagc tacgaggaat ccgtgtacaa cagcggccgg   2520

aagggcccag gccctcctag ctctgacgcc tctacagccg ccccacccta caccaacgag   2580

caggcctacc agatgctgct ggccctggct agactggacg ccgagcagag agcccagcag   2640

aacggaaccg acagcctgga tggccagacc ggcacccagg acaagggcca gaagcccaac   2700

ctgctggacc ggctgcggca cagaaagaac ggctaccggc acctgaagga cagcgacgaa   2760

gaggaaaacg tgtaccccta cgacgtgccc gactacgctt ga                     2802
```

<210> SEQ ID NO 42
<211> LENGTH: 933
<212> TYPE: PRT
<213> ORGANISM: Artificial Sequence
<220> FEATURE:
<223> OTHER INFORMATION: IgE leader + gB consensus + HA Tag amino acid sequence

<400> SEQUENCE: 42

```
Met Asp Trp Thr Trp Ile Leu Phe Leu Val Ala Ala Ala Thr Arg Val
1               5                   10                  15

His Ser Glu Ser Arg Ile Trp Cys Leu Val Val Cys Val Asn Leu Cys
            20                  25                  30

Ile Val Cys Leu Gly Ala Ala Val Ser Ser Ser Ser Thr Arg Gly Thr
        35                  40                  45

Ser Ala Thr His Ser His His Ser Ser His Thr Thr Ser Ala Ala His
    50                  55                  60

Ser Arg Ser Gly Ser Val Ser Ser Gln Arg Val Thr Ser Ser Glu Ala
65                  70                  75                  80

Val Ser His Arg Ala Asn Glu Thr Ile Tyr Asn Thr Thr Leu Lys Tyr
                85                  90                  95

Gly Asp Val Val Gly Val Asn Thr Thr Lys Tyr Pro Tyr Arg Val Cys
            100                 105                 110
```

```
Ser Met Ala Gln Gly Thr Asp Leu Ile Arg Phe Glu Arg Asn Ile Val
        115                 120                 125

Cys Thr Ser Met Lys Pro Ile Asn Glu Asp Leu Asp Glu Gly Ile Met
    130                 135                 140

Val Val Tyr Lys Arg Asn Ile Val Ala His Thr Phe Lys Val Arg Val
145                 150                 155                 160

Tyr Gln Lys Val Leu Thr Phe Arg Arg Ser Tyr Ala Tyr Ile His Thr
                165                 170                 175

Thr Tyr Leu Leu Gly Ser Asn Thr Glu Tyr Val Ala Pro Pro Met Trp
            180                 185                 190

Glu Ile His His Ile Asn Ser His Ser Gln Cys Tyr Ser Ser Tyr Ser
        195                 200                 205

Arg Val Ile Ala Gly Thr Val Phe Val Ala Tyr His Arg Asp Ser Tyr
    210                 215                 220

Glu Asn Lys Thr Met Gln Leu Met Pro Asp Asp Tyr Ser Asn Thr His
225                 230                 235                 240

Ser Thr Arg Tyr Val Thr Val Lys Asp Gln Trp His Ser Arg Gly Ser
                245                 250                 255

Thr Trp Leu Tyr Arg Glu Thr Cys Asn Leu Asn Cys Met Val Thr Ile
            260                 265                 270

Thr Thr Ala Arg Ser Lys Tyr Pro Tyr His Phe Phe Ala Thr Ser Thr
        275                 280                 285

Gly Asp Val Val Asp Ile Ser Pro Phe Tyr Asn Gly Thr Asn Arg Asn
    290                 295                 300

Ala Ser Tyr Phe Gly Glu Asn Ala Asp Lys Phe Phe Ile Phe Pro Asn
305                 310                 315                 320

Tyr Thr Ile Val Ser Asp Phe Gly Arg Pro Asn Ser Ala Leu Glu Thr
                325                 330                 335

His Arg Leu Val Ala Phe Leu Glu Arg Ala Asp Ser Val Ile Ser Trp
            340                 345                 350

Asp Ile Gln Asp Glu Lys Asn Val Thr Cys Gln Leu Thr Phe Trp Glu
        355                 360                 365

Ala Ser Glu Arg Thr Ile Arg Ser Glu Ala Glu Asp Ser Tyr His Phe
    370                 375                 380

Ser Ser Ala Lys Met Thr Ala Thr Phe Leu Ser Lys Lys Gln Glu Val
385                 390                 395                 400

Asn Met Ser Asp Ser Ala Leu Asp Cys Val Arg Asp Glu Ala Ile Asn
                405                 410                 415

Lys Leu Gln Gln Ile Phe Asn Thr Ser Tyr Asn Gln Thr Tyr Glu Lys
            420                 425                 430

Tyr Gly Asn Val Ser Val Phe Glu Thr Thr Gly Gly Leu Val Val Phe
        435                 440                 445

Trp Gln Gly Ile Lys Gln Lys Ser Leu Val Glu Leu Glu Arg Leu Ala
    450                 455                 460

Asn Arg Ser Ser Leu Asn Leu Thr His Arg Thr Lys Arg Ser Thr Asp
465                 470                 475                 480

Gly Asn Asn Thr Thr His Leu Ser Asn Met Glu Ser Val His Asn Leu
                485                 490                 495

Val Tyr Ala Gln Leu Gln Phe Thr Tyr Asp Thr Leu Arg Gly Tyr Ile
            500                 505                 510

Asn Arg Ala Leu Ala Gln Ile Ala Glu Ala Trp Cys Val Asp Gln Arg
        515                 520                 525
```

-continued

```
Arg Thr Leu Glu Val Phe Lys Glu Leu Ser Lys Ile Asn Pro Ser Ala
    530                 535                 540

Ile Leu Ser Ala Ile Tyr Asn Lys Pro Ile Ala Ala Arg Phe Met Gly
545                 550                 555                 560

Asp Val Leu Gly Leu Ala Ser Cys Val Thr Ile Asn Gln Thr Ser Val
                565                 570                 575

Lys Val Leu Arg Asp Met Asn Val Lys Glu Ser Pro Gly Arg Cys Tyr
            580                 585                 590

Ser Arg Pro Val Val Ile Phe Asn Phe Ala Asn Ser Ser Tyr Val Gln
        595                 600                 605

Tyr Gly Gln Leu Gly Glu Asp Asn Glu Ile Leu Leu Gly Asn His Arg
    610                 615                 620

Thr Glu Glu Cys Gln Leu Pro Ser Leu Lys Ile Phe Ile Ala Gly Asn
625                 630                 635                 640

Ser Ala Tyr Glu Tyr Val Asp Tyr Leu Phe Lys Arg Met Ile Asp Leu
                645                 650                 655

Ser Ser Ile Ser Thr Val Asp Ser Met Ile Ala Leu Asp Ile Asp Pro
            660                 665                 670

Leu Glu Asn Thr Asp Phe Arg Val Leu Glu Leu Tyr Ser Gln Lys Glu
        675                 680                 685

Leu Arg Ser Ser Asn Val Phe Asp Leu Glu Glu Ile Met Arg Glu Phe
    690                 695                 700

Asn Ser Tyr Lys Gln Arg Val Lys Tyr Val Glu Asp Lys Val Val Asp
705                 710                 715                 720

Pro Leu Pro Pro Tyr Leu Lys Gly Leu Asp Asp Leu Met Ser Gly Leu
                725                 730                 735

Gly Ala Ala Gly Lys Ala Val Gly Val Ala Ile Gly Ala Val Gly Gly
            740                 745                 750

Ala Val Ala Ser Val Val Glu Gly Val Ala Thr Phe Leu Lys Asn Pro
        755                 760                 765

Phe Gly Ala Phe Thr Ile Ile Leu Val Ala Ile Ala Val Val Ile Ile
    770                 775                 780

Thr Tyr Leu Ile Tyr Thr Arg Gln Arg Arg Leu Cys Thr Gln Pro Leu
785                 790                 795                 800

Gln Asn Leu Phe Pro Tyr Leu Val Ser Ala Asp Gly Thr Thr Val Thr
                805                 810                 815

Ser Gly Ser Thr Lys Asp Thr Ser Leu Gln Ala Pro Pro Ser Tyr Glu
            820                 825                 830

Glu Ser Val Tyr Asn Ser Gly Arg Lys Gly Pro Gly Pro Pro Ser Ser
        835                 840                 845

Asp Ala Ser Thr Ala Ala Pro Pro Tyr Thr Asn Glu Gln Ala Tyr Gln
    850                 855                 860

Met Leu Leu Ala Leu Ala Arg Leu Asp Ala Glu Gln Arg Ala Gln Gln
865                 870                 875                 880

Asn Gly Thr Asp Ser Leu Asp Gly Gln Thr Gly Thr Gln Asp Lys Gly
                885                 890                 895

Gln Lys Pro Asn Leu Leu Asp Arg Leu Arg His Arg Lys Asn Gly Tyr
            900                 905                 910

Arg His Leu Lys Asp Ser Asp Glu Glu Glu Asn Val Tyr Pro Tyr Asp
        915                 920                 925

Val Pro Asp Tyr Ala
    930
```

-continued

<210> SEQ ID NO 43
<211> LENGTH: 1197
<212> TYPE: DNA
<213> ORGANISM: Artificial Sequence
<220> FEATURE:
<223> OTHER INFORMATION: IgE leader + gM consensus + HA Tag nucleic acid sequence

<400> SEQUENCE: 43

```
atggattgga cctggatcct gttcctggtg gccgctgcta cccgggtcca cagtgcaccc     60

agccacgtgg acaaagtgaa cacccggact tggagcgcca gcatcgtgtt catggtgctg    120

accttcgtga atgtgtccgt ccacctggtg ctgagcaact tcccccacct gggctacccc    180

tgcgtgtact accacgtggt ggacttcgag cggctgaaca tgagcgccta caacgtgatg    240

catctgcaca cccccatgct gtttctggac agcgtgcagc tcgtgtgcta cgccgtgttt    300

atgcagctgg tgttcctggc cgtgaccatc tactacctcg tgtgctggat caagatttct    360

atgcggaagg acaagggcat gagcctgaac cagagcaccc gggacatcag ctacatgggc    420

gacagcctga ccgccttcct gttcatcctg agcatggaca ccttccagct gttcaccctg    480

accatgagct tccggctgcc cagcatgatc gcctttatgg ccgccgtcca cttcttctgt    540

ctgaccatct tcaacgtgtc catggtcacc cagtacagaa gctacaagcg gagcctgttc    600

ttcttcagtc ggctgcaccc caagctgaag ggcaccgtcc agttccggac cctgatcgtg    660

aacctggtgg aagtggccct gggcttcaac accaccgtgg tggctatggc tctgtgctac    720

ggcttcggca acaacttctt cgtgcggaca ggccacatgg tgctggccgt gttcgtggtg    780

tacgccatta tcagcatcat ctactttctg ctgatcgagg ccgtgttctt ccagtacgtg    840

aaggtgcagt tcggctacca cctgggcgcc tttttcggcc tgtgcggcct gatctacccc    900

atcgtgcagt acgacacctt cctgagcaac gagtaccgga ccggcatcag ctggtccttc    960

ggcatgctgt tcttcatctg ggccatgttc accacctgtc gggccgtgcg gtacttcaga   1020

ggcagaggca gcggctccgt gaagtaccag gccctggcca cagccagcgg cgaagaagtg   1080

gccgccctga gccaccacga cagcctggaa agcagacggc tgagagagga agaggacgac   1140

gacgacgatg aggacttcga ggacgcctac ccctacgacg tgcccgacta tgcctga      1197
```

<210> SEQ ID NO 44
<211> LENGTH: 398
<212> TYPE: PRT
<213> ORGANISM: Artificial Sequence
<220> FEATURE:
<223> OTHER INFORMATION: IgE leader + gM consensus + HA Tag amino acid sequence

<400> SEQUENCE: 44

```
Met Asp Trp Thr Trp Ile Leu Phe Leu Val Ala Ala Ala Thr Arg Val
1               5                   10                  15

His Ser Ala Pro Ser His Val Asp Lys Val Asn Thr Arg Thr Trp Ser
            20                  25                  30

Ala Ser Ile Val Phe Met Val Leu Thr Phe Val Asn Val Ser Val His
        35                  40                  45

Leu Val Leu Ser Asn Phe Pro His Leu Gly Tyr Pro Cys Val Tyr Tyr
    50                  55                  60

His Val Val Asp Phe Glu Arg Leu Asn Met Ser Ala Tyr Asn Val Met
65                  70                  75                  80

His Leu His Thr Pro Met Leu Phe Leu Asp Ser Val Gln Leu Val Cys
                85                  90                  95
```

```
Tyr Ala Val Phe Met Gln Leu Val Phe Leu Ala Val Thr Ile Tyr Tyr
            100                 105                 110

Leu Val Cys Trp Ile Lys Ile Ser Met Arg Lys Asp Lys Gly Met Ser
        115                 120                 125

Leu Asn Gln Ser Thr Arg Asp Ile Ser Tyr Met Gly Asp Ser Leu Thr
    130                 135                 140

Ala Phe Leu Phe Ile Leu Ser Met Asp Thr Phe Gln Leu Phe Thr Leu
145                 150                 155                 160

Thr Met Ser Phe Arg Leu Pro Ser Met Ile Ala Phe Met Ala Ala Val
                165                 170                 175

His Phe Phe Cys Leu Thr Ile Phe Asn Val Ser Met Val Thr Gln Tyr
            180                 185                 190

Arg Ser Tyr Lys Arg Ser Leu Phe Phe Phe Ser Arg Leu His Pro Lys
        195                 200                 205

Leu Lys Gly Thr Val Gln Phe Arg Thr Leu Ile Val Asn Leu Val Glu
    210                 215                 220

Val Ala Leu Gly Phe Asn Thr Thr Val Val Ala Met Ala Leu Cys Tyr
225                 230                 235                 240

Gly Phe Gly Asn Asn Phe Phe Val Arg Thr Gly His Met Val Leu Ala
                245                 250                 255

Val Phe Val Val Tyr Ala Ile Ile Ser Ile Ile Tyr Phe Leu Leu Ile
            260                 265                 270

Glu Ala Val Phe Phe Gln Tyr Val Lys Val Gln Phe Gly Tyr His Leu
        275                 280                 285

Gly Ala Phe Phe Gly Leu Cys Gly Leu Ile Tyr Pro Ile Val Gln Tyr
    290                 295                 300

Asp Thr Phe Leu Ser Asn Glu Tyr Arg Thr Gly Ile Ser Trp Ser Phe
305                 310                 315                 320

Gly Met Leu Phe Phe Ile Trp Ala Met Phe Thr Thr Cys Arg Ala Val
                325                 330                 335

Arg Tyr Phe Arg Gly Arg Gly Ser Gly Ser Val Lys Tyr Gln Ala Leu
            340                 345                 350

Ala Thr Ala Ser Gly Glu Glu Val Ala Ala Leu Ser His His Asp Ser
        355                 360                 365

Leu Glu Ser Arg Arg Leu Arg Glu Glu Glu Asp Asp Asp Asp Asp Glu
    370                 375                 380

Asp Phe Glu Asp Ala Tyr Pro Tyr Asp Val Pro Asp Tyr Ala
385                 390                 395


<210> SEQ ID NO 45
<211> LENGTH: 489
<212> TYPE: DNA
<213> ORGANISM: Artificial Sequence
<220> FEATURE:
<223> OTHER INFORMATION: IgE leader + gN consensus + HA Tag nucleic acid
      sequence

<400> SEQUENCE: 45

atggattgga cctggatcct gttcctggtg gccgctgcta cccgggtcca cagtgagtgg     60

aacaccctgg tgctgggtct gctggtgctg tctgtggccg ccagcagcaa caacaccagc    120

actgccagca cccccagccc tagcagcagc acccacacct ccaccaccgt gaaggccacc    180

accaccgcca ccacaagcac cacaacagcc accagcacca cctcttccac caccagcaca    240

aagcccggca gcaccactca cgaccccaac gtgatgaggc cccacgccca caacgacttc    300

tacaaggccc actgcaccag ccatatgtac gagctgagcc tgagcagctt cgccgcctgg    360
```

tggaccatgc tgaacgccct gatcctgatg ggcgccttct gcatcgtgct gcggcactgc 420
tgcttccaga acttcaccgc cacaaccacc aagggctact acccttacga tgtgcctgat 480
tatgcctga 489

<210> SEQ ID NO 46
<211> LENGTH: 162
<212> TYPE: PRT
<213> ORGANISM: Artificial Sequence
<220> FEATURE:
<223> OTHER INFORMATION: IgE leader + gN consensus + HA Tag amino acid sequence

<400> SEQUENCE: 46

Met Asp Trp Thr Trp Ile Leu Phe Leu Val Ala Ala Ala Thr Arg Val
1 5 10 15

His Ser Glu Trp Asn Thr Leu Val Leu Gly Leu Leu Val Leu Ser Val
20 25 30

Ala Ala Ser Ser Asn Asn Thr Ser Thr Ala Ser Thr Pro Ser Pro Ser
35 40 45

Ser Ser Thr His Thr Ser Thr Thr Val Lys Ala Thr Thr Thr Ala Thr
50 55 60

Thr Ser Thr Thr Thr Ala Thr Ser Thr Thr Ser Ser Thr Thr Ser Thr
65 70 75 80

Lys Pro Gly Ser Thr Thr His Asp Pro Asn Val Met Arg Pro His Ala
85 90 95

His Asn Asp Phe Tyr Lys Ala His Cys Thr Ser His Met Tyr Glu Leu
100 105 110

Ser Leu Ser Ser Phe Ala Ala Trp Trp Thr Met Leu Asn Ala Leu Ile
115 120 125

Leu Met Gly Ala Phe Cys Ile Val Leu Arg His Cys Cys Phe Gln Asn
130 135 140

Phe Thr Ala Thr Thr Thr Lys Gly Tyr Tyr Pro Tyr Asp Val Pro Asp
145 150 155 160

Tyr Ala

<210> SEQ ID NO 47
<211> LENGTH: 2310
<212> TYPE: DNA
<213> ORGANISM: Artificial Sequence
<220> FEATURE:
<223> OTHER INFORMATION: IgE leader + gH consensus + HA Tag nucleic acid sequence

<400> SEQUENCE: 47
atggactgga cctggatcct gttcctggtg gccgctgcta cccgggtgca cagtcgaccc 60
ggcctgccca gctacctgac cgtgttcgcc gtgtacctgc tgagccatct gcccagccag 120
agatacggcg ccgatgccgc ctctgaggcc ctggatcctc acgccttcca tctgctgctg 180
aacacctacg gcagacctat ccggttcctg cgcgagaaca ccacccagtg cacctacaac 240
agcagcctgc ggaacagcac cgtcgtgcgc gagaatgcta tcagcttcaa cttcttccag 300
agctacaacc agtactacgt gttccacatg ccccggtgcc tgttcgccgg acctctggcc 360
gagcagttcc tgaaccaggt ggacctgacc gagacactgg aaagatacca gcagcggctg 420
aatacctacg ccctggtgtc caaggacctg gccagctacc ggtccttcag ccagcagctg 480
aaggctcagg acagcctggg cgagcagcct accaccgtgc cccctccaat cgacctgagc 540

-continued

```
atcccccacg tgtggatgcc cccccagacc acacctcacg gctggaaaga gagccacacc    600
accagcggcc tgcacagacc ccacttcaac cagacctgca ttctgttcga cggccacgac    660
ctgctgttca gcaccgtgac cccctgcctg caccagggct tctacctgat cgacgagctg    720
agatacgtga agatcaccct gaccgaggat ttcttcgtgg tcaccgtgtc catcgacgac    780
gacaccccca tgctgctgat cttcggccat ctgcctcggg tgctgttcaa ggcccccctac   840
cagcgggaca acttcatcct gcggcagacc gagaagcacg agctgctggt gctggtcaag    900
aaggaccagc tgaaccggca ctcctacctg aaggaccccg acttcctgga cgccgccctg    960
gacttcaact acctggacct gagcgccctg ctgagaaaca gcttccacag atacgccgtg   1020
gacgtgctga agtccggccg gtgccagatg ctggacagac ggaccgtgga aatggccttc   1080
gcctatgccc tggccctgtt tgccgccgct cggcaggaag aggctggcgc tgaagtgtcc   1140
gtgcccagag ccctggacag acaggccgct ctgctgcaga tccaggaatt catgatcacc   1200
tgtctgagcc agacccccc  tcggaccacc ctgctgctgt accctaccgc cgtggatctg   1260
gccaagcggg ccctgtggac ccccaaccag atcaccgaca tcacaagcct cgtgcggctg   1320
gtgtacatcc tgagcaagca gaaccagcag cacctgatcc cccagtgggc cctgagacag   1380
atcgccgact tcgccctgaa gctgcacaag acccacctgg ctagctttct gagcgccttc   1440
gctaggcagg aactgtacct gatgggcagc ctggtgcact ccatgctggt gcacaccacc   1500
gagaggcggg aaatcttcat cgtggaaacc ggcctgtgca gcctggccga gctgagccac   1560
ttcacccagc tgctggccca cccccaccac gagtacctga gcgacctgta cacccccctgc  1620
agctctagcg gcagacggga tcacagcctg gaacggctga cccggctgtt ccccgatgcc   1680
acagtgcctg ccactgtgcc agccgccctg tccatcctgt ccaccatgca gcccagcacc   1740
ctggaaacct tccccgacct gttctgcctg cccctgggcg agagcttcag cgccctgaca   1800
gtgtccgagc acgtgtccta cgtggtcacc aaccagtacc tgatcaaggg catcagctac   1860
cccgtgtcca ccaccgtcgt gggccagagc ctgatcatca cccagaccga cagccagacc   1920
aagtgcgagc tgacccggaa catgcacacc acacacagca tcactgccgc cctgaacatc   1980
agcctggaaa actgcgcctt ctgccagtct gccctgctgg aatacgacga tacccagggc   2040
gtgatcaaca tcatgtacat gcacgacagc gacgacgtgc tgttcgccct ggacccctac   2100
aacgaggtgg tggtgtccag cccccggacc cactacctga tgctgctgaa gaacggcacc   2160
gtgctggaag tgaccgacgt ggtggtggac gccaccgaca gcagactgct gatgatgagc   2220
gtgtacgccc tgagcgccat catcggcatc tacctgctgt accggatgct gaaaacctgc   2280
taccccctacg acgtgcccga ctacgcctga                                   2310
```

<210> SEQ ID NO 48
<211> LENGTH: 769
<212> TYPE: PRT
<213> ORGANISM: Artificial Sequence
<220> FEATURE:
<223> OTHER INFORMATION: IgE leader + gH consensus + HA Tag amino acid sequence

<400> SEQUENCE: 48

```
Met Asp Trp Thr Trp Ile Leu Phe Leu Val Ala Ala Ala Thr Arg Val
1               5                   10                  15

His Ser Arg Pro Gly Leu Pro Ser Tyr Leu Thr Val Phe Ala Val Tyr
            20                  25                  30

Leu Leu Ser His Leu Pro Ser Gln Arg Tyr Gly Ala Asp Ala Ala Ser
        35                  40                  45
```

-continued

```
Glu Ala Leu Asp Pro His Ala Phe His Leu Leu Leu Asn Thr Tyr Gly
    50                  55                  60

Arg Pro Ile Arg Phe Leu Arg Glu Asn Thr Thr Gln Cys Thr Tyr Asn
65                  70                  75                  80

Ser Ser Leu Arg Asn Ser Thr Val Val Arg Glu Asn Ala Ile Ser Phe
                85                  90                  95

Asn Phe Phe Gln Ser Tyr Asn Gln Tyr Tyr Val Phe His Met Pro Arg
            100                 105                 110

Cys Leu Phe Ala Gly Pro Leu Ala Glu Gln Phe Leu Asn Gln Val Asp
        115                 120                 125

Leu Thr Glu Thr Leu Glu Arg Tyr Gln Gln Arg Leu Asn Thr Tyr Ala
    130                 135                 140

Leu Val Ser Lys Asp Leu Ala Ser Tyr Arg Ser Phe Ser Gln Gln Leu
145                 150                 155                 160

Lys Ala Gln Asp Ser Leu Gly Glu Gln Pro Thr Thr Val Pro Pro Pro
                165                 170                 175

Ile Asp Leu Ser Ile Pro His Val Trp Met Pro Pro Gln Thr Thr Pro
            180                 185                 190

His Gly Trp Lys Glu Ser His Thr Thr Ser Gly Leu His Arg Pro His
        195                 200                 205

Phe Asn Gln Thr Cys Ile Leu Phe Asp Gly His Asp Leu Leu Phe Ser
    210                 215                 220

Thr Val Thr Pro Cys Leu His Gln Gly Phe Tyr Leu Ile Asp Glu Leu
225                 230                 235                 240

Arg Tyr Val Lys Ile Thr Leu Thr Glu Asp Phe Phe Val Val Thr Val
                245                 250                 255

Ser Ile Asp Asp Asp Thr Pro Met Leu Leu Ile Phe Gly His Leu Pro
            260                 265                 270

Arg Val Leu Phe Lys Ala Pro Tyr Gln Arg Asp Asn Phe Ile Leu Arg
        275                 280                 285

Gln Thr Glu Lys His Glu Leu Leu Val Leu Val Lys Lys Asp Gln Leu
    290                 295                 300

Asn Arg His Ser Tyr Leu Lys Asp Pro Asp Phe Leu Asp Ala Ala Leu
305                 310                 315                 320

Asp Phe Asn Tyr Leu Asp Leu Ser Ala Leu Leu Arg Asn Ser Phe His
                325                 330                 335

Arg Tyr Ala Val Asp Val Leu Lys Ser Gly Arg Cys Gln Met Leu Asp
            340                 345                 350

Arg Arg Thr Val Glu Met Ala Phe Ala Tyr Ala Leu Ala Leu Phe Ala
        355                 360                 365

Ala Ala Arg Gln Glu Glu Ala Gly Ala Glu Val Ser Val Pro Arg Ala
    370                 375                 380

Leu Asp Arg Gln Ala Ala Leu Leu Gln Ile Gln Glu Phe Met Ile Thr
385                 390                 395                 400

Cys Leu Ser Gln Thr Pro Pro Arg Thr Thr Leu Leu Leu Tyr Pro Thr
                405                 410                 415

Ala Val Asp Leu Ala Lys Arg Ala Leu Trp Thr Pro Asn Gln Ile Thr
            420                 425                 430

Asp Ile Thr Ser Leu Val Arg Leu Val Tyr Ile Leu Ser Lys Gln Asn
        435                 440                 445

Gln Gln His Leu Ile Pro Gln Trp Ala Leu Arg Gln Ile Ala Asp Phe
    450                 455                 460
```

-continued

```
Ala Leu Lys Leu His Lys Thr His Leu Ala Ser Phe Leu Ser Ala Phe
465                 470                 475                 480

Ala Arg Gln Glu Leu Tyr Leu Met Gly Ser Leu Val His Ser Met Leu
                485                 490                 495

Val His Thr Thr Glu Arg Arg Glu Ile Phe Ile Val Glu Thr Gly Leu
            500                 505                 510

Cys Ser Leu Ala Glu Leu Ser His Phe Thr Gln Leu Leu Ala His Pro
        515                 520                 525

His His Glu Tyr Leu Ser Asp Leu Tyr Thr Pro Cys Ser Ser Ser Gly
    530                 535                 540

Arg Arg Asp His Ser Leu Glu Arg Leu Thr Arg Leu Phe Pro Asp Ala
545                 550                 555                 560

Thr Val Pro Ala Thr Val Pro Ala Ala Leu Ser Ile Leu Ser Thr Met
                565                 570                 575

Gln Pro Ser Thr Leu Glu Thr Phe Pro Asp Leu Phe Cys Leu Pro Leu
            580                 585                 590

Gly Glu Ser Phe Ser Ala Leu Thr Val Ser Glu His Val Ser Tyr Val
        595                 600                 605

Val Thr Asn Gln Tyr Leu Ile Lys Gly Ile Ser Tyr Pro Val Ser Thr
    610                 615                 620

Thr Val Val Gly Gln Ser Leu Ile Ile Thr Gln Thr Asp Ser Gln Thr
625                 630                 635                 640

Lys Cys Glu Leu Thr Arg Asn Met His Thr Thr His Ser Ile Thr Ala
                645                 650                 655

Ala Leu Asn Ile Ser Leu Glu Asn Cys Ala Phe Cys Gln Ser Ala Leu
            660                 665                 670

Leu Glu Tyr Asp Asp Thr Gln Gly Val Ile Asn Ile Met Tyr Met His
        675                 680                 685

Asp Ser Asp Asp Val Leu Phe Ala Leu Asp Pro Tyr Asn Glu Val Val
    690                 695                 700

Val Ser Ser Pro Arg Thr His Tyr Leu Met Leu Leu Lys Asn Gly Thr
705                 710                 715                 720

Val Leu Glu Val Thr Asp Val Val Val Asp Ala Thr Asp Ser Arg Leu
                725                 730                 735

Leu Met Met Ser Val Tyr Ala Leu Ser Ala Ile Ile Gly Ile Tyr Leu
            740                 745                 750

Leu Tyr Arg Met Leu Lys Thr Cys Tyr Pro Tyr Asp Val Pro Asp Tyr
        755                 760                 765

Ala
```

<210> SEQ ID NO 49
<211> LENGTH: 915
<212> TYPE: DNA
<213> ORGANISM: Artificial Sequence
<220> FEATURE:
<223> OTHER INFORMATION: IgE leader + gL consensus + HA Tag nucleic acid sequence

<400> SEQUENCE: 49

```
atggattgga cctggatcct gtttctggtg gccgctgcaa caagggtcca ctcttgcagg      60

cggcccgact gcggcttcag cttcagccct ggccccgtga tcctgctgtg gtgctgcctg     120

ctgctgccca tcgtgtcctc tgccgccgtg tctgtggccc ctacagccgc cgagaaggtg     180

ccagccgagt gccctgagct gaccagacgg tgtctgctgg gcgaggtgtt ccagggcgat     240

aagtacgaga gctggctgcg gcccctggtc aacgtgaccg gcagagatgg ccccctgagc     300
```

```
cagctgatcc ggtacagacc cgtgacccct gaggccgcca acagcgtgct gctggacgaa    360

gcctttctgg acacactggc cctgctgtac aacaaccccg accagctgcg ggccctgctg    420

acactgctga gcagcgatac cgcccccaga tggatgaccg tgatgcgggg ctacagcgag    480

tgcggcgacg gatctcccgc cgtgtacacc tgtgtggacg acctgtgccg gggctacgac    540

ctgaccagac tgagctacgg ccggtccatc ttcacagagc acgtgctggg cttcgagctg    600

gtgcccccca gcctgttcaa tgtggtggtg gccatccgga acgaggccac ccggaccaac    660

agagcagtgc ggctgcctgt gtccaccgct gctgctccag agggcatcac cctgttctac    720

ggcctgtaca acgccgtgaa agagttctgc ctgagacacc agctggaccc cccccctgctg    780

cggcacctgg acaagtacta cgccggcctg cctcccgagc tgaagcagac cagagtgaac    840

ctgcccgccc acagcagata cggccctcag gccgtggacg ccagataccc ttacgatgtg    900

cctgattatg cctga                                                      915
```

```
<210> SEQ ID NO 50
<211> LENGTH: 304
<212> TYPE: PRT
<213> ORGANISM: Artificial Sequence
<220> FEATURE:
<223> OTHER INFORMATION: IgE leader + gL Consensus + HA Tag amino acid
      sequence

<400> SEQUENCE: 50

Met Asp Trp Thr Trp Ile Leu Phe Leu Val Ala Ala Ala Thr Arg Val
1               5                   10                  15

His Ser Cys Arg Arg Pro Asp Cys Gly Phe Ser Phe Ser Pro Gly Pro
            20                  25                  30

Val Ile Leu Leu Trp Cys Cys Leu Leu Leu Pro Ile Val Ser Ser Ala
        35                  40                  45

Ala Val Ser Val Ala Pro Thr Ala Ala Glu Lys Val Pro Ala Glu Cys
    50                  55                  60

Pro Glu Leu Thr Arg Arg Cys Leu Leu Gly Glu Val Phe Gln Gly Asp
65                  70                  75                  80

Lys Tyr Glu Ser Trp Leu Arg Pro Leu Val Asn Val Thr Gly Arg Asp
                85                  90                  95

Gly Pro Leu Ser Gln Leu Ile Arg Tyr Arg Pro Val Thr Pro Glu Ala
            100                 105                 110

Ala Asn Ser Val Leu Leu Asp Glu Ala Phe Leu Asp Thr Leu Ala Leu
        115                 120                 125

Leu Tyr Asn Asn Pro Asp Gln Leu Arg Ala Leu Leu Thr Leu Leu Ser
    130                 135                 140

Ser Asp Thr Ala Pro Arg Trp Met Thr Val Met Arg Gly Tyr Ser Glu
145                 150                 155                 160

Cys Gly Asp Gly Ser Pro Ala Val Tyr Thr Cys Val Asp Asp Leu Cys
                165                 170                 175

Arg Gly Tyr Asp Leu Thr Arg Leu Ser Tyr Gly Arg Ser Ile Phe Thr
            180                 185                 190

Glu His Val Leu Gly Phe Glu Leu Val Pro Pro Ser Leu Phe Asn Val
        195                 200                 205

Val Val Ala Ile Arg Asn Glu Ala Thr Arg Thr Asn Arg Ala Val Arg
    210                 215                 220

Leu Pro Val Ser Thr Ala Ala Ala Pro Glu Gly Ile Thr Leu Phe Tyr
225                 230                 235                 240
```

```
Gly Leu Tyr Asn Ala Val Lys Glu Phe Cys Leu Arg His Gln Leu Asp
                245                 250                 255

Pro Pro Leu Leu Arg His Leu Asp Lys Tyr Tyr Ala Gly Leu Pro Pro
            260                 265                 270

Glu Leu Lys Gln Thr Arg Val Asn Leu Pro Ala His Ser Arg Tyr Gly
        275                 280                 285

Pro Gln Ala Val Asp Ala Arg Tyr Pro Tyr Asp Val Pro Asp Tyr Ala
    290                 295                 300
```

<210> SEQ ID NO 51
<211> LENGTH: 1497
<212> TYPE: DNA
<213> ORGANISM: Artificial Sequence
<220> FEATURE:
<223> OTHER INFORMATION: IgE leader + gO consensus + HA Tag nucleic acid sequence

<400> SEQUENCE: 51

```
atggactgga cctggatcct gttcctggtc gccgctgcaa ctagagtgca cagcggcaag     60

aaagaaatga tcatggtcaa gggcatcccc aagatcatgc tgctgatcag catcaccttt    120

ctgctgctga gcctgatcaa ctgcaacgtg ctggtcaaca gcaagggcac acggcggagc    180

tggccctaca ccgtgctgag ctaccggggc aaagagatcc tgaagaagca gaaagaggac    240

atcctgaagc ggctgatgag caccagcagc gacggctacc ggttcctgat gtaccccagc    300

cagcagaaat tccacgccat cgtgatcagc atggacaagt tcccccagga ctacatcctg    360

gccggaccca tccggaacga cagcatcacc cacatgtggt tcgacttcta cagcacccag    420

ctgcggaagc ccgccaaata cgtgtacagc gagtacaacc acaccgccca caagatcacc    480

ctgcggcctc cccccttgcgg caccgtgccc agcatgaact gcctgagcga gatgctgaac    540

gtgtccaagc ggaacgacac cggcgagaag ggctgcggca acttcaccac cttcaacccc    600

atgttcttca acgtgccccg gtggaacacc aagctgtaca tcggcagcaa caaagtgaac    660

gtggacagcc agaccatcta ctttctgggc ctgaccgccc tgctgctgcg ctacgcccag    720

agaaactgca cccggtcctt ctacctggtc aacgccatga gccggaacct gttccgggtg    780

cccaagtaca tcaacggcac caagctgaag aacaccatgc ggaagctgaa gcggaagcag    840

gccctggtca aagagcagcc ccagaagaag aacaagaagt cccagagcac caccaccccc    900

tacctgagct acaccaccag caccgccttc aacgtgacca ccaacgtgac ctacagcgcc    960

acagccgccg tgaccagagt ggccacctcc accaccggct accggcccga cagcaacttc   1020

atgaagtcca tcatggccac ccagctgagg gacctggcca cctgggtgta caccaccctg   1080

cggtacagaa acgagccctt ctgcaagccc gaccggaaca gaaccgccgt gtccgagttc   1140

atgaagaata cccacgtgct gatccgcaac gagacaccct acaccatcta cggcaccctg   1200

gacatgagca gcctgtacta caacgagaca atgagcgtcg agaacgagac agccagcgac   1260

aacaacgaaa ccacccccac cagccccagc acccggttcc agcggacctt catcgacccc   1320

ctgtgggact acctggacag cctgctgttc ctggacaaga tccggaactt cagcctgcag   1380

ctgcccgcct acggcaacct gacccccccct gaacacagaa gggccgccaa cctgagcacc   1440

ctgaacagcc tgtggtggtg gctgcagtac ccctacgacg tgcccgacta cgcctga      1497
```

<210> SEQ ID NO 52
<211> LENGTH: 498
<212> TYPE: PRT
<213> ORGANISM: Artificial Sequence
<220> FEATURE:

<223> OTHER INFORMATION: IgE leader + g0 consensus + HA Tag amino acid
      sequence

<400> SEQUENCE: 52

Met Asp Trp Thr Trp Ile Leu Phe Leu Val Ala Ala Ala Thr Arg Val
1               5                   10                  15

His Ser Gly Lys Lys Glu Met Ile Met Val Lys Gly Ile Pro Lys Ile
            20                  25                  30

Met Leu Leu Ile Ser Ile Thr Phe Leu Leu Leu Ser Leu Ile Asn Cys
        35                  40                  45

Asn Val Leu Val Asn Ser Lys Gly Thr Arg Arg Ser Trp Pro Tyr Thr
    50                  55                  60

Val Leu Ser Tyr Arg Gly Lys Glu Ile Leu Lys Lys Gln Lys Glu Asp
65                  70                  75                  80

Ile Leu Lys Arg Leu Met Ser Thr Ser Ser Asp Gly Tyr Arg Phe Leu
                85                  90                  95

Met Tyr Pro Ser Gln Gln Lys Phe His Ala Ile Val Ile Ser Met Asp
            100                 105                 110

Lys Phe Pro Gln Asp Tyr Ile Leu Ala Gly Pro Ile Arg Asn Asp Ser
        115                 120                 125

Ile Thr His Met Trp Phe Asp Phe Tyr Ser Thr Gln Leu Arg Lys Pro
    130                 135                 140

Ala Lys Tyr Val Tyr Ser Glu Tyr Asn His Thr Ala His Lys Ile Thr
145                 150                 155                 160

Leu Arg Pro Pro Pro Cys Gly Thr Val Pro Ser Met Asn Cys Leu Ser
                165                 170                 175

Glu Met Leu Asn Val Ser Lys Arg Asn Asp Thr Gly Glu Lys Gly Cys
            180                 185                 190

Gly Asn Phe Thr Thr Phe Asn Pro Met Phe Phe Asn Val Pro Arg Trp
        195                 200                 205

Asn Thr Lys Leu Tyr Ile Gly Ser Asn Lys Val Asn Val Asp Ser Gln
    210                 215                 220

Thr Ile Tyr Phe Leu Gly Leu Thr Ala Leu Leu Leu Arg Tyr Ala Gln
225                 230                 235                 240

Arg Asn Cys Thr Arg Ser Phe Tyr Leu Val Asn Ala Met Ser Arg Asn
                245                 250                 255

Leu Phe Arg Val Pro Lys Tyr Ile Asn Gly Thr Lys Leu Lys Asn Thr
            260                 265                 270

Met Arg Lys Leu Lys Arg Lys Gln Ala Leu Val Lys Glu Gln Pro Gln
        275                 280                 285

Lys Lys Asn Lys Lys Ser Gln Ser Thr Thr Thr Pro Tyr Leu Ser Tyr
    290                 295                 300

Thr Thr Ser Thr Ala Phe Asn Val Thr Thr Asn Val Thr Tyr Ser Ala
305                 310                 315                 320

Thr Ala Ala Val Thr Arg Val Ala Thr Ser Thr Thr Gly Tyr Arg Pro
                325                 330                 335

Asp Ser Asn Phe Met Lys Ser Ile Met Ala Thr Gln Leu Arg Asp Leu
            340                 345                 350

Ala Thr Trp Val Tyr Thr Thr Leu Arg Tyr Arg Asn Glu Pro Phe Cys
        355                 360                 365

Lys Pro Asp Arg Asn Arg Thr Ala Val Ser Glu Phe Met Lys Asn Thr
    370                 375                 380

His Val Leu Ile Arg Asn Glu Thr Pro Tyr Thr Ile Tyr Gly Thr Leu
385                 390                 395                 400

```
Asp Met Ser Ser Leu Tyr Tyr Asn Glu Thr Met Ser Val Glu Asn Glu
                405                 410                 415

Thr Ala Ser Asp Asn Asn Glu Thr Thr Pro Thr Ser Pro Ser Thr Arg
            420                 425                 430

Phe Gln Arg Thr Phe Ile Asp Pro Leu Trp Asp Tyr Leu Asp Ser Leu
        435                 440                 445

Leu Phe Leu Asp Lys Ile Arg Asn Phe Ser Leu Gln Leu Pro Ala Tyr
    450                 455                 460

Gly Asn Leu Thr Pro Pro Glu His Arg Arg Ala Ala Asn Leu Ser Thr
465                 470                 475                 480

Leu Asn Ser Leu Trp Trp Trp Leu Gln Tyr Pro Tyr Asp Val Pro Asp
                485                 490                 495

Tyr Ala


<210> SEQ ID NO 53
<211> LENGTH: 594
<212> TYPE: DNA
<213> ORGANISM: Artificial Sequence
<220> FEATURE:
<223> OTHER INFORMATION: IgE leader + UL128 consensus + HA Tag nucleic
      acid sequence

<400> SEQUENCE: 53

atggattgga cctggatcct gtttctggtg gccgctgcaa caagggtcca ctctagcccc     60

aaggatctga cccctttcct gaccgccctg tggctgctcc tgggccacag cagagtgcct    120

agagtgcggg ccgaggaatg ctgcgagttc atcaacgtga accacccccc cgagcggtgc    180

tacgacttca agatgtgcaa ccggttcacc gtggctctga gatgccccga cggcgaagtg    240

tgctacagcc ccgagaaaac cgccgagatc cggggcatcg tgaccaccat gacccacagc    300

ctgaccagac aggtggtgca taacaagctg accagttgca actacaaccc cctgtacctg    360

gaagccgacg gccggatcag atgcggcaaa gtgaacgaca aggcccagta cctgctgggc    420

gctgcaggca gtgtgcccta cagatggatc aacctggaat acgacaagat cacccggatc    480

gtgggcctgg accagtacct ggaaagcgtg aagaagcaca agcggctgga cgtgtgccgg    540

gccaagatgg gctacatgct gcagtaccca tatgacgtcc ccgattacgc ttga          594


<210> SEQ ID NO 54
<211> LENGTH: 197
<212> TYPE: PRT
<213> ORGANISM: Artificial Sequence
<220> FEATURE:
<223> OTHER INFORMATION: IgE leader + UL128 consensus + HA Tag amino
      acid sequence

<400> SEQUENCE: 54

Met Asp Trp Thr Trp Ile Leu Phe Leu Val Ala Ala Ala Thr Arg Val
1               5                   10                  15

His Ser Ser Pro Lys Asp Leu Thr Pro Phe Leu Thr Ala Leu Trp Leu
            20                  25                  30

Leu Leu Gly His Ser Arg Val Pro Arg Val Arg Ala Glu Glu Cys Cys
        35                  40                  45

Glu Phe Ile Asn Val Asn His Pro Pro Glu Arg Cys Tyr Asp Phe Lys
    50                  55                  60

Met Cys Asn Arg Phe Thr Val Ala Leu Arg Cys Pro Asp Gly Glu Val
65                  70                  75                  80

Cys Tyr Ser Pro Glu Lys Thr Ala Glu Ile Arg Gly Ile Val Thr Thr
```

```
                85                  90                  95

Met Thr His Ser Leu Thr Arg Gln Val Val His Asn Lys Leu Thr Ser
            100                 105                 110

Cys Asn Tyr Asn Pro Leu Tyr Leu Glu Ala Asp Gly Arg Ile Arg Cys
        115                 120                 125

Gly Lys Val Asn Asp Lys Ala Gln Tyr Leu Leu Gly Ala Ala Gly Ser
    130                 135                 140

Val Pro Tyr Arg Trp Ile Asn Leu Glu Tyr Asp Lys Ile Thr Arg Ile
145                 150                 155                 160

Val Gly Leu Asp Gln Tyr Leu Glu Ser Val Lys Lys His Lys Arg Leu
                165                 170                 175

Asp Val Cys Arg Ala Lys Met Gly Tyr Met Leu Gln Tyr Pro Tyr Asp
            180                 185                 190

Val Pro Asp Tyr Ala
        195


<210> SEQ ID NO 55
<211> LENGTH: 723
<212> TYPE: DNA
<213> ORGANISM: Artificial Sequence
<220> FEATURE:
<223> OTHER INFORMATION: IgE leader + UL130 consensus + HA Tag nucleic
      acid sequence

<400> SEQUENCE: 55

atggactgga cctggatcct gttcctggtc gccgctgcta cccgggtgca cagcctgcgg      60

ctgctgctgc ggcaccactt ccactgcctg ctgctgtgtg ccgtgtgggc cacccccttgt    120

ctggccagcc cttggagcac cctgaccgcc aaccagaacc ctagcccccc ctggtccaag     180

ctgacctaca gcaagcccca cgacgccgct accttctact gcccattcct gtaccccagc     240

cctcccagaa gccccctgca gttcagcggc ttccagcggg tgtccaccgg ccctgagtgc     300

cggaacgaga cactgtacct gctgtacaac cgcgagggcc agaccctggt ggaacggtct     360

agcacctggg tcaagaaagt gatctggtat ctgagcggcc ggaaccagac catcctgcag     420

cggatgcctc ggaccgccag caagcctagc gacggcaacg tgcagatcag cgtggaagat     480

gccaaaatct tcggcgccca catggtgccc aagcagacca agctgctgag attcgtggtc     540

aacgacggca ccagatacca gatgtgcgtg atgaagctgg aaagctgggc ccacgtgttc     600

cgggactaca gcgtgtcatt ccaggtccga ctgaccttca ccgaggccaa caaccagacc     660

tacaccttct gcacccaccc caacctgatc gtctaccctt acgacgtgcc agattatgcc     720

tga                                                                   723


<210> SEQ ID NO 56
<211> LENGTH: 240
<212> TYPE: PRT
<213> ORGANISM: Artificial Sequence
<220> FEATURE:
<223> OTHER INFORMATION: IgE leader + UL130 consensus + HA Tag amino
      acid sequence

<400> SEQUENCE: 56

Met Asp Trp Thr Trp Ile Leu Phe Leu Val Ala Ala Ala Thr Arg Val
1               5                   10                  15

His Ser Leu Arg Leu Leu Leu Arg His His Phe His Cys Leu Leu Leu
            20                  25                  30

Cys Ala Val Trp Ala Thr Pro Cys Leu Ala Ser Pro Trp Ser Thr Leu
        35                  40                  45
```

```
Thr Ala Asn Gln Asn Pro Ser Pro Pro Trp Ser Lys Leu Thr Tyr Ser
    50                  55                  60

Lys Pro His Asp Ala Ala Thr Phe Tyr Cys Pro Phe Leu Tyr Pro Ser
65                  70                  75                  80

Pro Pro Arg Ser Pro Leu Gln Phe Ser Gly Phe Gln Arg Val Ser Thr
                85                  90                  95

Gly Pro Glu Cys Arg Asn Glu Thr Leu Tyr Leu Leu Tyr Asn Arg Glu
            100                 105                 110

Gly Gln Thr Leu Val Glu Arg Ser Ser Thr Trp Val Lys Lys Val Ile
        115                 120                 125

Trp Tyr Leu Ser Gly Arg Asn Gln Thr Ile Leu Gln Arg Met Pro Arg
    130                 135                 140

Thr Ala Ser Lys Pro Ser Asp Gly Asn Val Gln Ile Ser Val Glu Asp
145                 150                 155                 160

Ala Lys Ile Phe Gly Ala His Met Val Pro Lys Gln Thr Lys Leu Leu
                165                 170                 175

Arg Phe Val Val Asn Asp Gly Thr Arg Tyr Gln Met Cys Val Met Lys
            180                 185                 190

Leu Glu Ser Trp Ala His Val Phe Arg Asp Tyr Ser Val Ser Phe Gln
        195                 200                 205

Val Arg Leu Thr Phe Thr Glu Ala Asn Asn Gln Thr Tyr Thr Phe Cys
    210                 215                 220

Thr His Pro Asn Leu Ile Val Tyr Pro Tyr Asp Val Pro Asp Tyr Ala
225                 230                 235                 240


<210> SEQ ID NO 57
<211> LENGTH: 468
<212> TYPE: DNA
<213> ORGANISM: Artificial Sequence
<220> FEATURE:
<223> OTHER INFORMATION: IgE leader + UL131a consensus + HA Tag nucleic
      acid sequence

<400> SEQUENCE: 57

atggactgga cctggatcct gttcctggtc gccgctgcta cccgggtgca cagcagactg      60

tgcagagtgt ggctgagcgt gtgcctgtgc gccgtggtgc tgggccagtg ccagagagag     120

acagccgaga agaacgacta ctaccgggtg ccccactact gggacgcctg ctctagagcc     180

ctgcccgacc agacccggta caaatacgtg gaacagctgg tggacctgac cctgaactac     240

cactacgacg ccagccacgg cctggacaac ttcgacgtgc tgaagcggat caacgtgacc     300

gaggtgtccc tgctgatcag cgacttccgg cggcagaaca gaagaggcgg caccaacaag     360

cggactacct tcaacgccgc tggcagcctg gcccctcacg ccagatccct ggaattcagc     420

gtgcggctgt tcgccaacta tccgtacgac gtcccagact acgcctga                  468


<210> SEQ ID NO 58
<211> LENGTH: 155
<212> TYPE: PRT
<213> ORGANISM: Artificial Sequence
<220> FEATURE:
<223> OTHER INFORMATION: IgE leader + UL131a consensus + HA Tag amino
      acid sequence

<400> SEQUENCE: 58

Met Asp Trp Thr Trp Ile Leu Phe Leu Val Ala Ala Ala Thr Arg Val
1               5                   10                  15

His Ser Arg Leu Cys Arg Val Trp Leu Ser Val Cys Leu Cys Ala Val
```

```
            20                  25                  30

Val Leu Gly Gln Cys Gln Arg Glu Thr Ala Glu Lys Asn Asp Tyr Tyr
        35                  40                  45

Arg Val Pro His Tyr Trp Asp Ala Cys Ser Arg Ala Leu Pro Asp Gln
    50                  55                  60

Thr Arg Tyr Lys Tyr Val Glu Gln Leu Val Asp Leu Thr Leu Asn Tyr
65                  70                  75                  80

His Tyr Asp Ala Ser His Gly Leu Asp Asn Phe Asp Val Leu Lys Arg
                85                  90                  95

Ile Asn Val Thr Glu Val Ser Leu Leu Ile Ser Asp Phe Arg Arg Gln
            100                 105                 110

Asn Arg Arg Gly Gly Thr Asn Lys Arg Thr Thr Phe Asn Ala Ala Gly
        115                 120                 125

Ser Leu Ala Pro His Ala Arg Ser Leu Glu Phe Ser Val Arg Leu Phe
    130                 135                 140

Ala Asn Tyr Pro Tyr Asp Val Pro Asp Tyr Ala
145                 150                 155


<210> SEQ ID NO 59
<211> LENGTH: 1764
<212> TYPE: DNA
<213> ORGANISM: Artificial Sequence
<220> FEATURE:
<223> OTHER INFORMATION: IgE leader + UL83 consensus + HA Tag nucleic
      acid sequence

<400> SEQUENCE: 59

atggattgga cctggatcct gtttctggtg gccgctgcaa caagggtcca ctctgagagt      60

cgcgggcgga gatgccctga aatgatcagc gtgctgggcc caatttccgg gcatgtgctg     120

aaggccgtct tctcccgcgg agacaccccc gtgctgcctc acgagacaag actgctgcag     180

actggcatcc atgtgagggt ctcccagcca tctctgattc tggtgtctca gtacacccca     240

gatagtacac cctgccacag aggggacaac cagctgcagg tgcagcatac ctacttcacc     300

ggatcagagg tcgaaaatgt gagcgtcaac gtgcacaatc ccacaggcag gagtatctgt     360

ccttcacagg agccaatgag catctacgtg tacgccctgc ccctgaaaat gctgaacatc     420

cctagcatta atgtgcacca ttacccctcc gccgctgaac gaaagcaccg gcatctgcct     480

gtggcagatg ccgtcatcca tgcttcaggc aaacagatgt ggcaggcacg actgaccgtg     540

agcggactgg catggacacg acagcagaac cagtggaagg agccagacgt gtactatact     600

agcgccttcg tgttccccac caaagacgtg gccctgcgac acgtggtctg cgcacatgag     660

ctggtgtgct ctatggaaaa tactcgggcc accaagatgc aggtcattgg cgatcagtac     720

gtcaaagtgt atctggagtc cttttgtgaa gacgtgccct ctgggaagct gttcatgcac     780

gtgaccctgg gaagcgatgt cgaggaagac ctgactatga cccggaaccc acagcccttt     840

atgagacctc acgagaggaa cggcttcact gtgctgtgcc caaagaatat gatcattaag     900

cccgggaaaa tctctcatat tatgctggat gtggccttta caagtcacga gcatttcgga     960

ctgctgtgcc ccaaaagcat ccctgggctg tcaattagcg gaaacctgct gatgaatggc    1020

cagcagatct ttctggaagt gcaggccatt cgagagaccg tcgaactgcg acagtacgac    1080

ccagtggcag ccctgttctt tttcgatatc gacctgctgc tgcagagagg ccctcagtat    1140

agtgagcacc caacattcac ttcacagtac aggattcagg ggaagctgga gtatcggcac    1200

acttgggata gacatgacga aggagctgca cagggcgacg atgacgtgtg gacctccggc    1260
```

-continued

```
tctgatagtg acgaggaact ggtgaccaca gagcgaaaaa ctccccgggt gaccggagga   1320

ggagctatgg caggagcatc aaccagcgcc ggacgaaaga gaaaaagcgc cagcagcgcc   1380

acagcatgca ctgcaggcgt gatgacaagg gggcgcctga aggcagaatc cacagtcgcc   1440

cctgaggaag atactgacga ggattctgac aacgaaatcc acaatccagc cgtgttcacc   1500

tggccacctt ggcaggcagg aattctggct cgcaatctgg tccctatggt ggccactgtc   1560

cagggacaga acctgaagta ccaggagttt ttctgggatg ctaatgacat ctatcggatt   1620

ttcgcagagc tggaaggcgt gtggcagcca gcagctcagc caaaaaggcg ccgacacaga   1680

caggacgcac tgcctggacc atgtatcgcc tccaccccaa agaaacatag gggctaccct   1740

tacgatgtgc ctgattatgc ctga                                          1764
```

<210> SEQ ID NO 60
<211> LENGTH: 587
<212> TYPE: PRT
<213> ORGANISM: Artificial Sequence
<220> FEATURE:
<223> OTHER INFORMATION: IgE leader + UL83 consensus + HA Tag amino acid sequence

<400> SEQUENCE: 60

```
Met Asp Trp Thr Trp Ile Leu Phe Leu Val Ala Ala Ala Thr Arg Val
1               5                   10                  15

His Ser Glu Ser Arg Gly Arg Arg Cys Pro Glu Met Ile Ser Val Leu
            20                  25                  30

Gly Pro Ile Ser Gly His Val Leu Lys Ala Val Phe Ser Arg Gly Asp
        35                  40                  45

Thr Pro Val Leu Pro His Glu Thr Arg Leu Leu Gln Thr Gly Ile His
    50                  55                  60

Val Arg Val Ser Gln Pro Ser Leu Ile Leu Val Ser Gln Tyr Thr Pro
65                  70                  75                  80

Asp Ser Thr Pro Cys His Arg Gly Asp Asn Gln Leu Gln Val Gln His
                85                  90                  95

Thr Tyr Phe Thr Gly Ser Glu Val Glu Asn Val Ser Val Asn Val His
            100                 105                 110

Asn Pro Thr Gly Arg Ser Ile Cys Pro Ser Gln Glu Pro Met Ser Ile
        115                 120                 125

Tyr Val Tyr Ala Leu Pro Leu Lys Met Leu Asn Ile Pro Ser Ile Asn
    130                 135                 140

Val His His Tyr Pro Ser Ala Ala Glu Arg Lys His Arg His Leu Pro
145                 150                 155                 160

Val Ala Asp Ala Val Ile His Ala Ser Gly Lys Gln Met Trp Gln Ala
                165                 170                 175

Arg Leu Thr Val Ser Gly Leu Ala Trp Thr Arg Gln Gln Asn Gln Trp
            180                 185                 190

Lys Glu Pro Asp Val Tyr Tyr Thr Ser Ala Phe Val Phe Pro Thr Lys
        195                 200                 205

Asp Val Ala Leu Arg His Val Val Cys Ala His Glu Leu Val Cys Ser
    210                 215                 220

Met Glu Asn Thr Arg Ala Thr Lys Met Gln Val Ile Gly Asp Gln Tyr
225                 230                 235                 240

Val Lys Val Tyr Leu Glu Ser Phe Cys Glu Asp Val Pro Ser Gly Lys
                245                 250                 255

Leu Phe Met His Val Thr Leu Gly Ser Asp Val Glu Glu Asp Leu Thr
            260                 265                 270
```

```
Met Thr Arg Asn Pro Gln Pro Phe Met Arg Pro His Glu Arg Asn Gly
        275                 280                 285

Phe Thr Val Leu Cys Pro Lys Asn Met Ile Ile Lys Pro Gly Lys Ile
    290                 295                 300

Ser His Ile Met Leu Asp Val Ala Phe Thr Ser His Glu His Phe Gly
305                 310                 315                 320

Leu Leu Cys Pro Lys Ser Ile Pro Gly Leu Ser Ile Ser Gly Asn Leu
                325                 330                 335

Leu Met Asn Gly Gln Gln Ile Phe Leu Glu Val Gln Ala Ile Arg Glu
            340                 345                 350

Thr Val Glu Leu Arg Gln Tyr Asp Pro Val Ala Ala Leu Phe Phe Phe
        355                 360                 365

Asp Ile Asp Leu Leu Leu Gln Arg Gly Pro Gln Tyr Ser Glu His Pro
    370                 375                 380

Thr Phe Thr Ser Gln Tyr Arg Ile Gln Gly Lys Leu Glu Tyr Arg His
385                 390                 395                 400

Thr Trp Asp Arg His Asp Glu Gly Ala Ala Gln Gly Asp Asp Asp Val
                405                 410                 415

Trp Thr Ser Gly Ser Asp Ser Asp Glu Glu Leu Val Thr Thr Glu Arg
            420                 425                 430

Lys Thr Pro Arg Val Thr Gly Gly Gly Ala Met Ala Gly Ala Ser Thr
        435                 440                 445

Ser Ala Gly Arg Lys Arg Lys Ser Ala Ser Ser Ala Thr Ala Cys Thr
    450                 455                 460

Ala Gly Val Met Thr Arg Gly Arg Leu Lys Ala Glu Ser Thr Val Ala
465                 470                 475                 480

Pro Glu Glu Asp Thr Asp Glu Asp Ser Asp Asn Glu Ile His Asn Pro
                485                 490                 495

Ala Val Phe Thr Trp Pro Pro Trp Gln Ala Gly Ile Leu Ala Arg Asn
            500                 505                 510

Leu Val Pro Met Val Ala Thr Val Gln Gly Gln Asn Leu Lys Tyr Gln
        515                 520                 525

Glu Phe Phe Trp Asp Ala Asn Asp Ile Tyr Arg Ile Phe Ala Glu Leu
    530                 535                 540

Glu Gly Val Trp Gln Pro Ala Ala Gln Pro Lys Arg Arg Arg His Arg
545                 550                 555                 560

Gln Asp Ala Leu Pro Gly Pro Cys Ile Ala Ser Thr Pro Lys Lys His
                565                 570                 575

Arg Gly Tyr Pro Tyr Asp Val Pro Asp Tyr Ala
            580                 585
```

<210> SEQ ID NO 61
<211> LENGTH: 18
<212> TYPE: PRT
<213> ORGANISM: Artificial Sequence
<220> FEATURE:
<223> OTHER INFORMATION: IgE leader amino acid sequence

<400> SEQUENCE: 61

```
Met Asp Trp Thr Trp Ile Leu Phe Leu Val Ala Ala Ala Thr Arg Val
1               5                   10                  15

His Ser
```

<210> SEQ ID NO 62
<211> LENGTH: 9

<212> TYPE: PRT
<213> ORGANISM: Artificial Sequence
<220> FEATURE:
<223> OTHER INFORMATION: HA Tag amino acid sequence

<400> SEQUENCE: 62

Tyr Pro Tyr Asp Val Pro Asp Tyr Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Furin protease cleavage site amino acid sequence

<400> SEQUENCE: 63

Arg Gly Arg Lys Arg Arg Ser
1               5

<210> SEQ ID NO 64
<211> LENGTH: 1650
<212> TYPE: DNA
<213> ORGANISM: Artificial Sequence
<220> FEATURE:
<223> OTHER INFORMATION: Plasmid 2 insert - IgE leader + gM consensus + HA Tag + Furin + gN consensus - HA Tag nucleic acid sequence

<400> SEQUENCE: 64
atggattgga cctggatcct gttcctggtg gccgctgcta cccgggtcca cagtgcaccc 60
agccacgtgg acaaagtgaa cacccggact tggagcgcca gcatcgtgtt catggtgctg 120
accttcgtga atgtgtccgt ccacctggtg ctgagcaact tcccccacct gggctacccc 180
tgcgtgtact accacgtggt ggacttcgag cggctgaaca tgagcgccta caacgtgatg 240
catctgcaca cccccatgct gtttctggac agcgtgcagc tcgtgtgcta cgccgtgttt 300
atgcagctgg tgttcctggc cgtgaccatc tactacctcg tgtgctggat caagatttct 360
atgcggaagg acaagggcat gagcctgaac cagagcaccc gggacatcag ctacatgggc 420
gacagcctga ccgccttcct gttcatcctg agcatggaca ccttccagct gttcaccctg 480
accatgagct tccggctgcc cagcatgatc gcctttatgg ccgccgtcca cttcttctgt 540
ctgaccatct tcaacgtgtc catggtcacc cagtacagaa gctacaagcg gagcctgttc 600
ttcttcagtc ggctgcaccc caagctgaag ggcaccgtcc agttccggac cctgatcgtg 660
aacctggtgg aagtggccct gggcttcaac accaccgtgg tggctatggc tctgtgctac 720
ggcttcggca acaacttctt cgtgcggaca ggccacatgg tgctggccgt gttcgtggtg 780
tacgccatta tcagcatcat ctactttctg ctgatcgagg ccgtgttctt ccagtacgtg 840
aaggtgcagt tcggctacca cctgggcgcc tttttcggcc tgtgcggcct gatctacccc 900
atcgtgcagt acgacacctt cctgagcaac gagtaccgga ccggcatcag ctggtccttc 960
ggcatgctgt tcttcatctg ggccatgttc accacctgtc gggccgtgcg gtacttcaga 1020
ggcagaggca gcggctccgt gaagtaccag gccctggcca cagccagcgg cgaagaagtg 1080
gccgccctga gccaccacga cagcctggaa agcagacggc tgagagagga agaggacgac 1140
gacgacgatg aggacttcga ggacgcctac ccctacgacg tgcccgacta tgcccgcggc 1200
agaaagcgga gatctgagtg gaacaccctg gtgctgggtc tgctggtgct gtctgtggcc 1260
gccagcagca acaacaccag cactgccagc acccccagcc ctagcagcag cacccacacc 1320

```
tccaccaccg tgaaggccac caccaccgcc accacaagca ccacaacagc caccagcacc   1380

acctcttcca ccaccagcac aaagcccggc agcaccactc acgaccccaa cgtgatgagg   1440

ccccacgccc acaacgactt ctacaaggcc cactgcacca gccatatgta cgagctgagc   1500

ctgagcagct tcgccgcctg gtggaccatg ctgaacgccc tgatcctgat gggcgccttc   1560

tgcatcgtgc tgcggcactg ctgcttccag aacttcaccg ccacaaccac caagggctac   1620

taccettacg atgtgcctga ttatgcctga                                    1650
```

<210> SEQ ID NO 65
<211> LENGTH: 549
<212> TYPE: PRT
<213> ORGANISM: Artificial Sequence
<220> FEATURE:
<223> OTHER INFORMATION: Plasmid 2 amino acid sequence - IgE leader + gM consensus + HA Tag + Furin + gN consensus + HA Tag amino acid sequence

<400> SEQUENCE: 65

```
Met Asp Trp Thr Trp Ile Leu Phe Leu Val Ala Ala Ala Thr Arg Val
1               5                   10                  15

His Ser Ala Pro Ser His Val Asp Lys Val Asn Thr Arg Thr Trp Ser
            20                  25                  30

Ala Ser Ile Val Phe Met Val Leu Thr Phe Val Asn Val Ser Val His
        35                  40                  45

Leu Val Leu Ser Asn Phe Pro His Leu Gly Tyr Pro Cys Val Tyr Tyr
    50                  55                  60

His Val Val Asp Phe Glu Arg Leu Asn Met Ser Ala Tyr Asn Val Met
65                  70                  75                  80

His Leu His Thr Pro Met Leu Phe Leu Asp Ser Val Gln Leu Val Cys
                85                  90                  95

Tyr Ala Val Phe Met Gln Leu Val Phe Leu Ala Val Thr Ile Tyr Tyr
            100                 105                 110

Leu Val Cys Trp Ile Lys Ile Ser Met Arg Lys Asp Lys Gly Met Ser
        115                 120                 125

Leu Asn Gln Ser Thr Arg Asp Ile Ser Tyr Met Gly Asp Ser Leu Thr
    130                 135                 140

Ala Phe Leu Phe Ile Leu Ser Met Asp Thr Phe Gln Leu Phe Thr Leu
145                 150                 155                 160

Thr Met Ser Phe Arg Leu Pro Ser Met Ile Ala Phe Met Ala Ala Val
                165                 170                 175

His Phe Phe Cys Leu Thr Ile Phe Asn Val Ser Met Val Thr Gln Tyr
            180                 185                 190

Arg Ser Tyr Lys Arg Ser Leu Phe Phe Phe Ser Arg Leu His Pro Lys
        195                 200                 205

Leu Lys Gly Thr Val Gln Phe Arg Thr Leu Ile Val Asn Leu Val Glu
    210                 215                 220

Val Ala Leu Gly Phe Asn Thr Thr Val Val Ala Met Ala Leu Cys Tyr
225                 230                 235                 240

Gly Phe Gly Asn Asn Phe Phe Val Arg Thr Gly His Met Val Leu Ala
                245                 250                 255

Val Phe Val Val Tyr Ala Ile Ile Ser Ile Ile Tyr Phe Leu Leu Ile
            260                 265                 270

Glu Ala Val Phe Phe Gln Tyr Val Lys Val Gln Phe Gly Tyr His Leu
        275                 280                 285

Gly Ala Phe Phe Gly Leu Cys Gly Leu Ile Tyr Pro Ile Val Gln Tyr
```

290 295 300

Asp Thr Phe Leu Ser Asn Glu Tyr Arg Thr Gly Ile Ser Trp Ser Phe
305 310 315 320

Gly Met Leu Phe Phe Ile Trp Ala Met Phe Thr Thr Cys Arg Ala Val
325 330 335

Arg Tyr Phe Arg Gly Arg Gly Ser Gly Ser Val Lys Tyr Gln Ala Leu
340 345 350

Ala Thr Ala Ser Gly Glu Glu Val Ala Ala Leu Ser His His Asp Ser
355 360 365

Leu Glu Ser Arg Arg Leu Arg Glu Glu Glu Asp Asp Asp Asp Asp Glu
370 375 380

Asp Phe Glu Asp Ala Tyr Pro Tyr Asp Val Pro Asp Tyr Ala Arg Gly
385 390 395 400

Arg Lys Arg Arg Ser Glu Trp Asn Thr Leu Val Leu Gly Leu Leu Val
405 410 415

Leu Ser Val Ala Ala Ser Ser Asn Asn Thr Ser Thr Ala Ser Thr Pro
420 425 430

Ser Pro Ser Ser Ser Thr His Thr Ser Thr Thr Val Lys Ala Thr Thr
435 440 445

Thr Ala Thr Thr Ser Thr Thr Thr Ala Thr Ser Thr Thr Ser Ser Thr
450 455 460

Thr Ser Thr Lys Pro Gly Ser Thr Thr His Asp Pro Asn Val Met Arg
465 470 475 480

Pro His Ala His Asn Asp Phe Tyr Lys Ala His Cys Thr Ser His Met
485 490 495

Tyr Glu Leu Ser Leu Ser Ser Phe Ala Ala Trp Trp Thr Met Leu Asn
500 505 510

Ala Leu Ile Leu Met Gly Ala Phe Cys Ile Val Leu Arg His Cys Cys
515 520 525

Phe Gln Asn Phe Thr Ala Thr Thr Thr Lys Gly Tyr Tyr Pro Tyr Asp
530 535 540

Val Pro Asp Tyr Ala
545

<210> SEQ ID NO 66
<211> LENGTH: 3189
<212> TYPE: DNA
<213> ORGANISM: Artificial Sequence
<220> FEATURE:
<223> OTHER INFORMATION: Plasmid 3 insert - IgE leader + gH consensus + HA Tag + Furin + gL consensus +HA Tag nucleic acid sequence

<400> SEQUENCE: 66
atggactgga cctggatcct gttcctggtg gccgctgcta cccgggtgca cagtcgaccc 60
ggcctgccca gctacctgac cgtgttcgcc gtgtacctgc tgagccatct gcccagccag 120
agatacggcg ccgatgccgc ctctgaggcc ctggatcctc acgccttcca tctgctgctg 180
aacacctacg gcagacctat ccggttcctg cgcgagaaca ccacccagtg cacctacaac 240
agcagcctgc ggaacagcac cgtcgtgcgc gagaatgcta tcagcttcaa cttcttccag 300
agctacaacc agtactacgt gttccacatg ccccggtgcc tgttcgccgg acctctggcc 360
gagcagttcc tgaaccaggt ggacctgacc gagacactgg aaagatacca gcagcggctg 420
aatacctacg ccctggtgtc caaggacctg gccagctacc ggtccttcag ccagcagctg 480
aaggctcagg acagcctggg cgagcagcct accaccgtgc cccctccaat cgacctgagc 540

-continued

```
atcccccacg tgtggatgcc cccccagacc acacctcacg gctggaaaga gagccacacc    600
accagcggcc tgcacagacc ccacttcaac cagacctgca ttctgttcga cggccacgac    660
ctgctgttca gcaccgtgac cccctgcctg caccagggct tctacctgat cgacgagctg    720
agatacgtga agatcaccct gaccgaggat ttcttcgtgg tcaccgtgtc catcgacgac    780
gacaccccca tgctgctgat cttcggccat ctgcctcggg tgctgttcaa ggcccccctac    840
cagcgggaca acttcatcct gcggcagacc gagaagcacg agctgctggt gctggtcaag    900
aaggaccagc tgaaccggca ctcctacctg aaggaccccg acttcctgga cgccgccctg    960
gacttcaact acctggacct gagcgccctg ctgagaaaca gcttccacag atacgccgtg   1020
gacgtgctga agtccggccg gtgccagatg ctggacagac ggaccgtgga aatggccttc   1080
gcctatgccc tggccctgtt tgccgccgct cggcaggaag aggctggcgc tgaagtgtcc   1140
gtgcccagag ccctggacag acaggccgct ctgctgcaga tccaggaatt catgatcacc   1200
tgtctgagcc agaccccccc tcggaccacc ctgctgctgt accctaccgc cgtggatctg   1260
gccaagcggg ccctgtggac ccccaaccag atcaccgaca tcacaagcct cgtgcggctg   1320
gtgtacatcc tgagcaagca gaaccagcag cacctgatcc cccagtgggc cctgagacag   1380
atcgccgact tcgccctgaa gctgcacaag acccacctgg ctagctttct gagcgccttc   1440
gctaggcagg aactgtacct gatgggcagc ctggtgcact ccatgctggt gcacaccacc   1500
gagaggcggg aaatcttcat cgtggaaacc ggcctgtgca gcctggccga gctgagccac   1560
ttcacccagc tgctggccca cccccaccac gagtacctga gcgacctgta cacccccctgc   1620
agctctagcg gcagacggga tcacagcctg gaacggctga cccggctgtt ccccgatgcc   1680
acagtgcctg ccactgtgcc agccgccctg tccatcctgt ccaccatgca gcccagcacc   1740
ctggaaacct tccccgacct gttctgcctg cccctgggcg agagcttcag cgccctgaca   1800
gtgtccgagc acgtgtccta cgtggtcacc aaccagtacc tgatcaaggg catcagctac   1860
cccgtgtcca ccaccgtcgt gggccagagc ctgatcatca cccagaccga cagccagacc   1920
aagtgcgagc tgacccggaa catgcacacc acacacagca tcactgccgc cctgaacatc   1980
agcctggaaa actgcgcctt ctgccagtct gccctgctgg aatacgacga tacccagggc   2040
gtgatcaaca tcatgtacat gcacgacagc gacgacgtgc tgttcgccct ggacccctac   2100
aacgaggtgg tggtgtccag cccccggacc cactacctga tgctgctgaa gaacggcacc   2160
gtgctggaag tgaccgacgt ggtggtggac gccaccgaca gcagactgct gatgatgagc   2220
gtgtacgccc tgagcgccat catcggcatc tacctgctgt accggatgct gaaaacctgc   2280
taccccctacg acgtgcccga ctacgcccgc ggcagaaagc ggagatcctg caggcggccc   2340
gactgcggct tcagcttcag ccctggcccc gtgatcctgc tgtggtgctg cctgctgctg   2400
cccatcgtgt cctctgccgc cgtgtctgtg gcccctacag ccgccgagaa ggtgccagcc   2460
gagtgccctg agctgaccag acggtgtctg ctgggcgagg tgttccaggg cgataagtac   2520
gagagctggc tgcggcccct ggtcaacgtg accggcagag atggcccccct gagccagctg   2580
atccggtaca gacccgtgac ccctgaggcc gccaacagcg tgctgctgga cgaagccttt   2640
ctggacacac tggccctgct gtacaacaac cccgaccagc tgcgggccct gctgacactg   2700
ctgagcagcg ataccgcccc cagatggatg accgtgatgc ggggctacag cgagtgcggc   2760
gacggatctc ccgccgtgta cacctgtgtg gacgacctgt gccggggcta cgacctgacc   2820
agactgagct acggccggtc catcttcaca gagcacgtgc tgggcttcga gctggtgccc   2880
cccagcctgt tcaatgtggt ggtggccatc cggaacgagg ccacccggac caacagagca   2940
```

-continued gtgcggctgc ctgtgtccac cgctgctgct ccagagggca tcaccctgtt ctacggcctg 3000
tacaacgccg tgaaagagtt ctgcctgaga caccagctgg accccccct gctgcggcac 3060 ctggacaagt actacgccgg cctgcctccc gagctgaagc agaccagagt gaacctgccc 3120
gcccacagca gatacggccc tcaggccgtg gacgccagat acccttacga tgtgcctgat 3180
tatgcctga 3189

<210> SEQ ID NO 67
<211> LENGTH: 1062
<212> TYPE: PRT
<213> ORGANISM: Artificial Sequence
<220> FEATURE:
<223> OTHER INFORMATION: Plasmid 3 amino acid sequence - IgE leader + gH consensus + HA Tag + Furin + gL consensus + HA Tag amino acid sequence

<400> SEQUENCE: 67

Met Asp Trp Thr Trp Ile Leu Phe Leu Val Ala Ala Ala Thr Arg Val
1 5 10 15

His Ser Arg Pro Gly Leu Pro Ser Tyr Leu Thr Val Phe Ala Val Tyr
20 25 30

Leu Leu Ser His Leu Pro Ser Gln Arg Tyr Gly Ala Asp Ala Ala Ser
35 40 45

Glu Ala Leu Asp Pro His Ala Phe His Leu Leu Leu Asn Thr Tyr Gly
50 55 60

Arg Pro Ile Arg Phe Leu Arg Glu Asn Thr Thr Gln Cys Thr Tyr Asn
65 70 75 80

Ser Ser Leu Arg Asn Ser Thr Val Val Arg Glu Asn Ala Ile Ser Phe
85 90 95

Asn Phe Phe Gln Ser Tyr Asn Gln Tyr Tyr Val Phe His Met Pro Arg
100 105 110

Cys Leu Phe Ala Gly Pro Leu Ala Glu Gln Phe Leu Asn Gln Val Asp
115 120 125

Leu Thr Glu Thr Leu Glu Arg Tyr Gln Gln Arg Leu Asn Thr Tyr Ala
130 135 140

Leu Val Ser Lys Asp Leu Ala Ser Tyr Arg Ser Phe Ser Gln Gln Leu
145 150 155 160

Lys Ala Gln Asp Ser Leu Gly Glu Gln Pro Thr Thr Val Pro Pro Pro
165 170 175

Ile Asp Leu Ser Ile Pro His Val Trp Met Pro Pro Gln Thr Thr Pro
180 185 190

His Gly Trp Lys Glu Ser His Thr Thr Ser Gly Leu His Arg Pro His
195 200 205

Phe Asn Gln Thr Cys Ile Leu Phe Asp Gly His Asp Leu Leu Phe Ser
210 215 220

Thr Val Thr Pro Cys Leu His Gln Gly Phe Tyr Leu Ile Asp Glu Leu
225 230 235 240

Arg Tyr Val Lys Ile Thr Leu Thr Glu Asp Phe Phe Val Val Thr Val
245 250 255

Ser Ile Asp Asp Asp Thr Pro Met Leu Leu Ile Phe Gly His Leu Pro
260 265 270

Arg Val Leu Phe Lys Ala Pro Tyr Gln Arg Asp Asn Phe Ile Leu Arg
275 280 285

Gln Thr Glu Lys His Glu Leu Leu Val Leu Val Lys Lys Asp Gln Leu
290 295 300

-continued

```
Asn Arg His Ser Tyr Leu Lys Asp Pro Asp Phe Leu Asp Ala Ala Leu
305                 310                 315                 320

Asp Phe Asn Tyr Leu Asp Leu Ser Ala Leu Leu Arg Asn Ser Phe His
                325                 330                 335

Arg Tyr Ala Val Asp Val Leu Lys Ser Gly Arg Cys Gln Met Leu Asp
            340                 345                 350

Arg Arg Thr Val Glu Met Ala Phe Ala Tyr Ala Leu Ala Leu Phe Ala
        355                 360                 365

Ala Ala Arg Gln Glu Glu Ala Gly Ala Glu Val Ser Val Pro Arg Ala
    370                 375                 380

Leu Asp Arg Gln Ala Ala Leu Leu Gln Ile Gln Glu Phe Met Ile Thr
385                 390                 395                 400

Cys Leu Ser Gln Thr Pro Pro Arg Thr Thr Leu Leu Leu Tyr Pro Thr
                405                 410                 415

Ala Val Asp Leu Ala Lys Arg Ala Leu Trp Thr Pro Asn Gln Ile Thr
            420                 425                 430

Asp Ile Thr Ser Leu Val Arg Leu Val Tyr Ile Leu Ser Lys Gln Asn
        435                 440                 445

Gln Gln His Leu Ile Pro Gln Trp Ala Leu Arg Gln Ile Ala Asp Phe
    450                 455                 460

Ala Leu Lys Leu His Lys Thr His Leu Ala Ser Phe Leu Ser Ala Phe
465                 470                 475                 480

Ala Arg Gln Glu Leu Tyr Leu Met Gly Ser Leu Val His Ser Met Leu
                485                 490                 495

Val His Thr Thr Glu Arg Arg Glu Ile Phe Ile Val Glu Thr Gly Leu
            500                 505                 510

Cys Ser Leu Ala Glu Leu Ser His Phe Thr Gln Leu Leu Ala His Pro
        515                 520                 525

His His Glu Tyr Leu Ser Asp Leu Tyr Thr Pro Cys Ser Ser Ser Gly
    530                 535                 540

Arg Arg Asp His Ser Leu Glu Arg Leu Thr Arg Leu Phe Pro Asp Ala
545                 550                 555                 560

Thr Val Pro Ala Thr Val Pro Ala Ala Leu Ser Ile Leu Ser Thr Met
                565                 570                 575

Gln Pro Ser Thr Leu Glu Thr Phe Pro Asp Leu Phe Cys Leu Pro Leu
            580                 585                 590

Gly Glu Ser Phe Ser Ala Leu Thr Val Ser Glu His Val Ser Tyr Val
        595                 600                 605

Val Thr Asn Gln Tyr Leu Ile Lys Gly Ile Ser Tyr Pro Val Ser Thr
    610                 615                 620

Thr Val Val Gly Gln Ser Leu Ile Ile Thr Gln Thr Asp Ser Gln Thr
625                 630                 635                 640

Lys Cys Glu Leu Thr Arg Asn Met His Thr Thr His Ser Ile Thr Ala
                645                 650                 655

Ala Leu Asn Ile Ser Leu Glu Asn Cys Ala Phe Cys Gln Ser Ala Leu
            660                 665                 670

Leu Glu Tyr Asp Asp Thr Gln Gly Val Ile Asn Ile Met Tyr Met His
        675                 680                 685

Asp Ser Asp Asp Val Leu Phe Ala Leu Asp Pro Tyr Asn Glu Val Val
    690                 695                 700

Val Ser Ser Pro Arg Thr His Tyr Leu Met Leu Leu Lys Asn Gly Thr
705                 710                 715                 720
```

```
Val Leu Glu Val Thr Asp Val Val Val Asp Ala Thr Asp Ser Arg Leu
                725                 730                 735

Leu Met Met Ser Val Tyr Ala Leu Ser Ala Ile Ile Gly Ile Tyr Leu
            740                 745                 750

Leu Tyr Arg Met Leu Lys Thr Cys Tyr Pro Tyr Asp Val Pro Asp Tyr
        755                 760                 765

Ala Arg Gly Arg Lys Arg Arg Ser Cys Arg Arg Pro Asp Cys Gly Phe
    770                 775                 780

Ser Phe Ser Pro Gly Pro Val Ile Leu Leu Trp Cys Cys Leu Leu Leu
785                 790                 795                 800

Pro Ile Val Ser Ser Ala Ala Val Ser Val Ala Pro Thr Ala Ala Glu
                805                 810                 815

Lys Val Pro Ala Glu Cys Pro Glu Leu Thr Arg Arg Cys Leu Leu Gly
            820                 825                 830

Glu Val Phe Gln Gly Asp Lys Tyr Glu Ser Trp Leu Arg Pro Leu Val
        835                 840                 845

Asn Val Thr Gly Arg Asp Gly Pro Leu Ser Gln Leu Ile Arg Tyr Arg
    850                 855                 860

Pro Val Thr Pro Glu Ala Ala Asn Ser Val Leu Leu Asp Glu Ala Phe
865                 870                 875                 880

Leu Asp Thr Leu Ala Leu Leu Tyr Asn Asn Pro Asp Gln Leu Arg Ala
                885                 890                 895

Leu Leu Thr Leu Leu Ser Ser Asp Thr Ala Pro Arg Trp Met Thr Val
            900                 905                 910

Met Arg Gly Tyr Ser Glu Cys Gly Asp Gly Ser Pro Ala Val Tyr Thr
        915                 920                 925

Cys Val Asp Asp Leu Cys Arg Gly Tyr Asp Leu Thr Arg Leu Ser Tyr
    930                 935                 940

Gly Arg Ser Ile Phe Thr Glu His Val Leu Gly Phe Glu Leu Val Pro
945                 950                 955                 960

Pro Ser Leu Phe Asn Val Val Val Ala Ile Arg Asn Glu Ala Thr Arg
                965                 970                 975

Thr Asn Arg Ala Val Arg Leu Pro Val Ser Thr Ala Ala Ala Pro Glu
            980                 985                 990

Gly Ile Thr Leu Phe Tyr Gly Leu  Tyr Asn Ala Val Lys  Glu Phe Cys
        995                 1000                1005

Leu Arg  His Gln Leu Asp Pro  Pro Leu Leu Arg His  Leu Asp Lys
    1010                1015                1020

Tyr Tyr  Ala Gly Leu Pro Pro  Glu Leu Lys Gln Thr  Arg Val Asn
    1025                1030                1035

Leu Pro  Ala His Ser Arg Tyr  Gly Pro Gln Ala Val  Asp Ala Arg
    1040                1045                1050

Tyr Pro  Tyr Asp Val Pro Asp  Tyr Ala
    1055                1060


<210> SEQ ID NO 68
<211> LENGTH: 1713
<212> TYPE: DNA
<213> ORGANISM: Artificial Sequence
<220> FEATURE:
<223> OTHER INFORMATION: Plasmid 5 insert - IgE leader + UL131a
      consensus + HA Tag + Furin + UL130 consensus + HA Tag + Furin +
      UL128 consensus + HA Tag nucleic acid sequence

<400> SEQUENCE: 68

atggactgga cctggatcct gttcctggtc gccgctgcta cccgggtgca cagcagactg     60
```

```
tgcagagtgt ggctgagcgt gtgcctgtgc gccgtggtgc tgggccagtg ccagagagag    120
acagccgaga agaacgacta ctaccgggtg ccccactact gggacgcctg ctctagagcc    180
ctgcccgacc agacccggta caaatacgtg gaacagctgg tggacctgac cctgaactac    240
cactacgacg ccagccacgg cctggacaac ttcgacgtgc tgaagcggat caacgtgacc    300
gaggtgtccc tgctgatcag cgacttccgg cggcagaaca gaagaggcgg caccaacaag    360
cggactacct tcaacgccgc tggcagcctg gcccctcacg ccagatccct ggaattcagc    420
gtgcggctgt tcgccaacta tccgtacgac gtcccagact acgccagagg ccggaagcgg    480
agatctctgc ggctgctgct gcggcaccac ttccactgcc tgctgctgtg tgccgtgtgg    540
gccacccctt gtctggccag cccttggagc accctgaccg ccaaccagaa ccctagcccc    600
ccctggtcca agctgaccta cagcaagccc cacgacgccg ctaccttcta ctgcccattc    660
ctgtacccca gccctcccag aagcccccctg cagttcagcg gcttccagcg ggtgtccacc    720
ggccctgagt gccggaacga gacactgtac ctgctgtaca accgcgaggg ccagaccctg    780
gtggaacggt ctagcacctg ggtcaagaaa gtgatctggt atctgagcgg ccggaaccag    840
accatcctgc agcggatgcc tcggaccgcc agcaagccta gcgacggcaa cgtgcagatc    900
agcgtggaag atgccaaaat cttcggcgcc cacatggtgc ccaagcagac caagctgctg    960
agattcgtgg tcaacgacgg caccagatac cagatgtgcg tgatgaagct ggaaagctgg   1020
gcccacgtgt tccgggacta cagcgtgtca ttccaggtcc gactgacctt caccgaggcc   1080
aacaaccaga cctacacctt ctgcacccac cccaacctga tcgtctaccc ttacgacgtg   1140
ccagattatg ccaggggcag aaaaaggagg agcagcccca aggatctgac ccctttcctg   1200
accgccctgt ggctgctcct gggccacagc agagtgccta gagtgcgggc cgaggaatgc   1260
tgcgagttca tcaacgtgaa ccaccccccc gagcggtgct acgacttcaa gatgtgcaac   1320
cggttcaccg tggctctgag atgccccgac ggcgaagtgt gctacagccc cgagaaaacc   1380
gccgagatcc ggggcatcgt gaccaccatg acccacagcc tgaccagaca ggtggtgcat   1440
aacaagctga ccagttgcaa ctacaacccc ctgtacctgg aagccgacgg ccggatcaga   1500
tgcggcaaag tgaacgacaa ggcccagtac ctgctgggcg ctgcaggcag tgtgccctac   1560
agatggatca acctggaata cgacaagatc acccggatcg tgggcctgga ccagtacctg   1620
gaaagcgtga agaagcacaa gcggctggac gtgtgccggg ccaagatggg ctacatgctg   1680
cagtacccat atgacgtccc cgattacgct tga                                 1713
```

<210> SEQ ID NO 69
<211> LENGTH: 570
<212> TYPE: PRT
<213> ORGANISM: Artificial Sequence
<220> FEATURE:
<223> OTHER INFORMATION: Plasmid 5 amino aciud sequence - IgE leader + UL131a consensus + HA Tag + Furin + UL130 consensus + HA Tag + Furin + UL128 consensus + HA Tag

<400> SEQUENCE: 69

```
Met Asp Trp Thr Trp Ile Leu Phe Leu Val Ala Ala Ala Thr Arg Val
1               5                   10                  15

His Ser Arg Leu Cys Arg Val Trp Leu Ser Val Cys Leu Cys Ala Val
            20                  25                  30

Val Leu Gly Gln Cys Gln Arg Glu Thr Ala Glu Lys Asn Asp Tyr Tyr
        35                  40                  45

Arg Val Pro His Tyr Trp Asp Ala Cys Ser Arg Ala Leu Pro Asp Gln
```

-continued

```
    50                  55                  60

Thr Arg Tyr Lys Tyr Val Glu Gln Leu Val Asp Leu Thr Leu Asn Tyr
65                  70                  75                  80

His Tyr Asp Ala Ser His Gly Leu Asp Asn Phe Asp Val Leu Lys Arg
                85                  90                  95

Ile Asn Val Thr Glu Val Ser Leu Leu Ile Ser Asp Phe Arg Arg Gln
            100                 105                 110

Asn Arg Arg Gly Gly Thr Asn Lys Arg Thr Thr Phe Asn Ala Ala Gly
        115                 120                 125

Ser Leu Ala Pro His Ala Arg Ser Leu Glu Phe Ser Val Arg Leu Phe
    130                 135                 140

Ala Asn Tyr Pro Tyr Asp Val Pro Asp Tyr Ala Arg Gly Arg Lys Arg
145                 150                 155                 160

Arg Ser Leu Arg Leu Leu Leu Arg His His Phe His Cys Leu Leu Leu
                165                 170                 175

Cys Ala Val Trp Ala Thr Pro Cys Leu Ala Ser Pro Trp Ser Thr Leu
            180                 185                 190

Thr Ala Asn Gln Asn Pro Ser Pro Pro Trp Ser Lys Leu Thr Tyr Ser
        195                 200                 205

Lys Pro His Asp Ala Ala Thr Phe Tyr Cys Pro Phe Leu Tyr Pro Ser
    210                 215                 220

Pro Pro Arg Ser Pro Leu Gln Phe Ser Gly Phe Gln Arg Val Ser Thr
225                 230                 235                 240

Gly Pro Glu Cys Arg Asn Glu Thr Leu Tyr Leu Leu Tyr Asn Arg Glu
                245                 250                 255

Gly Gln Thr Leu Val Glu Arg Ser Ser Thr Trp Val Lys Lys Val Ile
            260                 265                 270

Trp Tyr Leu Ser Gly Arg Asn Gln Thr Ile Leu Gln Arg Met Pro Arg
        275                 280                 285

Thr Ala Ser Lys Pro Ser Asp Gly Asn Val Gln Ile Ser Val Glu Asp
    290                 295                 300

Ala Lys Ile Phe Gly Ala His Met Val Pro Lys Gln Thr Lys Leu Leu
305                 310                 315                 320

Arg Phe Val Val Asn Asp Gly Thr Arg Tyr Gln Met Cys Val Met Lys
                325                 330                 335

Leu Glu Ser Trp Ala His Val Phe Arg Asp Tyr Ser Val Ser Phe Gln
            340                 345                 350

Val Arg Leu Thr Phe Thr Glu Ala Asn Asn Gln Thr Tyr Thr Phe Cys
        355                 360                 365

Thr His Pro Asn Leu Ile Val Tyr Pro Tyr Asp Val Pro Asp Tyr Ala
    370                 375                 380

Arg Gly Arg Lys Arg Arg Ser Ser Pro Lys Asp Leu Thr Pro Phe Leu
385                 390                 395                 400

Thr Ala Leu Trp Leu Leu Leu Gly His Ser Arg Val Pro Arg Val Arg
                405                 410                 415

Ala Glu Glu Cys Cys Glu Phe Ile Asn Val Asn His Pro Pro Glu Arg
            420                 425                 430

Cys Tyr Asp Phe Lys Met Cys Asn Arg Phe Thr Val Ala Leu Arg Cys
        435                 440                 445

Pro Asp Gly Glu Val Cys Tyr Ser Pro Glu Lys Thr Ala Glu Ile Arg
    450                 455                 460

Gly Ile Val Thr Thr Met Thr His Ser Leu Thr Arg Gln Val Val His
465                 470                 475                 480
```

-continued

```
Asn Lys Leu Thr Ser Cys Asn Tyr Asn Pro Leu Tyr Leu Glu Ala Asp
                485                 490                 495

Gly Arg Ile Arg Cys Gly Lys Val Asn Asp Lys Ala Gln Tyr Leu Leu
            500                 505                 510

Gly Ala Ala Gly Ser Val Pro Tyr Arg Trp Ile Asn Leu Glu Tyr Asp
        515                 520                 525

Lys Ile Thr Arg Ile Val Gly Leu Asp Gln Tyr Leu Glu Ser Val Lys
    530                 535                 540

Lys His Lys Arg Leu Asp Val Cys Arg Ala Lys Met Gly Tyr Met Leu
545                 550                 555                 560

Gln Tyr Pro Tyr Asp Val Pro Asp Tyr Ala
                565                 570


<210> SEQ ID NO 70
<211> LENGTH: 1596
<212> TYPE: DNA
<213> ORGANISM: Artificial Sequence
<220> FEATURE:
<223> OTHER INFORMATION: Plasmid 2 insert version 2 - IgE leader + gM
      consensus + Furin + gN consensus nucleic acid sequence

<400> SEQUENCE: 70

atggattgga cctggatcct gttcctggtg gccgctgcta cccgggtcca cagtgcaccc     60

agccacgtgg acaaagtgaa cacccggact tggagcgcca gcatcgtgtt catggtgctg    120

accttcgtga atgtgtccgt ccacctggtg ctgagcaact tcccccacct gggctacccc    180

tgcgtgtact accacgtggt ggacttcgag cggctgaaca tgagcgccta caacgtgatg    240

catctgcaca cccccatgct gtttctggac agcgtgcagc tcgtgtgcta cgccgtgttt    300

atgcagctgg tgttcctggc cgtgaccatc tactacctcg tgtgctggat caagatttct    360

atgcggaagg acaagggcat gagcctgaac cagagcaccc gggacatcag ctacatgggc    420

gacagcctga ccgccttcct gttcatcctg agcatggaca ccttccagct gttcaccctg    480

accatgagct tccggctgcc cagcatgatc gcctttatgg ccgccgtcca cttcttctgt    540

ctgaccatct tcaacgtgtc catggtcacc cagtacagaa gctacaagcg gagcctgttc    600

ttcttcagtc ggctgcaccc caagctgaag ggcaccgtcc agttccggac cctgatcgtg    660

aacctggtgg aagtggccct gggcttcaac accaccgtgg tggctatggc tctgtgctac    720

ggcttcggca acaacttctt cgtgcggaca ggccacatgg tgctggccgt gttcgtggtg    780

tacgccatta tcagcatcat ctactttctg ctgatcgagg ccgtgttctt ccagtacgtg    840

aaggtgcagt tcggctacca cctgggcgcc tttttcggcc tgtgcggcct gatctacccc    900

atcgtgcagt acgacacctt cctgagcaac gagtaccgga ccggcatcag ctggtccttc    960

ggcatgctgt tcttcatctg ggccatgttc accacctgtc gggccgtgcg gtacttcaga   1020

ggcagaggca gcggctccgt gaagtaccag gccctggcca cagccagcgg cgaagaagtg   1080

gccgccctga gccaccacga cagcctggaa agcagacggc tgagagagga agaggacgac   1140

gacgacgatg aggacttcga ggacgcccgc ggcagaaagc ggagatctga gtggaacacc   1200

ctggtgctgg gtctgctggt gctgtctgtg gccgccagca gcaacaacac cagcactgcc   1260

agcaccccca gccctagcag cagcacccac acctccacca ccgtgaaggc caccaccacc   1320

gccaccacaa gcaccacaac agccaccagc accacctctt ccaccaccag cacaaagccc   1380

ggcagcacca ctcacgaccc caacgtgatg aggccccacg cccacaacga cttctacaag   1440

gcccactgca ccagccatat gtacgagctg agcctgagca gcttcgccgc ctggtggacc   1500
```

atgctgaacg ccctgatcct gatgggcgcc ttctgcatcg tgctgcggca ctgctgcttc 1560
cagaacttca ccgccacaac caccaagggc tactga 1596

<210> SEQ ID NO 71
<211> LENGTH: 531
<212> TYPE: PRT
<213> ORGANISM: Artificial Sequence
<220> FEATURE:
<223> OTHER INFORMATION: Plasmid 2 amino acid sequence version 2 - IgE
leader + gM consensus + Furin + gN consensus amino acid sequence

<400> SEQUENCE: 71

Met Asp Trp Thr Trp Ile Leu Phe Leu Val Ala Ala Ala Thr Arg Val
1 5 10 15

His Ser Ala Pro Ser His Val Asp Lys Val Asn Thr Arg Thr Trp Ser
20 25 30

Ala Ser Ile Val Phe Met Val Leu Thr Phe Val Asn Val Ser Val His
35 40 45

Leu Val Leu Ser Asn Phe Pro His Leu Gly Tyr Pro Cys Val Tyr Tyr
50 55 60

His Val Val Asp Phe Glu Arg Leu Asn Met Ser Ala Tyr Asn Val Met
65 70 75 80

His Leu His Thr Pro Met Leu Phe Leu Asp Ser Val Gln Leu Val Cys
85 90 95

Tyr Ala Val Phe Met Gln Leu Val Phe Leu Ala Val Thr Ile Tyr Tyr
100 105 110

Leu Val Cys Trp Ile Lys Ile Ser Met Arg Lys Asp Lys Gly Met Ser
115 120 125

Leu Asn Gln Ser Thr Arg Asp Ile Ser Tyr Met Gly Asp Ser Leu Thr
130 135 140

Ala Phe Leu Phe Ile Leu Ser Met Asp Thr Phe Gln Leu Phe Thr Leu
145 150 155 160

Thr Met Ser Phe Arg Leu Pro Ser Met Ile Ala Phe Met Ala Ala Val
165 170 175

His Phe Phe Cys Leu Thr Ile Phe Asn Val Ser Met Val Thr Gln Tyr
180 185 190

Arg Ser Tyr Lys Arg Ser Leu Phe Phe Phe Ser Arg Leu His Pro Lys
195 200 205

Leu Lys Gly Thr Val Gln Phe Arg Thr Leu Ile Val Asn Leu Val Glu
210 215 220

Val Ala Leu Gly Phe Asn Thr Thr Val Val Ala Met Ala Leu Cys Tyr
225 230 235 240

Gly Phe Gly Asn Asn Phe Phe Val Arg Thr Gly His Met Val Leu Ala
245 250 255

Val Phe Val Val Tyr Ala Ile Ile Ser Ile Ile Tyr Phe Leu Leu Ile
260 265 270

Glu Ala Val Phe Phe Gln Tyr Val Lys Val Gln Phe Gly Tyr His Leu
275 280 285

Gly Ala Phe Phe Gly Leu Cys Gly Leu Ile Tyr Pro Ile Val Gln Tyr
290 295 300

Asp Thr Phe Leu Ser Asn Glu Tyr Arg Thr Gly Ile Ser Trp Ser Phe
305 310 315 320

Gly Met Leu Phe Phe Ile Trp Ala Met Phe Thr Thr Cys Arg Ala Val
325 330 335

```
Arg Tyr Phe Arg Gly Arg Gly Ser Gly Ser Val Lys Tyr Gln Ala Leu
            340                 345                 350

Ala Thr Ala Ser Gly Glu Glu Val Ala Ala Leu Ser His His Asp Ser
        355                 360                 365

Leu Glu Ser Arg Arg Leu Arg Glu Glu Glu Asp Asp Asp Asp Asp Glu
    370                 375                 380

Asp Phe Glu Asp Ala Arg Gly Arg Lys Arg Arg Ser Glu Trp Asn Thr
385                 390                 395                 400

Leu Val Leu Gly Leu Leu Val Leu Ser Val Ala Ala Ser Ser Asn Asn
                405                 410                 415

Thr Ser Thr Ala Ser Thr Pro Ser Pro Ser Ser Ser Thr His Thr Ser
            420                 425                 430

Thr Thr Val Lys Ala Thr Thr Thr Ala Thr Thr Ser Thr Thr Thr Ala
        435                 440                 445

Thr Ser Thr Thr Ser Ser Thr Thr Ser Thr Lys Pro Gly Ser Thr Thr
    450                 455                 460

His Asp Pro Asn Val Met Arg Pro His Ala His Asn Asp Phe Tyr Lys
465                 470                 475                 480

Ala His Cys Thr Ser His Met Tyr Glu Leu Ser Leu Ser Ser Phe Ala
                485                 490                 495

Ala Trp Trp Thr Met Leu Asn Ala Leu Ile Leu Met Gly Ala Phe Cys
            500                 505                 510

Ile Val Leu Arg His Cys Cys Phe Gln Asn Phe Thr Ala Thr Thr Thr
        515                 520                 525

Lys Gly Tyr
    530
```

<210> SEQ ID NO 72
<211> LENGTH: 3135
<212> TYPE: DNA
<213> ORGANISM: Artificial Sequence
<220> FEATURE:
<223> OTHER INFORMATION: Plasmid 3 insert version 2 - IgE leader + gH consensus + Furin + gL consensus nucleic acid sequence

<400> SEQUENCE: 72

```
atggactgga cctggatcct gttcctggtg gccgctgcta cccgggtgca cagtcgaccc      60

ggcctgccca gctacctgac cgtgttcgcc gtgtacctgc tgagccatct gcccagccag     120

agatacggcg ccgatgccgc ctctgaggcc ctggatcctc acgccttcca tctgctgctg     180

aacacctacg gcagacctat ccggttcctg cgcgagaaca ccacccagtg cacctacaac     240

agcagcctgc ggaacagcac cgtcgtgcgc gagaatgcta tcagcttcaa cttcttccag     300

agctacaacc agtactacgt gttccacatg ccccggtgcc tgttcgccgg acctctggcc     360

gagcagttcc tgaaccaggt ggacctgacc gagacactgg aaagatacca gcagcggctg     420

aatacctacg ccctggtgtc caaggacctg gccagctacc ggtccttcag ccagcagctg     480

aaggctcagg acagcctggg cgagcagcct accaccgtgc cccctccaat cgacctgagc     540

atcccccacg tgtggatgcc cccccagacc acacctcacg gctggaaaga gagccacacc     600

accagcggcc tgcacagacc ccacttcaac cagacctgca ttctgttcga cggccacgac     660

ctgctgttca gcaccgtgac cccctgcctg caccagggct tctacctgat cgacgagctg     720

agatacgtga agatcaccct gaccgaggat ttcttcgtgg tcaccgtgtc catcgacgac     780

gacacccccca tgctgctgat cttcggccat ctgcctcggg tgctgttcaa ggccccctac     840

cagcgggaca acttcatcct gcggcagacc gagaagcacg agctgctggt gctggtcaag     900
```

aaggaccagc tgaaccggca ctcctacctg aaggaccccg acttcctgga cgccgccctg 960
gacttcaact acctggacct gagcgccctg ctgagaaaca gcttccacag atacgccgtg 1020
gacgtgctga agtccggccg gtgccagatg ctggacagac ggaccgtgga aatggccttc 1080
gcctatgccc tggccctgtt tgccgccgct cggcaggaag aggctggcgc tgaagtgtcc 1140
gtgcccagag ccctggacag acaggccgct ctgctgcaga tccaggaatt catgatcacc 1200
tgtctgagcc agaccccccc tcggaccacc ctgctgctgt accctaccgc cgtggatctg 1260
gccaagcggg ccctgtggac ccccaaccag atcaccgaca tcacaagcct cgtgcggctg 1320
gtgtacatcc tgagcaagca gaaccagcag cacctgatcc cccagtgggc cctgagacag 1380
atcgccgact tcgccctgaa gctgcacaag acccacctgg ctagctttct gagcgccttc 1440
gctaggcagg aactgtacct gatgggcagc ctggtgcact ccatgctggt gcacaccacc 1500
gagaggcggg aaatcttcat cgtggaaacc ggcctgtgca gcctggccga gctgagccac 1560
ttcacccagc tgctggccca cccccaccac gagtacctga gcgacctgta cacccccctgc 1620 agctctagcg gcagacggga tcacagcctg gaacggctga cccggctgtt ccccgatgcc 1680
acagtgcctg ccactgtgcc agccgccctg tccatcctgt ccaccatgca gcccagcacc 1740
ctggaaacct tccccgacct gttctgcctg cccctgggcg agagcttcag cgccctgaca 1800
gtgtccgagc acgtgtccta cgtggtcacc aaccagtacc tgatcaaggg catcagctac 1860
cccgtgtcca ccaccgtcgt gggccagagc ctgatcatca cccagaccga cagccagacc 1920
aagtgcgagc tgacccggaa catgcacacc acacacagca tcactgccgc cctgaacatc 1980
agcctggaaa actgcgcctt ctgccagtct gccctgctgg aatacgacga tacccagggc 2040
gtgatcaaca tcatgtacat gcacgacagc gacgacgtgc tgttcgccct ggacccctac 2100
aacgaggtgg tggtgtccag cccccggacc cactacctga tgctgctgaa gaacggcacc 2160
gtgctggaag tgaccgacgt ggtggtggac gccaccgaca gcagactgct gatgatgagc 2220
gtgtacgccc tgagcgccat catcggcatc tacctgctgt accggatgct gaaaacctgc 2280
cgcggcagaa agcggagatc ctgcaggcgg cccgactgcg gcttcagctt cagccctggc 2340
cccgtgatcc tgctgtggtg ctgcctgctg ctgcccatcg tgtcctctgc cgccgtgtct 2400
gtggccccta cagccgccga gaaggtgcca gccgagtgcc ctgagctgac cagacggtgt 2460
ctgctgggcg aggtgttcca gggcgataag tacgagagct ggctgcggcc cctggtcaac 2520
gtgaccggca gagatggccc cctgagccag ctgatccggt acagacccgt gacccctgag 2580
gccgccaaca gcgtgctgct ggacgaagcc tttctggaca cactggccct gctgtacaac 2640
aaccccgacc agctgcgggc cctgctgaca ctgctgagca gcgataccgc ccccagatgg 2700
atgaccgtga tgcggggcta cagcgagtgc ggcgacggat ctcccgccgt gtacacctgt 2760
gtggacgacc tgtgccgggg ctacgacctg accagactga gctacggccg gtccatcttc 2820
acagagcacg tgctgggctt cgagctggtg ccccccagcc tgttcaatgt ggtggtggcc 2880
atccggaacg aggccacccg gaccaacaga gcagtgcggc tgcctgtgtc caccgctgct 2940
gctccagagg gcatcaccct gttctacggc ctgtacaacg ccgtgaaaga gttctgcctg 3000
agacaccagc tggacccccc cctgctgcgg cacctggaca agtactacgc cggcctgcct 3060
cccgagctga agcagaccag agtgaacctg cccgcccaca gcagatacgg ccctcaggcc 3120
gtggacgcca gatga 3135

<210> SEQ ID NO 73

<211> LENGTH: 1044
<212> TYPE: PRT
<213> ORGANISM: Artificial Sequence
<220> FEATURE:
<223> OTHER INFORMATION: Plasmid 3 amino acid sequence version 2 - IgE leader + gH consensus + Furin + gL consensus nucleic acid sequence

<400> SEQUENCE: 73

```
Met Asp Trp Thr Trp Ile Leu Phe Leu Val Ala Ala Ala Thr Arg Val
1               5                   10                  15

His Ser Arg Pro Gly Leu Pro Ser Tyr Leu Thr Val Phe Ala Val Tyr
            20                  25                  30

Leu Leu Ser His Leu Pro Ser Gln Arg Tyr Gly Ala Asp Ala Ala Ser
        35                  40                  45

Glu Ala Leu Asp Pro His Ala Phe His Leu Leu Leu Asn Thr Tyr Gly
    50                  55                  60

Arg Pro Ile Arg Phe Leu Arg Glu Asn Thr Thr Gln Cys Thr Tyr Asn
65                  70                  75                  80

Ser Ser Leu Arg Asn Ser Thr Val Val Arg Glu Asn Ala Ile Ser Phe
                85                  90                  95

Asn Phe Phe Gln Ser Tyr Asn Gln Tyr Tyr Val Phe His Met Pro Arg
            100                 105                 110

Cys Leu Phe Ala Gly Pro Leu Ala Glu Gln Phe Leu Asn Gln Val Asp
        115                 120                 125

Leu Thr Glu Thr Leu Glu Arg Tyr Gln Gln Arg Leu Asn Thr Tyr Ala
    130                 135                 140

Leu Val Ser Lys Asp Leu Ala Ser Tyr Arg Ser Phe Ser Gln Gln Leu
145                 150                 155                 160

Lys Ala Gln Asp Ser Leu Gly Glu Gln Pro Thr Thr Val Pro Pro Pro
                165                 170                 175

Ile Asp Leu Ser Ile Pro His Val Trp Met Pro Pro Gln Thr Thr Pro
            180                 185                 190

His Gly Trp Lys Glu Ser His Thr Thr Ser Gly Leu His Arg Pro His
        195                 200                 205

Phe Asn Gln Thr Cys Ile Leu Phe Asp Gly His Asp Leu Leu Phe Ser
    210                 215                 220

Thr Val Thr Pro Cys Leu His Gln Gly Phe Tyr Leu Ile Asp Glu Leu
225                 230                 235                 240

Arg Tyr Val Lys Ile Thr Leu Thr Glu Asp Phe Phe Val Val Thr Val
                245                 250                 255

Ser Ile Asp Asp Asp Thr Pro Met Leu Leu Ile Phe Gly His Leu Pro
            260                 265                 270

Arg Val Leu Phe Lys Ala Pro Tyr Gln Arg Asp Asn Phe Ile Leu Arg
        275                 280                 285

Gln Thr Glu Lys His Glu Leu Leu Val Leu Val Lys Lys Asp Gln Leu
    290                 295                 300

Asn Arg His Ser Tyr Leu Lys Asp Pro Asp Phe Leu Asp Ala Ala Leu
305                 310                 315                 320

Asp Phe Asn Tyr Leu Asp Leu Ser Ala Leu Leu Arg Asn Ser Phe His
                325                 330                 335

Arg Tyr Ala Val Asp Val Leu Lys Ser Gly Arg Cys Gln Met Leu Asp
            340                 345                 350

Arg Arg Thr Val Glu Met Ala Phe Ala Tyr Ala Leu Ala Leu Phe Ala
        355                 360                 365

Ala Ala Arg Gln Glu Glu Ala Gly Ala Glu Val Ser Val Pro Arg Ala
```

```
    370                 375                 380

Leu Asp Arg Gln Ala Ala Leu Leu Gln Ile Gln Glu Phe Met Ile Thr
385                 390                 395                 400

Cys Leu Ser Gln Thr Pro Pro Arg Thr Thr Leu Leu Leu Tyr Pro Thr
                405                 410                 415

Ala Val Asp Leu Ala Lys Arg Ala Leu Trp Thr Pro Asn Gln Ile Thr
            420                 425                 430

Asp Ile Thr Ser Leu Val Arg Leu Val Tyr Ile Leu Ser Lys Gln Asn
        435                 440                 445

Gln Gln His Leu Ile Pro Gln Trp Ala Leu Arg Gln Ile Ala Asp Phe
    450                 455                 460

Ala Leu Lys Leu His Lys Thr His Leu Ala Ser Phe Leu Ser Ala Phe
465                 470                 475                 480

Ala Arg Gln Glu Leu Tyr Leu Met Gly Ser Leu Val His Ser Met Leu
                485                 490                 495

Val His Thr Thr Glu Arg Arg Glu Ile Phe Ile Val Glu Thr Gly Leu
            500                 505                 510

Cys Ser Leu Ala Glu Leu Ser His Phe Thr Gln Leu Leu Ala His Pro
        515                 520                 525

His His Glu Tyr Leu Ser Asp Leu Tyr Thr Pro Cys Ser Ser Ser Gly
    530                 535                 540

Arg Arg Asp His Ser Leu Glu Arg Leu Thr Arg Leu Phe Pro Asp Ala
545                 550                 555                 560

Thr Val Pro Ala Thr Val Pro Ala Ala Leu Ser Ile Leu Ser Thr Met
                565                 570                 575

Gln Pro Ser Thr Leu Glu Thr Phe Pro Asp Leu Phe Cys Leu Pro Leu
            580                 585                 590

Gly Glu Ser Phe Ser Ala Leu Thr Val Ser Glu His Val Ser Tyr Val
        595                 600                 605

Val Thr Asn Gln Tyr Leu Ile Lys Gly Ile Ser Tyr Pro Val Ser Thr
    610                 615                 620

Thr Val Val Gly Gln Ser Leu Ile Ile Thr Gln Thr Asp Ser Gln Thr
625                 630                 635                 640

Lys Cys Glu Leu Thr Arg Asn Met His Thr Thr His Ser Ile Thr Ala
                645                 650                 655

Ala Leu Asn Ile Ser Leu Glu Asn Cys Ala Phe Cys Gln Ser Ala Leu
            660                 665                 670

Leu Glu Tyr Asp Asp Thr Gln Gly Val Ile Asn Ile Met Tyr Met His
        675                 680                 685

Asp Ser Asp Asp Val Leu Phe Ala Leu Asp Pro Tyr Asn Glu Val Val
    690                 695                 700

Val Ser Ser Pro Arg Thr His Tyr Leu Met Leu Leu Lys Asn Gly Thr
705                 710                 715                 720

Val Leu Glu Val Thr Asp Val Val Val Asp Ala Thr Asp Ser Arg Leu
                725                 730                 735

Leu Met Met Ser Val Tyr Ala Leu Ser Ala Ile Ile Gly Ile Tyr Leu
            740                 745                 750

Leu Tyr Arg Met Leu Lys Thr Cys Arg Gly Arg Lys Arg Arg Ser Cys
        755                 760                 765

Arg Arg Pro Asp Cys Gly Phe Ser Phe Ser Pro Gly Pro Val Ile Leu
    770                 775                 780

Leu Trp Cys Cys Leu Leu Leu Pro Ile Val Ser Ser Ala Ala Val Ser
785                 790                 795                 800
```

```
Val Ala Pro Thr Ala Ala Glu Lys Val Pro Ala Glu Cys Pro Glu Leu
                805                 810                 815

Thr Arg Arg Cys Leu Leu Gly Glu Val Phe Gln Gly Asp Lys Tyr Glu
            820                 825                 830

Ser Trp Leu Arg Pro Leu Val Asn Val Thr Gly Arg Asp Gly Pro Leu
        835                 840                 845

Ser Gln Leu Ile Arg Tyr Arg Pro Val Thr Pro Glu Ala Ala Asn Ser
    850                 855                 860

Val Leu Leu Asp Glu Ala Phe Leu Asp Thr Leu Ala Leu Leu Tyr Asn
865                 870                 875                 880

Asn Pro Asp Gln Leu Arg Ala Leu Leu Thr Leu Leu Ser Ser Asp Thr
                885                 890                 895

Ala Pro Arg Trp Met Thr Val Met Arg Gly Tyr Ser Glu Cys Gly Asp
            900                 905                 910

Gly Ser Pro Ala Val Tyr Thr Cys Val Asp Asp Leu Cys Arg Gly Tyr
        915                 920                 925

Asp Leu Thr Arg Leu Ser Tyr Gly Arg Ser Ile Phe Thr Glu His Val
    930                 935                 940

Leu Gly Phe Glu Leu Val Pro Pro Ser Leu Phe Asn Val Val Val Ala
945                 950                 955                 960

Ile Arg Asn Glu Ala Thr Arg Thr Asn Arg Ala Val Arg Leu Pro Val
                965                 970                 975

Ser Thr Ala Ala Ala Pro Glu Gly Ile Thr Leu Phe Tyr Gly Leu Tyr
            980                 985                 990

Asn Ala Val Lys Glu Phe Cys Leu  Arg His Gln Leu Asp  Pro Pro Leu
        995                 1000                 1005

Leu Arg  His Leu Asp Lys Tyr  Tyr Ala Gly Leu Pro  Pro Glu Leu
    1010                 1015                 1020

Lys Gln  Thr Arg Val Asn Leu  Pro Ala His Ser Arg  Tyr Gly Pro
    1025                 1030                 1035

Gln Ala  Val Asp Ala Arg
    1040
```

<210> SEQ ID NO 74
<211> LENGTH: 1632
<212> TYPE: DNA
<213> ORGANISM: Artificial Sequence
<220> FEATURE:
<223> OTHER INFORMATION: Plasmid 5 insert version 2 - IgE leader + UL131a consensus + Furin + UL130 consensus + Furin + UL128 consensus nucleic acid sequence

<400> SEQUENCE: 74

```
atggactgga cctggatcct gttcctggtc gccgctgcta cccgggtgca cagcagactg      60

tgcagagtgt ggctgagcgt gtgcctgtgc gccgtggtgc tgggccagtg ccagagagag     120

acagccgaga agaacgacta ctaccgggtg ccccactact gggacgcctg ctctagagcc     180

ctgcccgacc agacccggta caaatacgtg gaacagctgg tggacctgac cctgaactac     240

cactacgacg ccagccacgg cctggacaac ttcgacgtgc tgaagcggat caacgtgacc     300

gaggtgtccc tgctgatcag cgacttccgg cggcagaaca gaagaggcgg caccaacaag     360

cggactacct tcaacgccgc tggcagcctg gcccctcacg ccagatccct ggaattcagc     420

gtgcggctgt tcgccaacag aggccggaag cggagatctc tgcggctgct gctgcggcac     480

cacttccact gcctgctgct gtgtgccgtg tgggccaccc cttgtctggc cagcccttgg     540
```

```
agcaccctga ccgccaacca gaaccctagc ccccccctggt ccaagctgac ctacagcaag    600

ccccacgacg ccgctacctt ctactgccca ttcctgtacc ccagccctcc cagaagcccc    660

ctgcagttca gcggcttcca gcgggtgtcc accggccctg agtgccggaa cgagacactg    720

tacctgctgt acaaccgcga gggccagacc ctggtggaac ggtctagcac ctgggtcaag    780

aaagtgatct ggtatctgag cggccggaac cagaccatcc tgcagcggat gcctcggacc    840

gccagcaagc ctagcgacgg caacgtgcag atcagcgtgg aagatgccaa aatcttcggc    900

gcccacatgg tgcccaagca gaccaagctg ctgagattcg tggtcaacga cggcaccaga    960

taccagatgt gcgtgatgaa gctggaaagc tgggcccacg tgttccggga ctacagcgtg   1020

tcattccagg tccgactgac cttcaccgag gccaacaacc agacctacac cttctgcacc   1080

cacccccaacc tgatcgtcag gggcagaaaa aggaggagca gccccaagga tctgacccct   1140

ttcctgaccg ccctgtggct gctcctgggc cacagcagag tgcctagagt gcgggccgag   1200

gaatgctgcg agttcatcaa cgtgaaccac ccccccgagc ggtgctacga cttcaagatg   1260

tgcaaccggt tcaccgtggc tctgagatgc cccgacggcg aagtgtgcta cagccccgag   1320

aaaaccgccg agatccgggg catcgtgacc accatgaccc acagcctgac cagacaggtg   1380

gtgcataaca agctgaccag ttgcaactac aaccccctgt acctggaagc cgacggccgg   1440

atcagatgcg gcaaagtgaa cgacaaggcc cagtacctgc tgggcgctgc aggcagtgtg   1500

ccctacagat ggatcaacct ggaatacgac aagatcaccc ggatcgtggg cctggaccag   1560

tacctggaaa gcgtgaagaa gcacaagcgg ctggacgtgt gccgggccaa gatgggctac   1620

atgctgcagt ga                                                         1632
```

<210> SEQ ID NO 75
<211> LENGTH: 543
<212> TYPE: PRT
<213> ORGANISM: Artificial Sequence
<220> FEATURE:
<223> OTHER INFORMATION: Plasmid 5 amino acid sequence version 2 - IgE leader + UL131a consensus + Furin + UL130 consensus + Furin + UL128 consensus amino acid sequence

<400> SEQUENCE: 75

```
Met Asp Trp Thr Trp Ile Leu Phe Leu Val Ala Ala Ala Thr Arg Val
1               5                   10                  15

His Ser Arg Leu Cys Arg Val Trp Leu Ser Val Cys Leu Cys Ala Val
            20                  25                  30

Val Leu Gly Gln Cys Gln Arg Glu Thr Ala Glu Lys Asn Asp Tyr Tyr
        35                  40                  45

Arg Val Pro His Tyr Trp Asp Ala Cys Ser Arg Ala Leu Pro Asp Gln
    50                  55                  60

Thr Arg Tyr Lys Tyr Val Glu Gln Leu Val Asp Leu Thr Leu Asn Tyr
65                  70                  75                  80

His Tyr Asp Ala Ser His Gly Leu Asp Asn Phe Asp Val Leu Lys Arg
                85                  90                  95

Ile Asn Val Thr Glu Val Ser Leu Leu Ile Ser Asp Phe Arg Arg Gln
            100                 105                 110

Asn Arg Arg Gly Gly Thr Asn Lys Arg Thr Thr Phe Asn Ala Ala Gly
        115                 120                 125

Ser Leu Ala Pro His Ala Arg Ser Leu Glu Phe Ser Val Arg Leu Phe
    130                 135                 140

Ala Asn Arg Gly Arg Lys Arg Arg Ser Leu Arg Leu Leu Leu Arg His
145                 150                 155                 160
```

His Phe His Cys Leu Leu Leu Cys Ala Val Trp Ala Thr Pro Cys Leu
165 170 175

Ala Ser Pro Trp Ser Thr Leu Thr Ala Asn Gln Asn Pro Ser Pro Pro
180 185 190

Trp Ser Lys Leu Thr Tyr Ser Lys Pro His Asp Ala Ala Thr Phe Tyr
195 200 205

Cys Pro Phe Leu Tyr Pro Ser Pro Pro Arg Ser Pro Leu Gln Phe Ser
210 215 220

Gly Phe Gln Arg Val Ser Thr Gly Pro Glu Cys Arg Asn Glu Thr Leu
225 230 235 240

Tyr Leu Leu Tyr Asn Arg Glu Gly Gln Thr Leu Val Glu Arg Ser Ser
245 250 255

Thr Trp Val Lys Lys Val Ile Trp Tyr Leu Ser Gly Arg Asn Gln Thr
260 265 270

Ile Leu Gln Arg Met Pro Arg Thr Ala Ser Lys Pro Ser Asp Gly Asn
275 280 285

Val Gln Ile Ser Val Glu Asp Ala Lys Ile Phe Gly Ala His Met Val
290 295 300

Pro Lys Gln Thr Lys Leu Leu Arg Phe Val Val Asn Asp Gly Thr Arg
305 310 315 320

Tyr Gln Met Cys Val Met Lys Leu Glu Ser Trp Ala His Val Phe Arg
325 330 335

Asp Tyr Ser Val Ser Phe Gln Val Arg Leu Thr Phe Thr Glu Ala Asn
340 345 350

Asn Gln Thr Tyr Thr Phe Cys Thr His Pro Asn Leu Ile Val Arg Gly
355 360 365

Arg Lys Arg Arg Ser Ser Pro Lys Asp Leu Thr Pro Phe Leu Thr Ala
370 375 380

Leu Trp Leu Leu Leu Gly His Ser Arg Val Pro Arg Val Arg Ala Glu
385 390 395 400

Glu Cys Cys Glu Phe Ile Asn Val Asn His Pro Pro Glu Arg Cys Tyr
405 410 415

Asp Phe Lys Met Cys Asn Arg Phe Thr Val Ala Leu Arg Cys Pro Asp
420 425 430

Gly Glu Val Cys Tyr Ser Pro Glu Lys Thr Ala Glu Ile Arg Gly Ile
435 440 445

Val Thr Thr Met Thr His Ser Leu Thr Arg Gln Val Val His Asn Lys
450 455 460

Leu Thr Ser Cys Asn Tyr Asn Pro Leu Tyr Leu Glu Ala Asp Gly Arg
465 470 475 480

Ile Arg Cys Gly Lys Val Asn Asp Lys Ala Gln Tyr Leu Leu Gly Ala
485 490 495

Ala Gly Ser Val Pro Tyr Arg Trp Ile Asn Leu Glu Tyr Asp Lys Ile
500 505 510

Thr Arg Ile Val Gly Leu Asp Gln Tyr Leu Glu Ser Val Lys Lys His
515 520 525

Lys Arg Leu Asp Val Cys Arg Ala Lys Met Gly Tyr Met Leu Gln
530 535 540

<210> SEQ ID NO 76
<211> LENGTH: 2934
<212> TYPE: DNA
<213> ORGANISM: Artificial Sequence
<220> FEATURE:

<223> OTHER INFORMATION: modified pVax1 backbone nucleic acid sequence

<400> SEQUENCE: 76

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
ctatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagctttaa    720
ctcgagtcta gagggcccgt ttaaacccgc tgatcagcct cgactgtgcc ttctagttgc    780
cagccatctg ttgtttgccc ctcccccgtg ccttccttga ccctggaagg tgccactccc    840
actgtccttt cctaataaaa tgaggaaatt gcatcgcatt gtctgagtag gtgtcattct    900
attctggggg gtggggtggg gcaggacagc aagggggagg attgggaaga caatagcagg    960
catgctgggg atgcggtggg ctctatggct tctactgggc ggttttatgg acagcaagcg   1020
aaccggaatt gccagctggg gcgccctctg gtaaggttgg gaagccctgc aaagtaaact   1080
ggatggcttt ctcgccgcca aggatctgat ggcgcagggg atcaagctct gatcaagaga   1140
caggatgagg atcgtttcgc atgattgaac aagatggatt gcacgcaggt tctccggccg   1200
cttgggtgga gaggctattc ggctatgact gggcacaaca gacaatcggc tgctctgatg   1260
ccgccgtgtt ccggctgtca gcgcaggggc gcccggttct ttttgtcaag accgacctgt   1320
ccggtgccct gaatgaactg caagacgagg cagcgcggct atcgtggctg gccacgacgg   1380
gcgttccttg cgcagctgtg ctcgacgttg tcactgaagc gggaagggac tggctgctat   1440
tgggcgaagt gccggggcag gatctcctgt catctcacct tgctcctgcc gagaaagtat   1500
ccatcatggc tgatgcaatg cggcggctgc atacgcttga tccggctacc tgcccattcg   1560
accaccaagc gaaacatcgc atcgagcgag cacgtactcg gatggaagcc ggtcttgtcg   1620
atcaggatga tctggacgaa gagcatcagg ggctcgcgcc agccgaactg ttcgccaggc   1680
tcaaggcgag catgcccgac ggcgaggatc tcgtcgtgac ccatggcgat gcctgcttgc   1740
cgaatatcat ggtggaaaat ggccgctttt ctggattcat cgactgtggc cggctgggtg   1800
tggcggaccg ctatcaggac atagcgttgg ctacccgtga tattgctgaa gagcttggcg   1860
gcgaatgggc tgaccgcttc ctcgtgcttt acggtatcgc cgctcccgat tcgcagcgca   1920
tcgccttcta tcgccttctt gacgagttct tctgaattat taacgcttac aatttcctga   1980
tgcggtattt tctccttacg catctgtgcg gtatttcaca ccgcatacag gtggcacttt   2040
tcggggaaat gtgcgcggaa cccctatttg tttatttttc taaatacatt caaatatgta   2100
tccgctcatg agacaataac cctgataaat gcttcaataa tagcacgtgc taaaacttca   2160
tttttaattt aaaaggatct aggtgaagat cctttttgat aatctcatga ccaaaatccc   2220
ttaacgtgag ttttcgttcc actgagcgtc agaccccgta gaaaagatca aaggatcttc   2280
```

ttgagatcct ttttttctgc gcgtaatctg ctgcttgcaa acaaaaaaac caccgctacc 2340
agcggtggtt tgtttgccgg atcaagagct accaactctt tttccgaagg taactggctt 2400
cagcagagcg cagataccaa atactgtcct tctagtgtag ccgtagttag gccaccactt 2460
caagaactct gtagcaccgc ctacatacct cgctctgcta atcctgttac cagtggctgc 2520
tgccagtggc gataagtcgt gtcttaccgg gttggactca agacgatagt taccggataa 2580
ggcgcagcgg tcgggctgaa cggggggttc gtgcacacag cccagcttgg agcgaacgac 2640
ctacaccgaa ctgagatacc tacagcgtga gctatgagaa agcgccacgc ttcccgaagg 2700
gagaaaggcg gacaggtatc cggtaagcgg cagggtcgga acaggagagc gcacgaggga 2760
gcttccaggg ggaaacgcct ggtatcttta tagtcctgtc gggtttcgcc acctctgact 2820
tgagcgtcga tttttgtgat gctcgtcagg ggggcggagc ctatggaaaa acgccagcaa 2880
cgcggccttt ttacggttcc tgggcttttg ctggcctttt gctcacatgt tctt 2934

<210> SEQ ID NO 77
<211> LENGTH: 5742
<212> TYPE: DNA
<213> ORGANISM: Artificial Sequence
<220> FEATURE:
<223> OTHER INFORMATION: 1011932_pHCMVgB_pVAX1 (LTGA)

<400> SEQUENCE: 77
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
ctatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttgcc 720
accatggact ggacctggat cctgttcctg gtggccgctg ccacacgggt gcacagcgag 780
agcagaatct ggtgcctggt cgtgtgcgtg aacctgtgca tcgtgtgcct gggagccgcc 840
gtgtccagca gcagcacccg gggcacaagc gccacacaca gccaccacag cagccacacc 900
accagcgccg cccacagccg gagcggaagc gtgagcagcc agcgggtgac cagcagcgag 960
gccgtgtccc accgggccaa cgagacaatc tacaacacca ccctgaagta cggcgacgtc 1020
gtgggagtga acaccaccaa gtacccctac agagtgtgca gcatggccca gggcaccgac 1080
ctgatcagat tcgagcggaa catcgtgtgt accagcatga agcccatcaa cgaggacctg 1140
gacgagggca tcatggtggt gtacaagaga aacatcgtgg cccacacctt caaagtgcgg 1200
gtgtaccaga aggtgctgac cttccggcgg agctacgcct acatccacac cacctacctg 1260
ctgggcagca acaccgagta cgtggcccct cccatgtggg agatccacca catcaacagc 1320
cacagccagt gctacagcag ctacagccgc gtgatcgccg gcaccgtgtt cgtggcctac 1380

-continued

```
caccgggaca gctacgagaa caagaccatg cagctgatgc ccgacgacta cagcaacacc   1440
cacagcacca gatacgtgac cgtgaaggac cagtggcaca gccggggaag cacctggctg   1500
tacagagaga catgcaacct gaactgcatg gtcaccatca ccaccgccag aagcaagtac   1560
ccttaccact tcttcgccac cagcaccggc gacgtggtgg acatcagccc cttctacaac   1620
ggcaccaacc ggaacgccag ctacttcggc gagaacgccg acaagttctt catcttcccc   1680
aactacacca tcgtgtccga cttcggcaga cccaacagcg cccctgagac acaccggctg   1740
gtggcctttc tggaacgggc cgacagcgtg atcagctggg acatccagga cgagaagaac   1800
gtgacctgcc agctgacctt ctgggaggct agcgagcgga ccatcagaag cgaggccgag   1860
gacagctacc acttcagcag cgccaagatg accgccacct tcctgagcaa gaaacaggaa   1920
gtgaacatga gcgacagcgc cctggactgc gtgcgggatg aggccatcaa caagctgcag   1980
cagatcttca acaccagcta caaccagacc tacgagaagt atggcaacgt gtccgtgttc   2040
gagacaacag gcggcctggt ggtgttctgg cagggcatca agcagaagtc cctggtcgag   2100
ctggaacggc tggccaacag aagcagcctg aacctgaccc accggaccaa gcggagcacc   2160
gacggcaaca ataccaccca cctgagcaac atggaaagcg tccacaacct ggtgtacgcc   2220
cagctgcagt tcacctacga caccctgcgg ggctacatca accgggccct ggcccagatc   2280
gccgaggctt ggtgtgtgga ccagcggcgg accctggaag tgttcaaaga gctgagcaag   2340
atcaacccca gcgccatcct gagcgccatc tacaacaagc ctatcgccgc cagattcatg   2400
ggcgacgtgc tgggcctggc cagctgcgtg accatcaacc agaccagcgt gaaggtgctg   2460
cgggacatga acgtgaaaga aagccccggc agatgctact ccagacccgt ggtcatcttc   2520
aacttcgcca acagctccta cgtgcagtac ggccagctgg gcgaggacaa cgagatcctg   2580
ctgggaaacc accggaccga ggaatgccag ctgcccagcc tgaagatctt tatcgccggc   2640
aacagcgcct acgagtatgt ggactacctg ttcaagcgga tgatcgacct gagcagcatc   2700
agcaccgtgg acagcatgat cgccctggac atcgaccccc tggaaaacac cgacttccgg   2760
gtgctggaac tgtacagcca gaaagagctg cggagcagca acgtgttcga cctggaagag   2820
atcatgcgcg agttcaacag ctacaagcag cgcgtgaaat acgtcgagga caaggtggtg   2880
gacccccctgc ccccctacct gaagggcctg gacgacctga tgagcggcct gggagctgct   2940
ggcaaggccg tgggagtggc cattggagct gtgggcggag ccgtggccag cgtggtggaa   3000
ggcgtggcca cctttctgaa gaacccccttc ggcgccttca ccatcatcct ggtggctatc   3060
gccgtcgtga tcatcaccta cctgatctac acccggcagc ggcggctgtg tacccagcct   3120
ctgcagaacc tgttccccta cctggtgtcc gccgacggca ccaccgtgac aagcggctcc   3180
accaaggaca ccagcctgca ggccccaccc agctacgagg aatccgtgta caacagcggc   3240
cggaagggcc caggccctcc tagctctgac gcctctacag ccgccccacc ctacaccaac   3300
gagcaggcct accagatgct gctggccctg gctagactgg acgccgagca gagagcccag   3360
cagaacggaa ccgacagcct ggatggccag accggcaccc aggacaaggg ccagaagccc   3420
aacctgctgg accggctgcg gcacagaaag aacggctacc ggcacctgaa ggacagcgac   3480
gaagaggaaa acgtgtaccc ctacgacgtg cccgactacg cttgatgact cgagtctaga   3540
gggcccgttt aaacccgctg atcagcctcg actgtgcctt ctagttgcca gccatctgtt   3600
gtttgcccct cccccgtgcc ttccttgacc ctggaaggtg ccactcccac tgtcctttcc   3660
taataaaatg aggaaattgc atcgcattgt ctgagtaggt gtcattctat tctggggggt   3720
ggggtggggc aggacagcaa gggggaggat tgggaagaca atagcaggca tgctggggat   3780
```

gcggtgggct ctatggcttc tactgggcgg ttttatggac agcaagcgaa ccggaattgc 3840
cagctggggc gccctctggt aaggttggga agccctgcaa agtaaactgg atggctttct 3900
cgccgccaag gatctgatgg cgcaggggat caagctctga tcaagagaca ggatgaggat 3960
cgtttcgcat gattgaacaa gatggattgc acgcaggttc tccggccgct tgggtggaga 4020
ggctattcgg ctatgactgg gcacaacaga caatcggctg ctctgatgcc gccgtgttcc 4080
ggctgtcagc gcaggggcgc ccggttcttt ttgtcaagac cgacctgtcc ggtgccctga 4140
atgaactgca agacgaggca gcgcggctat cgtggctggc cacgacgggc gttccttgcg 4200
cagctgtgct cgacgttgtc actgaagcgg gaagggactg gctgctattg ggcgaagtgc 4260
cggggcagga tctcctgtca tctcaccttg ctcctgccga gaaagtatcc atcatggctg 4320
atgcaatgcg gcggctgcat acgcttgatc cggctacctg cccattcgac caccaagcga 4380
aacatcgcat cgagcgagca cgtactcgga tggaagccgg tcttgtcgat caggatgatc 4440
tggacgaaga gcatcagggg ctcgcgccag ccgaactgtt cgccaggctc aaggcgagca 4500
tgcccgacgg cgaggatctc gtcgtgaccc atggcgatgc ctgcttgccg aatatcatgg 4560
tggaaaatgg ccgcttttct ggattcatcg actgtggccg gctgggtgtg gcggaccgct 4620
atcaggacat agcgttggct acccgtgata ttgctgaaga gcttggcggc gaatgggctg 4680
accgcttcct cgtgctttac ggtatcgccg ctcccgattc gcagcgcatc gccttctatc 4740
gccttcttga cgagttcttc tgaattatta acgcttacaa tttcctgatg cggtattttc 4800
tccttacgca tctgtgcggt atttcacacc gcatacaggt ggcacttttc ggggaaatgt 4860
gcgcggaacc cctatttgtt tatttttcta aatacattca aatatgtatc cgctcatgag 4920
acaataaccc tgataaatgc ttcaataata gcacgtgcta aaacttcatt tttaatttaa 4980
aaggatctag gtgaagatcc tttttgataa tctcatgacc aaaatccctt aacgtgagtt 5040
ttcgttccac tgagcgtcag accccgtaga aaagatcaaa ggatcttctt gagatccttt 5100
ttttctgcgc gtaatctgct gcttgcaaac aaaaaaacca ccgctaccag cggtggtttg 5160
tttgccggat caagagctac caactctttt tccgaaggta actggcttca gcagagcgca 5220
gataccaaat actgtccttc tagtgtagcc gtagttaggc caccacttca agaactctgt 5280
agcaccgcct acatacctcg ctctgctaat cctgttacca gtggctgctg ccagtggcga 5340
taagtcgtgt cttaccgggt tggactcaag acgatagtta ccggataagg cgcagcggtc 5400
gggctgaacg gggggttcgt gcacacagcc cagcttggag cgaacgacct acaccgaact 5460
gagataccta cagcgtgagc tatgagaaag cgccacgctt cccgaaggga gaaaggcgga 5520
caggtatccg gtaagcggca gggtcggaac aggagagcgc acgagggagc ttccaggggg 5580
aaacgcctgg tatctttata gtcctgtcgg gtttcgccac ctctgacttg agcgtcgatt 5640
tttgtgatgc tcgtcagggg ggcggagcct atggaaaaac gccagcaacg cggccttttt 5700
acggttcctg gccttttgct ggccttttgc tcacatgttc tt 5742

<210> SEQ ID NO 78
<211> LENGTH: 4590
<212> TYPE: DNA
<213> ORGANISM: Artificial Sequence
<220> FEATURE:
<223> OTHER INFORMATION: 1007652_pHCMVgMgN_pVAX1 (LTGA)

<400> SEQUENCE: 78
gactcttcgc gatgtacggg ccagatatac gcgttgacat tgattattga ctagttatta 60

-continued

```
atagtaatca attacggggt cattagttca tagcccatat atggagttcc gcgttacata    120

acttacggta aatggcccgc ctggctgacc gcccaacgac ccccgcccat tgacgtcaat    180

aatgacgtat gttcccatag taacgccaat agggactttc cattgacgtc aatgggtgga    240

ctatttacgg taaactgccc acttggcagt acatcaagtg tatcatatgc caagtacgcc    300

ccctattgac gtcaatgacg gtaaatggcc cgcctggcat tatgcccagt acatgacctt    360

atgggacttt cctacttggc agtacatcta cgtattagtc atcgctatta ccatggtgat    420

gcggttttgg cagtacatca atgggcgtgg atagcggttt gactcacggg gatttccaag    480

tctccacccc attgacgtca atgggagttt gttttggcac caaaatcaac gggactttcc    540

aaaatgtcgt aacaactccg ccccattgac gcaaatgggc ggtaggcgtg tacggtggga    600

ggtctatata agcagagctc tctggctaac tagagaaccc actgcttact ggcttatcga    660

aattaatacg actcactata gggagaccca agctggctag cgtttaaact taagcttgcc    720

accatggatt ggacctggat cctgttcctg gtggccgctg ctacccgggt ccacagtgca    780

cccagccacg tggacaaagt gaacacccgg acttggagcg ccagcatcgt gttcatggtg    840

ctgaccttcg tgaatgtgtc cgtccacctg gtgctgagca acttccccca cctgggctac    900

ccctgcgtgt actaccacgt ggtggacttc gagcggctga acatgagcgc ctacaacgtg    960

atgcatctgc acacccccat gctgtttctg gacagcgtgc agctcgtgtg ctacgccgtg   1020

tttatgcagc tggtgttcct ggccgtgacc atctactacc tcgtgtgctg gatcaagatt   1080

tctatgcgga aggacaaggg catgagcctg aaccagagca cccgggacat cagctacatg   1140

ggcgacagcc tgaccgcctt cctgttcatc ctgagcatgg acaccttcca gctgttcacc   1200

ctgaccatga gcttccggct gcccagcatg atcgccttta tggccgccgt ccacttcttc   1260

tgtctgacca tcttcaacgt gtccatggtc acccagtaca gaagctacaa gcggagcctg   1320

ttcttcttca gtcggctgca ccccaagctg aagggcaccg tccagttccg gaccctgatc   1380

gtgaacctgg tggaagtggc cctgggcttc aacaccaccg tggtggctat ggctctgtgc   1440

tacggcttcg gcaacaactt cttcgtgcgg acaggccaca tggtgctggc cgtgttcgtg   1500

gtgtacgcca ttatcagcat catctacttt ctgctgatcg aggccgtgtt cttccagtac   1560

gtgaaggtgc agttcggcta ccacctgggc gcctttttcg gcctgtgcgg cctgatctac   1620

cccatcgtgc agtacgacac cttcctgagc aacgagtacc ggaccggcat cagctggtcc   1680

ttcggcatgc tgttcttcat ctgggccatg ttcaccacct gtcgggccgt gcggtacttc   1740

agaggcagag gcagcggctc cgtgaagtac caggccctgg ccacagccag cggcgaagaa   1800

gtggccgccc tgagccacca cgacagcctg gaaagcagac ggctgagaga ggaagaggac   1860

gacgacgacg atgaggactt cgaggacgcc taccccctacg acgtgcccga ctatgcccgc   1920

ggcagaaagc ggagatctga gtggaacacc ctggtgctgg gtctgctggt gctgtctgtg   1980

gccgccagca gcaacaacac cagcactgcc agcaccccca gccctagcag cagcacccac   2040

acctccacca ccgtgaaggc caccaccacc gccaccacaa gcaccacaac agccaccagc   2100

accacctctt ccaccaccag cacaaagccc ggcagcacca ctcacgaccc caacgtgatg   2160

aggccccacg cccacaacga cttctacaag gcccactgca ccagccatat gtacgagctg   2220

agcctgagca gcttcgccgc ctggtggacc atgctgaacg ccctgatcct gatgggcgcc   2280

ttctgcatcg tgctgcggca ctgctgcttc cagaacttca ccgccacaac caccaagggc   2340

tactaccctt acgatgtgcc tgattatgcc tgatgactcg agtctagagg gcccgtttaa   2400

acccgctgat cagcctcgac tgtgccttct agttgccagc catctgttgt ttgcccctcc   2460
```

cccgtgcctt ccttgaccct ggaaggtgcc actcccactg tcctttccta ataaaatgag 2520
gaaattgcat cgcattgtct gagtaggtgt cattctattc tggggggtgg ggtggggcag 2580
gacagcaagg gggaggattg ggaagacaat agcaggcatg ctggggatgc ggtgggctct 2640
atggcttcta ctgggcggtt ttatggacag caagcgaacc ggaattgcca gctggggcgc 2700
cctctggtaa ggttgggaag ccctgcaaag taaactggat ggctttctcg ccgccaagga 2760
tctgatggcg caggggatca agctctgatc aagagacagg atgaggatcg tttcgcatga 2820
ttgaacaaga tggattgcac gcaggttctc cggccgcttg ggtggagagg ctattcggct 2880
atgactgggc acaacagaca atcggctgct ctgatgccgc cgtgttccgg ctgtcagcgc 2940
aggggcgccc ggttcttttt gtcaagaccg acctgtccgg tgccctgaat gaactgcaag 3000
acgaggcagc gcggctatcg tggctggcca cgacgggcgt tccttgcgca gctgtgctcg 3060
acgttgtcac tgaagcggga agggactggc tgctattggg cgaagtgccg gggcaggatc 3120
tcctgtcatc tcaccttgct cctgccgaga aagtatccat catggctgat gcaatgcggc 3180
ggctgcatac gcttgatccg gctacctgcc cattcgacca ccaagcgaaa catcgcatcg 3240
agcgagcacg tactcggatg gaagccggtc ttgtcgatca ggatgatctg gacgaagagc 3300
atcaggggct cgcgccagcc gaactgttcg ccaggctcaa ggcgagcatg cccgacggcg 3360
aggatctcgt cgtgacccat ggcgatgcct gcttgccgaa tatcatggtg gaaaatggcc 3420
gcttttctgg attcatcgac tgtggccggc tgggtgtggc ggaccgctat caggacatag 3480
cgttggctac ccgtgatatt gctgaagagc ttggcggcga atgggctgac cgcttcctcg 3540
tgctttacgg tatcgccgct cccgattcgc agcgcatcgc cttctatcgc cttcttgacg 3600
agttcttctg aattattaac gcttacaatt tcctgatgcg gtattttctc cttacgcatc 3660
tgtgcggtat ttcacaccgc atacaggtgg cacttttcgg ggaaatgtgc gcggaacccc 3720
tatttgttta tttttctaaa tacattcaaa tatgtatccg ctcatgagac aataaccctg 3780
ataaatgctt caataatagc acgtgctaaa acttcatttt taatttaaaa ggatctaggt 3840
gaagatcctt tttgataatc tcatgaccaa aatcccttaa cgtgagtttt cgttccactg 3900
agcgtcagac cccgtagaaa agatcaaagg atcttcttga gatccttttt ttctgcgcgt 3960
aatctgctgc ttgcaaacaa aaaaaccacc gctaccagcg gtggtttgtt tgccggatca 4020
agagctacca actctttttc cgaaggtaac tggcttcagc agagcgcaga taccaaatac 4080
tgtccttcta gtgtagccgt agttaggcca ccacttcaag aactctgtag caccgcctac 4140
atacctcgct ctgctaatcc tgttaccagt ggctgctgcc agtggcgata agtcgtgtct 4200
taccgggttg gactcaagac gatagttacc ggataaggcg cagcggtcgg gctgaacggg 4260
gggttcgtgc acacagccca gcttggagcg aacgacctac accgaactga gatacctaca 4320
gcgtgagcta tgagaaagcg ccacgcttcc cgaagggaga aaggcggaca ggtatccggt 4380
aagcggcagg gtcggaacag gagagcgcac gagggagctt ccagggggaa acgcctggta 4440
tctttatagt cctgtcgggt ttcgccacct ctgacttgag cgtcgatttt tgtgatgctc 4500
gtcagggggg cggagcctat ggaaaaacgc cagcaacgcg gcctttttac ggttcctggg 4560
cttttgctgg ccttttgctc acatgttctt 4590

<210> SEQ ID NO 79
<211> LENGTH: 6129
<212> TYPE: DNA
<213> ORGANISM: Artificial Sequence
<220> FEATURE:

<223> OTHER INFORMATION: 0958364_pCMVgHgL_pVAX1 (LTGA)

<400> SEQUENCE: 79

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
ctatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttgcc    720
accatggact ggacctggat cctgttcctg gtggccgctg ctacccgggt gcacagtcga    780
cccggcctgc ccagctacct gaccgtgttc gccgtgtacc tgctgagcca tctgcccagc    840
cagagatacg gcgccgatgc cgcctctgag gccctggatc ctcacgcctt ccatctgctg    900
ctgaacacct acggcagacc tatccggttc ctgcgcgaga acaccaccca gtgcacctac    960
aacagcagcc tgcggaacag caccgtcgtg cgcgagaatg ctatcagctt caacttcttc   1020
cagagctaca accagtacta cgtgttccac atgccccggt gcctgttcgc cggacctctg   1080
gccgagcagt tcctgaacca ggtggacctg accgagacac tggaaagata ccagcagcgg   1140
ctgaatacct acgccctggt gtccaaggac ctggccagct accggtcctt cagccagcag   1200
ctgaaggctc aggacagcct gggcgagcag cctaccaccg tgccccctcc aatcgacctg   1260
agcatccccc acgtgtggat gcccccccag accacacctc acggctggaa agagagccac   1320
accaccagcg gcctgcacag accccacttc aaccagacct gcattctgtt cgacggccac   1380
gacctgctgt tcagcaccgt gacccccctgc ctgcaccagg gcttctacct gatcgacgag   1440
ctgagatacg tgaagatcac cctgaccgag gatttcttcg tggtcaccgt gtccatcgac   1500
gacgacaccc ccatgctgct gatcttcggc catctgcctc gggtgctgtt caaggccccc   1560
taccagcggg acaacttcat cctgcggcag accgagaagc acgagctgct ggtgctggtc   1620
aagaaggacc agctgaaccg gcactcctac ctgaaggacc ccgacttcct ggacgccgcc   1680
ctggacttca actacctgga cctgagcgcc ctgctgagaa acagcttcca cagatacgcc   1740
gtggacgtgc tgaagtccgg ccggtgccag atgctggaca gacggaccgt ggaaatggcc   1800
ttcgcctatg ccctggccct gtttgccgcc gctcggcagg aagaggctgg cgctgaagtg   1860
tccgtgccca gagccctgga cagacaggcc gctctgctgc agatccagga attcatgatc   1920
acctgtctga gccagacccc ccctcggacc accctgctgc tgtaccctac cgccgtggat   1980
ctggccaagc gggccctgtg gacccccaac cagatcaccg acatcacaag cctcgtgcgg   2040
ctggtgtaca tcctgagcaa gcagaaccag cagcacctga tcccccagtg ggccctgaga   2100
cagatcgccg acttcgccct gaagctgcac aagacccacc tggctagctt tctgagcgcc   2160
ttcgctaggc aggaactgta cctgatgggc agcctggtgc actccatgct ggtgcacacc   2220
accgagaggc gggaaatctt catcgtggaa accggcctgt gcagcctggc cgagctgagc   2280
```

```
cacttcaccc agctgctggc ccaccccac cacgagtacc tgagcgacct gtacaccccc   2340
tgcagctcta gcggcagacg ggatcacagc ctggaacggc tgacccggct gttccccgat   2400
gccacagtgc ctgccactgt gccagccgcc ctgtccatcc tgtccaccat gcagcccagc   2460
accctggaaa ccttccccga cctgttctgc ctgcccctgg gcgagagctt cagcgccctg   2520
acagtgtccg agcacgtgtc ctacgtggtc accaaccagt acctgatcaa gggcatcagc   2580
taccccgtgt ccaccaccgt cgtgggccag agcctgatca tcacccagac cgacagccag   2640
accaagtgcg agctgacccg gaacatgcac accacacaca gcatcactgc cgccctgaac   2700
atcagcctgg aaaactgcgc cttctgccag tctgccctgc tggaatacga cgatacccag   2760
ggcgtgatca acatcatgta catgcacgac agcgacgacg tgctgttcgc cctggacccc   2820
tacaacgagg tggtggtgtc cagcccccgg acccactacc tgatgctgct gaagaacggc   2880
accgtgctgg aagtgaccga cgtggtggtg gacgccaccg acagcagact gctgatgatg   2940
agcgtgtacg ccctgagcgc catcatcggc atctacctgc tgtaccggat gctgaaaacc   3000
tgctacccct acgacgtgcc cgactacgcc cgcggcagaa agcggagatc ctgcaggcgg   3060
cccgactgcg gcttcagctt cagccctggc cccgtgatcc tgctgtggtg ctgcctgctg   3120
ctgcccatcg tgtcctctgc cgccgtgtct gtggccccta cagccgccga gaaggtgcca   3180
gccgagtgcc ctgagctgac cagacggtgt ctgctgggcg aggtgttcca gggcgataag   3240
tacgagagct ggctgcggcc cctggtcaac gtgaccggca gagatggccc cctgagccag   3300
ctgatccggt acagacccgt gacccctgag gccgccaaca gcgtgctgct ggacgaagcc   3360
tttctggaca cactggccct gctgtacaac aaccccgacc agctgcgggc cctgctgaca   3420
ctgctgagca gcgataccgc cccccagatgg atgaccgtga tgcggggcta cagcgagtgc   3480
ggcgacggat ctcccgccgt gtacacctgt gtggacgacc tgtgccgggg ctacgacctg   3540
accagactga gctacggccg gtccatcttc acagagcacg tgctgggctt cgagctggtg   3600
ccccccagcc tgttcaatgt ggtggtggcc atccggaacg aggccacccg gaccaacaga   3660
gcagtgcggc tgcctgtgtc caccgctgct gctccagagg gcatcaccct gttctacggc   3720
ctgtacaacg ccgtgaaaga gttctgcctg agacaccagc tggaccccc cctgctgcgg   3780
cacctggaca agtactacgc cggcctgcct cccgagctga agcagaccag agtgaacctg   3840
cccgcccaca gcagatacgg ccctcaggcc gtggacgcca gataccctta cgatgtgcct   3900
gattatgcct gatgactcga gtctagaggg cccgtttaaa cccgctgatc agcctcgact   3960
gtgccttcta gttgccagcc atctgttgtt tgcccctccc ccgtgccttc cttgaccctg   4020
gaaggtgcca ctcccactgt cctttcctaa taaaatgagg aaattgcatc gcattgtctg   4080
agtaggtgtc attctattct ggggggtggg gtggggcagg acagcaaggg ggaggattgg   4140
gaagacaata gcaggcatgc tggggatgcg gtgggctcta tggcttctac tgggcggttt   4200
tatggacagc aagcgaaccg gaattgccag ctggggcgcc ctctggtaag gttgggaagc   4260
cctgcaaagt aaactggatg gctttctcgc cgccaaggat ctgatggcgc aggggatcaa   4320
gctctgatca agagacagga tgaggatcgt ttcgcatgat tgaacaagat ggattgcacg   4380
caggttctcc ggccgcttgg gtggagaggc tattcggcta tgactgggca caacagacaa   4440
tcggctgctc tgatgccgcc gtgttccggc tgtcagcgca ggggcgcccg gttctttttg   4500
tcaagaccga cctgtccggt gccctgaatg aactgcaaga cgaggcagcg cggctatcgt   4560
ggctggccac gacgggcgtt ccttgcgcag ctgtgctcga cgttgtcact gaagcgggaa   4620
```

gggactggct gctattgggc gaagtgccgg ggcaggatct cctgtcatct caccttgctc 4680
ctgccgagaa agtatccatc atggctgatg caatgcggcg gctgcatacg cttgatccgg 4740
ctacctgccc attcgaccac caagcgaaac atcgcatcga gcgagcacgt actcggatgg 4800
aagccggtct tgtcgatcag gatgatctgg acgaagagca tcaggggctc gcgccagccg 4860
aactgttcgc caggctcaag gcgagcatgc ccgacggcga ggatctcgtc gtgacccatg 4920
gcgatgcctg cttgccgaat atcatggtgg aaaatggccg cttttctgga ttcatcgact 4980
gtggccggct gggtgtggcg gaccgctatc aggacatagc gttggctacc cgtgatattg 5040
ctgaagagct tggcggcgaa tgggctgacc gcttcctcgt gctttacggt atcgccgctc 5100
ccgattcgca gcgcatcgcc ttctatcgcc ttcttgacga gttcttctga attattaacg 5160
cttacaattt cctgatgcgg tattttctcc ttacgcatct gtgcggtatt tcacaccgca 5220
tacaggtggc acttttcggg gaaatgtgcg cggaacccct atttgtttat ttttctaaat 5280
acattcaaat atgtatccgc tcatgagaca ataaccctga taaatgcttc aataatagca 5340
cgtgctaaaa cttcattttt aatttaaaag gatctaggtg aagatccttt ttgataatct 5400
catgaccaaa atcccttaac gtgagttttc gttccactga gcgtcagacc ccgtagaaaa 5460
gatcaaagga tcttcttgag atcctttttt tctgcgcgta atctgctgct tgcaaacaaa 5520
aaaaccaccg ctaccagcgg tggtttgttt gccggatcaa gagctaccaa ctctttttcc 5580
gaaggtaact ggcttcagca gagcgcagat accaaatact gtccttctag tgtagccgta 5640
gttaggccac cacttcaaga actctgtagc accgcctaca tacctcgctc tgctaatcct 5700
gttaccagtg gctgctgcca gtggcgataa gtcgtgtctt accgggttgg actcaagacg 5760
atagttaccg gataaggcgc agcggtcggg ctgaacgggg ggttcgtgca cacagcccag 5820
cttggagcga acgacctaca ccgaactgag atacctacag cgtgagctat gagaaagcgc 5880
cacgcttccc gaagggagaa aggcggacag gtatccggta agcggcaggg tcggaacagg 5940
agagcgcacg agggagcttc caggggg aaa cgcctggtat ctttatagtc ctgtcgggtt 6000
tcgccacctc tgacttgagc gtcgattttt gtgatgctcg tcaggggggc ggagcctatg 6060
gaaaaacgcc agcaacgcgg cctttttacg gttcctgggc ttttgctggc cttttgctca 6120
catgttctt 6129

<210> SEQ ID NO 80
<211> LENGTH: 4437
<212> TYPE: DNA
<213> ORGANISM: Artificial Sequence
<220> FEATURE:
<223> OTHER INFORMATION: 1007654_pHCMVgO_pVAX1 (LTGA)

<400> SEQUENCE: 80
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
ctatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540

-continued

```
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttgcc    720
accatggact ggacctggat cctgttcctg gtcgccgctg caactagagt gcacagcggc    780
aagaaagaaa tgatcatggt caagggcatc cccaagatca tgctgctgat cagcatcacc    840
tttctgctgc tgagcctgat caactgcaac gtgctggtca acagcaaggg cacacggcgg    900
agctggccct acaccgtgct gagctaccgg ggcaaagaga tcctgaagaa gcagaaagag    960
gacatcctga agcggctgat gagcaccagc agcgacggct accggttcct gatgtacccc   1020
agccagcaga aattccacgc catcgtgatc agcatggaca agttccccca ggactacatc   1080
ctggccggac ccatccggaa cgacagcatc acccacatgt ggttcgactt ctacagcacc   1140
cagctgcgga agcccgccaa atacgtgtac agcgagtaca accacaccgc ccacaagatc   1200
accctgcggc ctcccccttg cggcaccgtg cccagcatga actgcctgag cgagatgctg   1260
aacgtgtcca agcggaacga caccggcgag aagggctgcg gcaacttcac caccttcaac   1320
cccatgttct tcaacgtgcc ccggtggaac accaagctgt acatcggcag caacaaagtg   1380
aacgtggaca gccagaccat ctactttctg ggcctgaccg ccctgctgct gcgctacgcc   1440
cagagaaact gcacccggtc cttctacctg gtcaacgcca tgagccggaa cctgttccgg   1500
gtgcccaagt acatcaacgg caccaagctg aagaacacca tgcggaagct gaagcggaag   1560
caggccctgg tcaaagagca gccccagaag aagaacaaga agtcccagag caccaccacc   1620
ccctacctga gctacaccac cagcaccgcc ttcaacgtga ccaccaacgt gacctacagc   1680
gccacagccg ccgtgaccag agtggccacc tccaccaccg gctaccggcc cgacagcaac   1740
ttcatgaagt ccatcatggc cacccagctg agggacctgg ccacctgggt gtacaccacc   1800
ctgcggtaca gaaacgagcc cttctgcaag cccgaccgga acagaaccgc cgtgtccgag   1860
ttcatgaaga atacccacgt gctgatccgc aacgagacac cctacaccat ctacggcacc   1920
ctggacatga gcagcctgta ctacaacgag acaatgagcg tcgagaacga gacagccagc   1980
gacaacaacg aaaccacccc caccagcccc agcacccggt tccagcggac cttcatcgac   2040
cccctgtggg actacctgga cagcctgctg ttcctggaca agatccggaa cttcagcctg   2100
cagctgcccg cctacggcaa cctgaccccc cctgaacaca gaagggccgc caacctgagc   2160
accctgaaca gcctgtggtg gtggctgcag taccccctacg acgtgcccga ctacgcctga   2220
tgactcgagt ctagagggcc cgtttaaacc cgctgatcag cctcgactgt gccttctagt   2280
tgccagccat ctgttgtttg cccctccccc gtgccttcct tgaccctgga aggtgccact   2340
cccactgtcc tttcctaata aaatgaggaa attgcatcgc attgtctgag taggtgtcat   2400
tctattctgg ggggtggggt ggggcaggac agcaaggggg aggattggga agacaatagc   2460
aggcatgctg gggatgcggt gggctctatg gcttctactg ggcggtttta tggacagcaa   2520
gcgaaccgga attgccagct ggggcgccct ctggtaaggt tgggaagccc tgcaaagtaa   2580
actggatggc tttctcgccg ccaaggatct gatggcgcag gggatcaagc tctgatcaag   2640
agacaggatg aggatcgttt cgcatgattg aacaagatgg attgcacgca ggttctccgg   2700
ccgcttgggt ggagaggcta ttcggctatg actgggcaca acagacaatc ggctgctctg   2760
atgccgccgt gttccggctg tcagcgcagg ggcgcccggt tctttttgtc aagaccgacc   2820
tgtccggtgc cctgaatgaa ctgcaagacg aggcagcgcg gctatcgtgg ctggccacga   2880
```

cgggcgttcc ttgcgcagct gtgctcgacg ttgtcactga agcgggaagg gactggctgc 2940
tattgggcga agtgccgggg caggatctcc tgtcatctca ccttgctcct gccgagaaag 3000
tatccatcat ggctgatgca atgcggcggc tgcatacgct tgatccggct acctgcccat 3060
tcgaccacca agcgaaacat cgcatcgagc gagcacgtac tcggatggaa gccggtcttg 3120
tcgatcagga tgatctggac gaagagcatc aggggctcgc gccagccgaa ctgttcgcca 3180
ggctcaaggc gagcatgccc gacggcgagg atctcgtcgt gacccatggc gatgcctgct 3240
tgccgaatat catggtggaa aatggccgct tttctggatt catcgactgt ggccggctgg 3300
gtgtggcgga ccgctatcag gacatagcgt tggctacccg tgatattgct gaagagcttg 3360
gcggcgaatg ggctgaccgc ttcctcgtgc tttacggtat cgccgctccc gattcgcagc 3420
gcatcgcctt ctatcgcctt cttgacgagt tcttctgaat tattaacgct tacaatttcc 3480
tgatgcggta ttttctcctt acgcatctgt gcggtatttc acaccgcata caggtggcac 3540
ttttcgggga aatgtgcgcg gaacccctat ttgtttattt ttctaaatac attcaaatat 3600
gtatccgctc atgagacaat aaccctgata aatgcttcaa taatagcacg tgctaaaact 3660
tcatttttaa tttaaaagga tctaggtgaa gatccttttt gataatctca tgaccaaaat 3720
cccttaacgt gagttttcgt tccactgagc gtcagacccc gtagaaaaga tcaaaggatc 3780
ttcttgagat cctttttttc tgcgcgtaat ctgctgcttg caaacaaaaa aaccaccgct 3840
accagcggtg gtttgtttgc cggatcaaga gctaccaact ctttttccga aggtaactgg 3900
cttcagcaga gcgcagatac caaatactgt ccttctagtg tagccgtagt taggccacca 3960
cttcaagaac tctgtagcac cgcctacata cctcgctctg ctaatcctgt taccagtggc 4020
tgctgccagt ggcgataagt cgtgtcttac cgggttggac tcaagacgat agttaccgga 4080
taaggcgcag cggtcgggct gaacgggggg ttcgtgcaca cagcccagct tggagcgaac 4140
gacctacacc gaactgagat acctacagcg tgagctatga gaaagcgcca cgcttcccga 4200
agggagaaag gcggacaggt atccggtaag cggcagggtc ggaacaggag agcgcacgag 4260
ggagcttcca gggggaaacg cctggtatct ttatagtcct gtcgggtttc gccacctctg 4320
acttgagcgt cgatttttgt gatgctcgtc aggggggcgg agcctatgga aaaacgccag 4380
caacgcggcc tttttacggt tcctgggctt ttgctggcct tttgctcaca tgttctt 4437

<210> SEQ ID NO 81
<211> LENGTH: 4653
<212> TYPE: DNA
<213> ORGANISM: Artificial Sequence
<220> FEATURE:
<223> OTHER INFORMATION: 1007656_pHCMVgUL_pVAX1 (LTGA)

<400> SEQUENCE: 81
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
ctatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttgcc 720
accatggact ggacctggat cctgttcctg gtcgccgctg ctacccgggt gcacagcaga 780
ctgtgcagag tgtggctgag cgtgtgcctg tgcgccgtgg tgctgggcca gtgccagaga 840
gagacagccg agaagaacga ctactaccgg gtgccccact actgggacgc ctgctctaga 900
gccctgcccg accagacccg gtacaaatac gtggaacagc tggtggacct gaccctgaac 960
taccactacg acgccagcca cggcctggac aacttcgacg tgctgaagcg gatcaacgtg 1020
accgaggtgt ccctgctgat cagcgacttc cggcggcaga acagaagagg cggcaccaac 1080
aagcggacta ccttcaacgc cgctggcagc ctggcccctc acgccagatc cctggaattc 1140
agcgtgcggc tgttcgccaa ctatccgtac gacgtcccag actacgccag aggccggaag 1200
cggagatctc tgcggctgct gctgcggcac cacttccact gcctgctgct gtgtgccgtg 1260
tgggccaccc cttgtctggc cagcccttgg agcaccctga ccgccaacca gaaccctagc 1320
cccccctggt ccaagctgac ctacagcaag ccccacgacg ccgctacctt ctactgccca 1380
ttcctgtacc ccagccctcc cagaagcccc ctgcagttca gcggcttcca gcgggtgtcc 1440
accggccctg agtgccggaa cgagacactg tacctgctgt acaaccgcga gggccagacc 1500
ctggtggaac ggtctagcac ctgggtcaag aaagtgatct ggtatctgag cggccggaac 1560
cagaccatcc tgcagcggat gcctcggacc gccagcaagc ctagcgacgg caacgtgcag 1620
atcagcgtgg aagatgccaa aatcttcggc gcccacatgg tgcccaagca gaccaagctg 1680
ctgagattcg tggtcaacga cggcaccaga taccagatgt gcgtgatgaa gctggaaagc 1740
tgggcccacg tgttccggga ctacagcgtg tcattccagg tccgactgac cttcaccgag 1800
gccaacaacc agacctacac cttctgcacc caccccaacc tgatcgtcta cccttacgac 1860
gtgccagatt atgccagggg cagaaaaagg aggagcagcc ccaaggatct gacccctttc 1920
ctgaccgccc tgtggctgct cctgggccac agcagagtgc ctagagtgcg ggccgaggaa 1980
tgctgcgagt tcatcaacgt gaaccacccc cccgagcggt gctacgactt caagatgtgc 2040
aaccggttca ccgtggctct gagatgcccc gacggcgaag tgtgctacag ccccgagaaa 2100
accgccgaga tccggggcat cgtgaccacc atgacccaca gcctgaccag acaggtggtg 2160
cataacaagc tgaccagttg caactacaac cccctgtacc tggaagccga cggccggatc 2220
agatgcggca aagtgaacga caaggcccag tacctgctgg gcgctgcagg cagtgtgccc 2280
tacagatgga tcaacctgga atacgacaag atcacccgga tcgtgggcct ggaccagtac 2340
ctggaaagcg tgaagaagca caagcggctg gacgtgtgcc gggccaagat gggctacatg 2400
ctgcagtacc catatgacgt ccccgattac gcttgatgac tcgagtctag agggcccgtt 2460
taaacccgct gatcagcctc gactgtgcct tctagttgcc agccatctgt tgtttgcccc 2520
tcccccgtgc cttccttgac cctggaaggt gccactccca ctgtcctttc ctaataaaat 2580
gaggaaattg catcgcattg tctgagtagg tgtcattcta ttctgggggg tggggtgggg 2640
caggacagca agggggagga ttgggaagac aatagcaggc atgctgggga tgcggtgggc 2700
tctatggctt ctactgggcg gttttatgga cagcaagcga accggaattg ccagctgggg 2760
cgccctctgg taaggttggg aagccctgca aagtaaactg gatggctttc tcgccgccaa 2820
ggatctgatg gcgcagggga tcaagctctg atcaagagac aggatgagga tcgtttcgca 2880

```
tgattgaaca agatggattg cacgcaggtt ctccggccgc ttgggtggag aggctattcg   2940

gctatgactg ggcacaacag acaatcggct gctctgatgc cgccgtgttc cggctgtcag   3000

cgcaggggcg cccggttctt tttgtcaaga ccgacctgtc cggtgccctg aatgaactgc   3060

aagacgaggc agcgcggcta tcgtggctgg ccacgacggg cgttccttgc gcagctgtgc   3120

tcgacgttgt cactgaagcg ggaagggact ggctgctatt gggcgaagtg ccggggcagg   3180

atctcctgtc atctcacctt gctcctgccg agaaagtatc catcatggct gatgcaatgc   3240

ggcggctgca tacgcttgat ccggctacct gcccattcga ccaccaagcg aaacatcgca   3300

tcgagcgagc acgtactcgg atggaagccg gtcttgtcga tcaggatgat ctggacgaag   3360

agcatcaggg gctcgcgcca gccgaactgt tcgccaggct caaggcgagc atgcccgacg   3420

gcgaggatct cgtcgtgacc catggcgatg cctgcttgcc gaatatcatg gtggaaaatg   3480

gccgcttttc tggattcatc gactgtggcc ggctgggtgt ggcggaccgc tatcaggaca   3540

tagcgttggc tacccgtgat attgctgaag agcttggcgg cgaatgggct gaccgcttcc   3600

tcgtgcttta cggtatcgcc gctcccgatt cgcagcgcat cgccttctat cgccttcttg   3660

acgagttctt ctgaattatt aacgcttaca atttcctgat gcggtatttt ctccttacgc   3720

atctgtgcgg tatttcacac cgcatacagg tggcactttt cggggaaatg tgcgcggaac   3780

ccctatttgt ttatttttct aaatacattc aaatatgtat ccgctcatga gacaataacc   3840

ctgataaatg cttcaataat agcacgtgct aaaacttcat ttttaattta aaaggatcta   3900

ggtgaagatc ctttttgata atctcatgac caaaatccct taacgtgagt tttcgttcca   3960

ctgagcgtca gaccccgtag aaaagatcaa aggatcttct tgagatcctt tttttctgcg   4020

cgtaatctgc tgcttgcaaa caaaaaaacc accgctacca gcggtggttt gtttgccgga   4080

tcaagagcta ccaactcttt ttccgaaggt aactggcttc agcagagcgc agataccaaa   4140

tactgtcctt ctagtgtagc cgtagttagg ccaccacttc aagaactctg tagcaccgcc   4200

tacatacctc gctctgctaa tcctgttacc agtggctgct gccagtggcg ataagtcgtg   4260

tcttaccggg ttggactcaa gacgatagtt accggataag gcgcagcggt cgggctgaac   4320

gggggggttcg tgcacacagc ccagcttgga gcgaacgacc tacaccgaac tgagatacct   4380

acagcgtgag ctatgagaaa gcgccacgct tcccgaaggg agaaaggcgg acaggtatcc   4440

ggtaagcggc agggtcggaa caggagagcg cacgagggag cttccagggg gaaacgcctg   4500

gtatctttat agtcctgtcg ggtttcgcca cctctgactt gagcgtcgat ttttgtgatg   4560

ctcgtcaggg gggcggagcc tatggaaaaa cgccagcaac gcggcctttt tacggttcct   4620

gggcttttgc tggccttttg ctcacatgtt ctt                                4653
```

<210> SEQ ID NO 82
<211> LENGTH: 5715
<212> TYPE: DNA
<213> ORGANISM: Artificial Sequence
<220> FEATURE:
<223> OTHER INFORMATION: 1028044_pHCMV_gB_pVAX1 (LGA)

<400> SEQUENCE: 82

```
gactcttcgc gatgtacggg ccagatatac gcgttgacat tgattattga ctagttatta     60

atagtaatca attacggggt cattagttca tagcccatat atggagttcc gcgttacata    120

acttacggta aatggcccgc ctggctgacc gcccaacgac ccccgcccat tgacgtcaat    180

aatgacgtat gttcccatag taacgccaat agggactttc cattgacgtc aatgggtgga    240

ctatttacgg taaactgccc acttggcagt acatcaagtg tatcatatgc caagtacgcc    300
```

```
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttgcc    720
accatggact ggacctggat cctgttcctg gtggccgctg ccacacgggt gcacagcgag    780
agcagaatct ggtgcctggt cgtgtgcgtg aacctgtgca tcgtgtgcct gggagccgcc    840
gtgtccagca gcagcacccg gggcacaagc gccacacaca gccaccacag cagccacacc    900
accagcgccg cccacagccg gagcggaagc gtgagcagcc agcgggtgac cagcagcgag    960
gccgtgtccc accgggccaa cgagacaatc tacaacacca ccctgaagta cggcgacgtc   1020
gtgggagtga acaccaccaa gtacccctac agagtgtgca gcatggccca gggcaccgac   1080
ctgatcagat tcgagcggaa catcgtgtgt accagcatga agcccatcaa cgaggacctg   1140
gacgagggca tcatggtggt gtacaagaga aacatcgtgg cccacacctt caaagtgcgg   1200
gtgtaccaga aggtgctgac cttccggcgg agctacgcct acatccacac cacctacctg   1260
ctgggcagca acaccgagta cgtggcccct cccatgtggg agatccacca catcaacagc   1320
cacagccagt gctacagcag ctacagccgc gtgatcgccg gcaccgtgtt cgtggcctac   1380
caccgggaca gctacgagaa caagaccatg cagctgatgc ccgacgacta cagcaacacc   1440
cacagcacca gatacgtgac cgtgaaggac cagtggcaca gccggggaag cacctggctg   1500
tacagagaga catgcaacct gaactgcatg gtcaccatca ccaccgccag aagcaagtac   1560
ccttaccact tcttcgccac cagcaccggc gacgtggtgg acatcagccc cttctacaac   1620
ggcaccaacc ggaacgccag ctacttcggc gagaacgccg acaagttctt catcttcccc   1680
aactacacca tcgtgtccga cttcggcaga cccaacagcg cccctgagac acaccggctg   1740
gtggcctttc tggaacgggc cgacagcgtg atcagctggg acatccagga cgagaagaac   1800
gtgacctgcc agctgacctt ctgggaggct agcgagcgga ccatcagaag cgaggccgag   1860
gacagctacc acttcagcag cgccaagatg accgccacct tcctgagcaa gaaacaggaa   1920
gtgaacatga gcgacagcgc cctggactgc gtgcgggatg aggccatcaa caagctgcag   1980
cagatcttca acaccagcta caaccagacc tacgagaagt atggcaacgt gtccgtgttc   2040
gagacaacag gcggcctggt ggtgttctgg cagggcatca agcagaagtc cctggtcgag   2100
ctggaacggc tggccaacag aagcagcctg aacctgaccc accggaccaa gcggagcacc   2160
gacggcaaca ataccaccca cctgagcaac atggaaagcg tccacaacct ggtgtacgcc   2220
cagctgcagt tcacctacga caccctgcgg ggctacatca accgggccct ggcccagatc   2280
gccgaggctt ggtgtgtgga ccagcggcgg accctggaag tgttcaaaga gctgagcaag   2340
atcaacccca gcgccatcct gagcgccatc tacaacaagc ctatcgccgc cagattcatg   2400
ggcgacgtgc tgggcctggc cagctgcgtg accatcaacc agaccagcgt gaaggtgctg   2460
cgggacatga acgtgaaaga aagccccggc agatgctact ccagacccgt ggtcatcttc   2520
aacttcgcca acagctccta cgtgcagtac ggccagctgg gcgaggacaa cgagatcctg   2580
ctgggaaacc accggaccga ggaatgccag ctgcccagcc tgaagatctt tatcgccggc   2640
```

```
aacagcgcct acgagtatgt ggactacctg ttcaagcgga tgatcgacct gagcagcatc   2700
agcaccgtgg acagcatgat cgccctggac atcgaccccc tggaaaacac cgacttccgg   2760
gtgctggaac tgtacagcca gaaagagctg cggagcagca acgtgttcga cctggaagag   2820
atcatgcgcg agttcaacag ctacaagcag cgcgtgaaat acgtcgagga caaggtggtg   2880
gaccccctgc ccccctacct gaagggcctg gacgacctga tgagcggcct gggagctgct   2940
ggcaaggccg tgggagtggc cattggagct gtgggcggag ccgtggccag cgtggtggaa   3000
ggcgtggcca cctttctgaa gaacccttc ggcgccttca ccatcatcct ggtggctatc    3060
gccgtcgtga tcatcaccta cctgatctac acccggcagc ggcggctgtg tacccagcct   3120
ctgcagaacc tgttccccta cctggtgtcc gccgacggca ccaccgtgac aagcggctcc   3180
accaaggaca ccagcctgca ggccccaccc agctacgagg aatccgtgta caacagcggc   3240
cggaagggcc caggccctcc tagctctgac gcctctacag ccgcccccacc ctacaccaac  3300
gagcaggcct accagatgct gctggccctg gctagactgg acgccgagca gagagcccag   3360
cagaacggaa ccgacagcct ggatggccag accggcaccc aggacaaggg ccagaagccc   3420
aacctgctgg accggctgcg gcacagaaag aacggctacc ggcacctgaa ggacagcgac   3480
gaagaggaaa acgtgtgatg actcgagtct agagggcccg tttaaacccg ctgatcagcc   3540
tcgactgtgc cttctagttg ccagccatct gttgtttgcc cctcccccgt gccttccttg   3600
accctggaag gtgccactcc cactgtcctt tcctaataaa atgaggaaat tgcatcgcat   3660
tgtctgagta ggtgtcattc tattctgggg ggtggggtgg ggcaggacag caagggggag   3720
gattgggaag acaatagcag gcatgctggg gatgcggtgg gctctatggc ttctactggg   3780
cggttttatg gacagcaagc gaaccggaat tgccagctgg ggcgccctct ggtaaggttg   3840
ggaagccctg caaagtaaac tggatggctt tctcgccgcc aaggatctga tggcgcaggg   3900
gatcaagctc tgatcaagag acaggatgag gatcgtttcg catgattgaa caagatggat   3960
tgcacgcagg ttctccggcc gcttgggtgg agaggctatt cggctatgac tgggcacaac   4020
agacaatcgg ctgctctgat gccgccgtgt tccggctgtc agcgcagggg cgcccggttc   4080
tttttgtcaa gaccgacctg tccggtgccc tgaatgaact gcaagacgag gcagcgcggc   4140
tatcgtggct ggccacgacg ggcgttcctt gcgcagctgt gctcgacgtt gtcactgaag   4200
cgggaaggga ctggctgcta ttgggcgaag tgccggggca ggatctcctg tcatctcacc   4260
ttgctcctgc cgagaaagta tccatcatgg ctgatgcaat gcggcggctg catacgcttg   4320
atccggctac ctgcccattc gaccaccaag cgaaacatcg catcgagcga gcacgtactc   4380
ggatggaagc cggtcttgtc gatcaggatg atctggacga agagcatcag gggctcgcgc   4440
cagccgaact gttcgccagg ctcaaggcga gcatgcccga cggcgaggat ctcgtcgtga   4500
cccatggcga tgcctgcttg ccgaatatca tggtggaaaa tggccgcttt tctggattca   4560
tcgactgtgg ccggctgggt gtggcggacc gctatcagga catagcgttg gctacccgtg   4620
atattgctga agagcttggc ggcgaatggg ctgaccgctt cctcgtgctt tacggtatcg   4680
ccgctcccga ttcgcagcgc atcgccttct atcgccttct tgacgagttc ttctgaatta   4740
ttaacgctta caatttcctg atgcggtatt ttctccttac gcatctgtgc ggtatttcac   4800
accgcataca ggtggcactt ttcggggaaa tgtgcgcgga acccctattt gtttattttt   4860
ctaaatacat tcaaatatgt atccgctcat gagacaataa ccctgataaa tgcttcaata   4920
atagcacgtg ctaaaacttc atttttaatt taaaaggatc taggtgaaga tcctttttga   4980
taatctcatg accaaaatcc cttaacgtga gttttcgttc cactgagcgt cagaccccgt   5040
```

```
agaaaagatc aaaggatctt cttgagatcc ttttttctg cgcgtaatct gctgcttgca   5100

aacaaaaaaa ccaccgctac cagcggtggt ttgtttgccg gatcaagagc taccaactct   5160

ttttccgaag gtaactggct tcagcagagc gcagatacca aatactgtcc ttctagtgta   5220

gccgtagtta ggccaccact tcaagaactc tgtagcaccg cctacatacc tcgctctgct   5280

aatcctgtta ccagtggctg ctgccagtgg cgataagtcg tgtcttaccg ggttggactc   5340

aagacgatag ttaccggata aggcgcagcg gtcgggctga acggggggtt cgtgcacaca   5400

gcccagcttg gagcgaacga cctacaccga actgagatac ctacagcgtg agctatgaga   5460

aagcgccacg cttcccgaag ggagaaaggc ggacaggtat ccggtaagcg gcagggtcgg   5520

aacaggagag cgcacgaggg agcttccagg gggaaacgcc tggtatcttt atagtcctgt   5580

cgggtttcgc cacctctgac ttgagcgtcg atttttgtga tgctcgtcag gggggcggag   5640

cctatggaaa aacgccagca acgcggcctt tttacggttc ctgggctttt gctggccttt   5700

tgctcacatg ttctt                                                   5715
```

<210> SEQ ID NO 83
<211> LENGTH: 6075
<212> TYPE: DNA
<213> ORGANISM: Artificial Sequence
<220> FEATURE:
<223> OTHER INFORMATION: 1028046_pHCMV_gHgL_pVAX1 (LGA)

<400> SEQUENCE: 83

```
gactcttcgc gatgtacggg ccagatatac gcgttgacat tgattattga ctagttatta     60

atagtaatca attacggggt cattagttca tagcccatat atggagttcc gcgttacata    120

acttacggta aatggcccgc ctggctgacc gcccaacgac ccccgcccat tgacgtcaat    180

aatgacgtat gttcccatag taacgccaat agggactttc cattgacgtc aatgggtgga    240

ctatttacgg taaactgccc acttggcagt acatcaagtg tatcatatgc caagtacgcc    300

ccctattgac gtcaatgacg gtaaatggcc cgcctggcat tatgcccagt acatgacctt    360

atgggacttt cctacttggc agtacatcta cgtattagtc atcgctatta ccatggtgat    420

gcggttttgg cagtacatca atgggcgtgg atagcggttt gactcacggg gatttccaag    480

tctccacccc attgacgtca atgggagttt gttttggcac caaaatcaac gggactttcc    540

aaaatgtcgt aacaactccg ccccattgac gcaaatgggc ggtaggcgtg tacggtggga    600

ggtctatata agcagagctc tctggctaac tagagaaccc actgcttact ggcttatcga    660

aattaatacg actcactata gggagaccca agctggctag cgtttaaact taagcttgcc    720

accatggact ggacctggat cctgttcctg gtggccgctg ctacccgggt gcacagtcga    780

cccggcctgc ccagctacct gaccgtgttc gccgtgtacc tgctgagcca tctgcccagc    840

cagagatacg gcgccgatgc cgcctctgag gccctggatc ctcacgcctt ccatctgctg    900

ctgaacacct acggcagacc tatccggttc ctgcgcgaga acaccaccca gtgcacctac    960

aacagcagcc tgcggaacag caccgtcgtg cgcgagaatg ctatcagctt caacttcttc   1020

cagagctaca accagtacta cgtgttccac atgccccggt gcctgttcgc cggacctctg   1080

gccgagcagt tcctgaacca ggtggacctg accgagacac tggaaagata ccagcagcgg   1140

ctgaatacct acgccctggt gtccaaggac ctggccagct accggtcctt cagccagcag   1200

ctgaaggctc aggacagcct gggcgagcag cctaccaccg tgccccctcc aatcgacctg   1260

agcatccccc acgtgtggat gcccccccag accacacctc acggctggaa agagagccac   1320
```

-continued

```
accaccagcg gcctgcacag accccacttc aaccagacct gcattctgtt cgacggccac   1380
gacctgctgt tcagcaccgt gaccccctgc ctgcaccagg gcttctacct gatcgacgag   1440
ctgagatacg tgaagatcac cctgaccgag gatttcttcg tggtcaccgt gtccatcgac   1500
gacgacaccc ccatgctgct gatcttcggc catctgcctc gggtgctgtt caaggccccc   1560
taccagcggg acaacttcat cctgcggcag accgagaagc acgagctgct ggtgctggtc   1620
aagaaggacc agctgaaccg gcactcctac ctgaaggacc ccgacttcct ggacgccgcc   1680
ctggacttca actacctgga cctgagcgcc ctgctgagaa acagcttcca cagatacgcc   1740
gtggacgtgc tgaagtccgg ccggtgccag atgctggaca gacggaccgt ggaaatggcc   1800
ttcgcctatg ccctggccct gtttgccgcc gctcggcagg aagaggctgg cgctgaagtg   1860
tccgtgccca gagccctgga cagacaggcc gctctgctgc agatccagga attcatgatc   1920
acctgtctga gccagacccc ccctcggacc accctgctgc tgtaccctac cgccgtggat   1980
ctggccaagc gggccctgtg gacccccaac cagatcaccg acatcacaag cctcgtgcgg   2040
ctggtgtaca tcctgagcaa gcagaaccag cagcacctga tcccccagtg ggccctgaga   2100
cagatcgccg acttcgccct gaagctgcac aagacccacc tggctagctt tctgagcgcc   2160
ttcgctaggc aggaactgta cctgatgggc agcctggtgc actccatgct ggtgcacacc   2220
accgagaggc gggaaatctt catcgtggaa accggcctgt gcagcctggc cgagctgagc   2280
cacttcaccc agctgctggc ccaccccccac cacgagtacc tgagcgacct gtacaccccc   2340
tgcagctcta gcggcagacg ggatcacagc ctggaacggc tgacccggct gttccccgat   2400
gccacagtgc ctgccactgt gccagccgcc ctgtccatcc tgtccaccat gcagcccagc   2460
accctggaaa ccttccccga cctgttctgc ctgcccctgg gcgagagctt cagcgccctg   2520
acagtgtccg agcacgtgtc ctacgtggtc accaaccagt acctgatcaa gggcatcagc   2580
taccccgtgt ccaccaccgt cgtgggccag agcctgatca tcacccagac cgacagccag   2640
accaagtgcg agctgacccg gaacatgcac accacacaca gcatcactgc cgccctgaac   2700
atcagcctgg aaaactgcgc cttctgccag tctgccctgc tggaatacga cgatacccag   2760
ggcgtgatca acatcatgta catgcacgac agcgacgacg tgctgttcgc cctggacccc   2820
tacaacgagg tggtggtgtc cagcccccgg acccactacc tgatgctgct gaagaacggc   2880
accgtgctgg aagtgaccga cgtggtggtg gacgccaccg acagcagact gctgatgatg   2940
agcgtgtacg ccctgagcgc catcatcggc atctacctgc tgtaccggat gctgaaaacc   3000
tgccgcggca gaaagcggag atcctgcagg cggcccgact gcggcttcag cttcagccct   3060
ggccccgtga tcctgctgtg gtgctgcctg ctgctgccca tcgtgtcctc tgccgccgtg   3120
tctgtggccc ctacagccgc cgagaaggtg ccagccgagt gccctgagct gaccagacgg   3180
tgtctgctgg gcgaggtgtt ccagggcgat aagtacgaga gctggctgcg gccccctggtc   3240
aacgtgaccg gcagagatgg cccccctgagc cagctgatcc ggtacagacc cgtgacccct   3300
gaggccgcca acagcgtgct gctggacgaa gcctttctgg acacactggc cctgctgtac   3360
aacaaccccg accagctgcg ggccctgctg acactgctga gcagcgatac cgcccccaga   3420
tggatgaccg tgatgcgggg ctacagcgag tgcggcgacg gatctcccgc cgtgtacacc   3480
tgtgtggacg acctgtgccg gggctacgac ctgaccagac tgagctacgg ccggtccatc   3540
ttcacagagc acgtgctggg cttcgagctg gtgcccccca gcctgttcaa tgtggtggtg   3600
gccatccgga acgaggccac ccggaccaac agagcagtgc ggctgcctgt gtccaccgct   3660
gctgctccag agggcatcac cctgttctac ggcctgtaca acgccgtgaa agagttctgc   3720
```

-continued ctgagacacc agctggaccc ccccctgctg cggcacctgg acaagtacta cgccggcctg 3780
cctcccgagc tgaagcagac cagagtgaac ctgcccgccc acagcagata cggccctcag 3840
gccgtggacg ccagatgatg actcgagtct agagggcccg tttaaacccg ctgatcagcc 3900
tcgactgtgc cttctagttg ccagccatct gttgtttgcc cctcccccgt gccttccttg 3960
accctggaag gtgccactcc cactgtcctt tcctaataaa atgaggaaat tgcatcgcat 4020
tgtctgagta ggtgtcattc tattctgggg ggtggggtgg ggcaggacag caagggggag 4080
gattgggaag acaatagcag gcatgctggg gatgcggtgg gctctatggc ttctactggg 4140
cggttttatg gacagcaagc gaaccggaat tgccagctgg ggcgccctct ggtaaggttg 4200
ggaagccctg caaagtaaac tggatggctt tctcgccgcc aaggatctga tggcgcaggg 4260
gatcaagctc tgatcaagag acaggatgag gatcgtttcg catgattgaa caagatggat 4320
tgcacgcagg ttctccggcc gcttgggtgg agaggctatt cggctatgac tgggcacaac 4380
agacaatcgg ctgctctgat gccgccgtgt tccggctgtc agcgcagggg cgcccggttc 4440
tttttgtcaa gaccgacctg tccggtgccc tgaatgaact gcaagacgag gcagcgcggc 4500
tatcgtggct ggccacgacg ggcgttcctt gcgcagctgt gctcgacgtt gtcactgaag 4560
cgggaaggga ctggctgcta ttgggcgaag tgccggggca ggatctcctg tcatctcacc 4620
ttgctcctgc cgagaaagta tccatcatgg ctgatgcaat gcggcggctg catacgcttg 4680
atccggctac ctgcccattc gaccaccaag cgaaacatcg catcgagcga gcacgtactc 4740
ggatggaagc cggtcttgtc gatcaggatg atctggacga agagcatcag gggctcgcgc 4800
cagccgaact gttcgccagg ctcaaggcga gcatgcccga cggcgaggat ctcgtcgtga 4860
cccatggcga tgcctgcttg ccgaatatca tggtggaaaa tggccgcttt tctggattca 4920
tcgactgtgg ccggctgggt gtggcggacc gctatcagga catagcgttg gctacccgtg 4980
atattgctga agagcttggc ggcgaatggg ctgaccgctt cctcgtgctt tacggtatcg 5040
ccgctcccga ttcgcagcgc atcgccttct atcgccttct tgacgagttc ttctgaatta 5100
ttaacgctta caatttcctg atgcggtatt ttctccttac gcatctgtgc ggtatttcac 5160
accgcataca ggtggcactt ttcggggaaa tgtgcgcgga acccctattt gtttattttt 5220
ctaaatacat tcaaatatgt atccgctcat gagacaataa ccctgataaa tgcttcaata 5280
atagcacgtg ctaaaacttc atttttaatt taaaaggatc taggtgaaga tcctttttga 5340
taatctcatg accaaaatcc cttaacgtga gttttcgttc cactgagcgt cagaccccgt 5400
agaaaagatc aaaggatctt cttgagatcc tttttttctg cgcgtaatct gctgcttgca 5460
aacaaaaaaa ccaccgctac cagcggtggt ttgtttgccg gatcaagagc taccaactct 5520
ttttccgaag gtaactggct tcagcagagc gcagatacca aatactgtcc ttctagtgta 5580
gccgtagtta ggccaccact tcaagaactc tgtagcaccg cctacatacc tcgctctgct 5640
aatcctgtta ccagtggctg ctgccagtgg cgataagtcg tgtcttaccg ggttggactc 5700
aagacgatag ttaccggata aggcgcagcg gtcgggctga acggggggtt cgtgcacaca 5760
gcccagcttg gagcgaacga cctacaccga actgagatac ctacagcgtg agctatgaga 5820
aagcgccacg cttcccgaag ggagaaaggc ggacaggtat ccggtaagcg gcagggtcgg 5880
aacaggagag cgcacgaggg agcttccagg gggaaacgcc tggtatcttt atagtcctgt 5940
cgggtttcgc cacctctgac ttgagcgtcg atttttgtga tgctcgtcag gggggcggag 6000
cctatggaaa aacgccagca acgcggcctt tttacggttc ctgggctttt gctggccttt 6060
tgctcacatg ttctt 6075

<210> SEQ ID NO 84
<211> LENGTH: 4671
<212> TYPE: DNA
<213> ORGANISM: Artificial Sequence
<220> FEATURE:
<223> OTHER INFORMATION: 103600_pHCMV_UL83_pVAX1 (LGS)

<400> SEQUENCE: 84
gactcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
ctatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttatg 720
gattggacct ggatcctgtt tctggtggcc gctgcaacaa gggtccactc tgagagtcgc 780
gggcggagat gccctgaaat gatcagcgtg ctgggcccaa tttccgggca tgtgctgaag 840
gccgtcttct cccgcggaga cacccccgtg ctgcctcacg agacaagact gctgcagact 900
ggcatccatg tgagggtctc ccagccatct ctgattctgg tgtctcagta caccccagat 960
agtacaccct gccacagagg ggacaaccag ctgcaggtgc agcataccta cttcaccgga 1020
tcagaggtcg aaaatgtgag cgtcaacgtg cacaatccca caggcaggag tatctgtcct 1080
tcacaggagc caatgagcat ctacgtgtac gccctgcccc tgaaaatgct gaacatccct 1140
agcattaatg tgcaccatta cccctccgcc gctgaacgaa agcaccggca tctgcctgtg 1200
gcagatgccg tcatccatgc ttcaggcaaa cagatgtggc aggcacgact gaccgtgagc 1260
ggactggcat ggacacgaca gcagaaccag tggaaggagc cagacgtgta ctatactagc 1320
gccttcgtgt tccccaccaa agacgtggcc ctgcgacacg tggtctgcgc acatgagctg 1380
gtgtgctcta tggaaaatac tcgggccacc aagatgcagg tcattggcga tcagtacgtc 1440
aaagtgtatc tggagtcctt ttgtgaagac gtgccctctg ggaagctgtt catgcacgtg 1500
accctgggaa gcgatgtcga ggaagacctg actatgaccc ggaacccaca gccctttatg 1560
agacctcacg agaggaacgg cttcactgtg ctgtgcccaa agaatatgat cattaagccc 1620
gggaaaatct ctcatattat gctggatgtg gcctttacaa gtcacgagca tttcggactg 1680
ctgtgcccca aaagcatccc tgggctgtca attagcggaa acctgctgat gaatggccag 1740
cagatctttc tggaagtgca ggccattcga gagaccgtcg aactgcgaca gtacgaccca 1800
gtggcagccc tgttcttttt cgatatcgac ctgctgctgc agagaggccc tcagtatagt 1860
gagcacccaa cattcacttc acagtacagg attcagggga agctggagta tcggcacact 1920
tgggatagac atgacgaagg agctgcacag ggcgacgatg acgtgtggac ctccggctct 1980
gatagtgacg aggaactggt gaccacagag cgaaaaactc cccgggtgac cggaggagga 2040
gctatggcag gagcatcaac cagcgccgga cgaaagagaa aaagcgccag cagcgccaca 2100
gcatgcactg caggcgtgat gacaaggggg cgcctgaagg cagaatccac agtcgcccct 2160
gaggaagata ctgacgagga ttctgacaac gaaatccaca atccagccgt gttcacctgg 2220
ccaccttggc aggcaggaat tctggctcgc aatctggtcc ctatggtggc cactgtccag 2280
ggacagaacc tgaagtacca ggagtttttc tgggatgcta atgacatcta tcggattttc 2340
gcagagctgg aaggcgtgtg gcagccagca gctcagccaa aaaggcgccg acacagacag 2400
gacgcactgc ctggaccatg tatcgcctcc accccaaaga aacatagggg ctgataactc 2460
gagtctagag ggcccgttta aacccgctga tcagcctcga ctgtgccttc tagttgccag 2520
ccatctgttg tttgcccctc ccccgtgcct tccttgaccc tggaaggtgc cactcccact 2580
gtcctttcct aataaaatga ggaaattgca tcgcattgtc tgagtaggtg tcattctatt 2640
ctggggggtg gggtggggca ggacagcaag ggggaggatt gggaagacaa tagcaggcat 2700
gctggggatg cggtgggctc tatggcttct actgggcggt tttatggaca gcaagcgaac 2760
cggaattgcc agctggggcg ccctctggta aggttgggaa gccctgcaaa gtaaactgga 2820
tggctttctc gccgccaagg atctgatggc gcaggggatc aagctctgat caagagacag 2880
gatgaggatc gtttcgcatg attgaacaag atggattgca cgcaggttct ccggccgctt 2940
gggtggagag gctattcggc tatgactggg cacaacagac aatcggctgc tctgatgccg 3000
ccgtgttccg gctgtcagcg caggggcgcc cggttctttt tgtcaagacc gacctgtccg 3060
gtgccctgaa tgaactgcaa gacgaggcag cgcggctatc gtggctggcc acgacgggcg 3120
ttccttgcgc agctgtgctc gacgttgtca ctgaagcggg aagggactgg ctgctattgg 3180
gcgaagtgcc ggggcaggat ctcctgtcat ctcaccttgc tcctgccgag aaagtatcca 3240
tcatggctga tgcaatgcgg cggctgcata cgcttgatcc ggctacctgc ccattcgacc 3300
accaagcgaa acatcgcatc gagcgagcac gtactcggat ggaagccggt cttgtcgatc 3360
aggatgatct ggacgaagag catcaggggc tcgcgccagc cgaactgttc gccaggctca 3420
aggcgagcat gcccgacggc gaggatctcg tcgtgaccca tggcgatgcc tgcttgccga 3480
atatcatggt ggaaaatggc cgcttttctg gattcatcga ctgtggccgg ctgggtgtgg 3540
cggaccgcta tcaggacata gcgttggcta cccgtgatat tgctgaagag cttggcggcg 3600
aatgggctga ccgcttcctc gtgctttacg gtatcgccgc tcccgattcg cagcgcatcg 3660
ccttctatcg ccttcttgac gagttcttct gaattattaa cgcttacaat ttcctgatgc 3720
ggtattttct ccttacgcat ctgtgcggta tttcacaccg catacaggtg gcacttttcg 3780
gggaaatgtg cgcggaaccc ctatttgttt atttttctaa atacattcaa atatgtatcc 3840
gctcatgaga caataaccct gataaatgct tcaataatag cacgtgctaa aacttcattt 3900
ttaatttaaa aggatctagg tgaagatcct ttttgataat ctcatgacca aaatccctta 3960
acgtgagttt tcgttccact gagcgtcaga ccccgtagaa aagatcaaag gatcttcttg 4020
agatcctttt tttctgcgcg taatctgctg cttgcaaaca aaaaaaccac cgctaccagc 4080
ggtggtttgt ttgccggatc aagagctacc aactcttttt ccgaaggtaa ctggcttcag 4140
cagagcgcag ataccaaata ctgtccttct agtgtagccg tagttaggcc accacttcaa 4200
gaactctgta gcaccgccta catacctcgc tctgctaatc ctgttaccag tggctgctgc 4260
cagtggcgat aagtcgtgtc ttaccgggtt ggactcaaga cgatagttac cggataaggc 4320
gcagcggtcg ggctgaacgg ggggttcgtg cacacagccc agcttggagc gaacgaccta 4380
caccgaactg agatacctac agcgtgagct atgagaaagc gccacgcttc ccgaagggag 4440
aaaggcggac aggtatccgg taagcggcag ggtcggaaca ggagagcgca cgagggagct 4500
tccaggggga aacgcctggt atctttatag tcctgtcggg tttcgccacc tctgacttga 4560
gcgtcgattt ttgtgatgct cgtcaggggg gcggagccta tggaaaaacg ccagcaacgc 4620
ggccttttta cggttcctgg gcttttgctg gccttttgct cacatgttct t 4671

<210> SEQ ID NO 85
<211> LENGTH: 904
<212> TYPE: PRT
<213> ORGANISM: Artificial Sequence
<220> FEATURE:
<223> OTHER INFORMATION: pHSV1-gB Amino Acid Sequence

<400> SEQUENCE: 85

Met Arg Gln Gly Ala Pro Ala Arg Gly Arg Arg Trp Phe Val Val Trp
1 5 10 15

Ala Leu Leu Gly Leu Thr Leu Gly Val Leu Val Ala Ser Ala Ala Pro
20 25 30

Ser Ser Pro Gly Thr Pro Gly Val Ala Ala Ala Thr Gln Ala Ala Asn
35 40 45

Gly Gly Pro Ala Thr Pro Ala Pro Pro Ala Pro Gly Pro Ala Pro Thr
50 55 60

Gly Asp Thr Lys Pro Lys Lys Asn Lys Lys Pro Lys Pro Pro Pro Pro
65 70 75 80

Pro Arg Pro Ala Gly Asp Asn Ala Thr Val Ala Ala Gly His Ala Thr
85 90 95

Leu Arg Glu His Leu Arg Asp Ile Lys Ala Glu Asn Thr Asp Ala Asn
100 105 110

Phe Tyr Val Cys Pro Pro Pro Thr Gly Ala Thr Val Val Gln Phe Glu
115 120 125

Gln Pro Arg Arg Cys Pro Thr Arg Pro Glu Gly Gln Asn Tyr Thr Glu
130 135 140

Gly Ile Ala Val Val Phe Lys Glu Asn Ile Ala Pro Tyr Lys Phe Lys
145 150 155 160

Ala Thr Met Tyr Tyr Lys Asp Val Thr Val Ser Gln Val Trp Phe Gly
165 170 175

His Arg Tyr Ser Gln Phe Met Gly Ile Phe Glu Asp Arg Ala Pro Val
180 185 190

Pro Phe Glu Glu Val Ile Asp Lys Ile Asn Ala Lys Gly Val Cys Arg
195 200 205

Ser Thr Ala Lys Tyr Val Arg Asn Asn Leu Glu Thr Thr Ala Phe His
210 215 220

Arg Asp Asp His Glu Thr Asp Met Glu Leu Lys Pro Ala Asn Ala Ala
225 230 235 240

Thr Arg Thr Ser Arg Gly Trp His Thr Thr Asp Leu Lys Tyr Asn Pro
245 250 255

Ser Arg Val Glu Ala Phe His Arg Tyr Gly Thr Thr Val Asn Cys Ile
260 265 270

Val Glu Glu Val Asp Ala Arg Ser Val Tyr Pro Tyr Asp Glu Phe Val
275 280 285

Leu Ala Thr Gly Asp Phe Val Tyr Met Ser Pro Phe Tyr Gly Tyr Arg
290 295 300

Glu Gly Ser His Thr Glu His Thr Ser Tyr Ala Ala Asp Arg Phe Lys
305 310 315 320

```
Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Leu Ala Asn Gly Gly Phe
        435                 440                 445

Leu Ile Ala Tyr Gln Pro Leu Leu Ser Asn Thr Leu Ala Glu Leu Tyr
    450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
    530                 535                 540

Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735
```

```
Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900


<210> SEQ ID NO 86
<211> LENGTH: 2715
<212> TYPE: DNA
<213> ORGANISM: Artificial Sequence
<220> FEATURE:
<223> OTHER INFORMATION: pHSV1-gB nucleic acid sequence

<400> SEQUENCE: 86

atgcgacagg gcgcacctgc tcggggaaga agatggttcg tggtctgggc actgctgggg     60

ctgacactgg gagtcctggt ggcctcagca gctcccagct cccctggaac tccaggagtg    120

gcagcagcta cccaggcagc aaacggcgga ccagctaccc ctgcaccccc tgcacctgga    180

ccagcaccaa ctggcgatac caaaccaaag aaaaacaaga aaccaaagcc accccctcca    240

cccaggccag caggagacaa tgctacagtg gctgcaggcc acgccactct gagagagcat    300

ctgagggaca tcaaggcaga aaacacagat gccaatttct acgtgtgccc tccacccaca    360

ggagcaactg tggtccagtt tgagcagcca cggagatgtc caacacgacc agagggccag    420

aactacactg aagggatcgc tgtggtcttc aaagaaaata ttgcccctta taagttcaag    480

gctaccatgt actataagga cgtgacagtc tcccaagtgt ggttcgggca caggtactct    540

cagttcatgg gaatttttga ggatcgcgcc cctgtgccat ttgaggaagt catcgacaaa    600

attaacgcta agggcgtctg ccgcagcacc gcaaagtatg tgcgaaacaa tctggagacc    660

acagctttcc accgggacga tcatgagaca gatatggaac tgaaaccagc aaatgccgct    720

acaaggacta gtcgcggctg gcacactacc gacctgaagt acaacccctc acgagtcgag    780

gccttccatc ggtatgggac aactgtgaat tgtatcgtgg aggaagtcga cgccagatcc    840

gtgtacccct atgatgaatt tgtcctggct accggagact tcgtgtacat gtctcctttt    900

tacggatata gggagggctc tcacaccgaa catacaagtt acgcagccga tcgcttcaaa    960

caggtggacg gcttttatgc ccgggatctg accacaaagg caagagccac tgctccaact   1020

accaggaatc tgctgacaac tcccaagttc accgtggctt gggattgggt ccctaaacgg   1080
```

ccaagcgtct gcaccatgac aaagtggcag gaagtggatg aaatgctgcg cagtgagtac 1140
ggaggctcat tccgattttc tagtgacgcc atcagcacca ccttcaccac caacctgacc 1200
gaatatcctc tgtccagagt ggacctgggg gattgtattg gaaaagacgc tagggatgca 1260
atggaccgca tcttcgctag gcgctacaat gcaacacaca ttaaggtcgg ccagcctcag 1320
tactatctgg caaacggggg atttctgatc gcctaccagc cactgctgtc aaatactctg 1380
gccgagctgt atgtgcgcga gcatctgcga gaacagagcc ggaaacctcc aaacccaaca 1440
ccccctccac ccggagcatc tgccaatgct agtgtggagc ggatcaagac aacttcaagc 1500
attgaattcg ccagactgca gtttacctat aaccacatcc agcggcatgt caatgacatg 1560
ctgggaagag tggcaattgc ctggtgcgag ctgcagaacc acgaactgac actgtggaat 1620
gaggcccgga agctgaaccc aaatgctatc gcatcagcca ctgtgggccg acgggtcagc 1680
gccagaatgc tgggggatgt gatggctgtc tctacctgcg tgcccgtcgc tgcagacaac 1740
gtgatcgtcc agaatagtat gagaatttcc tctaggcccg ggcctgtta cagcagacct 1800 ctggtgtcct tcaggtacga ggatcaggga cctctggtgg aaggccagct gggggagaac 1860
aatgaactgc gactgacccg ggacgccatt gagccatgta cagtgggcca cagaaggtac 1920
ttcacttttg gcgggggata cgtgtatttc gaggaatacg catattcaca tcagctgagc 1980
agggccgata tcaccacagt gagcactttc atcgatctga acattaccat gctggaggac 2040
cacgaatttg tgcccctgga ggtctacacc aggcatgaga tcaaggattc cgggctgctg 2100
gactatacag aggtgcagcg ccgaaaccag ctgcacgatc tgcgcttcgc cgacatcgat 2160
accgtgattc atgctgacgc aaatgccgct atgtttgcag ggctgggagc cttctttgag 2220
ggaatggggg acctgggacg agcagtcggg aaggtggtca tgggaatcgt gggcggcgtg 2280
gtgagcgccg tgagcggcgt cagttcattc atgtctaacc cttttggggc cctggctgtg 2340
ggactgctgg tcctggctgg actggcagcc gctttctttg cattccgcta cgtgatgcga 2400
ctgcagagta atcctatgaa agccctgtat ccactgacta ccaaagagct gaagaacccc 2460
accaatcctg atgcaagcgg agagggagag gaaggcggcg actttgatga agccaaactg 2520
gcagaggccc gggaaatgat cagatacatg gctctggtgt ccgcaatgga gcggaccgaa 2580
cacaaggcca agaaaaaggg cacatccgcc ctgctgtctg ctaaagtgac tgacatggtc 2640
atgcggaaga gacggaatac caattacacc caggtcccca ataaggatgg agacgccgat 2700
gaagacgatc tgtga 2715

<210> SEQ ID NO 87
<211> LENGTH: 1068
<212> TYPE: PRT
<213> ORGANISM: Artificial Sequence
<220> FEATURE:
<223> OTHER INFORMATION: pHSV1-gHgL amino acid sequence

<400> SEQUENCE: 87

Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro

-continued

```
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Pro Asn Ala Ser Leu Pro Ala Pro Thr Thr
        115                 120                 125

Val Glu Pro Thr Ala Gln Pro Pro Pro Ser Val Ala Pro Leu Lys Gly
    130                 135                 140

Leu Leu His Asn Pro Ala Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
        195                 200                 205

Leu Asp Ile Thr His Leu His Asn Ala Ser Thr Thr Trp Leu Ala Thr
    210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
            260                 265                 270

Gly Leu Val Ile Ser Met His Asp Ser Pro Pro Val Glu Val Met Val
        275                 280                 285

Val Pro Ala Gly Gln Thr Leu Asp Arg Val Gly Asp Pro Ala Asp Glu
    290                 295                 300

Asn Pro Pro Gly Ala Leu Pro Gly Pro Pro Gly Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Pro Leu Phe Trp Arg Leu Thr Gly
    370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
            420                 425                 430

Ser Val Phe Phe Asn Val Ser Val Leu Asp Pro Thr Ala Arg Leu Gln
        435                 440                 445

Leu Glu Ala Arg Leu Gln His Leu Val Ala Glu Ile Leu Glu Arg Glu
    450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495
```

Ile Asp Ala Leu Tyr Ala Glu Phe Leu Gly Gly Arg Val Leu Thr Thr
500 505 510

Pro Val Val His Arg Ala Leu Phe Tyr Ala Ser Ala Val Leu Arg Gln
515 520 525

Pro Phe Leu Ala Gly Val Pro Ser Ala Val Gln Arg Glu Arg Ala Arg
530 535 540

Arg Ser Leu Leu Ile Ala Ser Ala Leu Cys Thr Ser Asp Val Ala Ala
545 550 555 560

Ala Thr Asn Ala Asp Leu Arg Thr Ala Leu Ala Arg Ala Asp His Gln
565 570 575

Lys Thr Leu Phe Trp Leu Pro Asp His Phe Ser Pro Cys Ala Ala Ser
580 585 590

Leu Arg Phe Asp Leu Asp Glu Ser Val Phe Ile Leu Asp Ala Leu Ala
595 600 605

Gln Ala Thr Arg Ser Glu Thr Pro Val Glu Val Leu Ala Gln Gln Thr
610 615 620

His Gly Leu Ala Ser Thr Leu Thr Arg Trp Ala His Tyr Asn Ala Leu
625 630 635 640

Ile Arg Ala Phe Val Pro Glu Ala Ser His Arg Cys Gly Gly Gln Ser
645 650 655

Ala Asn Val Glu Pro Arg Ile Leu Val Pro Ile Thr His Asn Ala Ser
660 665 670

Tyr Val Val Thr His Ser Pro Leu Pro Arg Gly Ile Gly Tyr Lys Leu
675 680 685

Thr Gly Val Asp Val Arg Arg Pro Leu Phe Leu Thr Tyr Leu Thr Ala
690 695 700

Thr Cys Glu Gly Ser Thr Arg Asp Ile Glu Ser Lys Arg Leu Val Arg
705 710 715 720

Thr Gln Asn Gln Arg Asp Leu Gly Leu Val Gly Ala Val Phe Met Arg
725 730 735

Tyr Thr Pro Ala Gly Glu Val Met Ser Val Leu Leu Val Asp Thr Asp
740 745 750

Asn Thr Gln Gln Gln Ile Ala Ala Gly Pro Thr Glu Gly Ala Pro Ser
755 760 765

Val Phe Ser Ser Asp Val Pro Ser Thr Ala Leu Leu Leu Phe Pro Asn
770 775 780

Gly Thr Val Ile His Leu Leu Ala Phe Asp Thr Gln Pro Val Ala Ala
785 790 795 800

Ile Ala Pro Gly Phe Leu Ala Ala Ser Ala Leu Gly Val Val Met Ile
805 810 815

Thr Ala Ala Leu Ala Gly Ile Leu Lys Val Leu Arg Thr Ser Val Pro
820 825 830

Phe Phe Trp Arg Arg Glu Arg Gly Arg Lys Arg Arg Ser Gly Ile Leu
835 840 845

Gly Trp Val Gly Leu Ile Ala Val Gly Val Leu Cys Val Arg Gly Gly
850 855 860

Leu Pro Ser Thr Glu Tyr Val Ile Arg Ser Arg Val Ala Arg Glu Val
865 870 875 880

Gly Asp Ile Leu Lys Val Pro Cys Val Pro Leu Pro Ser Asp Asp Leu
885 890 895

Asp Trp Arg Tyr Glu Thr Pro Ser Ala Ile Asn Tyr Ala Leu Ile Asp
900 905 910

```
Gly Ile Phe Leu Arg Tyr His Cys Pro Gly Leu Asp Thr Val Leu Trp
        915                 920                 925

Asp Arg His Ala Gln Lys Ala Tyr Trp Val Asn Pro Phe Leu Phe Val
    930                 935                 940

Ala Gly Phe Leu Glu Asp Leu Ser His Pro Ala Phe Pro Ala Asn Thr
945                 950                 955                 960

Gln Glu Thr Glu Thr Arg Leu Ala Leu Tyr Lys Glu Ile Arg Gln Ala
                965                 970                 975

Leu Asp Ser Arg Lys Gln Ala Ala Ser His Thr Pro Val Lys Ala Gly
            980                 985                 990

Cys Val Asn Phe Asp Tyr Ser Arg  Thr Arg Arg Cys Val  Gly Arg Gln
        995                 1000                 1005

Asp Leu  Gly Pro Thr Asn Gly  Thr Ser Gly Arg Thr  Pro Val Leu
    1010                 1015                 1020

Pro Pro  Asp Asp Glu Ala Gly  Leu Gln Pro Lys Pro  Leu Thr Thr
    1025                 1030                 1035

Pro Pro  Pro Ile Ile Ala Thr  Ser Asp Pro Thr Pro  Arg Arg Asp
    1040                 1045                 1050

Ala Ala  Thr Lys Ser Arg Arg  Arg Arg Pro His Ser  Arg Arg Leu
    1055                 1060                 1065


<210> SEQ ID NO 88
<211> LENGTH: 3207
<212> TYPE: DNA
<213> ORGANISM: Artificial Sequence
<220> FEATURE:
<223> OTHER INFORMATION: pHSV1-gHgL nucleic acid sequence

<400> SEQUENCE: 88

atggggaacg ggctgtggtt tgtcggagtg attatcctgg gcgtcgcatg gggacaggtg     60

catgactgga ctgaacagac tgatccttgg ttcctggacg ggctgggaat ggatcgcatg    120

tactggcgag acacaaacac tggcaggctg tggctgccaa ataccccaga tcctcagaag    180

ccccctcgcg ggtttctggc tccacccgac gagctgaacc tgaccacagc cagcctgcca    240

ctgctgcgat ggtatgagga acgattctgc tttgtgctgg tcactaccgc agaattcccc    300

cgggaccctg gacagctgct gtacatccct aagacctatc tgctgggaag acctccaaac    360

gctagtctgc cagcacccac aactgtcgag ccaacagctc agccccctcc atccgtggca    420

ccactgaaag gcctgctgca caatccagca gcttccgtgc tgctgcgatc tcgggcctgg    480

gtcacattct ccgctgtgcc tgacccagag gcactgacct ttccccgggg agataacgtg    540

gcaacagcct ctcacccaag tggccccagg gacacccctc ctccccggcc tcccgtggga    600

gcacggagac atcccaccac agaactggat atcacacacc tgcataatgc cagcactacc    660

tggctggcta ctcggggcct gctgagatcc cctgggaggt acgtgtattt ttctcccagt    720

gcctcaacat ggcctgtggg aatctggaca actggcgagc tggtcctggg gtgtgatgca    780

gccctggtga gagccagata cggacgggag ttcatgggcc tggtcatctc aatgcacgac    840

agcccacccg tggaagtcat ggtggtccct gccgggcaga ccctggatag agtgggagac    900

ccagccgatg aaaaccctcc aggggctctg ccaggacccc ctggcgggcc acgctaccga    960

gtgtttgtcc tgggcagcct gactagggcc gacaacgggt ccgctctgga tgcactgagg   1020

cgcgtgggag gctaccctga ggaaggcacc aattatgccc agttcctgtc tcgcgcttat   1080

gcagagttct ttagtggaga cgcaggagct gaacagggac cacgaccacc cctgttttgg   1140

cggctgaccg gactgctggc aacaagcggc ttcgcctttg tcaacgctgc acacgccaat   1200
```

```
ggggccgtgt gcctgtccga tctgctggga ttcctggcac attctagggc actggcagga   1260
ctggcagctc gcggggcagc aggatgtgct gcagacagcg tgttcttcaa cgtgagcgtg   1320
ctggatccca ccgcaagact gcagctggag gcaaggctgc agcacctggt ggccgaaatc   1380
ctggagaggg aacagagcct ggcactgcat gccctggggt accagctggc tttcgtcctg   1440
gacagccctt ccgcatatga tgctgtggca ccatccgccg ctcacctgat tgacgctctg   1500
tacgcagagt tcctgggcgg ccgagtgctg accacaccag tggtccatag ggccctgttc   1560
tatgcctctg ctgtgctgcg ccagcctttt ctggctggcg tcccaagtgc agtgcagcgg   1620
gaaagagctc gacggagtct gctgatcgca tcagccctgt gcacaagcga cgtggcagcc   1680
gctactaacg ccgatctgcg gaccgctctg gcaagagccg accaccagaa gactctgttc   1740
tggctgcccg atcatttttc cccttgtgca gcctctctgc ggttcgacct ggatgagtca   1800
gtgtttatcc tggacgctct ggcacaggcc acaagaagcg agactcccgt ggaagtcctg   1860
gcacagcaga cacacggact ggcatccacc ctgacacgat gggcccatta caatgctctg   1920
attcgggcat tcgtgcctga ggcttcccac agatgcggcg gacagtctgc caacgtcgaa   1980
ccaaggatcc tggtgcccat tacacacaat gccagctacg tggtcactca tagccccctg   2040
cctcgcggca tcgggtataa gctgaccggg gtggatgtca gaaggcctct gtttctgact   2100
tacctgactg ccacctgtga gggatctacc agagatattg aaagtaaaag actggtgagg   2160
acacagaacc agagggacct gggcctggtg gggccgtct tcatgcgcta tactccagct   2220
ggcgaagtga tgagcgtgct gctggtcgac accgataata cacagcagca gatcgctgca   2280
ggccctaccg aaggggctcc atcagtcttt agctccgacg tgccaagcac tgccctgctg   2340
ctgttcccta acggaaccgt gatccacctg ctggcctttg atacacagcc cgtggccgct   2400
attgcacctg gattcctggc agcaagcgcc ctgggagtgg tcatgatcac cgctgcactg   2460
gccggcattc tgaaggtcct gagaacatcc gtgccattct tttggcgccg agagagggga   2520
cgcaaacgga gatctggaat cctgggatgg gtgggactga ttgcagtggg cgtcctgtgc   2580
gtgaggggag gcctgcccag taccgagtac gtgatccgat cacgggtcgc ccgcgaagtg   2640
ggcgatattc tgaaggtccc ctgcgtgcca ctgcccagtg acgatctgga ctggagatac   2700
gagacccctt cagccatcaa ttatgctctg atcgatggca tttttctgcg gtaccactgc   2760
ccagggctgg acacagtgct gtgggataga catgcccaga aggcttattg ggtcaacccc   2820
ttcctgtttg tggccggctt cctggaggac ctgtctcacc ctgcatttcc agccaatacc   2880
caggagacag aaactcggct ggctctgtac aaagaaattc gccaggcact ggattcacga   2940
aagcaggccg ctagccatac tcctgtcaaa gccgggtgcg tgaacttcga ctattctcgg   3000
acccggcggt gcgtggggag acaggatctg ggaccaacta atggaaccag cggcagaact   3060
cccgtgctgc ctccagacga tgaggctgga ctgcagccta aaccactgac taccctccc   3120
ccaatcattg ccaccagcga ccccacaccc cgacgagatg ctgccaccaa gtcaagacgc   3180
cgacgccccc actcaagacg cctgtga                                        3207
```

<210> SEQ ID NO 89
<211> LENGTH: 911
<212> TYPE: PRT
<213> ORGANISM: Artificial Sequence
<220> FEATURE:
<223> OTHER INFORMATION: pHSV1-gCgD amino acid sequence

<400> SEQUENCE: 89

-continued

```
Met Ala Pro Gly Arg Val Gly Leu Ala Val Val Leu Trp Ser Leu Leu
1               5                   10                  15

Trp Leu Gly Ala Gly Val Ser Gly Gly Ser Glu Thr Ala Ser Thr Gly
            20                  25                  30

Pro Thr Ile Thr Ala Gly Ala Val Thr Asn Ala Ser Glu Ala Pro Thr
        35                  40                  45

Ser Gly Ser Pro Gly Ser Ala Ala Ser Pro Glu Val Thr Pro Thr Ser
    50                  55                  60

Thr Pro Asn Pro Asn Asn Val Thr Gln Asn Lys Thr Thr Pro Thr Glu
65                  70                  75                  80

Pro Ala Ser Pro Pro Thr Thr Pro Lys Pro Thr Ser Thr Pro Lys Ser
                85                  90                  95

Pro Pro Thr Ser Thr Pro Asp Pro Lys Pro Lys Asn Asn Thr Thr Pro
            100                 105                 110

Ala Lys Ser Gly Arg Pro Thr Lys Pro Pro Gly Pro Val Trp Cys Asp
        115                 120                 125

Arg Arg Asp Pro Leu Ala Arg Tyr Gly Ser Arg Val Gln Ile Arg Cys
    130                 135                 140

Arg Phe Arg Asn Ser Thr Arg Met Glu Phe Arg Leu Gln Ile Trp Arg
145                 150                 155                 160

Tyr Ser Met Gly Pro Ser Pro Pro Ile Ala Pro Ala Pro Asp Leu Glu
                165                 170                 175

Glu Val Leu Thr Asn Ile Thr Ala Pro Pro Gly Gly Leu Leu Val Tyr
            180                 185                 190

Asp Ser Ala Pro Asn Leu Thr Asp Pro His Val Leu Trp Ala Glu Gly
        195                 200                 205

Ala Gly Pro Gly Ala Asp Pro Pro Leu Tyr Ser Val Thr Gly Pro Leu
    210                 215                 220

Pro Thr Gln Arg Leu Ile Ile Gly Glu Val Thr Pro Ala Thr Gln Gly
225                 230                 235                 240

Met Tyr Tyr Leu Ala Trp Gly Arg Met Asp Ser Pro His Glu Tyr Gly
                245                 250                 255

Thr Trp Val Arg Val Arg Met Phe Arg Pro Pro Ser Leu Thr Leu Gln
            260                 265                 270

Pro His Ala Val Met Glu Gly Gln Pro Phe Lys Ala Thr Cys Thr Ala
        275                 280                 285

Ala Ala Tyr Tyr Pro Arg Asn Pro Val Glu Phe Val Trp Phe Glu Asp
    290                 295                 300

Asp Arg Gln Val Phe Asn Pro Gly Gln Ile Asp Thr Gln Thr His Glu
305                 310                 315                 320

His Pro Asp Gly Phe Thr Thr Val Ser Thr Val Thr Ser Glu Ala Val
                325                 330                 335

Gly Gly Gln Val Pro Pro Arg Thr Phe Thr Cys Gln Met Thr Trp His
            340                 345                 350

Arg Asp Ser Val Thr Phe Ser Arg Arg Asn Ala Thr Gly Leu Ala Leu
        355                 360                 365

Val Leu Pro Arg Pro Thr Ile Thr Met Glu Phe Gly Val Arg His Val
    370                 375                 380

Val Cys Thr Ala Gly Cys Val Pro Glu Gly Val Thr Phe Ala Trp Phe
385                 390                 395                 400

Leu Gly Asp Asp Pro Ser Pro Ala Ala Lys Ser Ala Val Thr Ala Gln
                405                 410                 415

Glu Ser Cys Asp His Pro Gly Leu Ala Thr Val Arg Ser Thr Leu Pro
```

```
            420                 425                 430

Ile Ser Tyr Asp Tyr Ser Glu Tyr Ile Cys Arg Leu Thr Gly Tyr Pro
        435                 440                 445

Ala Gly Ile Pro Val Leu Glu His His Gly Ser His Gln Pro Pro Pro
    450                 455                 460

Arg Asp Pro Thr Glu Arg Gln Val Ile Glu Ala Ile Glu Trp Val Gly
465                 470                 475                 480

Ile Gly Ile Gly Val Leu Ala Ala Gly Val Leu Val Val Thr Ala Ile
                485                 490                 495

Val Tyr Val Val Arg Thr Ser Gln Ser Arg Gln Arg His Arg Arg Arg
            500                 505                 510

Gly Arg Lys Arg Arg Ser Gly Gly Ala Ala Ala Arg Leu Gly Ala Val
        515                 520                 525

Ile Leu Phe Val Val Ile Val Gly Leu His Gly Val Arg Gly Lys Tyr
    530                 535                 540

Ala Leu Ala Asp Ala Ser Leu Lys Met Ala Asp Pro Asn Arg Phe Arg
545                 550                 555                 560

Gly Lys Asp Leu Pro Val Leu Asp Gln Leu Thr Asp Pro Pro Gly Val
                565                 570                 575

Arg Arg Val Tyr His Ile Gln Ala Gly Leu Pro Asn Pro Phe Gln Pro
            580                 585                 590

Pro Ser Leu Pro Ile Thr Val Tyr Tyr Ala Val Leu Glu Arg Ala Cys
        595                 600                 605

Arg Ser Val Leu Leu Asn Ala Pro Ser Glu Ala Pro Gln Ile Val Arg
    610                 615                 620

Gly Ala Ser Glu Asp Val Arg Lys Gln Pro Tyr Asn Leu Thr Ile Ala
625                 630                 635                 640

Trp Phe Arg Met Gly Gly Asn Cys Ala Ile Pro Ile Thr Val Met Glu
                645                 650                 655

Tyr Thr Glu Cys Ser Tyr Asn Lys Ser Leu Gly Ala Cys Pro Ile Arg
            660                 665                 670

Thr Gln Pro Arg Trp Asn Tyr Tyr Asp Ser Phe Ser Ala Val Ser Glu
        675                 680                 685

Asp Asn Leu Gly Phe Leu Met His Ala Pro Ala Phe Glu Thr Ala Gly
    690                 695                 700

Thr Tyr Leu Arg Leu Val Lys Ile Asn Asp Trp Thr Glu Ile Thr Gln
705                 710                 715                 720

Phe Ile Leu Glu His Arg Ala Lys Gly Ser Cys Lys Tyr Ala Leu Pro
                725                 730                 735

Leu Arg Ile Pro Pro Ser Ala Cys Leu Ser Pro Gln Ala Tyr Gln Gln
            740                 745                 750

Gly Val Thr Val Asp Ser Ile Gly Met Leu Pro Arg Phe Ile Pro Glu
        755                 760                 765

Asn Gln Arg Thr Val Ala Val Tyr Ser Leu Lys Ile Ala Gly Trp His
    770                 775                 780

Gly Pro Lys Ala Pro Tyr Thr Ser Thr Leu Leu Pro Pro Glu Leu Ser
785                 790                 795                 800

Glu Thr Pro Asn Ala Thr Gln Pro Glu Leu Ala Pro Glu Asp Pro Glu
                805                 810                 815

Asp Ser Ala Leu Leu Glu Asp Pro Val Gly Thr Val Ala Pro Gln Ile
            820                 825                 830

Pro Pro Asn Trp His Ile Pro Ser Ile Gln Asp Ala Ala Thr Pro Tyr
        835                 840                 845
```

```
His Pro Pro Ala Thr Pro Asn Asn Met Gly Leu Ile Ala Gly Ala Val
    850                 855                 860

Gly Gly Ser Leu Leu Ala Ala Leu Val Ile Cys Gly Ile Val Tyr Trp
865                 870                 875                 880

Met Arg Arg Arg Thr Arg Lys Ala Pro Lys Arg Ile Arg Leu Pro His
                885                 890                 895

Ile Arg Glu Asp Asp Gln Pro Ser Ser His Gln Pro Leu Phe Tyr
            900                 905                 910


<210> SEQ ID NO 90
<211> LENGTH: 2736
<212> TYPE: DNA
<213> ORGANISM: Artificial Sequence
<220> FEATURE:
<223> OTHER INFORMATION: pHSV1-gCgD nucleic acid sequence

<400> SEQUENCE: 90

atggcacccg ggcgcgtcgg actggctgtc gtgctgtggt cactgctgtg gctgggggct     60

ggcgtgagcg gcggatcaga aactgcaagt accggaccta ctatcaccgc tggcgcagtg    120

accaacgcct cagaggctcc tacaagcgga tccccaggat ccgccgcttc tccagaagtg    180

acacccactt ctacccctaa cccaaacaat gtcactcaga ataagaccac accaaccgag    240

cctgcaagtc cccctactac ccccaagcct acaagtactc caaaatcacc acccaccagc    300

acaccagacc ccaagcctaa aaacaataca actcccgcca agagcgggcg ccctaccaaa    360

cctccaggac cagtgtggtg cgaccggaga gatcccctgg ctcggtacgg atcaagagtg    420

cagatccgat gtcggttcag aaatagcaca aggatggagt ttcgcctgca gatctggcgg    480

tattccatgg gcccttctcc ccctattgcc ccagctcccg atctggagga agtgctgact    540

aacattaccg ctccacccgg cgggctgctg gtgtacgaca gtgcacccaa tctgaccgat    600

cctcacgtcc tgtgggcaga gggagcagga ccaggagcag accctccact gtatagcgtg    660

actggacctc tgccaaccca gcgcctgatc attggagagg tgacaccagc cactcagggc    720

atgtactatc tggcttgggg gcgcatggat agcccccacg aatacggcac atgggtgagg    780

gtccgcatgt tccggccccc ttccctgact ctgcagcctc atgcagtgat ggaggggcag    840

cccttcaagg ccacttgcac cgcagccgct tactatccaa gaaaccccgt ggagttcgtc    900

tggtttgaag acgataggca ggtgttcaat cctggacaga tcgacacaca gactcacgag    960

catccagatg gctttaccac agtgagtacc gtcacatcag aagcagtggg aggccaggtc   1020

ccaccccgaa ctttcacctg tcagatgaca tggcaccggg acagcgtgac tttttccagg   1080

cgcaacgcaa ccggactggc tctggtgctg ccaagaccta caatcactat ggagttcggc   1140

gtcaggcatg tggtctgcac tgccggctgc gtgcctgaag ggtcacctt cgcttggttt    1200

ctgggggacg atccaagtcc cgcagccaaa tcagctgtga ccgcacagga gtcctgcgac   1260

cacccaggac tggccacagt gagatctact ctgcccatct cttacgatta cagtgaatac   1320

atctgtaggc tgactggata tcctgccggc atcccagtgc tggagcacca tgggtcccat   1380

cagcctccac ccagagaccc cacagaaagg caggtcatcg aggccattga atgggtcggg   1440

atcggaattg gcgtgctggc tgcaggcgtc ctggtggtca ccgctatcgt gtacgtggtc   1500

agaacatctc agagtcgaca gcgacaccga cggagaggac gaaagaggcg ctccggggga   1560

gccgctgcac gactgggagc cgtgatcctg ttcgtggtca ttgtgggcct gcatggggtc   1620

aggggaaagt acgcactggc cgacgcttct ctgaaaatgg ccgatcccaa tcggttccgg   1680
```

```
ggcaaagacc tgcctgtgct ggaccagctg accgatcctc caggcgtgcg acgggtctat   1740

cacatccagg caggactgcc taacccattc cagcccccta gcctgcccat tacagtgtac   1800

tatgctgtcc tggagcgcgc atgccgaagc gtgctgctga atgcaccatc cgaggcccct   1860

cagatcgtgc ggggcgccag cgaagatgtc agaaagcagc cttacaacct gaccattgct   1920

tggtttagaa tgggcgggaa ttgtgcaatc ccaattacag tgatggagta cactgaatgc   1980

tcatataaca aaagcctggg agcatgtcca atccgaaccc agccacggtg gaactactat   2040

gacagcttca gcgccgtgag cgaggataat ctggggttcc tgatgcacgc acccgccttt   2100

gaaaccgccg gaacatatct gaggctggtg aagatcaatg actggactga gatcacccag   2160

tttattctgg aacatcgcgc taagggctct tgcaaatacg cactgccact gcgaattcca   2220

ccctccgcct gtctgtctcc tcaggcttat cagcagggag tgaccgtcga ttcaatcggc   2280

atgctgccaa ggttcattcc cgagaaccag cgcacagtgg ccgtctacag cctgaagatc   2340

gctggctggc acgggcctaa agcaccatat acctctacac tgctgcctcc agagctgagt   2400

gaaaccccta acgcaacaca gccagagctg gcaccagagg accctgaaga ttccgcactg   2460

ctggaagacc cagtgggaac cgtcgcccct cagatccctc ccaattggca catcccatct   2520

attcaggatg ccgctacacc ataccatcca cccgccactc ccaacaatat ggggctgatt   2580

gctggagcag tgggaggcag cctgctggcc gccctggtca tctgcggcat tgtctattgg   2640

atgagaaggc gcacccgcaa ggcccccaaa cgaatccgcc tgcctcacat ccgcgaggac   2700

gaccagccat cttcccacca gccactgttc tattga                             2736
```

<210> SEQ ID NO 91
<211> LENGTH: 901
<212> TYPE: PRT
<213> ORGANISM: Artificial Sequence
<220> FEATURE:
<223> OTHER INFORMATION: pHSV2-gB amino acid sequence

<400> SEQUENCE: 91

```
Met Arg Gly Gly Gly Leu Ile Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Gln Pro Pro
        35                  40                  45

Pro Val Pro Ser Pro Ala Thr Thr Lys Ala Arg Lys Arg Lys Thr Lys
    50                  55                  60

Lys Pro Pro Lys Arg Pro Glu Ala Thr Pro Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175
```

```
Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
    210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
    290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
                325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
    370                 375                 380

Thr Thr Phe Thr Thr Asn Leu Thr Glu Tyr Ser Leu Ser Arg Val Asp
385                 390                 395                 400

Leu Gly Asp Cys Ile Gly Arg Asp Ala Arg Glu Ala Ile Asp Arg Met
                405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
        435                 440                 445

Ser Asn Thr Leu Ala Glu Leu Tyr Val Arg Glu Tyr Met Arg Glu Gln
    450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
        515                 520                 525

Glu Leu Thr Leu Trp Asn Glu Ala Arg Lys Leu Asn Pro Asn Ala Ile
    530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
```

```
        595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
        675                 680                 685

Lys Asp Ser Gly Leu Leu Asp Tyr Thr Glu Val Gln Arg Arg Asn Gln
    690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met
                725                 730                 735

Gly Asp Leu Gly Arg Ala Val Gly Lys Val Val Met Gly Val Val Gly
            740                 745                 750

Gly Val Val Ser Ala Val Ser Gly Val Ser Ser Phe Met Ser Asn Pro
        755                 760                 765

Phe Gly Ala Leu Ala Val Gly Leu Leu Val Leu Ala Gly Leu Val Ala
    770                 775                 780

Ala Phe Phe Ala Phe Arg Tyr Val Leu Gln Leu Gln Arg Asn Pro Met
785                 790                 795                 800

Lys Ala Leu Tyr Pro Leu Thr Thr Lys Glu Leu Lys Thr Ser Asp Pro
                805                 810                 815

Gly Gly Val Gly Gly Glu Gly Glu Glu Gly Ala Glu Gly Gly Gly Phe
            820                 825                 830

Asp Glu Ala Lys Leu Ala Glu Ala Arg Glu Met Ile Arg Tyr Met Ala
        835                 840                 845

Leu Val Ser Ala Met Glu Arg Thr Glu His Lys Ala Arg Lys Lys Gly
    850                 855                 860

Thr Ser Ala Leu Leu Ser Ser Lys Val Thr Asn Met Val Leu Arg Lys
865                 870                 875                 880

Arg Asn Lys Ala Arg Tyr Ser Pro Leu His Asn Glu Asp Glu Ala Gly
                885                 890                 895

Asp Glu Asp Glu Leu
            900
```

<210> SEQ ID NO 92
<211> LENGTH: 2706
<212> TYPE: DNA
<213> ORGANISM: Artificial Sequence
<220> FEATURE:
<223> OTHER INFORMATION: pHSV2-gB nucleic acid sequence

<400> SEQUENCE: 92

```
atgagaggcg gaggactgat ctgtgcactg gtcgtcggag cactggtcgc tgctgtcgca      60

tctgctgccc ccgccgcacc ccgggccagc ggcggggtgg cagctaccgt cgcagcaaac     120

ggaggcccag catctcagcc ccctccagtg ccaagtcccg ctaccacaaa ggcacgcaag     180

cgaaaaacca agaaaccccc taaacgacca gaggcaacac caccccctga cgcaaacgct     240

actgtggctg caggacacgc caccctgcga gctcatctga gagagatcaa ggtcgaaaat     300
```

-continued

```
gcagatgccc agttctacgt gtgcccaccc cctacaggag ccactgtggt ccagtttgag    360
cagccccgga gatgtccaac tagacccgag gggcagaact acaccgaagg aatcgccgtg    420
gtcttcaagg aaaacatcgc accttacaag tttaaagcca caatgtacta caaagacgtg    480
actgtctccc aagtgtggtt cggccacaga tactctcagt tcatggggat tttgaggac     540
agggcccctg tgccatttga ggaagtcatc gataagatta atgcaaaagg cgtctgcaga    600
agcacagcca agtatgtgag gaacaatatg gaaactaccg ccttccacag ggacgatcat    660
gagactgaca tggaactgaa gccagctaaa gtggcaacca ggacaagccg cggatggcac    720
acaactgatc tgaaatacaa cccctcccgg gtggaggcct tccatagata tggcaccaca    780
gtgaattgta tcgtggagga agtcgatgcc cgctccgtgt acccctatga cgaatttgtc    840
ctggctaccg gcgatttcgt gtacatgtct cctttttacg gatataggga gggcagccac    900
accgaacata catcctacgc cgctgaccgc ttcaagcagg tggatgggtt ttatgcccgc    960
gacctgacta ccaaagcccg ggccaccagc ccaacaactc gaaacctgct gaccacacct   1020
aagttcacag tggcttggga ctgggtccct aagcggccag cagtctgcac tatgaccaaa   1080
tggcaggaag tggacgaaat gctgcgagca gagtacggcg gcagcttccg gttcagcagc   1140
gatgctattt caactacctt tacaactaat ctgaccgagt atagcctgtc cagagtggac   1200
ctgggggatt gtatcggacg agatgcccgg gaagctattg acaggatgtt cgcccgcaag   1260
tacaacgcta ctcacatcaa agtgggccag cctcagtact atctggctac cggcgggttt   1320
ctgattgcat atcagccact gctgtccaat acactggccg agctgtacgt gcgagagtat   1380
atgcgggaac aggacagaaa gccaaggaac gcaaccccag cccctctgcg agaagcaccc   1440
tcagccaatg ctagcgtgga gcggatcaaa accacatcta gtattgaatt cgctagactg   1500
cagtttacct acaaccacat ccagagacat gtcaatgata tgctgggcag gattgcagtg   1560
gcctggtgcg agctgcagaa ccatgaactg actctgtgga atgaggcccg gaagctgaac   1620
cctaatgcta tcgcatcagc caccgtgggc cggcgggtga gcgccagaat gctgggcgac   1680
gtgatggcag tctctacatg cgtgcccgtc gcccctgata acgtgattgt ccagaatagt   1740
atgagagtgt caagcaggcc tggcacctgt tacagtaggc cactggtgtc attccgctat   1800
gaagaccagg gacctctgat cgagggacag ctgggagaga acaatgaact gcgcctgaca   1860
cgagatgccc tggagccatg cactgtgggc caccgacggt atttcatttt tggaggcggg   1920
tacgtgtatt tcgaggaata cgcttattcc catcagctgt ctagggcaga cgtgactacc   1980
gtcagtacct tcatcgacct gaacattaca atgctggagg atcacgaatt tgtgcccctg   2040
gaggtctaca cacgccatga aatcaaggac agcggactgc tggattatac tgaggtgcag   2100
agaaggaacc agctgcacga cctgcgcttc gccgacatcg atacagtgat tcgggctgat   2160
gcaaatgcag ccatgtttgc aggcctgtgc gccttctttg agggaatggg cgatctggga   2220
cgagcagtgg ggaaagtggt catgggggtg gtcggaggcg tggtctctgc tgtgagtgga   2280
gtctcctctt tcatgagcaa cccttttgga gccctggctg tgggactgct ggtcctggca   2340
ggcctggtgg ccgcattctt tgctttcaga tacgtgctgc agctgcagag gaatccaatg   2400
aaggccctgt atcccctgac aactaaggag ctgaaaacct ccgacccagg gggagtgggc   2460
ggggagggag aggaaggggc agagggcggc ggctttgatg aggcaaagct ggcagaggcc   2520
cgcgaaatga tccgatacat ggctctggtg tcagcaatgg agcgaaccga acacaaagcc   2580
cggaagaaag gcaccagcgc cctgctgagt tcaaaagtga ctaacatggt cctgcggaaa   2640
agaaacaaag cccgctattc cccactgcat aatgaggatg aagccggcga tgaggacgaa   2700
```

ctgtga 2706

<210> SEQ ID NO 93
<211> LENGTH: 1068
<212> TYPE: PRT
<213> ORGANISM: Artificial Sequence
<220> FEATURE:
<223> OTHER INFORMATION: pHSV2-gHgL amino acid sequence

<400> SEQUENCE: 93

```
Met Gly Pro Gly Leu Trp Val Val Met Gly Val Leu Val Gly Val Ala
1               5                   10                  15

Gly Gly His Asp Thr Tyr Trp Thr Glu Gln Ile Asp Pro Trp Phe Leu
            20                  25                  30

His Gly Leu Gly Leu Ala Arg Thr Tyr Trp Arg Asp Thr Asn Thr Gly
        35                  40                  45

Arg Leu Trp Leu Pro Asn Thr Pro Asp Ala Ser Asp Pro Gln Arg Gly
    50                  55                  60

Arg Leu Ala Pro Pro Gly Glu Leu Asn Leu Thr Thr Ala Ser Val Pro
65                  70                  75                  80

Met Leu Arg Trp Tyr Ala Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Arg Asn Ala Ser Leu Pro Glu Leu Pro Glu
        115                 120                 125

Ala Gly Pro Thr Ser Arg Pro Pro Ala Glu Val Thr Gln Leu Lys Gly
    130                 135                 140

Leu Ser His Asn Pro Gly Ala Ser Ala Leu Leu Arg Ser Arg Ala Trp
145                 150                 155                 160

Val Thr Phe Ala Ala Ala Pro Asp Arg Glu Gly Leu Thr Phe Pro Arg
                165                 170                 175

Gly Asp Asp Gly Ala Thr Glu Arg His Pro Asp Gly Arg Arg Asn Ala
            180                 185                 190

Pro Pro Pro Gly Pro Pro Ala Gly Thr Pro Arg His Pro Thr Thr Asn
        195                 200                 205

Leu Ser Ile Ala His Leu His Asn Ala Ser Val Thr Trp Leu Ala Ala
    210                 215                 220

Arg Gly Leu Leu Arg Thr Pro Gly Arg Tyr Val Tyr Leu Ser Pro Ser
225                 230                 235                 240

Ala Ser Thr Trp Pro Val Gly Val Trp Thr Thr Gly Gly Leu Ala Phe
                245                 250                 255

Gly Cys Asp Ala Ala Leu Val Arg Ala Arg Tyr Gly Lys Gly Phe Met
            260                 265                 270

Gly Leu Val Ile Ser Met Arg Asp Ser Pro Pro Ala Glu Ile Ile Val
        275                 280                 285

Val Pro Ala Asp Lys Thr Leu Ala Arg Val Gly Asn Pro Thr Asp Glu
    290                 295                 300

Asn Ala Pro Ala Val Leu Pro Gly Pro Pro Ala Gly Pro Arg Tyr Arg
305                 310                 315                 320

Val Phe Val Leu Gly Ala Pro Thr Pro Ala Asp Asn Gly Ser Ala Leu
                325                 330                 335

Asp Ala Leu Arg Arg Val Ala Gly Tyr Pro Glu Glu Ser Thr Asn Tyr
            340                 345                 350
```

```
Ala Gln Tyr Met Ser Arg Ala Tyr Ala Glu Phe Leu Gly Glu Asp Pro
        355                 360                 365

Gly Ser Gly Thr Asp Ala Arg Pro Ser Leu Phe Trp Arg Leu Ala Gly
    370                 375                 380

Leu Leu Ala Ser Ser Gly Phe Ala Phe Val Asn Ala Ala His Ala His
385                 390                 395                 400

Asp Ala Ile Arg Leu Ser Asp Leu Leu Gly Phe Leu Ala His Ser Arg
                405                 410                 415

Val Leu Ala Gly Leu Ala Ala Arg Gly Ala Ala Gly Cys Ala Ala Asp
            420                 425                 430

Ser Val Phe Leu Asn Val Ser Val Leu Asp Pro Ala Ala Arg Leu Arg
        435                 440                 445

Leu Glu Ala Arg Leu Gly His Leu Val Ala Ala Ile Leu Glu Arg Glu
    450                 455                 460

Gln Ser Leu Val Ala His Ala Leu Gly Tyr Gln Leu Ala Phe Val Leu
465                 470                 475                 480

Asp Ser Pro Ala Ala Tyr Gly Ala Val Ala Pro Ser Ala Ala Arg Leu
                485                 490                 495

Ile Asp Ala Leu Tyr Ala Glu Phe Leu Gly Gly Arg Ala Leu Thr Ala
            500                 505                 510

Pro Met Val Arg Arg Ala Leu Phe Tyr Ala Thr Ala Val Leu Arg Ala
        515                 520                 525

Pro Phe Leu Ala Gly Ala Pro Ser Ala Glu Gln Arg Glu Arg Ala Arg
    530                 535                 540

Arg Gly Leu Leu Ile Thr Thr Ala Leu Cys Thr Ser Asp Val Ala Ala
545                 550                 555                 560

Ala Thr His Ala Asp Leu Arg Ala Ala Leu Ala Arg Thr Asp His Gln
                565                 570                 575

Lys Asn Leu Phe Trp Leu Pro Asp His Phe Ser Pro Cys Ala Ala Ser
            580                 585                 590

Leu Arg Phe Asp Leu Ala Glu Gly Gly Phe Ile Leu Asp Ala Leu Ala
        595                 600                 605

Met Ala Thr Arg Ser Asp Ile Pro Ala Asp Val Met Ala Gln Gln Thr
    610                 615                 620

Arg Gly Val Ala Ser Val Leu Thr Arg Trp Ala His Tyr Asn Ala Leu
625                 630                 635                 640

Ile Arg Ala Phe Val Pro Glu Ala Thr His Gln Cys Ser Gly Pro Ser
                645                 650                 655

His Asn Ala Glu Pro Arg Ile Leu Val Pro Ile Thr His Asn Ala Ser
            660                 665                 670

Tyr Val Val Thr His Thr Pro Leu Pro Arg Gly Ile Gly Tyr Lys Leu
        675                 680                 685

Thr Gly Val Asp Val Arg Arg Pro Leu Phe Ile Thr Tyr Leu Thr Ala
    690                 695                 700

Thr Cys Glu Gly His Ala Arg Glu Ile Glu Pro Lys Arg Leu Val Arg
705                 710                 715                 720

Thr Glu Asn Arg Arg Asp Leu Gly Leu Val Gly Ala Val Phe Leu Arg
                725                 730                 735

Tyr Thr Pro Ala Gly Glu Val Met Ser Val Leu Leu Val Asp Thr Asp
            740                 745                 750

Ala Thr Gln Gln Gln Leu Ala Gln Gly Pro Val Ala Gly Thr Pro Asn
        755                 760                 765

Val Phe Ser Ser Asp Val Pro Ser Val Ala Leu Leu Leu Phe Pro Asn
```

```
    770                 775                 780

Gly Thr Val Ile His Leu Leu Ala Phe Asp Thr Leu Pro Ile Ala Thr
785                 790                 795                 800

Ile Ala Pro Gly Phe Leu Ala Ala Ser Ala Leu Gly Val Val Met Ile
                805                 810                 815

Thr Ala Ala Leu Ala Gly Ile Leu Arg Val Val Arg Thr Cys Val Pro
            820                 825                 830

Phe Leu Trp Arg Arg Glu Arg Gly Arg Lys Arg Arg Ser Gly Phe Val
        835                 840                 845

Cys Leu Phe Gly Leu Val Val Met Gly Ala Trp Gly Ala Trp Gly Gly
    850                 855                 860

Ser Gln Ala Thr Glu Tyr Val Leu Arg Ser Val Ile Ala Lys Glu Val
865                 870                 875                 880

Gly Asp Ile Leu Arg Val Pro Cys Met Arg Thr Pro Ala Asp Asp Val
                885                 890                 895

Ser Trp Arg Tyr Glu Ala Pro Ser Val Ile Asp Tyr Ala Arg Ile Asp
            900                 905                 910

Gly Ile Phe Leu Arg Tyr His Cys Pro Gly Leu Asp Thr Phe Leu Trp
        915                 920                 925

Asp Arg His Ala Gln Arg Ala Tyr Leu Val Asn Pro Phe Leu Phe Ala
    930                 935                 940

Ala Gly Phe Leu Glu Asp Leu Ser His Ser Val Phe Pro Ala Asp Thr
945                 950                 955                 960

Gln Glu Thr Thr Thr Arg Arg Ala Leu Tyr Lys Glu Ile Arg Asp Ala
                965                 970                 975

Leu Gly Ser Arg Lys Gln Ala Val Ser His Ala Pro Val Arg Ala Gly
            980                 985                 990

Cys Val Asn Phe Asp Tyr Ser Arg  Thr Arg Arg Cys Val  Gly Arg Arg
        995                 1000                1005

Asp Leu  Arg Pro Ala Asn Thr  Thr Ser Thr Trp Glu  Pro Pro Val
    1010                 1015                 1020

Ser Ser  Asp Asp Glu Ala Ser  Ser Gln Ser Lys Pro  Leu Ala Thr
    1025                 1030                 1035

Gln Pro  Pro Val Leu Ala Leu  Ser Asn Ala Pro Pro  Arg Arg Val
    1040                 1045                 1050

Ser Pro  Thr Arg Gly Arg Arg  Arg His Thr Arg Leu  Arg Arg Asn
    1055                 1060                 1065


<210> SEQ ID NO 94
<211> LENGTH: 3207
<212> TYPE: DNA
<213> ORGANISM: Artificial Sequence
<220> FEATURE:
<223> OTHER INFORMATION: pHSV2-gHgL nucleic acid sequence

<400> SEQUENCE: 94

atggggcctg gactgtgggt cgtgatggga gtgctggtcg gcgtggctgg agggcatgat      60

acatactgga ctgaacagat tgatccttgg tttctgcatg gactgggcct ggccaggaca     120

tactggcgcg acaccaacac aggcaggctg tggctgccca atactcctga cgcatctgat     180

ccacagaggg gccgcctggc tccccctgga gagctgaacc tgaccacagc aagtgtgccc     240

atgctgcgat ggtatgctga gcggttctgc tttgtgctgg tcactaccgc cgaattccca     300

agggatcccg gccagctgct gtacatcccc aagacctatc tgctggggcg acctcgaaac     360

gcctcactgc ctgagctgcc agaagctgga cctaccagcc gcccacccgc agaggtgaca     420
```

-continued

```
cagctgaaag gactgagcca caatccaggc gcctctgctc tgctgagaag tagggcctgg    480
gtgaccttcg ccgctgcacc agaccgagag ggactgacct ttccccgggg cgacgatgga    540
gccacagaaa gacaccctga tgggcggaga aatgcccctc cacccggccc tccagctgga    600
acccccaggc atcctacaac taacctgtca atcgcccacc tgcataatgc tagcgtgact    660
tggctggcag ccagaggcct gctgcgaacc ccaggaagat acgtgtatct gagtccctca    720
gccagcacct ggcctgtggg agtctggacc acaggcgggc tggccttcgg ctgtgacgca    780
gccctggtgc gcgctcgata cgggaagggc ttcatgggcc tggtcattag catgagagat    840
agccctcccg ccgagatcat tgtggtcccc gcagacaaaa ctctggccag ggtggggaac    900
cctaccgatg aaaatgcacc agccgtcctg ccaggaccac ccgcaggacc acggtataga    960
gtgtttgtcc tgggagctcc aactcccgca gacaacggct ccgcactgga tgcactgagg   1020
cgcgtggcag gatacccaga ggaatccacc aattacgctc agtatatgtc tcgggcttat   1080
gcagagttcc tgggagaaga ccctggaagc ggaacagatg cacgaccatc cctgttttgg   1140
agactggcag gactgctggc tagctccgga ttcgcctttg tgaacgctgc acacgctcat   1200
gacgcaatca gactgagtga tctgctgggg ttcctggcac actcacgcgt gctggctgga   1260
ctggcagctc ggggcgcagc aggatgcgct gcagactccg tgtttctgaa cgtgagcgtg   1320
ctggatccag cagctaggct gcgactggag gcaagactgg gacacctggt ggcagccatc   1380
ctggagaggg aacagagcct ggtcgcccat gctctggggt accagctggc cttcgtgctg   1440
gactctcccg ctgcatatgg agcagtcgca cctagtgccg ctcgactgat tgatgccctg   1500
tacgctgaat ttctgggagg ccgggcactg accgcaccta tggtgcgacg ggccctgttc   1560
tatgctacag cagtcctgcg cgctccattt ctggcaggag ctccatccgc agagcagcga   1620
gaacgagcaa gaaggggcct gctgatcact accgccctgt gcacatctga cgtggcagcc   1680
gctactcacg cagatctgag agcagccctg gccaggaccg accaccagaa gaacctgttc   1740
tggctgcctg atcatttttc accatgtgct gcaagcctgc gattcgacct ggcagagggc   1800
ggcttcatcc tggatgcact ggccatggct acacggagtg acattcccgc agatgtgatg   1860
gcccagcaga caagaggagt ggcctcagtc ctgactagat gggctcatta caatgcactg   1920
atccgcgcct tcgtgcctga ggccacacac cagtgcagtg ggccatcaca taacgctgaa   1980
ccccggatcc tggtgcctat tactcacaat gcctcctacg tggtcactca taccccctctg   2040
ccaagaggaa ttggctataa gctgacagga gtggacgtgc ggcggcccct gttcatcact   2100
tacctgacag ctacttgtga gggccacgca agggagattg aaccaaaacg cctggtgcga   2160
accgaaaacc ggagagatct gggactggtg ggcgccgtct ttctgcgcta tacacccgct   2220
ggcgaagtga tgagcgtgct gctggtcgac accgatgcca cacagcagca gctggctcag   2280
ggaccagtgg caggaacccc caacgtcttc tctagtgacg tgccaagcgt ggccctgctg   2340
ctgttcccca atggcacagt gatccacctg ctggcctttg atactctgcc tatcgctacc   2400
attgcaccag ggttcctggc agcttccgcc ctgggagtgg tcatgatcac tgcagccctg   2460
gcaggaattc tgcgagtggt cagaacctgc gtgccctttc tgtggaggcg cgagagagga   2520
aggaagcgac ggtctggctt cgtgtgcctg tttggcctgg tggtcatggg agcatgggga   2580
gcttggggcg ggagccaggc aactgagtac gtcctgcggt ccgtgatcgc taaagaagtg   2640
ggcgacattc tgcgcgtccc ttgcatgcga acaccagccg acgacgtgag ctggagatac   2700
gaggctccca gtgtcatcga ctatgcaaga atcgatggca ttttcctgag gtaccactgt   2760
```

-continued

```
cctgggctgg acacctttct gtgggatagg catgcacagc gcgcctatct ggtgaaccca   2820

ttcctgtttg ctgcaggctt cctggaagac ctgtcccaca gcgtgttccc cgccgataca   2880

caggagacaa ctaccagaag ggcactgtac aaggaaatta gggacgccct gggcagtcgc   2940

aaacaggctg tctcacatgc acccgtgcgc gcaggatgcg tcaacttcga ctatagccgg   3000

actcggcggt gcgtgggacg gagagatctg aggcccgcca atacaacttc cacctgggag   3060

cctccagtgt caagcgacga tgaggccagc agccagtcca aacctctggc aacccagccc   3120

cctgtgctgg ctctgtctaa tgcaccaccc cgaagagtct cacctacaag aggacggcga   3180

cgacataccc gcctgcgacg gaattga                                         3207
```

<210> SEQ ID NO 95
<211> LENGTH: 879
<212> TYPE: PRT
<213> ORGANISM: Artificial Sequence
<220> FEATURE:
<223> OTHER INFORMATION: pHSV2-gCgD amino acid sequence

<400> SEQUENCE: 95

```
Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Phe Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
    210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
        275                 280                 285
```

Glu Asn Pro Asp Gly Phe Ser Thr Val Ser Thr Val Thr Ser Ala Ala
    290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480

Arg Gly Arg Lys Arg Arg Ser Gly Arg Leu Thr Ser Gly Val Gly Thr
                485                 490                 495

Ala Ala Leu Leu Val Val Ala Val Gly Leu Arg Val Val Cys Ala Lys
            500                 505                 510

Tyr Ala Leu Ala Asp Pro Ser Leu Lys Met Ala Asp Pro Asn Arg Phe
        515                 520                 525

Arg Gly Lys Asn Leu Pro Val Leu Asp Gln Leu Thr Asp Pro Pro Gly
    530                 535                 540

Val Lys Arg Val Tyr His Ile Gln Pro Ser Leu Glu Asp Pro Phe Gln
545                 550                 555                 560

Pro Pro Ser Ile Pro Ile Thr Val Tyr Tyr Ala Val Leu Glu Arg Ala
                565                 570                 575

Cys Arg Ser Val Leu Leu His Ala Pro Ser Glu Ala Pro Gln Ile Val
            580                 585                 590

Arg Gly Ala Ser Asp Glu Ala Arg Lys His Thr Tyr Asn Leu Thr Ile
        595                 600                 605

Ala Trp Tyr Arg Met Gly Asp Asn Cys Ala Ile Pro Ile Thr Val Met
    610                 615                 620

Glu Tyr Thr Glu Cys Pro Tyr Asn Lys Ser Leu Gly Val Cys Pro Ile
625                 630                 635                 640

Arg Thr Gln Pro Arg Trp Ser Tyr Tyr Asp Ser Phe Ser Ala Val Ser
                645                 650                 655

Glu Asp Asn Leu Gly Phe Leu Met His Ala Pro Ala Phe Glu Thr Ala
            660                 665                 670

Gly Thr Tyr Leu Arg Leu Val Lys Ile Asn Asp Trp Thr Glu Ile Thr
        675                 680                 685

Gln Phe Ile Leu Glu His Arg Ala Arg Ala Ser Cys Lys Tyr Ala Leu
    690                 695                 700

-continued

```
Pro Leu Arg Ile Pro Pro Ala Ala Cys Leu Thr Ser Lys Ala Tyr Gln
705                 710                 715                 720

Gln Gly Val Thr Val Asp Ser Ile Gly Met Leu Pro Arg Phe Ile Pro
                725                 730                 735

Glu Asn Gln Arg Thr Val Ala Leu Tyr Ser Leu Lys Ile Ala Gly Trp
            740                 745                 750

His Gly Pro Lys Pro Pro Tyr Thr Ser Thr Leu Leu Pro Pro Glu Leu
        755                 760                 765

Ser Asp Thr Thr Asn Ala Thr Gln Pro Glu Leu Val Pro Glu Asp Pro
    770                 775                 780

Glu Asp Ser Ala Leu Leu Glu Asp Pro Ala Gly Thr Val Ser Ser Gln
785                 790                 795                 800

Ile Pro Pro Asn Trp His Ile Pro Ser Ile Gln Asp Val Ala Pro His
                805                 810                 815

His Ala Pro Ala Ala Pro Ser Asn Pro Gly Leu Ile Ile Gly Ala Leu
            820                 825                 830

Ala Gly Ser Thr Leu Ala Val Leu Val Ile Gly Gly Ile Ala Phe Trp
        835                 840                 845

Val Arg Arg Arg Ala Gln Met Ala Pro Lys Arg Leu Arg Leu Pro His
    850                 855                 860

Ile Arg Asp Asp Asp Ala Pro Pro Ser His Gln Pro Leu Phe Tyr
865                 870                 875
```

<210> SEQ ID NO 96
<211> LENGTH: 2640
<212> TYPE: DNA
<213> ORGANISM: Artificial Sequence
<220> FEATURE:
<223> OTHER INFORMATION: pHSV2-gCgD nucleic acid sequence

<400> SEQUENCE: 96

```
atggcactgg gaagggtcgg gctggctgtc gggctgtggg ggctgctgtg ggtcggagtg     60

gtcgtggtcc tggctaatgc aagtccaggc agaacaatca ctgtgggacc caggggcaac    120

gctagtaatg ccgctccaag tgcatcaccc aggaacgcct cagctcctcg caccacacca    180

acccctcccc agcctagaaa ggccactaag agcaaagcat ccaccgccaa accagctcca    240

ccccctaaga ctggaccacc caaaaccagc tccgagcccg tgcgctgcaa ccgacacgac    300

cctctggcac gatacggctc acgggtgcag atccgctgtc gattccctaa tagcaccaga    360

acagagttta ggctgcagat ctggagatat gcaactgcca ccgatgctga aattggcacc    420

gcaccaagtc tggaggaagt gatggtcaac gtgtcagctc ctccaggcgg gcagctggtc    480

tacgacagcg ccccaaatcg cacagatccc catgtgatct gggcagaggg agcaggacca    540

ggagcaagtc ctcggctgta ttcagtggtc ggaccactgg gacggcagag actgatcatt    600

gaggaactga ccctggaaac acaggggatg tactattggg tgtggggacg gactgacaga    660

ccttctgcct acggaacctg ggtcagggtg cgcgtcttca gacccccctag tctgacaatc    720

cacccacatg ccgtgctgga gggacagccc tttaaggcta catgcactgc agccacttac    780

tatcccggaa acagggctga gttcgtctgg tttgaagacg gccggagagt gttcgatcca    840

gcccagattc acacccagac acaggaaaat cccgatggat tttctaccgt cagtactgtg    900

acctccgctg cagtgggagg ccagggccca cccagaacat tcacttgtca gctgacttgg    960

cacagggaca gcgtctcctt ttctaggcgc aatgcatccg ggaccgcctc tgtgctgcct   1020

agaccaacca tcacaatgga gttcaccgga gatcatgccg tgtgcacagc aggctgcgtg   1080
```

-continued

```
cccgaagggg tgaccttcgc ttggtttctg ggcgacgatt ctagtcctgc cgagaaggtg   1140

gctgtcgcat cacagacaag ctgcggccgc cctggaactg caaccattcg aagcacactg   1200

ccagtgtcct acgagcagac tgaatatatc tgtagactgg ccgggtaccc agacggaatt   1260

cccgtgctgg agcaccatgg atcccaccag cctccaccca gggatccaac cgagcgacag   1320

gtcatccgag cagtggaagg agctgggatt ggagtggcag tcctggtggc cgtggtcctg   1380

gctggaacag cagtggtcta cctgactcat gcctcaagcg tgcgctatcg acggctgaga   1440

aggggacgaa aacgccgatc tggccggctg acaagtggag tcggaactgc cgccctgctg   1500

gtcgtggcag tgggactgcg agtggtctgc gcaaagtacg cactggctga cccaagcctg   1560

aaaatggccg atcccaaccg attccggggc aagaatctgc cagtgctgga ccagctgacc   1620

gatcctccag ggtcaaacg cgtgtatcac atccagccta gcctggagga cccatttcag   1680

ccccccttcca tccccattac agtctactat gccgtgctgg aaagggcttg ccgctcagtc   1740

ctgctgcacg ctcctagcga ggcaccacag atcgtgagag gcgccagcga cgaagctagg   1800

aagcatacct acaacctgac aattgcatgg tatcggatgg gggataattg tgccatcccc   1860

attaccgtga tggagtacac agaatgccct tataacaaaa gcctgggcgt gtgcccaatc   1920

cgaacccagc ctagatggtc ttactatgac agtttctcag ccgtgagtga ggataacctg   1980

gggttcctga tgcacgcacc tgcctttgaa actgccggaa cctacctgcg cctggtgaag   2040

atcaatgact ggacagagat cactcagttt attctggaac atagagctag ggcatcctgc   2100

aagtacgctc tgccactgcg gattccaccc gcagcctgtc tgacctccaa agcctatcag   2160

cagggcgtca cagtggattc tatcgggatg ctgccccgct tcattcctga gaaccagcgg   2220

accgtggccc tgtactctct gaagatcgct ggatggcacg gccctaaacc tccatataca   2280

tccactctgc tgccccctga gctgtctgac actaccaatg ccactcagcc agaactggtg   2340

cccgaggacc ctgaagattc cgcactgctg gaggacccag caggaacagt gtcctctcag   2400

attccaccca actggcatat cccttctatt caggatgtgg caccacacca tgccccagct   2460

gcacccagca atcctggcct gatcattggg gccctggctg gatccaccct ggccgtgctg   2520

gtcatcggcg gcattgcatt ttgggtgcgg agaagggccc agatggctcc caagcggctg   2580

cgcctgcccc atattagaga cgacgacgct cctccatccc accagccact gttttactga   2640
```

```
<210> SEQ ID NO 97
<211> LENGTH: 931
<212> TYPE: PRT
<213> ORGANISM: Artificial Sequence
<220> FEATURE:
<223> OTHER INFORMATION: pVZV-gB amino acid sequence

<400> SEQUENCE: 97

Met Ser Pro Cys Gly Tyr Tyr Ser Lys Trp Arg Asn Arg Asp Arg Pro
1               5                   10                  15

Glu Tyr Arg Arg Asn Leu Arg Phe Arg Arg Phe Phe Ser Ser Ile His
            20                  25                  30

Pro Asn Ala Ala Ala Gly Ser Gly Phe Asn Gly Pro Gly Val Phe Ile
        35                  40                  45

Thr Ser Val Thr Gly Val Trp Leu Cys Phe Leu Cys Ile Phe Ser Met
    50                  55                  60

Phe Val Thr Ala Val Val Ser Val Ser Pro Ser Ser Phe Tyr Glu Ser
65                  70                  75                  80

Leu Gln Val Glu Pro Thr Gln Ser Glu Asp Ile Thr Arg Ser Ala His
                85                  90                  95
```

-continued

```
Leu Gly Asp Gly Asp Glu Ile Arg Glu Ala Ile His Lys Ser Gln Asp
            100                 105                 110

Ala Glu Thr Lys Pro Thr Phe Tyr Val Cys Pro Pro Pro Thr Gly Ser
        115                 120                 125

Thr Ile Val Arg Leu Glu Pro Thr Arg Thr Cys Pro Asp Tyr His Leu
    130                 135                 140

Gly Lys Asn Phe Thr Glu Gly Ile Ala Val Val Tyr Lys Glu Asn Ile
145                 150                 155                 160

Ala Ala Tyr Lys Phe Lys Ala Thr Val Tyr Tyr Lys Asp Val Ile Val
                165                 170                 175

Ser Thr Ala Trp Ala Gly Ser Ser Tyr Thr Gln Ile Thr Asn Arg Tyr
            180                 185                 190

Ala Asp Arg Val Pro Ile Pro Val Ser Glu Ile Thr Asp Thr Ile Asp
        195                 200                 205

Lys Phe Gly Lys Cys Ser Ser Lys Ala Thr Tyr Val Arg Asn Asn His
    210                 215                 220

Lys Val Glu Ala Phe Asn Glu Asp Lys Asn Pro Gln Asp Met Pro Leu
225                 230                 235                 240

Ile Ala Ser Lys Tyr Asn Ser Val Gly Ser Lys Ala Trp His Thr Thr
                245                 250                 255

Asn Asp Thr Tyr Met Val Ala Gly Thr Pro Gly Thr Tyr Arg Thr Gly
            260                 265                 270

Thr Ser Val Asn Cys Ile Ile Glu Glu Val Glu Ala Arg Ser Ile Phe
        275                 280                 285

Pro Tyr Asp Ser Phe Gly Leu Ser Thr Gly Asp Ile Ile Tyr Met Ser
    290                 295                 300

Pro Phe Phe Gly Leu Arg Asp Gly Ala Tyr Arg Glu His Ser Asn Tyr
305                 310                 315                 320

Ala Met Asp Arg Phe His Gln Phe Glu Gly Tyr Arg Gln Arg Asp Leu
                325                 330                 335

Asp Thr Arg Ala Leu Leu Glu Pro Ala Ala Arg Asn Phe Leu Val Thr
            340                 345                 350

Pro His Leu Thr Val Gly Trp Asn Trp Lys Pro Lys Arg Thr Glu Val
        355                 360                 365

Cys Ser Leu Val Lys Trp Arg Glu Val Glu Asp Val Val Arg Asp Glu
    370                 375                 380

Tyr Ala His Asn Phe Arg Phe Thr Met Lys Thr Leu Ser Thr Thr Phe
385                 390                 395                 400

Ile Ser Glu Thr Asn Glu Phe Asn Leu Asn Gln Ile His Leu Ser Gln
                405                 410                 415

Cys Val Lys Glu Glu Ala Arg Ala Ile Ile Asn Arg Ile Tyr Thr Thr
            420                 425                 430

Arg Tyr Asn Ser Ser His Val Arg Thr Gly Asp Ile Gln Thr Tyr Leu
        435                 440                 445

Ala Arg Gly Gly Phe Val Val Val Phe Gln Pro Leu Leu Ser Asn Ser
    450                 455                 460

Leu Ala Arg Leu Tyr Leu Gln Glu Leu Val Arg Glu Asn Thr Asn His
465                 470                 475                 480

Ser Pro Gln Lys His Pro Thr Arg Asn Thr Arg Ser Arg Arg Ser Val
                485                 490                 495

Pro Val Glu Leu Arg Ala Asn Arg Thr Ile Thr Thr Thr Ser Ser Val
            500                 505                 510
```

```
Glu Phe Ala Met Leu Gln Phe Thr Tyr Asp His Ile Gln Glu His Val
        515                 520                 525

Asn Glu Met Leu Ala Arg Ile Ser Ser Ser Trp Cys Gln Leu Gln Asn
    530                 535                 540

Arg Glu Arg Ala Leu Trp Ser Gly Leu Phe Pro Ile Asn Pro Ser Ala
545                 550                 555                 560

Leu Ala Ser Thr Ile Leu Asp Gln Arg Val Lys Ala Arg Ile Leu Gly
                565                 570                 575

Asp Val Ile Ser Val Ser Asn Cys Pro Glu Leu Gly Ser Asp Thr Arg
            580                 585                 590

Ile Ile Leu Gln Asn Ser Met Arg Val Ser Gly Ser Thr Thr Arg Cys
        595                 600                 605

Tyr Ser Arg Pro Leu Ile Ser Ile Val Ser Leu Asn Gly Ser Gly Thr
    610                 615                 620

Val Glu Gly Gln Leu Gly Thr Asp Asn Glu Leu Ile Met Ser Arg Asp
625                 630                 635                 640

Leu Leu Glu Pro Cys Val Ala Asn His Lys Arg Tyr Phe Leu Phe Gly
                645                 650                 655

His His Tyr Val Tyr Tyr Glu Asp Tyr Arg Tyr Val Arg Glu Ile Ala
            660                 665                 670

Val His Asp Val Gly Met Ile Ser Thr Tyr Val Asp Leu Asn Leu Thr
        675                 680                 685

Leu Leu Lys Asp Arg Glu Phe Met Pro Leu Gln Val Tyr Thr Arg Asp
    690                 695                 700

Glu Leu Arg Asp Thr Gly Leu Leu Asp Tyr Ser Glu Ile Gln Arg Arg
705                 710                 715                 720

Asn Gln Met His Ser Leu Arg Phe Tyr Asp Ile Asp Lys Val Val Gln
                725                 730                 735

Tyr Asp Ser Gly Thr Ala Ile Met Gln Gly Met Ala Gln Phe Phe Gln
            740                 745                 750

Gly Leu Gly Thr Ala Gly Gln Ala Val Gly His Val Val Leu Gly Ala
        755                 760                 765

Thr Gly Ala Leu Leu Ser Thr Val His Gly Phe Thr Thr Phe Leu Ser
    770                 775                 780

Asn Pro Phe Gly Ala Leu Ala Val Gly Leu Leu Val Leu Ala Gly Leu
785                 790                 795                 800

Val Ala Ala Phe Phe Ala Tyr Arg Tyr Val Leu Lys Leu Lys Thr Ser
                805                 810                 815

Pro Met Lys Ala Leu Tyr Pro Leu Thr Thr Lys Gly Leu Lys Gln Leu
            820                 825                 830

Pro Glu Gly Met Asp Pro Phe Ala Glu Lys Pro Asn Ala Thr Asp Thr
        835                 840                 845

Pro Ile Glu Glu Ile Gly Asp Ser Gln Asn Thr Glu Pro Ser Val Asn
    850                 855                 860

Ser Gly Phe Asp Pro Asp Lys Phe Arg Glu Ala Gln Glu Met Ile Lys
865                 870                 875                 880

Tyr Met Thr Leu Val Ser Ala Ala Glu Arg Gln Glu Ser Lys Ala Arg
                885                 890                 895

Lys Lys Asn Lys Thr Ser Ala Leu Leu Thr Ser Arg Leu Thr Gly Leu
            900                 905                 910

Ala Leu Arg Asn Arg Arg Gly Tyr Ser Arg Val Arg Thr Glu Asn Val
        915                 920                 925

Thr Gly Val
```

930

<210> SEQ ID NO 98
<211> LENGTH: 2817
<212> TYPE: DNA
<213> ORGANISM: Artificial Sequence
<220> FEATURE:
<223> OTHER INFORMATION: pVZV-gB nucleic acid sequence

<400> SEQUENCE: 98
aagcttgcca ccatgtcacc ttgcggatac tactcaaaat ggcggaatcg ggataggccc 60
gaatacaggc ggaatctgcg gtttaggcgg ttcttcagct ccatccaccc taacgccgct 120
gcaggatctg gcttcaatgg gccaggagtg tttatcacta gtgtcaccgg cgtgtggctg 180
tgcttcctgt gtattttctc aatgtttgtc accgctgtgg tcagtgtgtc acccagctcc 240
ttttacgagt ccctgcaggt ggaacctacc cagtctgagg acatcacacg aagtgcacac 300
ctgggcgacg gggatgagat ccgagaagcc attcataagt ctcaggatgc tgagacaaaa 360
cccactttct acgtctgccc ccctccaacc ggcagtacaa ttgtgagact ggaaccaacc 420
aggacatgtc ccgactatca cctgggaaag aacttcaccg aaggcatcgc agtggtctac 480
aaggagaaca tcgccgctta caagtttaaa gccacagtgt actacaagga cgtcatcgtg 540
agcactgcat gggccgggtc tagttacact cagatcacca accgctatgc cgatcgagtc 600
cccattcctg tgagcgagat cactgacacc attgataagt tcggaaaatg ctcaagcaaa 660
gctacctacg tccgcaacaa tcacaaggtg gaggccttca acgaagacaa aaatcctcag 720
gatatgccac tgatcgcatc taagtataac tccgtgggct ctaaagcctg gcataccaca 780
aatgatacat acatggtggc aggcacaccc gggacttatc gcacagggac ttcagtcaac 840
tgtatcattg aggaagtgga ggcccggagc attttcccat acgactcatt tggcctgagc 900
accggggata tcatctacat gagccccttc tttggactgc gcgacggcgc ataccgagag 960
cactccaatt atgccatgga tcggttccat cagtttgaag gatacagaca gagggacctg 1020
gatacacgag ccctgctgga gccagcagca cgaaacttcc tggtcacacc ccacctgact 1080
gtgggctgga attggaagcc taaaagaacc gaggtctgct ccctggtgaa gtggcgggag 1140
gtggaagacg tggtcagaga tgaatatgcc cataacttca ggtttaccat gaaaacactg 1200
agtactacct tcatctcaga gaccaatgag ttcaacctga atcagattca cctgtctcag 1260
tgtgtgaagg aggaagctcg ggcaatcatt aacagaatct acacaactag gtacaattcc 1320
tctcatgtga gaacaggcga cattcagact tacctggcca ggggcgggtt cgtggtcgtg 1380
tttcagcccc tgctgagcaa ctccctggct agactgtatc tgcaggagct ggtgagggaa 1440
aacaccaatc acagccccca gaagcatcct actaggaaca cccgcagtcg gagatcagtc 1500
cctgtggagc tgcgagccaa tcggaccatc accacaacta gttcagtgga attcgctatg 1560
ctgcagttta catacgacca catccaggag catgtgaatg aaatgctggc tagaattagc 1620
tcctcttggt gccagctgca gaaccgcgag cgagcactgt ggagcggcct gttcccaatc 1680
aatccctccg ccctggcttc tacaattctg gaccagcggg tgaaggccag aatcctgggg 1740
gatgtcattt ctgtgagtaa ctgccctgag ctgggaagtg atacccgcat cattctgcag 1800
aattcaatgc gggtgtcagg gagcaccaca aggtgttact cccgcccact gatcagcatt 1860
gtctccctga acggatctgg cacagtggaa ggacagctgg gcactgacaa tgagctgatc 1920
atgagcagag atctgctgga gccatgtgtg gctaaccaca agaggtactt cctgtttgga 1980
caccattatg tctactatga agactacaga tatgtgaggg agatcgccgt ccatgatgtg 2040

```
ggcatgatta gcacctacgt ggacctgaac ctgacactgc tgaaagatcg cgaattcatg   2100

cccctgcagg tgtacacccg ggacgagctg cgagataccg gactgctgga ctatagcgaa   2160

atccagaggc gcaatcagat gcactccctg cggttttacg acatcgataa ggtcgtgcag   2220

tatgatagcg ggactgctat tatgcaggga atggcacagt tctttcaggg actgggaacc   2280

gctggacagg cagtgggaca cgtcgtgctg ggagcaactg gagctctgct gtctaccgtg   2340

catgggttca ctacctttct gagtaaccct ttcggagcac tggcagtcgg actgctggtg   2400

ctggctggac tggtcgctgc attctttgca tacagatatg tgctgaagct gaaaacatcc   2460

cctatgaagg ccctgtaccc actgacaact aagggcctga aacagctgcc tgaagggatg   2520

gacccatttg cagagaaacc caacgccacc gacacaccaa tcgaggaaat tggcgattct   2580

cagaacaccg agccctctgt gaatagtggg ttcgaccctg ataagtttag ggaggcccag   2640

gaaatgatca aatacatgac actggtgtca gcagctgagc gacaggaaag caaggcacgg   2700

aagaagaaca agactagcgc tctgctgacc tccaggctga caggactggc actgcgaaac   2760

cgacgaggat atagccgggt gagaactgag aatgtcaccg gcgtgtgata actcgag      2817
```

<210> SEQ ID NO 99
<211> LENGTH: 1007
<212> TYPE: PRT
<213> ORGANISM: Artificial Sequence
<220> FEATURE:
<223> OTHER INFORMATION: pVZV-gHgL amino acid sequence

<400> SEQUENCE: 99

```
Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220
```

-continued

```
Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Leu Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335

Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
```

```
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Arg Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
                805                 810                 815

Val Gly Phe Gly Ile Ile Gly Trp Met Leu Cys Gly Asn Ser Arg Leu
            820                 825                 830

Arg Glu Tyr Asn Lys Ile Pro Leu Thr Arg Gly Arg Lys Arg Arg Ser
        835                 840                 845

Met Ala Ser His Lys Trp Leu Leu Gln Ile Val Phe Leu Lys Thr Ile
    850                 855                 860

Thr Ile Ala Tyr Cys Leu His Leu Gln Asp Asp Thr Pro Leu Phe Phe
865                 870                 875                 880

Gly Ala Lys Pro Leu Ser Asp Val Ser Leu Ile Ile Thr Glu Pro Cys
                885                 890                 895

Val Ser Ser Val Tyr Glu Ala Trp Asp Tyr Ala Ala Pro Pro Val Ser
            900                 905                 910

Asn Leu Ser Glu Ala Leu Ser Gly Ile Val Val Lys Thr Lys Cys Pro
        915                 920                 925

Val Pro Glu Val Ile Leu Trp Phe Lys Asp Lys Gln Met Ala Tyr Trp
    930                 935                 940

Thr Asn Pro Tyr Val Thr Leu Lys Gly Leu Ala Gln Ser Val Gly Glu
945                 950                 955                 960

Glu His Lys Ser Gly Asp Ile Arg Asp Ala Leu Leu Asp Ala Leu Ser
                965                 970                 975

Gly Val Trp Val Asp Ser Thr Pro Ser Ser Thr Asn Ile Pro Glu Asn
            980                 985                 990

Gly Cys Val Trp Gly Ala Asp Arg  Leu Phe Gln Arg Val  Cys Gln
        995                 1000                1005
```

<210> SEQ ID NO 100
<211> LENGTH: 3045
<212> TYPE: DNA
<213> ORGANISM: Artificial Sequence
<220> FEATURE:
<223> OTHER INFORMATION: pVZV-gHgL nucleic acid sequence

<400> SEQUENCE: 100
aagcttgcca ccatgttcgc actggtcctg gccgtcgtca tcctgcccct gtggacaact      60

```
gctaacaaat cttacgtcac tcctacccct gcaactcggt ctatcggcca catgagtgcc    120
ctgctgaggg aatactcaga tcgcaacatg agcctgaaac tggaggcttt ctatccccacc    180
ggatttgatg aggaactgat taagtctctg cactggggca acgaccggaa gcatgtgttc    240
ctggtcatcg tcaaagtgaa tcctaccaca cacgaagggg acgtcggact ggtcatcttt    300
ccaaaatacc tgctgagccc ctatcacttc aaggcagagc atcgggcccc atttcccgct    360
ggcagattcg ggtttctgag ccatccagtc acccccgacg tgtccttctt tgatagctcc    420
ttcgctccct acctgactac ccagcacctg gtggcattca caacttttcc ccctaaccct    480
ctggtgtggc atctggagag ggcagaaact gcagctaccg ctgagcgacc attcggcgtg    540
agcctgctgc ctgcaaggcc aacagtcccc aagaacacta tcctggaaca caaagctcat    600
tttgcaactt gggatgcact ggcccgccac accttctttt ctgctgaggc aatcattaca    660
aatagtactc tgcgcattca tgtccccctg ttcgggagtg tgtggcctat ccgatactgg    720
gccactggct cagtgctgct gacctctgac agtgggaggg tcgaagtgaa tattggagtg    780
ggctttatgt ctagtctgat cagcctgtca agcggcctgc caatcgagct gattgtggtc    840
ccccacacag tcaagctgaa cgccgtgact tccgatacca catggttcca gctgaatcca    900
ccaggacctg acccaggacc atcttaccga gtgtatctgc tggggcgagg actggacatg    960
aactttagta agcacgcaac cgtggatatc tgcgcctacc ccgaggaatc actggactac   1020
agatatcacc tgagcatggc acatacagag gccctgagga tgactaccaa agccgaccag   1080
cacgatatca acgaggaatc ttactaccat atcgcagcca ggattgctac ctccatcttc   1140
gcactgtctg agatgggccg cacaactgaa tattttctgc tggacgagat cgtcgatgtg   1200
cagtaccagc tgaagttcct gaactatatt ctgatgcgaa tcggagcagg agctcaccca   1260
aatacaattt caggaactag cgacctgatc tttgccgatc cttcacagct gcatgatgaa   1320
ctgagcctgc tgttcggcca ggtcaaaccc gcaaacgtgg actactttat ctcatatgac   1380
gaggcccgag atcagctgaa gaccgcatac gcactgagcc ggggccagga ccacgtgaat   1440
gctctgtccc tggcacggag agtcatcatg tctatctaca aggggctgct ggtgaaacag   1500
aacctgaatg ccacagagcg gcaggccctg ttctttgcta gcatgatcct gctgaacttc   1560
agagagggac tggaaaacag cagccgggtg ctggatggac gaaccacact gctgctgatg   1620
acctctatgt gcacagctgc acacgctact caggccgctc tgaacatcca ggaggggctg   1680
gcatacctga atcctagcaa gcatatgttt acaattccca acgtgtatag tccttgtatg   1740
ggatcactga ggaccgacct gacagaggaa attcacgtga tgaacctgct gagtgccatc   1800
cctacccgcc caggcctgaa tgaggtgctg catacacagc tggacgagag cgaaattttc   1860
gatgcagcct ttaaaacaat gatgatcttc actacctgga ctgccaagga tctgcacatc   1920
ctgcacaccc atgtcccaga agtgtttaca tgccaggacg ctgcagcccg gaatggcgag   1980
tacgtcctga ttctgccagc cgtgcagggg cattcctatg tcatcaccag aaacaagccc   2040
cagaggggcc tggtgtactc tctggctgac gtcgatgtgt acaatcccat cagcgtggtc   2100
tatctgtcca gagatacttg tgtgagcgag cacggggtca ttgaaaccgt ggccctgcct   2160
catccagaca acctgaaaga atgcctgtac tgtgggtccg tgttcctgcg gtatctgaca   2220
actggagcta tcatggatat cattatcatt gacagcaagg atacagagag acagctggct   2280
gcaatgggga actccactat tcctcccttc aaccctgaca tgcacggaga cgatagcaaa   2340
gccgtgctgc tgttcccaaa tgggactgtg gtcaccctgc tgggatttga aaggcgccag   2400
```

```
gccatcagga tgtccgggca gtacctggga gcttctctgg gaggagcctt cctggctgtg   2460

gtcggatttg gcatcattgg atggatgctg tgcggcaact ccagactgag ggagtataat   2520

aagatccccc tgacccgcgg acgaaaacga cggtccatgg cctctcacaa gtggctgctg   2580

cagattgtgt tcctgaaaac catcacaatt gcttactgcc tgcatctgca ggacgatacc   2640

cctctgttct ttggcgcaaa gccactgagt gatgtgtcac tgatcattac agaaccttgt   2700

gtcagttcag tgtacgaggc atgggactat gccgctcccc ctgtgagcaa cctgtccgaa   2760

gccctgtccg gcattgtggt caagaccaaa tgtcccgtcc ctgaagtgat cctgtggttc   2820

aaggataaac agatggccta ctggaccaat ccatatgtga cactgaaagg gctggctcag   2880

agtgtcggag aggaacacaa gtcaggcgac atcagagatg cactgctgga cgccctgtct   2940

ggcgtctggg tggatagtac tcctagctcc accaacattc cagagaatgg atgcgtgtgg   3000

ggagcagacc gactgttcca gagagtgtgt cagtgataac tcgag                  3045
```

```
<210> SEQ ID NO 101
<211> LENGTH: 529
<212> TYPE: PRT
<213> ORGANISM: Artificial Sequence
<220> FEATURE:
<223> OTHER INFORMATION: pVZV-gMgN amino acid sequence

<400> SEQUENCE: 101

Met Gly Thr Gln Lys Lys Gly Pro Arg Ser Glu Lys Val Ser Pro Tyr
1               5                   10                  15

Asp Thr Thr Thr Pro Glu Val Glu Ala Leu Asp His Gln Met Asp Thr
            20                  25                  30

Leu Asn Trp Arg Ile Trp Ile Ile Gln Val Met Met Phe Thr Leu Gly
        35                  40                  45

Ala Val Met Leu Leu Ala Thr Leu Ile Ala Ala Ser Ser Glu Tyr Thr
    50                  55                  60

Gly Ile Pro Cys Phe Tyr Ala Ala Val Val Asp Tyr Glu Leu Phe Asn
65                  70                  75                  80

Ala Thr Leu Asp Gly Gly Val Trp Ser Gly Asn Arg Gly Gly Tyr Ser
                85                  90                  95

Ala Pro Val Leu Phe Leu Glu Pro His Ser Val Val Ala Phe Thr Tyr
            100                 105                 110

Tyr Thr Ala Leu Thr Ala Met Ala Met Ala Val Tyr Thr Leu Ile Thr
        115                 120                 125

Ala Ala Ile Ile His Arg Glu Thr Lys Asn Gln Arg Val Arg Gln Ser
    130                 135                 140

Ser Gly Val Ala Trp Leu Val Val Asp Pro Thr Thr Leu Phe Trp Gly
145                 150                 155                 160

Leu Leu Ser Leu Trp Leu Leu Asn Ala Val Val Leu Leu Leu Ala Tyr
                165                 170                 175

Lys Gln Ile Gly Val Ala Ala Thr Leu Tyr Leu Gly His Phe Ala Thr
            180                 185                 190

Ser Val Ile Phe Thr Thr Tyr Phe Cys Gly Arg Gly Lys Leu Asp Glu
        195                 200                 205

Thr Asn Ile Lys Ala Val Ala Asn Leu Arg Gln Gln Ser Val Phe Leu
    210                 215                 220

Tyr Arg Leu Ala Gly Pro Thr Arg Ala Val Phe Val Asn Leu Met Ala
225                 230                 235                 240

Ala Leu Met Ala Ile Cys Ile Leu Phe Val Ser Leu Met Leu Glu Leu
                245                 250                 255
```

```
Val Val Ala Asn His Leu His Thr Gly Leu Trp Ser Ser Val Ser Val
            260                 265                 270

Ala Met Ser Thr Phe Ser Thr Leu Ser Val Val Tyr Leu Ile Val Ser
        275                 280                 285

Glu Leu Ile Leu Ala His Tyr Ile His Val Leu Ile Gly Pro Ser Leu
    290                 295                 300

Gly Thr Leu Val Ala Cys Ala Thr Leu Gly Thr Ala Ala His Ser Tyr
305                 310                 315                 320

Met Asp Arg Leu Tyr Asp Pro Ile Ser Val Gln Ser Pro Arg Leu Ile
                325                 330                 335

Pro Thr Thr Arg Gly Thr Leu Ala Cys Leu Ala Val Phe Ser Val Val
            340                 345                 350

Met Leu Leu Leu Arg Leu Met Arg Ala Tyr Val Tyr His Arg Gln Lys
        355                 360                 365

Arg Ser Arg Phe Tyr Gly Ala Val Arg Arg Val Pro Glu Arg Val Arg
    370                 375                 380

Gly Tyr Ile Arg Lys Val Lys Pro Ala His Arg Asn Ser Arg Arg Thr
385                 390                 395                 400

Asn Tyr Pro Ser Gln Gly Tyr Gly Tyr Val Tyr Glu Asn Asp Ser Thr
                405                 410                 415

Tyr Glu Thr Asp Arg Glu Asp Glu Leu Leu Tyr Glu Arg Ser Asn Ser
            420                 425                 430

Gly Trp Glu Arg Gly Arg Lys Arg Arg Ser Met Gly Ser Ile Thr Ala
        435                 440                 445

Ser Phe Ile Leu Ile Thr Met Gln Ile Leu Phe Phe Cys Glu Asp Ser
    450                 455                 460

Ser Gly Glu Pro Asn Phe Ala Glu Arg Asn Phe Trp His Ala Ser Cys
465                 470                 475                 480

Ser Ala Arg Gly Val Tyr Ile Asp Gly Ser Met Ile Thr Thr Leu Phe
                485                 490                 495

Phe Tyr Ala Ser Leu Leu Gly Val Cys Val Ala Leu Ile Ser Leu Ala
            500                 505                 510

Tyr His Ala Cys Phe Arg Leu Phe Thr Arg Ser Val Leu Arg Ser Thr
        515                 520                 525

Trp
```

<210> SEQ ID NO 102
<211> LENGTH: 1611
<212> TYPE: DNA
<213> ORGANISM: Artificial Sequence
<220> FEATURE:
<223> OTHER INFORMATION: pVZV-gMgN nucleic acid sequence

<400> SEQUENCE: 102

```
aagcttgcca ccatgggcac acagaagaag ggaccccgga gcgagaaagt ctcaccatac      60

gacacaacaa cccccgaggt ggaggcactg gatcatcaga tggacactct gaactggagg     120

atttggatca ttcaggtcat gatgttcaca ctgggagctg tcatgctgct ggcaactctg     180

atcgccgcta gctccgaata caccggcatt ccctgcttct atgcagccgt ggtcgactac     240

gagctgttta acgctacact ggatggagga gtgtggtccg gaaatcgagg aggatattct     300

gccccagtgc tgttcctgga accccacagc gtggtcgcct tcacctacta taccgccctg     360

acagccatgg ctatggcagt gtacactctg atcaccgctg caatcattca tcgggagacc     420

aagaaccaga gagtgaggca gtctagtgga gtcgcatggc tggtggtcga cccaaccaca     480
```

```
ctgttctggg ggctgctgag cctgtggctg ctgaatgctg tggtcctgct gctggcatat    540

aaacagatcg gagtggccgc tactctgtac ctgggccact ttgccacctc tgtgattttc    600

actacctatt tttgcgggag aggaaagctg gatgaaacaa acatcaaagc cgtggctaat    660

ctgaggcagc agagcgtctt cctgtaccga ctggcaggac caactcgggc tgtgtttgtc    720

aacctgatgg cagccctgat ggccatctgt attctgttcg tgagcctgat gctggaactg    780

gtggtcgcaa atcacctgca taccggcctg tggtcaagcg tgtccgtcgc catgtctacc    840

ttcagcactc tgtcagtggt ctatctgatc gtgagtgagc tgattctggc ccactacatc    900

catgtgctga ttggaccctc actgggaacc ctggtcgcat gcgcaaccct gggaacagct    960

gcacactcct atatggacag actgtacgat cctatcagcg tgcagtcccc cagactgatt   1020

cctacaacta gggggacact ggcttgtctg gcagtgttct ctgtggtcat gctgctgctg   1080

cgactgatgc gggcttacgt gtatcaccgg cagaagcgca gtcgatttta tggagcagtg   1140

cggagagtcc ctgagcgggt gagaggatac atccgcaagg tcaaacctgc ccatcgaaac   1200

agtaggcgca ccaattatcc atcacagggc tacggctatg tgtacgaaaa cgatagcact   1260

tatgagaccg acagagagga tgaactgctg tacgaaagga gtaattcagg gtgggagagg   1320

ggacgcaaac gacggtctat ggggagtatc acagcttcct tcatcctgat tactatgcag   1380

attctgttct tttgcgagga ctcctctgga gaaccaaact tcgccgagcg caatttttgg   1440

cacgcaagct gttccgccag aggcgtgtat atcgatggga gcatgattac cacactgttc   1500

ttttacgcct ccctgctggg agtgtgcgtc gctctgatct ctctggccta ccatgcttgt   1560

ttcagactgt ttaccagatc agtgctgcgc agcacatggt gataactcga g            1611
```

<210> SEQ ID NO 103
<211> LENGTH: 892
<212> TYPE: PRT
<213> ORGANISM: Artificial Sequence
<220> FEATURE:
<223> OTHER INFORMATION: pCeHV1-gB amino acid sequence

<400> SEQUENCE: 103

```
Met Arg Pro Arg Ala Gly Pro Leu Pro Leu Pro Ser Pro Leu Val Pro
1               5                   10                  15

Leu Leu Ala Leu Ala Leu Leu Ala Ala Thr Arg Pro Leu Gly Pro Ala
            20                  25                  30

Ala Ala Thr Pro Val Val Ser Pro Arg Ala Ser Pro Ala Pro Pro Val
        35                  40                  45

Pro Ala Ala Thr Pro Thr Phe Pro Asp Asp Asp Asn Asp Gly Glu Ala
    50                  55                  60

Gly Ala Ala Pro Gly Ala Pro Gly Thr Asn Ala Ser Val Glu Ala Gly
65                  70                  75                  80

His Ala Thr Leu Arg Glu Asn Leu Arg Asp Ile Lys Ala Leu Asp Gly
                85                  90                  95

Asp Ala Thr Phe Tyr Val Cys Pro Pro Pro Thr Gly Ala Thr Val Val
            100                 105                 110

Gln Phe Glu Gln Pro Arg Pro Cys Pro Arg Ala Pro Asp Gly Gln Asn
        115                 120                 125

Tyr Thr Glu Gly Ile Ala Val Ile Phe Lys Glu Asn Ile Ala Pro Tyr
    130                 135                 140

Lys Phe Lys Ala Thr Met Tyr Tyr Lys Asp Val Thr Val Ser Gln Val
145                 150                 155                 160
```

-continued

```
Trp Phe Gly His Arg Tyr Ser Gln Phe Met Gly Ile Phe Glu Asp Arg
                165                 170                 175

Ala Pro Val Pro Phe Glu Glu Val Ile Asp Lys Ile Asn Ala Arg Gly
            180                 185                 190

Val Cys Arg Ser Thr Ala Lys Tyr Val Arg Asn Asn Met Glu Ser Thr
        195                 200                 205

Ala Phe His Arg Asp Asp Asp Glu Ser Asp Met Lys Leu Lys Pro Ala
    210                 215                 220

Lys Ala Ala Thr Arg Thr Ser Arg Gly Trp His Thr Thr Asp Leu Lys
225                 230                 235                 240

Tyr Asn Pro Ser Arg Ile Glu Ala Phe His Arg Tyr Gly Thr Thr Val
                245                 250                 255

Asn Cys Ile Val Glu Glu Val Glu Ala Arg Ser Val Tyr Pro Tyr Asp
            260                 265                 270

Glu Phe Val Leu Ala Thr Gly Asp Phe Val Tyr Met Ser Pro Phe Tyr
        275                 280                 285

Gly Tyr Arg Asp Gly Ala His Ala Glu His Thr Ala Tyr Ala Ala Asp
    290                 295                 300

Arg Phe Arg Gln Val Asp Gly Tyr Tyr Glu Arg Asp Leu Ser Thr Gly
305                 310                 315                 320

Arg Arg Ala Ser Thr Pro Ala Thr Arg Asn Leu Leu Thr Thr Pro Lys
                325                 330                 335

Phe Thr Val Gly Trp Asp Trp Ala Pro Lys Arg Pro Ser Val Cys Thr
            340                 345                 350

Leu Thr Lys Trp Gln Glu Val Asp Glu Met Leu Arg Ala Glu Tyr Gly
        355                 360                 365

Pro Ser Phe Arg Phe Ser Ser Ser Ala Leu Ser Thr Thr Phe Thr Thr
    370                 375                 380

Asn Arg Thr Glu Tyr Ala Leu Ser Arg Val Asp Leu Gly Asp Cys Val
385                 390                 395                 400

Gly Arg Glu Ala Arg Glu Ala Val Asp Arg Ile Phe Leu Arg Arg Tyr
                405                 410                 415

Asn Gly Thr His Val Lys Val Gly Gln Val Gln Tyr Tyr Leu Ala Thr
            420                 425                 430

Gly Gly Phe Leu Ile Ala Tyr Gln Pro Leu Leu Ser Asn Ala Leu Val
        435                 440                 445

Glu Leu Tyr Val Arg Glu Leu Leu Arg Glu Gln Glu Arg Arg Pro Gly
    450                 455                 460

Asp Ala Ala Ala Thr Pro Lys Pro Ser Ala Asp Pro Pro Asp Val Glu
465                 470                 475                 480

Arg Ile Lys Thr Thr Ser Ser Val Glu Phe Ala Arg Leu Gln Phe Thr
                485                 490                 495

Tyr Asp His Ile Gln Arg His Val Asn Asp Met Leu Gly Arg Ile Ala
            500                 505                 510

Ile Ala Trp Cys Glu Leu Gln Asn His Glu Leu Thr Leu Trp Asn Glu
        515                 520                 525

Ala Arg Lys Leu Asn Pro Asn Ala Ile Ala Ser Ala Thr Val Gly Arg
    530                 535                 540

Arg Val Ser Ala Arg Met Leu Gly Asp Val Met Ala Val Ser Thr Cys
545                 550                 555                 560

Val Pro Val Thr Pro Asp Asn Val Ile Met Gln Asn Ser Met Arg Val
                565                 570                 575

Pro Ala Arg Pro Gly Thr Cys Tyr Ser Arg Pro Leu Val Ser Phe Arg
```

```
            580                 585                 590

Tyr Glu Glu Gly Gly Pro Leu Val Glu Gly Gln Leu Gly Glu Asp Asn
        595                 600                 605

Glu Ile Arg Leu Glu Arg Asp Ala Leu Glu Pro Cys Thr Val Gly His
    610                 615                 620

Arg Arg Tyr Phe Thr Phe Gly Ala Gly Tyr Val Tyr Phe Glu Asp Tyr
625                 630                 635                 640

Ala Tyr Ser His Gln Leu Gly Arg Ala Asp Val Thr Thr Val Ser Thr
                645                 650                 655

Phe Ile Asn Leu Asn Leu Thr Met Leu Glu Asp His Glu Phe Val Pro
            660                 665                 670

Leu Glu Val Tyr Thr Arg Gln Glu Ile Lys Asp Ser Gly Leu Leu Asp
        675                 680                 685

Tyr Thr Glu Val Gln Arg Arg Asn Gln Leu His Ala Leu Arg Phe Ala
    690                 695                 700

Asp Ile Asp Thr Val Ile Lys Ala Asp Ala His Ala Ala Leu Phe Ala
705                 710                 715                 720

Gly Leu Tyr Ser Phe Phe Glu Gly Leu Gly Asp Val Gly Arg Ala Val
                725                 730                 735

Gly Lys Val Val Met Gly Ile Val Gly Gly Val Val Ser Ala Val Ser
            740                 745                 750

Gly Val Ser Ser Phe Leu Ser Asn Pro Phe Gly Ala Leu Ala Val Gly
        755                 760                 765

Leu Leu Val Leu Ala Gly Leu Ala Ala Ala Phe Phe Ala Phe Arg Tyr
    770                 775                 780

Val Met Arg Leu Gln Arg Asn Pro Met Lys Ala Leu Tyr Pro Leu Thr
785                 790                 795                 800

Thr Lys Glu Leu Lys Ser Asp Gly Pro Ser Pro Ala Gly Asp Gly Gly
                805                 810                 815

Asp Gly Ala Ser Gly Gly Gly Glu Glu Asp Phe Asp Glu Ala Lys Leu
            820                 825                 830

Ala Gln Ala Arg Glu Met Ile Arg Tyr Met Ala Leu Val Ser Ala Met
        835                 840                 845

Glu Arg Thr Glu His Lys Ala Arg Lys Lys Gly Thr Ser Ala Leu Leu
    850                 855                 860

Ser Ala Lys Val Thr Asn Met Val Met Arg Lys Arg Ala Lys Pro Arg
865                 870                 875                 880

Tyr Ser Pro Leu Gly Asp Thr Asp Glu Glu Glu Leu
                885                 890


<210> SEQ ID NO 104
<211> LENGTH: 2679
<212> TYPE: DNA
<213> ORGANISM: Artificial Sequence
<220> FEATURE:
<223> OTHER INFORMATION: pCeHV1-gB  nucleic acid sequence

<400> SEQUENCE: 104

atgagacctc gcgccggacc cctgcccctg ccttcacccc tggtgcccct gctggccctg      60

gctctgctgg ctgcaacccg acccctgggc cctgccgctg caaccccagt ggtctcaccc     120

agagcaagcc ctgcccctcc cgtgccagca gctacaccta ctttcccaga cgatgacaac     180

gatggagagg caggagcagc accaggagct cctggcacaa acgcatccgt ggaggctggc     240

cacgcaactc tgagggaaaa tctgcgcgac atcaaggccc tggacggaga tgctacattc     300
```

-continued

```
tacgtgtgcc cacccctac aggagcaact gtggtccagt ttgagcagcc tcgaccatgt    360
ccccgggctc cagatggaca gaactacacc gagggcatcg cagtgatttt caaggaaaac   420
atcgcacctt acaagtttaa agccacaatg tactacaaag acgtgactgt ctcccaagtg   480
tggttcggcc accggtactc tcagttcatg gggatttttg aggatagagc ccctgtgcca   540
tttgaggaag tcatcgacaa gattaatgca agaggcgtct gcaggagcac cgccaaatat   600
gtgaggaaca atatggagag cacagctttc catcgcgatg acgatgaatc cgatatgaag   660
ctgaaaccag caaaggctgc aacccgaaca tcacgggggt ggcacaccac agacctgaaa   720
tacaacccca gccgaatcga ggccttccat cggtatggaa ctaccgtgaa ttgtattgtg   780
gaggaagtcg aggcccggag cgtgtaccca tatgatgaat ttgtcctggc tacaggcgac   840
ttcgtgtaca tgtcaccctt ttacggctat cgcgacgggg ctcacgcaga gcatactgcc   900
tatgccgctg acaggttccg ccaggtggat ggatactatg aacgggacct gtctactggc   960
cggagagcaa gtacccctgc cacaagaaac ctgctgacaa ctccaaagtt taccgtggga  1020
tgggattggg ccccaaagag gccctccgtc tgcactctga ccaaatggca ggaagtggac  1080
gaaatgctga gggcagagta cggcccaagt ttccgcttta gctcctctgc cctgtcaacc  1140
acattcacta ccaatcggac cgaatatgcc ctgtctagag tggacctggg agattgcgtg  1200
ggcagagagg ccagggaagc tgtggatcgc atcttcctga ggcgctacaa cgggactcac  1260
gtgaaagtcg gacaggtgca gtactatctg gctaccggcg ggtttctgat tgcataccag  1320
cctctgctgt ctaatgccct ggtggagctg tatgtccgcg aactgctgcg agagcaggaa  1380
cgacggccag gcgacgcagc agctacacca aagcctagtg ctgacccacc cgatgtcgag  1440
aggatcaaaa caactagttc agtggaattc gcccgcctgc agtttaccta tgatcacatt  1500
cagcggcatg tgaacgacat gctggggaga atcgccattg cttggtgcga gctgcagaac  1560
catgaactga ccctgtggaa tgaggccagg aagctgaacc ccaatgcaat cgcctcagct  1620
acagtgggcc ggcgggtgag cgcccgaatg ctgggagatg tgatggcagt ctccacttgc  1680
gtgcctgtca ccccagacaa cgtcattatg cagaattcta tgcgggtgcc cgccagacct  1740
ggcacctgtt acagcagacc cctggtgtcc ttcaggtatg aggaaggcgg ccctctggtg  1800
gagggacagc tgggagagga taacgaaatc cgcctggagc gagacgctct ggaaccctgt  1860
actgtgggcc accgccgata cttcaccttt ggagccggct acgtgtattt tgaggattac  1920
gcctattctc atcagctggg gcgggctgac gtgaccacag tcagtacctt catcaacctg  1980
aatctgacaa tgctggagga tcacgaattt gtgcctctgg aggtctacac acggcaggaa  2040
attaaggaca gcgggctgct ggattatact gaggtgcagc ggagaaatca gctgcacgct  2100
ctgagattcg cagacatcga taccgtgatt aaggcagatg cccatgcagc cctgtttgcc  2160
ggactgtaca gcttctttga aggactggga gacgtgggac gagctgtcgg aaaagtggtc  2220
atgggcatcg tgggcggcgt ggtgagcgcc gtgagcgggg tcagctcctt cctgagcaac  2280
ccttttggcg ctctggcagt gggactgctg gtcctggcag gactggctgc agccttcttt  2340
gccttcagat acgtgatgcg gctgcagaga aatccaatga aggccctgta tcccctgact  2400
accaaggagc tgaaatccga cggaccatct ccagcaggcg acggcgggga tggagctagc  2460
ggaggcgggg aggaagactt tgatgaggct aaactggccc aggctaggga aatgattcgc  2520
tacatggccc tggtgtccgc tatggagcgc acagaacaca aggcccgaaa gaaaggcact  2580
agtgcactgc tgtcagccaa agtgaccaac atggtcatga gaaagagagc caagccacga  2640
tattcaccac tgggcgatac cgacgaagag gaactgtga                         2679
```

<210> SEQ ID NO 105
<211> LENGTH: 1088
<212> TYPE: PRT
<213> ORGANISM: Artificial Sequence
<220> FEATURE:
<223> OTHER INFORMATION: pCeHV1-gHgL amino acid sequence

<400> SEQUENCE: 105

```
Met Ser Ala Arg Arg Arg Asp Arg Ser Thr Gly Met Pro Val Cys Trp
1               5                   10                  15

Ile Leu Ala Gly Leu Ala Ile Ala Ala Gly Ser Ala Ala Val Pro Ala
            20                  25                  30

Pro Met Arg Ala Leu Glu Arg Glu His Tyr Trp Val Ala Gln Ala Asp
        35                  40                  45

Ser Trp Tyr Arg Asp His Pro Arg Met Arg Ala Tyr Trp Arg Asp Gly
    50                  55                  60

Glu Pro Ser Arg Leu Trp Leu Pro Asn Leu Pro Asn Ala Thr Lys Leu
65                  70                  75                  80

Pro Leu Gly Leu Leu Ala Pro Pro Ala Glu Leu Asn Leu Thr Val Ala
                85                  90                  95

Thr Ala Pro Leu Leu Arg Trp Ala Thr Pro Arg Ser Cys Phe Leu Phe
            100                 105                 110

Ile Thr Thr Pro Glu Phe Pro Arg Asn Pro Gly Gln Leu Leu Tyr Val
        115                 120                 125

Asn Lys Thr Ala Leu Leu Gly Leu Pro Ala Asn Ala Ser Leu Pro Ala
    130                 135                 140

Ala Ala Pro Thr Pro Arg Ala Pro Gln Leu Val Ala Gln Leu Arg Gly
145                 150                 155                 160

Phe Leu Gly Asn Pro Ser Ala Ala Ala Leu Leu Arg Ser Arg Ala Trp
                165                 170                 175

Val Thr His Ala Pro Val Trp Asn Pro Arg Ser Leu Val Arg Pro Pro
            180                 185                 190

Val Asp Pro Ser Gly Asp Ile Ala Pro Thr His Ala Pro Arg Pro Pro
        195                 200                 205

Ala Gly Phe Pro Pro Asp Ala Gly Pro Ala Asp Ala Asp Pro Arg Ile
    210                 215                 220

Ser Phe Arg Glu Leu Ser Ala Ala His Leu Asn Asn Ala Ser Gly Thr
225                 230                 235                 240

Trp Leu Val Ala Ala Gly Leu Leu Arg Ala Pro Ser Ala Leu Val Tyr
                245                 250                 255

Arg Ser Pro Ser Ser Ala Thr Trp Pro Leu Ala Ile Trp Ala Thr Gly
            260                 265                 270

Glu Leu Ala Phe Gly Cys Asp Ala Ala Leu Val Arg Ala Arg Tyr Gly
        275                 280                 285

Leu Arg Phe Met Gly Leu Ser Leu Ser Met Arg Asp Ser Ala Pro Ala
    290                 295                 300

Glu Val Leu Val Val Pro Ala Ala Glu Thr Leu Ala Leu Ile Gly Pro
305                 310                 315                 320

Pro Ala Met Asn Glu Pro Leu Val Leu Pro Gly Pro Pro Pro Gly Lys
                325                 330                 335

Arg Tyr Arg Thr Phe Val Ile Gly Ser Val Val Asp Pro Arg Asn Val
            340                 345                 350

Ser Ala Ile Glu Ala Leu Arg Arg Ala Ala Arg Tyr Pro His Glu Asp
        355                 360                 365
```

-continued

Ala Gly His Glu His His Leu Ser Arg Ala Tyr Ala Glu Ile Phe Gly
370 375 380

Glu Gly Pro Ser Val Glu Pro Gly Pro Arg Pro Pro Leu Phe Trp Arg
385 390 395 400

Val Ser Ala Leu Leu Ala Thr Ser Gly Phe Ala Phe Thr Glu Thr Thr
405 410 415

Arg Ala Arg Gly Met Leu Arg Leu Ser Asp Leu Val Asp Phe Leu Ala
420 425 430

His Val Arg Val Ile Ala Asn Leu Ala Leu Arg Gly Ala Ala Gly Cys
435 440 445

Ala Pro Gly Thr Pro Phe Ala Arg Ala Pro Leu Trp Ala Ala Pro Ala
450 455 460

Arg Ala Glu Leu Glu Ser Arg Leu Gly Arg Leu Ala Ala Glu Ala Val
465 470 475 480

Ala Arg Asp Gln Arg Leu Ser Ala Leu Ala Val Ala Tyr Gln Val Ala
485 490 495

Phe Ala Leu Gly Asp Pro Ala Ile Ala Glu Ala Val Ala Pro Ser Ala
500 505 510

Ala His Thr Leu Asp Thr Leu Tyr Ala Glu Phe Leu Arg Gly Arg Gly
515 520 525

Leu Asp Ala Pro Ala Val Arg Arg Ala Leu Phe Tyr Ala Thr Ala Val
530 535 540

Leu Arg Ala Pro Ala Glu Arg Gly Gly Ala Pro Ser Asp Ala Gln Val
545 550 555 560

Thr Arg Gly Arg Arg Ser Leu Leu Leu Ala Ser Ala Met Cys Thr Ser
565 570 575

Asp Val Ala Val Ala Thr His Thr Asp Leu Arg Asp Ala Leu Asp Arg
580 585 590

Ser Asp His Arg Lys Thr Phe Phe Tyr Ala Pro Asp His Phe Ser Pro
595 600 605

Cys Ala Ala Ser Leu Arg Phe Asp Leu Ala Glu Arg Ser Phe Val Met
610 615 620

Asp Thr Leu Ala His Thr Pro Arg Ser Asn Val Ser Val Glu Ala Met
625 630 635 640

Ala Gln Lys Thr Gln Gly Val Ala Ser Ala Leu Thr Arg Trp Ala His
645 650 655

Ala Asn Ala Leu Ile Arg Ala Phe Val Pro Glu Ala Ala Gln Thr Cys
660 665 670

Ala Gly Pro Thr His Asn Ala Glu Pro Leu Val Val Leu Pro Val Thr
675 680 685

Trp Asn Ala Ser Tyr Val Val Thr His Ala Pro Leu Pro Arg Gly Val
690 695 700

Gly Tyr Arg Leu Ala Gly Val Asp Val Arg Arg Pro Leu Phe Leu Thr
705 710 715 720

Tyr Leu Thr Glu Thr Cys Glu Gly Arg Thr Arg Glu Ile Glu Pro Lys
725 730 735

Arg Leu Thr Arg Thr Glu Thr Arg Arg Asp Leu Gly Leu Val Gly Ala
740 745 750

Val Phe Met Arg Tyr Thr Pro Ala Gly Glu Ile Met Ser Ala Leu Val
755 760 765

Val Asp Ser Asp His Thr Gln Gln Gln Leu Ala Gly Gly Pro Leu Ala
770 775 780

-continued

```
Gly Gly Val Asp Val Phe Val Ser Asp Val Pro Ser Thr Ala Leu Leu
785                 790                 795                 800

Leu Phe Pro Asn Gly Thr Val Ile His Leu Leu Ala Phe Asp Thr Leu
                805                 810                 815

Pro Leu Ala Thr Ile Thr Pro Gly Val Leu Ala Ala Ser Val Leu Gly
            820                 825                 830

Val Val Leu Ile Ala Ala Ala Ile Val Gly Leu Ala Arg Val Ala Trp
        835                 840                 845

Thr Cys Val Pro Ser Leu Trp Ser Arg Glu Arg Gly Arg Lys Arg Arg
    850                 855                 860

Ser Phe Leu Arg Ser Val Ser Ala Ala Pro Ser Val Val Ser Pro Ala
865                 870                 875                 880

Ala Ser Pro Ser Pro Ser Pro Pro Val Glu Tyr Val Ile Arg Ser Val
                885                 890                 895

Ala Ala Arg Thr Val Gly Asp Ile Leu Lys Phe Ala Cys Leu Glu Leu
            900                 905                 910

Pro Ala Gly Gly Val Thr Trp Arg Tyr Glu Ala Pro Arg Ser Ile Asp
        915                 920                 925

Tyr Ala Arg Ile Asp Gly Ile Phe Leu Arg Tyr His Cys Pro Gly Leu
    930                 935                 940

Asp Thr Val Val Trp Asp Gly Lys Ala Gln Arg Ala Tyr Trp Val Asn
945                 950                 955                 960

Pro Phe Leu Phe Ala Ala Gly Phe Leu Glu Asp Leu Gly His Ala Leu
                965                 970                 975

Phe Pro Ala Asn Ala Leu Glu Thr Thr Thr Arg Phe Ala Leu Tyr Lys
            980                 985                 990

Glu Val Arg Leu Ala Leu Ala Ser  Arg Ser Asp Ala Ala  Ser Ser Thr
        995                 1000                1005

Pro Val  Pro Pro Gly Cys Val  Asp Ala Glu Tyr Ser  Arg Thr Arg
    1010                1015                1020

Asp Cys  Pro Asp Gly Arg Thr  Pro Gly Ile Trp Asn  Glu Pro Arg
    1025                1030                1035

Ile Arg  Arg Pro Phe Ser Ala  Pro Asn Asp Glu Ala  Ser Pro Gln
    1040                1045                1050

Pro Gln  Ser Leu Ala Pro Ala  Pro Thr Pro Thr Pro  Pro Gly Arg
    1055                1060                1065

Thr His  Glu Pro Ala Arg Lys  Pro Arg Gly Asn Ala  Thr Arg Thr
    1070                1075                1080

Ala Arg  Pro Arg Ala
    1085
```

<210> SEQ ID NO 106
<211> LENGTH: 3267
<212> TYPE: DNA
<213> ORGANISM: Artificial Sequence
<220> FEATURE:
<223> OTHER INFORMATION: pCeHV1-gHgL nucleic acid sequence

<400> SEQUENCE: 106

```
atgtccgcaa gaagacggga ccgaagcact ggaatgcctg tctgttggat cctggctgga     60

ctggctatcg ctgccgggag cgccgcagtg cccgctccta tgcgagcact ggagcgggaa    120

cactactggg tggctcaggc agactcctgg tatcgcgatc atccacgaat gcgagcatac    180

tggagggacg gagagccttc tcgcctgtgg ctgcccaacc tgcctaatgc cacaaagctg    240

ccactgggac tgctggcccc tcccgctgaa ctgaacctga ccgtggcaac agctcccctg    300
```

```
ctgagatggg caacccctcg cagctgcttc ctgtttatca ccacaccaga gtttccccgg    360
aaccctgggc agctgctgta tgtgaacaag accgccctgc tgggactgcc agcaaatgcc    420
agcctgcctg cagctgcacc aacccccaga gcccctcagc tggtcgccca gctgcgagga    480
ttcctgggaa acccatccgc cgctgcactg ctgagatcta gggcctgggt cacacacgct    540
cccgtgtgga atccaagaag cctggtcagg ccacccgtgg acccttccgg cgatatcgca    600
ccaactcatg ctcctcgccc tccagcagga ttccctcccg atgctggacc agctgacgca    660
gatcctcgca tttcctttcg agagctgtct gccgctcacc tgaacaatgc cagcggaacc    720
tggctggtcg ccgcaggact gctgcgagca ccaagcgccc tggtctatcg gtccccaagc    780
tccgccacat ggccactggc tatctgggca actggcgagc tggccttcgg gtgtgacgct    840
gcactggtgc gcgcacgata cggactgcgg ttcatgggcc tgtcactgag catgagggat    900
agcgccccag ctgaggtgct ggtcgtgcca gccgctgaaa cactggcact gattgggcca    960
cccgccatga acgagccact ggtgctgcca ggacctccac ccggcaagcg gtacagaacc   1020
tttgtgatcg gaagtgtggt cgaccccaga aatgtctcag ccattgaagc tctgcggaga   1080
gcagccaggt atcctcacga ggatgccggc catgaacacc atctgtctag agcatacgcc   1140
gagatcttcg gagaaggacc cagtgtggag cctggaccac gacctccact gttttggcgg   1200
gtgtctgcac tgctggccac tagtggattc gcttttaccg aaactaccag ggcccgcggc   1260
atgctgaggc tgagcgacct ggtggatttc ctggcccacg tgagagtcat tgctaacctg   1320
gcactgagag gcgccgcagg atgcgcacca ggaacccccct ttgctcgcgc accactgtgg   1380
gcagctccag cccgggctga gctggaatca cgactgggcc gactggcagc agaggcagtg   1440
gcccgggacc agagactgag cgccctggca gtcgcctatc aggtggcttt cgcactgggc   1500
gatccagcaa tcgctgaggc agtggcacct tccgctgcac acactctgga caccctgtat   1560
gccgaattcc tgcgaggacg aggactggat gctccagcag tgaggcgcgc cctgttttac   1620
gccacagctg tcctgcgagc acctgcagag cggggcgggg caccatctga cgcccaagtg   1680
actagaggcc gacggagtct gctgctggct tcagcaatgt gcaccagcga tgtggccgtc   1740
gctacacata ctgacctgag ggatgccctg gaccggagcg atcacagaaa gaccttcttt   1800
tacgccccctg accatttttc cccatgtgcc gcttctctga gattcgacct ggccgagagg   1860
tcctttgtga tggatacact ggcccacact cccagaagta acgtgtcagt cgaagcaatg   1920
gcccagaaaa cccagggcgt ggcttctgca ctgacaagat gggcccatgc taatgcactg   1980
attagggcct tcgtgcctga ggcagcacag acctgcgctg gaccaacaca caacgccgaa   2040
cccctggtgg tcctgcctgt gacttggaat gcttcctatg tggtcaccca tgcccctctg   2100
cctagaggcg tgggatacag gctggcagga gtggacgtgc ggcggcccct gttcctgacc   2160
tatctgaccg agacatgtga agggagaaca agggagatcg aaccaaaaag gctgactcgc   2220
accgagacac gccgagatct gggcctggtc ggggccgtgt ttatgaggta cacacccgct   2280
ggggaaatta tgtcagccct ggtggtcgac agcgatcaca ctcagcagca gctggccggc   2340
ggacctctgg ccgggggagt ggacgtgttc gtgagcgatg tgccaagcac cgccctgctg   2400
ctgttcccca atggcacagt gatccatctg ctggcttttg acactctgcc tctggccact   2460
attaccccag gggtcctggc tgcatccgtg ctgggagtgg tcctgatcgc cgctgcaatt   2520
gtcggactgg cccgcgtggc ttggacctgc gtgcctagcc tgtggtcccg cgagcgagga   2580
cgaaagcgga gaagtttcct gcggtccgtg tctgccgctc catctgtggt cagtccagca   2640
```

```
gcaagtccat caccaagccc tcccgtcgaa tacgtgatcc gctctgtggc tgcacgaact   2700

gtcggagaca ttctgaaatt cgcttgcctg gagctgccag ccggcggggt gacctggcgg   2760

tacgaagctc ccagaagcat cgactatgcc agaatcgatg gcatttttct gaggtatcac   2820

tgtccaggac tggacaccgt ggtctgggat gggaaggcac agcgcgccta ctgggtgaac   2880

ccattcctgt ttgccgctgg cttcctggag gatctggggc atgccctgtt tcccgccaat   2940

gctctggaga caactacccg gtttgccctg tataaagaag tgcgcctggc actggcctcc   3000

cggtctgacg cagcctctag taccccagtg ccacccggat gcgtcgatgc agagtacagt   3060

agaacaaggg actgtcctga tgggcgcact ccaggaatct ggaacgagcc ccggattagg   3120

cgcccttttct cagctccaaa tgacgaagca agtcctcagc cacagtcact ggctcccgca   3180

cctacaccaa ctcctccagg ccggacccat gaacccgcta ggaaaccaag aggaaatgct   3240

acccgaaccg ccagaccaag agcttga                                        3267
```

<210> SEQ ID NO 107
<211> LENGTH: 867
<212> TYPE: PRT
<213> ORGANISM: Artificial Sequence
<220> FEATURE:
<223> OTHER INFORMATION: pCeHV1-gCgD amino acid sequence

<400> SEQUENCE: 107

```
Met Ala Gly Trp Arg Ala Ala Gly Ser Gly Leu Cys Leu Phe Val Leu
1               5                   10                  15

Met Trp Leu Leu Cys Ala Gly Ala Gly Ala Pro Arg Gly Ala Ala Ser
            20                  25                  30

Thr Pro Ala Gly Arg Pro Gly Ala Ser Arg Pro Gly Gly Val Glu Arg
        35                  40                  45

Ala Asn Arg Thr Ala Ala Pro Ala Arg Gly Arg Gly Ser Ser Asn Gly
    50                  55                  60

Thr Gly Pro Gly Ser Thr Ser Ala Gln Phe Arg Cys Lys Arg Pro Asp
65                  70                  75                  80

Val Ser Ala Leu Tyr Gly Ser Arg Val Val Ile Gly Cys Arg Leu Pro
                85                  90                  95

Arg Pro Thr Ala Asp Phe Arg Leu Gln Ile Trp Arg Val Ala Ala Ala
            100                 105                 110

Ala His Thr Glu Pro Val Glu Pro Gly Ala Val Leu Val Asn Val Thr
        115                 120                 125

Ala Pro Pro Asp Gly Glu Leu Val Tyr Asp Ser Ala Pro Asn Arg Thr
    130                 135                 140

Glu Ala Arg Val Arg Trp Ala Glu Gly Ala Gly Pro Asp Ala Arg Pro
145                 150                 155                 160

Arg Val Tyr Ser Ile Glu Gly Thr Phe Pro Thr Gln Arg Leu Val Ile
                165                 170                 175

Gln Glu Leu Thr Val Ala Arg Gln Gly Leu Tyr Leu Trp Ile Arg Gly
            180                 185                 190

Pro Ala Glu Arg Pro Leu Arg Tyr Gly Thr Trp Thr Arg Val Arg Met
        195                 200                 205

Leu Arg Arg Pro Ser Leu Ser Ile Arg Ala His Thr Val Leu Glu Gly
    210                 215                 220

Glu Pro Phe Gly Ala Thr Cys Val Ala Ala Asn Tyr Tyr Pro Gly Asp
225                 230                 235                 240

Arg Ala Ala Phe Arg Trp Phe Glu Gly Gly Gly Glu Val Val Ala Pro
                245                 250                 255
```

-continued

```
Glu Arg Val Gln Thr Arg Val Asp Ala Gln Arg Asn Gly Phe Ser Ala
            260                 265                 270

Thr Ser Thr Leu Thr Ser Glu Ala Arg Ala Gly Leu Ala Pro Pro Arg
        275                 280                 285

Asn Leu Thr Cys Glu Phe Thr Trp His Arg Asp Ser Val Ser Phe Ser
    290                 295                 300

Arg Arg Asn Ala Thr Gly Ala Pro Thr Val Leu Pro Arg Pro Thr Ile
305                 310                 315                 320

Glu Met Glu Phe Gly Ser Gly Glu Ala Val Cys Thr Ala Ala Cys Val
                325                 330                 335

Pro Glu Gly Val Glu Leu Gln Trp Leu Leu Gly Ala Asp Pro Ala Pro
            340                 345                 350

Ala Glu Asp Ala Ala Ala Ser Gly Gly Pro Cys Pro Gly His Pro Gly
        355                 360                 365

Leu Ala Arg Val Arg Ser Ala Leu Pro Leu Ser Arg Glu His Ser Glu
    370                 375                 380

Tyr Thr Cys Arg Leu Val Gly Tyr Pro Pro Thr Val Pro Val Leu Glu
385                 390                 395                 400

His His Gly Arg His Glu Pro Ala Pro Arg Asp Pro Val Gly Gln Gln
                405                 410                 415

Val Thr Thr Ala Leu Glu Trp Ala Gly Ile Ala Ala Gly Ser Ala Ala
            420                 425                 430

Ala Ile Gly Leu Ala Val Gly Val Gly Val Tyr Val Arg Arg Ala Val
        435                 440                 445

Ala Arg Arg Arg Arg Val Arg Thr Gly Arg Trp Ala Gly Glu Pro Ala
    450                 455                 460

Arg Arg Gly Arg Gly Arg Lys Arg Arg Ser Gly Pro Gly Ile Ala Ala
465                 470                 475                 480

Val Leu Leu Ser Leu Ala Val Ala Leu Ala Arg Val Pro Ala Gly Gly
                485                 490                 495

Gly Glu Tyr Val Pro Val Glu Arg Ser Leu Thr Arg Val Asn Pro Gly
            500                 505                 510

Arg Phe Arg Gly Ala His Leu Ala Pro Leu Glu Gln Lys Thr Asp Pro
        515                 520                 525

Pro Asp Val Arg Arg Val Tyr His Val Gln Pro Phe Val Glu Asn Pro
    530                 535                 540

Phe Gln Thr Pro Ser Val Pro Val Ala Val Tyr Tyr Ala Val Leu Glu
545                 550                 555                 560

Arg Ala Cys Arg Ser Val Leu Leu Trp Ala Pro Thr Glu Ala Val Gln
                565                 570                 575

Val Val Arg Gly Ala Pro Glu Ala Thr Arg Pro Asp Ala Arg Tyr Asn
            580                 585                 590

Leu Thr Val Ala Trp Tyr Arg Thr Ser Asp Asp Cys Ala Ile Pro Ile
        595                 600                 605

Leu Val Met Glu Tyr Ala Glu Cys Pro Tyr Asp Arg Pro Leu Gly Ala
    610                 615                 620

Cys Pro Val Arg Asn Leu Pro Arg Trp Ser Phe Tyr Asp Asn Phe Ser
625                 630                 635                 640

Ala Thr Ser Asp Asp Asp Leu Gly Leu Val Met His Ala Pro Ala Phe
                645                 650                 655

Glu Thr Ala Gly Thr Tyr Val Arg Leu Val Lys Val Asn Gly Trp Val
            660                 665                 670
```

```
Glu Val Thr Gln Phe Ile Phe Glu His Arg Gly Lys Gly Pro Cys Arg
        675                 680                 685

Tyr Thr Leu Pro Leu Arg Ile Leu Pro Ala Ala Cys Leu Arg Gly Pro
    690                 695                 700

Val Phe Glu Gln Gly Val Thr Val Asp Gly Ile Gly Met Leu Pro Arg
705                 710                 715                 720

Phe Ile Pro Glu Asn Gln Arg Ile Val Ala Val Tyr Ser Leu Gln Ala
                725                 730                 735

Ala Gly Trp His Gly Pro Lys Ala Pro Phe Thr Ser Thr Leu Leu Pro
            740                 745                 750

Pro Glu Val Val Glu Thr Ala Asn Ala Thr Arg Pro Glu Leu Ala Pro
        755                 760                 765

Glu Asp Glu Asp Glu Gln Ala Pro Gly Asp Glu Pro Ala Pro Ala Val
    770                 775                 780

Ala Ala Gln Leu Pro Pro Asn Trp His Val Pro Glu Ala Ser Asp Val
785                 790                 795                 800

Thr Ile Gln Gly Pro Ala Pro Ala Pro Ser Gly His Thr Gly Ala Ile
                805                 810                 815

Val Gly Ala Leu Ala Gly Ala Gly Leu Ala Ala Gly Val Val Val Leu
            820                 825                 830

Ala Val Tyr Leu Val Arg Arg Arg Ala Arg Ala Ala Gly Lys His Val
        835                 840                 845

Arg Leu Pro Glu Leu Leu Asp Glu Gly Pro Gly Pro Ala Arg Arg Gly
    850                 855                 860

Ala Pro Tyr
865


<210> SEQ ID NO 108
<211> LENGTH: 2604
<212> TYPE: DNA
<213> ORGANISM: Artificial Sequence
<220> FEATURE:
<223> OTHER INFORMATION: pCeHV1-gCgD nucleic acid sequence

<400> SEQUENCE: 108

atggctggat ggagggctgc cgggagcgga ctgtgcctgt ttgtcctgat gtggctgctg      60

tgcgctggag ctggagcacc ccgaggggca gcttctacac cagctgggcg ccctggagca     120

agtcggccag gcggggtgga gcgagctaac cgaactgcag caccagcacg agggcgagga     180

agctccaatg gcacagggcc tggatctact agtgcccagt tccggtgcaa gagaccagac     240

gtgagcgccc tgtacggatc cagggtggtc atcggatgta ggctgccacg acctaccgca     300

gactttagac tgcagatttg gagggtggct gcagccgctc acactgaacc agtcgagcct     360

ggagccgtcc tggtgaacgt caccgctccc cctgatggag agctggtgta cgactccgca     420

cccaatcgga ctgaagccag agtgaggtgg gcagagggag ctggaccaga tgcacgaccc     480

cgagtgtatt ctatcgaagg caccttccct acacagcggc tggtcatcca ggagctgacc     540

gtcgcacgac agggactgta cctgtggatc agagggcctg ctgagcgacc actgcggtat     600

ggcacttgga cccgggtgag aatgctgcgg agaccttcac tgagcattcg agcacacaca     660

gtgctggagg gagaaccctt cggggctact tgcgtggcag ccaactacta tcctggcgat     720

cgggctgcat tcagatggtt tgagggcggc ggcgaggtgg tcgcaccaga gagggtgcag     780

acccgcgtcg acgcacagag aaatggcttt tcagccacaa gcactctgac ctccgaagct     840

cgggcaggac tggccccacc cagaaacctg acctgtgagt tcacttggca tcgggattcc     900
```

```
gtgtctttta gtaggcgcaa tgcaaccggc gcccctacag tgctgccaag acccacaatc    960

gagatggaat ttggatctgg cgaagccgtg tgcactgccg cttgcgtgcc agaaggagtc   1020

gagctgcagt ggctgctggg agcagatcct gcaccagctg aggacgcagc agctagtgga   1080

ggcccatgcc ctggacaccc tggactggcc agggtgcgct cagctctgcc actgagtagg   1140

gaacattcag agtacacttg tcgcctggtg ggctatcctc caaccgtgcc tgtcctggaa   1200

caccatggac gccacgagcc agcccccaga gacccagtgg gacagcaggt caccacagca   1260

ctggaatggg caggaatcgc agcaggaagc gccgcagcaa ttggactggc agtgggagtc   1320

ggagtgtacg tccgacgggc agtggcaaga aggcgccgag tcagaacagg gaggtgggct   1380

ggagagccag cacggagagg acgaggacga aagaggcgct caggaccagg cattgctgca   1440

gtgctgctga gcctggctgt ggcactggcc cgggtcccag ccgggggagg cgaatacgtg   1500

ccagtcgagc gaagcctgac ccgggtgaac ccaggccggt tccggggcgc ccacctggca   1560

cctctggagc agaaaacaga tccccctgac gtgcggcggg tgtaccatgt ccagcccttc   1620

gtggaaaatc cttttcagac cccatctgtg cccgtcgccg tgtactatgc tgtgctggag   1680

cgagcatgcc gaagtgtcct gctgtgggca ccaaccgaag cagtgcaggt ggtcaggggc   1740

gccccagagg ctacaagacc cgatgctagg tacaacctga ccgtggcatg gtatcgcaca   1800

agcgacgatt gtgccatccc catcctggtc atggaatacg ctgagtgccc ctatgataga   1860

cctctgggag cctgtcctgt gcgcaacctg ccacgatgga gcttctacga caatttttcc   1920

gccacatctg acgatgacct gggcctggtc atgcacgctc ccgcattcga gactgccggg   1980

acctatgtga ggctggtcaa ggtgaacgga tgggtcgaag tgactcagtt catctttgag   2040

catagaggga aaggaccatg caggtacacc ctgccactgc gaattctgcc tgcagcttgt   2100

ctgcgaggac ccgtgttcga acagggagtc accgtggacg gcatcgggat gctgccaagg   2160

tttatccccg agaatcagcg cattgtcgcc gtgtatagcc tgcaggcagc aggatggcac   2220

ggacctaagg cacccttcac ctccactctg ctgccacccg aagtggtcga gactgccaac   2280

gctaccaggc ctgaactggc ccagaggat gaagacgagc aggctccagg ggatgagcct    2340

gcaccagcag tggctgcaca gctgcctcca aattggcacg tgccagaggc ctccgacgtg   2400

accatccagg gaccagctcc tgcaccatct ggacatacag gagcaattgt gggcgccctg   2460

gctggagcag gactggcagc tggggtggtc gtgctggcag tgtacctggt cagaaggcgc   2520

gctcgcgcag caggcaaaca tgtgagactg cctgaactgc tggatgaagg acctggaccc   2580

gctcggagag gagccccata ctga                                          2604
```

```
<210> SEQ ID NO 109
<211> LENGTH: 984
<212> TYPE: PRT
<213> ORGANISM: Artificial Sequence
<220> FEATURE:
<223> OTHER INFORMATION: VZV-gEgI amino acid sequence

<400> SEQUENCE: 109

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60
```

```
Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480
```

-continued

```
Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg Arg
    610                 615                 620

Gly Arg Lys Arg Arg Ser Met Phe Leu Ile Gln Cys Leu Ile Ser Ala
625                 630                 635                 640

Val Ile Phe Tyr Ile Gln Val Thr Asn Ala Leu Ile Phe Lys Gly Asp
                645                 650                 655

His Val Ser Leu Gln Val Asn Ser Ser Leu Thr Ser Ile Leu Ile Pro
            660                 665                 670

Met Gln Asn Asp Asn Tyr Thr Glu Ile Lys Gly Gln Leu Val Phe Ile
        675                 680                 685

Gly Glu Gln Leu Pro Thr Gly Thr Asn Tyr Ser Gly Thr Leu Glu Leu
    690                 695                 700

Leu Tyr Ala Asp Thr Val Ala Phe Cys Phe Arg Ser Val Gln Val Ile
705                 710                 715                 720

Arg Tyr Asp Gly Cys Pro Arg Ile Arg Thr Ser Ala Phe Ile Ser Cys
                725                 730                 735

Arg Tyr Lys His Ser Trp His Tyr Gly Asn Ser Thr Asp Arg Ile Ser
            740                 745                 750

Thr Glu Pro Asp Ala Gly Val Met Leu Lys Ile Thr Lys Pro Gly Ile
        755                 760                 765

Asn Asp Ala Gly Val Tyr Val Leu Leu Val Arg Leu Asp His Ser Arg
    770                 775                 780

Ser Thr Asp Gly Phe Ile Leu Gly Val Asn Val Tyr Thr Ala Gly Ser
785                 790                 795                 800

His His Asn Ile His Gly Val Ile Tyr Thr Ser Pro Ser Leu Gln Asn
                805                 810                 815

Gly Tyr Ser Thr Arg Ala Leu Phe Gln Gln Ala Arg Leu Cys Asp Leu
            820                 825                 830

Pro Ala Thr Pro Lys Gly Ser Gly Thr Ser Leu Phe Gln His Met Leu
        835                 840                 845

Asp Leu Arg Ala Gly Lys Ser Leu Glu Asp Asn Pro Trp Leu His Glu
    850                 855                 860

Asp Val Val Thr Thr Glu Thr Lys Ser Val Val Lys Glu Gly Ile Glu
865                 870                 875                 880

Asn His Val Tyr Pro Thr Asp Met Ser Thr Leu Pro Glu Lys Ser Leu
                885                 890                 895

Asn Asp Pro Pro Glu Asn Leu Leu Ile Ile Ile Pro Ile Val Ala Ser
```

```
            900                 905                 910

Val Met Ile Leu Thr Ala Met Val Ile Val Ile Val Ile Ser Val Lys
        915                 920                 925

Arg Arg Arg Ile Lys Lys His Pro Ile Tyr Arg Pro Asn Thr Lys Thr
    930                 935                 940

Arg Arg Gly Ile Gln Asn Ala Thr Pro Glu Ser Asp Val Met Leu Glu
945                 950                 955                 960

Ala Ala Ile Ala Gln Leu Ala Thr Ile Arg Glu Glu Ser Pro Pro His
                965                 970                 975

Ser Val Val Asn Pro Phe Val Lys
            980


<210> SEQ ID NO 110
<211> LENGTH: 2976
<212> TYPE: DNA
<213> ORGANISM: Artificial Sequence
<220> FEATURE:
<223> OTHER INFORMATION: VZV-gEgI nucleic acid sequence

<400> SEQUENCE: 110

aagcttgcca ccatgggaac tgtcaacaaa cctgtcgtcg gcgtgctgat gggcttcggc     60

attattactg gaacactgag aatcacaaat cctgtccggg cctctgtgct gcggtacgac    120

gatttccaca tcgacgaaga taagctggac accaatagtg tgtatgagcc ctactatcac    180

tcagatcatg ctgaaagctc ctgggtcaac cgcggggagt ctagtcgaaa agcatacgac    240

cacaacagcc cctatatctg gcctagaaat gactacgatg gatttctgga aaacgcccat    300

gagcaccatg gcgtgtataa tcagggaagg ggcattgact ccggagaacg cctgatgcag    360

cccacccaga tgtctgctca ggaggatctg ggagacgata ctggcatcca cgtgattcct    420

accctgaatg gcgacgatag acataagatc gtcaacgtgg atcagaggca gtacggcgac    480

gtgttcaagg gggatctgaa tcctaaacca caggggcaga ggctgattga ggtcagcgtg    540

gaggaaaacc accctttcac cctgcgggcc ccaatccaga gaatctacgg cgtgaggtat    600

actgagacct ggagttttct gccatcactg acatgcactg gggacgcagc tccagctatc    660

cagcacattt gcctgaagca taccacatgt tttcaggacg tggtcgtgga cgtggattgt    720

gctgaaaata caaaagagga tcagctggca gaaatctctt acagattcca gggcaagaaa    780

gaggccgatc agccctggat tgtcgtgaac accagcacac tgtttgacga actggagctg    840

gatccccctg aaatcgagcc tggcgtgctg aaggtcctgc ggaccgagaa acagtacctg    900

ggggtgtata tttggaacat gagaggcagc gacgggactt ccacctacgc caccttcctg    960

gtgacatgga agggggatga aaaaactcgc aatcccaccc ctgcagtgac accacagccc   1020

cgaggggcag agtttcacat gtggaactat cactctcatg tgttcagtgt cggagacacc   1080

ttttctctgg ccatgcacct gcagtacaag atccatgaag ctcctttcga cctgctgctg   1140

gagtggctgt atgtgcctat tgatccaacc tgccagccaa tgaggctgta cagcacatgt   1200

ctgtatcacc ccaatgcccc tcagtgcctg tcacatatga acagcggctg taccttcacc   1260

agccctcacc tggcacagcg agtggcttcc accgtctacc agaactgcga acatgctgac   1320

aattacacag catattgtct gggcatcagc cacatggagc catccttcgg gctgattctg   1380

catgacggcg ggactaccct gaagtttgtg gatacacccg aaagtctgtc agggctgtac   1440

gtcttcgtcg tgtattttaa tggacacgtg gaggcagtcg cctacactgt cgtgagcacc   1500

gtggatcatt tcgtcaacgc catcgaggaa aggggatttc caccaaccgc aggacagcct   1560
```

```
ccagctacaa ctaagccaaa agagattact ccagtgaacc caggaacctc cccactgctg   1620

cgatatgcag catggaccgg aggactggct gcagtcgtgc tgctgtgcct ggtcatcttc   1680

ctgatttgta cagctaagcg aatgcgggtg aaagcataca gggtcgacaa gtctccttat   1740

aatcagagta tgtactatgc tggactgcca gtggacgatt tcgaagacag cgagtccacc   1800

gatacagagg aagagtttgg aaacgcaatc ggaggatccc acggagggtc aagctacaca   1860

gtgtatattg ataagactcg gagaggacgc aaaaggcgct ctatgtttct gatccagtgc   1920

ctgattagtg cagtgatctt ctacattcag gtcaccaatg ccctgatctt taagggcgac   1980

cacgtgtcac tgcaggtcaa ctcctctctg actagcattc tgatccctat gcagaacgat   2040

aattataccg aaatcaaagg acagctggtg ttcattggcg agcagctgcc aactggaacc   2100

aattacagcg gcacactgga gctgctgtat gcagacactg tggccttctg ttttcggtcc   2160

gtccaggtca tcagatacga tggctgcccc agaatcagga cttccgcctt tatttcttgt   2220

aggtacaagc acagctggca ttatggaaat tcaaccgacc gcatcagcac agagcccgat   2280

gccggcgtga tgctgaagat caccaaacct gggattaacg acgctggagt ctacgtgctg   2340

ctggtgcgcc tggaccactc tcgaagtaca gatgggttca tcctgggagt caatgtgtat   2400

actgccggga gccaccataa catccatggc gtgatctaca cttcacctag cctgcagaac   2460

ggctattcca cccgagcact gttccagcag gcacgactgt gcgacctgcc tgcaacccca   2520

aaggggtccg gaacatctct gtttcagcac atgctggatc tgcgggccgg gaaatctctg   2580

gaggacaatc catggctgca tgaagatgtc gtgaccacag agacaaagag tgtcgtgaaa   2640

gaaggaatcg agaaccacgt gtaccccaca gacatgtcca ctctgcctga aaagtctctg   2700

aacgatcccc ctgagaatct gctgatcatt atccccatcg tggccagtgt catgattctg   2760

accgctatgg tcattgtgat cgtcatttca gtgaagcgac ggagaatcaa gaaacaccca   2820

atctaccggc ccaatacaaa aactaggcgc ggcatccaga acgccacacc agaatccgac   2880

gtgatgctgg aggccgctat cgctcagctg gcaactatta gagaagagag tccaccccat   2940

tcagtcgtga accccttcgt gaaatgataa ctcgag                             2976
```

```
<210> SEQ ID NO 111
<211> LENGTH: 591
<212> TYPE: PRT
<213> ORGANISM: Artificial Sequence
<220> FEATURE:
<223> OTHER INFORMATION: VZV-gC amino acid sequence

<400> SEQUENCE: 111

Met Ser Lys Lys Thr Phe Pro Ser Phe Lys Phe Arg Gly Gly Cys Phe
1               5                   10                  15

Asn Leu Leu Phe Lys Gly Ser Val Asp Val Ser Ile Lys Thr Arg Met
            20                  25                  30

Lys Arg Ile Gln Ile Asn Leu Ile Leu Thr Ile Ala Cys Ile Gln Leu
        35                  40                  45

Ser Thr Glu Ser Gln Pro Thr Pro Val Ser Ile Thr Glu Leu Tyr Thr
    50                  55                  60

Ser Ala Ala Thr Arg Lys Pro Asp Pro Ala Val Ala Pro Thr Ser Ala
65                  70                  75                  80

Ala Ser Arg Lys Pro Asp Pro Ala Val Ala Pro Thr Ser Ala Ala Thr
                85                  90                  95

Arg Lys Pro Asp Pro Ala Val Ala Pro Thr Ser Ala Ala Thr Arg Lys
            100                 105                 110
```

-continued

```
Pro Asp Pro Ala Val Ala Pro Thr Ser Ala Ala Thr Arg Lys Pro Asp
        115                 120                 125

Pro Ala Val Ala Pro Thr Ser Ala Ala Thr Arg Lys Pro Asp Pro Ala
    130                 135                 140

Val Ala Pro Thr Ser Ala Ala Thr Arg Lys Pro Asp Pro Ala Val Ala
145                 150                 155                 160

Pro Thr Ser Ala Ala Ser Arg Lys Pro Asp Pro Ala Ala Asn Thr Gln
                165                 170                 175

His Ser Gln Pro Pro Phe Leu Tyr Glu Asn Ile Gln Cys Val His Gly
            180                 185                 190

Gly Ile Gln Ser Ile Pro Tyr Phe His Thr Phe Ile Met Pro Cys Tyr
        195                 200                 205

Met Arg Leu Thr Thr Gly Gln Gln Ala Ala Phe Lys Gln Gln Gln Lys
    210                 215                 220

Thr Tyr Glu Gln Tyr Ser Leu Asp Pro Glu Gly Ser Asn Ile Thr Arg
225                 230                 235                 240

Trp Lys Ser Leu Ile Arg Pro Asp Leu His Ile Glu Val Trp Phe Thr
                245                 250                 255

Arg His Leu Ile Asp Pro His Arg Gln Leu Gly Asn Ala Leu Ile Arg
            260                 265                 270

Met Pro Asp Leu Pro Val Met Leu Tyr Ser Asn Ser Ala Asp Leu Asn
        275                 280                 285

Leu Ile Asn Asn Pro Glu Ile Phe Thr His Ala Lys Glu Asn Tyr Val
    290                 295                 300

Ile Pro Asp Val Lys Thr Thr Ser Asp Phe Ser Val Thr Ile Leu Ser
305                 310                 315                 320

Met Asp Ala Thr Thr Glu Gly Thr Tyr Ile Trp Arg Val Val Asn Thr
                325                 330                 335

Lys Thr Lys Asn Val Ile Ser Glu His Ser Ile Thr Val Thr Thr Tyr
            340                 345                 350

Tyr Arg Pro Asn Ile Thr Val Val Gly Asp Pro Val Leu Thr Gly Gln
        355                 360                 365

Thr Tyr Ala Ala Tyr Cys Asn Val Ser Lys Tyr Tyr Pro Pro His Ser
    370                 375                 380

Val Arg Val Arg Trp Thr Ser Arg Phe Gly Asn Ile Gly Lys Asn Phe
385                 390                 395                 400

Ile Thr Asp Ala Ile Gln Glu Tyr Ala Asn Gly Leu Phe Ser Tyr Val
                405                 410                 415

Ser Ala Val Arg Ile Pro Gln Gln Lys Gln Met Asp Tyr Pro Pro Pro
            420                 425                 430

Ala Ile Gln Cys Asn Val Leu Trp Ile Arg Asp Gly Val Ser Asn Met
        435                 440                 445

Lys Tyr Ser Ala Val Val Thr Pro Asp Val Tyr Pro Phe Pro Asn Val
    450                 455                 460

Ser Ile Gly Ile Ile Asp Gly His Ile Val Cys Thr Ala Lys Cys Val
465                 470                 475                 480

Pro Arg Gly Val Val His Phe Val Trp Trp Val Asn Asp Ser Pro Ile
                485                 490                 495

Asn His Glu Asn Ser Glu Ile Thr Gly Val Cys Asp Gln Asn Lys Arg
            500                 505                 510

Phe Val Asn Met Gln Ser Ser Cys Pro Thr Ser Glu Leu Asp Gly Pro
        515                 520                 525
```

-continued

```
Ile Thr Tyr Ser Cys His Leu Asp Gly Tyr Pro Lys Lys Phe Pro Pro
    530                 535                 540

Phe Ser Ala Val Tyr Thr Tyr Asp Ala Ser Thr Tyr Ala Thr Thr Phe
545                 550                 555                 560

Ser Val Val Ala Val Ile Ile Gly Val Ile Ser Ile Leu Gly Thr Leu
                565                 570                 575

Gly Leu Ile Ala Val Ile Ala Thr Leu Cys Ile Arg Cys Cys Ser
            580                 585                 590


<210> SEQ ID NO 112
<211> LENGTH: 1797
<212> TYPE: DNA
<213> ORGANISM: Artificial Sequence
<220> FEATURE:
<223> OTHER INFORMATION: VZV-gC nucleic acid sequence

<400> SEQUENCE: 112

aagcttgcca ccatgtcaaa gaagactttt ccttcattca aattccgggg cggctgtttc     60

aacctgctgt tcaaagggag cgtggatgtg tcaatcaaaa ccaggatgaa gcgcatccag    120

attaacctga tcctgacaat tgcctgtatc cagctgtcaa ccgagagcca gcccacacct    180

gtgagcatca ctgaactgta cacctccgca gctacacgaa agccagaccc agctgtggca    240

ccaacctccg cagcctctcg aaaacctgat ccagccgtgg ctcctacttc cgctgcaacc    300

cgaaagccag accctgcagt ggcaccaaca tctgccgcta ctagaaaacc agatcccgct    360

gtggcaccca ccagtgcagc cacaaggaag cctgaccctg ctgtggctcc tacttctgct    420

gcaacccgca aacccgatcc tgcagtggcc ccaacaagcg ccgctactcg aaagccagac    480

cccgctgtgg cacccacaag tgcagcctca cggaaacctg atccagctgc aaacactcag    540

cacagccagc cccctttct gtacgagaat attcagtgtg tgcacggcgg gattcagtcc     600

atcccctact tccatacctt tatcatgcct tgctatatga ggctgaccac aggccagcag    660

gccgctttta agcagcagca gaaaacatac gagcagtata gtctggaccc tgaagggtca    720

aacatcaccc gatggaagtc cctgattcgg ccagacctgc acatcgaagt gtggttcaca    780

agacacctga ttgatcccca taggcagctg ggcaatgccc tgatccgcat gccagacctg    840

cccgtgatgc tgtactctaa cagtgccgat ctgaatctga ttaacaatcc tgagatcttc    900

acccatgcta aggaaaacta tgtgattcca gacgtcaaaa ctaccagcga tttttccgtg    960

acaattctga gcatggacgc cacaactgag gggacttaca tctggagagt ggtcaacaca   1020

aagactaaga acgtgatctc tgaacacagt atcactgtca ccacatacta taggccaaac   1080

atcaccgtgg tcggagatcc agtgctgacc ggacagacat acgcagccta ttgtaatgtc   1140

tctaagtact atccacccca tagtgtgcgg gtcagatgga cttcacggtt cggaaacatt   1200

ggcaaaaatt ttattaccga cgctatccag gagtacgcaa atgggctgtt ttcatatgtg   1260

agcgccgtcc gcatcccaca gcagaagcag atggactatc ctccacccgc tattcagtgc   1320

aacgtgctgt ggatccgaga tggagtctcc aatatgaaat actctgccgt ggtcacacct   1380

gacgtgtatc ccttccctaa cgtcagcatt ggcatcattg atgggcacat cgtgtgcacc   1440

gcaaagtgtg tcccccgggg agtggtccac tttgtgtggt gggtcaatga cagccctatt   1500

aaccatgaga attccgaaat caccggcgtg tgcgatcaga acaaaagatt cgtcaatatg   1560

cagagctcct gtcctacatc agagctggac gggccaatca cttacagctg ccatctggat   1620

ggatatccca agaaattccc tccattttcc gccgtgtaca cttatgatgc atctacctac   1680
```

-continued gccactacct tcagtgtggt cgccgtgatc attggcgtca tctctattct ggggaccctg 1740
ggactgattg ccgtgatcgc tacactgtgc atcagatgct gtagctgata actcgag 1797

<210> SEQ ID NO 113
<211> LENGTH: 340
<212> TYPE: PRT
<213> ORGANISM: Artificial Sequence
<220> FEATURE:
<223> OTHER INFORMATION: VZV-gK amino acid sequence

<400> SEQUENCE: 113

Met Gln Ala Leu Gly Ile Lys Thr Glu His Phe Ile Ile Met Cys Leu
1 5 10 15

Leu Ser Gly His Ala Val Phe Thr Leu Trp Tyr Thr Ala Arg Val Lys
20 25 30

Phe Glu His Glu Cys Val Tyr Ala Thr Thr Val Ile Asn Gly Gly Pro
35 40 45

Val Val Trp Gly Ser Tyr Asn Asn Ser Leu Ile Tyr Val Thr Phe Val
50 55 60

Asn His Ser Thr Phe Leu Asp Gly Leu Ser Gly Tyr Asp Tyr Ser Cys
65 70 75 80

Arg Glu Asn Leu Leu Ser Gly Asp Thr Met Val Lys Thr Ala Ile Ser
85 90 95

Thr Pro Leu His Asp Lys Ile Arg Ile Val Leu Gly Thr Arg Asn Cys
100 105 110

His Ala Tyr Phe Trp Cys Val Gln Leu Lys Met Ile Phe Phe Ala Trp
115 120 125

Phe Val Tyr Gly Met Tyr Leu Gln Phe Arg Arg Ile Arg Arg Met Phe
130 135 140

Gly Pro Phe Arg Ser Ser Cys Glu Leu Ile Ser Pro Thr Ser Tyr Ser
145 150 155 160

Leu Asn Tyr Val Thr Arg Val Ile Ser Asn Ile Leu Leu Gly Tyr Pro
165 170 175

Tyr Thr Lys Leu Ala Arg Leu Leu Cys Asp Val Ser Met Arg Arg Asp
180 185 190

Gly Met Ser Lys Val Phe Asn Ala Asp Pro Ile Ser Phe Leu Tyr Met
195 200 205

His Lys Gly Val Thr Leu Leu Met Leu Leu Glu Val Ile Ala His Ile
210 215 220

Ser Ser Gly Cys Ile Val Leu Leu Thr Leu Gly Val Ala Tyr Thr Pro
225 230 235 240

Cys Ala Leu Leu Tyr Pro Thr Tyr Ile Arg Ile Leu Ala Trp Val Val
245 250 255

Val Cys Thr Leu Ala Ile Val Glu Leu Ile Ser Tyr Val Arg Pro Lys
260 265 270

Pro Thr Lys Asp Asn His Leu Asn His Ile Asn Thr Gly Gly Ile Arg
275 280 285

Gly Ile Cys Thr Thr Cys Cys Ala Thr Val Met Ser Gly Leu Ala Ile
290 295 300

Lys Cys Phe Tyr Ile Val Ile Phe Ala Ile Ala Val Val Ile Phe Met
305 310 315 320

His Tyr Glu Gln Arg Val Gln Val Ser Leu Phe Gly Glu Ser Glu Asn
325 330 335

Ser Gln Lys His
340

-continued

```
<210> SEQ ID NO 114
<211> LENGTH: 1044
<212> TYPE: DNA
<213> ORGANISM: Artificial Sequence
<220> FEATURE:
<223> OTHER INFORMATION: VZV-gK nucleic acid sequence

<400> SEQUENCE: 114

aagcttgcca ccatgcaggc actgggaatc aaaaccgaac acttcatcat catgtgtctg     60

ctgtcagggc acgccgtctt cactctgtgg tacactgcta gggtgaagtt cgagcacgaa    120

tgcgtctacg ccaccacagt gatcaatggc gggccagtgg tctgggggag ttacaacaat    180

tcactgatct acgtcacatt cgtgaatcat tctacttttc tggacgggct gagcggatac    240

gattattcct gtcgcgagaa cctgctgtca ggagacacaa tggtgaagac tgctatcagc    300

acccccctgc acgataaaat cagaattgtg ctgggcacaa ggaactgcca tgcatatttt    360

tggtgtgtgc agctgaagat gatcttcttt gcctggttcg tgtacgggat gtatctgcag    420

tttcggagaa tcaggcgcat gttcggacct tttagaagct cctgcgaact gatttcccca    480

acttcataca gcctgaatta tgtcacccgc gtgatctcta acattctgct gggctacccc    540

tatactaaac tggctcgact gctgtgtgac gtctctatgc gacgggatgg catgagtaag    600

gtgttcaatg cagaccctat cagctttctg tacatgcaca aaggggtcac cctgctgatg    660

ctgctggaag tgatcgccca tatttctagt ggctgcattg tcctgctgac cctgggggtg    720

gcatacacac catgtgccct gctgtacccc acctatatcc gaattctggc ctgggtggtc    780

gtgtgcacac tggctatcgt cgaactgatt tcctatgtgc ggcccaagcc tacaaaagat    840

aaccacctga atcatatcaa cactggaggc atcagaggaa tttgcactac ctgctgtgct    900

accgtgatga gtggcctggc aattaagtgt ttctacatcg tgatttttgc catcgctgtc    960

gtgattttca tgcactatga gcagcgcgtc caggtgagcc tgtttggcga gtccgaaaac   1020

tctcagaaac attgataact cgag                                          1044
```